United States Patent
Miyata et al.

(10) Patent No.: US 8,415,479 B2
(45) Date of Patent: Apr. 9, 2013

(54) INHIBITOR OF PLASMINOGEN ACTIVATOR INHIBITOR-1

(75) Inventors: Toshio Miyata, Sendai (JP); Nagahisa Yamaoka, Osaka (JP); Hidehiko Kodama, Osaka (JP); Kenji Murano, Osaka (JP)

(73) Assignee: Renascience Co., Ltd., Tokyo (JP)

( * ) Notice: Subject to any disclaimer, the term of this patent is extended or adjusted under 35 U.S.C. 154(b) by 0 days.

(21) Appl. No.: 12/935,609

(22) PCT Filed: Mar. 31, 2009

(86) PCT No.: PCT/JP2009/056755
§ 371 (c)(1),
(2), (4) Date: Dec. 22, 2010

(87) PCT Pub. No.: WO2009/123241
PCT Pub. Date: Oct. 8, 2009

(65) Prior Publication Data
US 2011/0112140 A1    May 12, 2011

(30) Foreign Application Priority Data
Mar. 31, 2008   (JP) ................. 2008-093911

(51) Int. Cl.
*C07D 213/00*   (2006.01)
*A61K 31/44*    (2006.01)

(52) U.S. Cl.
USPC ............................... 546/308; 514/352

(58) Field of Classification Search ............ None
See application file for complete search history.

(56) References Cited

U.S. PATENT DOCUMENTS

| | | | |
|---|---|---|---|
| 5,532,276 | A | 7/1996 | Mederski et al. |
| 6,291,478 | B1 | 9/2001 | Galey et al. |
| 2005/0124667 | A1 | 6/2005 | Sartori et al. |
| 2008/0119402 | A1 | 5/2008 | Zheng et al. |
| 2009/0124620 | A1 | 5/2009 | Miyata et al. |

FOREIGN PATENT DOCUMENTS

| | | |
|---|---|---|
| EP | 0120352 | 10/1984 |
| EP | 0376166 | 7/1990 |
| JP | 56-7716 | 1/1981 |
| JP | 02-256667 | 10/1990 |
| JP | 07-196656 | 8/1995 |
| JP | 2000-503308 | 3/2000 |
| JP | 2000-290252 | 10/2000 |
| JP | 2005-275352 | 10/2005 |
| JP | 2007-22943 | 2/2007 |
| JP | 2007-502264 | 2/2007 |
| JP | 2008-502699 | 1/2008 |
| WO | 97/26244 | 7/1997 |
| WO | 2005/016870 | 2/2005 |
| WO | 2005/123072 | 12/2005 |
| WO | 2006/107719 | 10/2006 |
| WO | 2007/083689 | 7/2007 |
| WO | 2008/070831 | 6/2008 |
| WO | 2009/013915 | 1/2009 |
| WO | 2009/123241 | 10/2009 |

OTHER PUBLICATIONS

CAPLUS 1970 100715.*
Silverman, R. "The Organic Chemistry of Drug Design and Drug Action," 2004, Elsevier, pp. 29-32.*
CAPLUS 2008 564823.*
Vippagunta, S. et al., Adv. Drug Deliv. Rev. 2001, vol. 48, pp. 3-26.*
Aya, N, et al., Tissue-Type Plasminogen Activator and Its Inhibitor in Human Glomerulonephritis, J. Pathol., 166, 289-295, 1992.
Yoshida, Y, et al., Enhanced Expression of Plasminogen Activator Inhibitor 1 in Patients with Nephrotic Syndrome, Nephron, 88, 24-29, 2001.
Border, W.A., et al., t-PA promotes glomerular plasmin generation and matrix degradation in experimental glomerulonephritis, Kidney Int., 59, 2146-2155, 2001.
Egelund, R., et al., A Regulatory Hydrophobic Area in the Flexible Joint Region of Plasminogen Activator Inhiitor-1, Defined with Fluorescent Activity-neutralizing Ligands, J. Biol. Chem., 276, 13077-13086, 2001.
Eitzman, D. T., et al., Bleomycin-induced Pulmonary Fibrosis in Transgenic Mice That either Lack or Overexpress the Murine Plasminogen Activator Inhibitor-1 Gene, J. Clin. Invest. 97, 232-237, 1996.
Jacobsen, JS et al., Enhanced clearance of Aβ in brain by sustaining the plasmin proteolysis cascade, Proc Natl Acad Sci USA, 105(25), 8754-9, 2008.
Border, W.A. et al., A mutant, noninhibitory plasminogen activator inhibitor type 1 decreases matrix accumulation in experimental glomerulonephritis, J. Clin Invest. 112, 379-388, 2003.
International Search Report of PCT/JP2009/056755, dated Jun. 16, 2009.
Lassila, M. et al., Plasminogen activator inhibitor-1 production is pathogenetic in experimental murine diabetic renal disease, Diabetologia, 2007, vol. 50, pp. 1315-1326.

(Continued)

*Primary Examiner* — D M Seaman
*Assistant Examiner* — Heidi Reese
(74) *Attorney, Agent, or Firm* — Roylance, Abrams, Berdo & Goodman, L.L.P.

(57) ABSTRACT

The present invention relates to a novel compound having plasminogen activator inhibitor-1 (PAI-1) inhibitory activity, and a PAI-1 inhibitor comprising the compound as an active ingredient. The present invention further relates to a pharmaceutical composition that has an inhibitory action on PAI-1 activity and is useful in the prevention and treatment of various diseases whose onset is associated with PAI-1 activity. The novel compound is represented by the following general formula.

(I)

Each symbol is defined as those in the specification.

17 Claims, 9 Drawing Sheets

OTHER PUBLICATIONS

Oda, T. et al., PAI-1 deficiency attenuates the fibrogenic response to ureteral obstruction, Kidney International, 2001, vol. 30, pp. 587-596.

Matsuo, S. et al., Multifunctionality of PAI-1 in fibrogenesis: Evidence from obstructive nephropathy in PAI-1—overexpressing mice, Kidney International, 2005, vol. 67, pp. 2221-2238.

Huang, Y. et al., Noninhibitory PAI-1 enhances plasmin-mediated matrix degradation both in vitro and in experimental nephritis, Kidney International, 2006, vol. 70, pp. 515-522.

Eddy, A. et al., Plasminogen activator inhibitor-1 in chronic kidney disease: Evidence and mechanisms of action, Journal of American Society Nephrology, 2006, vol. 17, pp. 2999-3012.

Roelofs, J. et al., Plasminogen activator inhibitor-1 regulates neutrophil influx during acute pyelonephritis, Kidney International, 2009, vol. 75, pp. 52-59.

Ha, H. et al., The role of plasminogen activator inhibitor 1 in renal and cardiovascular diseases, Nephrology, 2009, vol. 5, pp. 203-211.

Durand, M. et al., Plasminogen activator inhibitor-I and tumour growth, invasion, and metastasis, Thromb Haemost, 2004, vol. 91, pp. 438-449.

Dan, J. et al., Plasminogen activator inhibitor-I in the aqueous humor of patients with and without glaucoma, Arch Ophthalmol, 2005, vol. 123, pp. 220-224.

Basu, A. et al., Plasminogen activator inhibitor-1 (PAI-1) facilitates retinal angiogenesis in a model of oxygen-induced retinopathy, Investigative Ophthalmology & Visual Science, 2009, vol. 50, No. 10, pp. 4974-4981.

Milliat, F. et al., Essential role of plasminogen activator inhibitor type-1 in radiation enteropathy, The American Journal of Pathology, 2008, vol. 172, No. 3, pp. 691-701.

Eren, M. et al., Reactive site-dependent phenotypic alterations in plasminogen activator inhibitor-1 transgenic mice, Journal of Thrombosis and Haemostasis, 2007, vol. 5, pp. 1500-1508.

Devin, J. et al., Transgenic overexpression of plasminogen activator inhibitor-1 promotes the development of polycystic ovarian changes in female mice, Journal of Molecular Endocrinology, 2007, vol. 39, pp. 9-16.

Suzuki, Y. et al., Unique secretory dynamics of tissue plasminogen activator and its modulation by plasminogen activator inhibitor-1 in vascular endothelial cells, Blood, 2009, vol. 113, No. 2, pp. 470-478.

Maemura, K. et al., Circadian rhythms in the CNS and peripheral clock disorders: Role of the biological clock in cardiovascular diseases, Journal of Pharmacological Sciences, 2007, vol. 103, pp. 134-138.

Schoenhard, J. et al., Plasminogen activator inhibitor-1 has a circadian rhythm in blind Individuals, Thromb Haemost, 2007, vol. 98, pp. 479-481.

Crandall, D. et al., Modulation of adipose tissue development by pharmacological inhibition of PAI-1, Arteriosclerosis, Thrombosis, and Vascular Biology, 2006, vol. 26, pp. 2209-2215.

Hattori, N. et al., Bleomycin-induced pulmonary fibrosis in fibrinogen-null mice, The Journal of Clinical Investigation, 2000, vol. 106, No. 11, pp. 1341-1350.

Kosaka, H. et al., Interferon-gamma is a therapeutic target molecule for prevention of postoperative adhesion formation, Nature Medicine, 2008, vol. 14, No. 4, pp. 437-441.

Matsuo, O. et al., Plasminogen activator in bronchoalveolar fluid, Haemostasis, 1986, vol. 16, pp. 43-50.

Kivirikko, K. et al., Modifications of a specific assay for hydroxyproline in urine, Analytical Biochemistry, 1967, vol. 19, pp. 249-255.

Ashcroft, T. et al., Simple method of estimating severity of pulmonary fibrosis on a numerical scale, Journal of Clinical Pathology, 1988, vol. 41, pp. 467-470.

Milton, J. et al, Biaryl acids: Novel non-nucleoside inhibitors of HIV reverse transcriptase types 1 and 2, Bioorganic & Medicinal Chemistry Letters, 1998, vol. 8, pp. 2623-2628.

International Search Report for PCT/IB2010/000731, dated Jul. 13, 2010.

International Search Report for PCT/JP2008/054543, dated Jun. 17, 2008.

Huang, Y. et al., A mutant, noninhibitory plasminogen activator inhibitor type 1 decreases matrix accumulation in experimental glomerulonephritis, The Journal of Clinical Investigation, 2003, vol. 112, pp. 379-388.

Haraguchi, M. et al., t-PA promotes glomerular plasmin generation and matrix degradation in experimental glomerulonephritis, Kidney International, 2001, vol. 59, pp. 2146-2155.

Lopez-Alvarado, P. et al., Versatile synthesis of malonamic acid derivatives from a beta-ketothioester, Tetrahedron Letters, 2001, vol. 42, No. 27, pp. 4479-4482.

Bezugly, P. et al., Amides of 4-carboxymalonanilic acid with anti-inflammatory and neurotropic activities, Farmacevticnij Zurnal, 1990, No. 4, pp. 37-41.

Petiunin, G. et al., Amides and hydrazides of oxalic acid. XXVI. Synthesis and properties of N-substituted oxamoyl) anthranilic acids, Farmacevticnij Zurnal, 1973, vol. 28, No. 6, pp. 21-24.

Supplementary European Search Report for EP Application No. 09729173.6, dated Dec. 20, 2011.

Vaughan, D. et al., PAI-1 antagonists: Predictable indications and unconventional applications, Current Drug Targets, 2007, vol. 8, pp. 962-970.

* cited by examiner

FIG. 1

| Example | Chemical name | Formula M.W. | PAI-1 activity % 50 μM | PAI-1 activity % 20 μM |
|---|---|---|---|---|
| 1 | 5-Chloro-2-([[(2-oxo-2-([4-(pyridin-4-yl)phenyl]amino)ethoxy]acetyl]amino)benzoic acid | C22H18ClN3O5 439.85 | 0.6 | 28.7 |
| 2 | 5-Chloro-2-([[(2-oxo-2-([[3-(pyridin-4-yl)phenyl]amino)ethoxy]acetyl]amino)benzoic acid | C22H18ClN3O5 439.85 | 12.8 | 14.6 |
| 3 | 5-Chloro-2-[((2-[(4'-fluorobiphenyl-2-yl)amino]-2-oxoethoxy)acetyl)amino]benzoic acid | C23H18ClFN2O5 456.85 | 39.6 | 82.4 |
| 4 | 5-Chloro-2-([[(2-oxo-2-([2-(pyridin-4-yl)phenyl]amino)ethoxy]acetyl]amino)benzoic acid hydrochloride | C22H19Cl2N3O5 476.31 | 24.3 | 65.1 |
| 5 | 5-Chloro-2-[((2-[(4'-fluoro-4-methylbiphenyl-3-yl)amino]-2-oxoethoxy)acetyl)amino]benzoic acid | C24H20ClFN2O5 470.88 | 8.1 | 48.6 |
| 6 | 5-Chloro-2-[((2-oxo-2-[(3',4,5'-trimethylbiphenyl-3-yl)amino]ethoxy)acetyl)amino]benzoic acid | C26H25ClN2O5 480.94 | 13.6 | 96.6 |
| 7 | 5-Chloro-2-[((2-[(4'-fluorobiphenyl-4-yl)amino]-2-oxoethoxy)acetyl)amino]benzoic acid sodium salt | C23H17ClFN2NaO5 478.83 | 15.6 | 92.2 |
| 8 | 5-Chloro-2-[((2-[(4'-fluorobiphenyl-3-yl)amino]-2-oxoethoxy)acetyl)amino]benzoic acid sodium salt | C23H17ClFN2NaO5 478.83 | 12.4 | 95.6 |
| 9 | 5-Chloro-2-(([2-(dicyclohexylamino)-2-oxoethoxy]acetyl)amino)benzoic acid sodium salt | C23H30ClN2NaO5 472.94 | 19.6 | 79.3 |
| 10 | 5-Chloro-2-[((2-[(4-cyclohexylphenyl)amino]-2-oxoethoxy)acetyl)amino]benzoic acid sodium salt | C23H24ClN2NaO5 466.89 | 31.9 | 93.2 |
| 11 | 5-Chloro-2-(([2-(cyclododecylamino)-2-oxoethoxy]acetyl)amino)benzoic acid | C23H33ClN2O5 452.97 | 11.5 | 64.7 |
| 12 | 5-Chloro-2-([([(2-[(4'-fluorobiphenyl-3-yl)amino]-2-oxoethyl)sulfanyl]acetyl)amino)benzoic acid sodium salt | C23H17ClFN2NaO4S 494.90 | 29.2 | 92.7 |

FIG. 2

| Example | Chemical name | Formula M.W. | PAI-1 activity % 50 μM | PAI-1 activity % 20 μM |
|---|---|---|---|---|
| 13 | 5-Chloro-2-([[(2-[(4'-fluorobiphenyl-3-yl)amino]-2-oxoethyl)sulfinyl]acetyl]amino)benzoic acid | C23H18ClFN2O5S 488.92 | 27.8 | 95.1 |
| 14 | 5-Chloro-2-([[(2-[(4'-fluorobiphenyl-3-yl)amino]-2-oxoethyl)sulfonyl]acetyl]amino)benzoic acid | C23H18ClFN2O6S 504.92 | 30.9 | 99.7 |
| 15 | 5-Chloro-2-[((2-[cyclohexyl(phenyl)amino]-2-oxoethoxy)acetyl]amino]benzoic acid sodium salt | C23H24ClN2NaO5 466.89 | 16.8 | 55.9 |
| 16 | 5-Chloro-2-([(2-oxo-2-([[3-(pyridin-4-yl)phenyl]amino]ethoxy)acetyl]amino)benzoic acid [(2,2-dimethylpropanoyl)oxy]methyl ester | C28H28ClN3O7 553.99 | 99.1 | 99.2 |
| 17 | 5-Chloro-2-([(2-oxo-2-([[3-(pyridin-4-yl)phenyl]amino]ethoxy)acetyl]amino)benzoic acid 1-([(cyclohexyloxy)carbonyl]oxy)ethylester | C31H32ClN3O8 610.05 | 99.3 | 99.8 |
| 18 | 5-Chloro-2-([(2-oxo-2-([[3-(pyridin-4-yl)phenyl]amino]ethoxy)acetyl]amino)benzoic acid (5-methyl-2-oxo-1,3-dioxol-4-yl)methyl ester | C27H22ClN3O8 551.93 | 94.0 | 97.7 |
| 19 | 5-Chloro-2-([[(2-oxo-2-([[3-(pyridin-3-yl)phenyl]amino]ethoxy)acetyl]amino]benzoic acid sodium salt | C22H17ClN3NaO5 461.83 | 22.0 | 74.2 |
| 20 | 5-Chloro-2-((([(4'-fluoro-4-methylbiphenyl-3-yl)amino](oxo)acetyl]amino)benzoic acid sodium salt | C22H15ClFN2NaO4 448.81 | 27.2 | 31.1 |
| 21 | 5-Chloro-2-([[(2-oxo-2-([[3-(pyridin-2-yl)phenyl]amino]ethoxy)acetyl]amino]benzoic acid sodium salt | C22H17ClN3NaO5 461.83 | 41.3 | 76.7 |
| 22 | 5-Chloro-2-[(((2-[(4'-fluoro-4-methylbiphenyl-3-yl)(2-methylpropyl)amino]-2-oxoethoxy)acetyl]amino]benzoic acid | C28H28ClFN2O5 526.98 | 6.7 | 42.6 |
| 23 | 4'-Fluoro-4-[(((2-[(4'-fluoro-4-methylbiphenyl-3-yl)amino]-2-oxoethoxy)acetyl]amino]biphenyl-3-carboxylic acid sodium salt | C30H23F2N2NaO5 552.50 | 7.6 | 96.8 |

FIG. 3

| Example | Chemical name | Formula M.W. | PAI-1 activity % 50 μM | PAI-1 activity % 20 μM |
|---|---|---|---|---|
| 24 | 5-Chloro-2-([[(2-oxo-2-[(3',4,5'-trimethylbiphenyl-3-yl)amino]ethyl)sulfanyl]acetyl]amino)benzoic acid | C26H25ClN2O4S 497.01 | 17.0 | 66.0 |
| 25 | 5-Chloro-2-((([(2-oxo-2-([3-(pyridin-4-yl)phenyl]amino)ethyl)sulfanyl]acetyl)amino)benzoic acid | C22H18ClN3O4S 455.91 | 18.4 | 16.4 |
| 26 | 5-Chloro-2-[((2-[(3-cyclohexylphenyl)amino]-2-oxoethoxy)acetyl)amino]benzoic acid | C23H25ClN2O5 444.91 | 6.4 | 34.9 |
| 27 | 5-Chloro-2-(([(2-[(4-cyclohexylphenyl)amino]-2-oxoethyl)sulfanyl]acetyl)amino)benzoic acid | C23H25ClN2O4S 460.97 | 24.5 | 72.5 |
| 28 | 5-Chloro-2-[(([2-(cyclododecylamino)-2-oxoethyl]sulfanyl)acetyl)amino]benzoic acid | C23H33ClN2O4S 469.04 | 10.3 | 51.6 |
| 29 | 5-Chloro-2-[([2-[ethyl(4'-fluoro-4-methylbiphenyl-3-yl)amino]-2-oxoethyl)acetyl)amino]benzoic acid | C26H24ClFN2O5 498.93 | 8.0 | 58.5 |
| 30 | 5-Chloro-2-(([(2-[ethyl(4'-fluoro-4-methylbiphenyl-3-yl)amino]-2-oxoethyl]sulfanyl)acetyl)amino)benzoic acid | C26H24ClFN2O4S 515.00 | 13.2 | 55.0 |
| 31 | 5-Chloro-2-((5-[ethyl(4'-fluoro-4-methylbiphenyl-3-yl)amino]-5-oxopentanoyl)amino)benzoic acid | C27H26ClFN2O4 496.96 | 12.5 | 75.4 |
| 32 | 5-Chloro-2-(([2-([5-(furan-3-yl)-2-methylphenyl]amino)-2-oxoethoxy)acetyl]amino)benzoic acid | C22H19ClN2O6 442.85 | 17.2 | 63.6 |
| 33 | 5-Chloro-2-(([(2-[[5-(furan-3-yl)-2-methylphenyl]amino]-2-oxoethyl]sulfanyl)acetyl)amino)benzoic acid | C22H19ClN2O5S 458.91 | 13.5 | 43.8 |
| 34 | 5-Chloro-2-[(5-([5-(furan-3-yl)-2-methylphenyl]amino)-5-oxopentanoyl)amino]benzoic acid | C23H21ClN2O5 440.88 | 23.6 | 74.0 |
| 35 | 5-Chloro-2-([[2-(ethyl[5-(furan-3-yl)-2-methylphenyl]amino)-2-oxoethoxy]acetyl)amino]benzoic acid | C24H23ClN2NaO6 470.90 | 30.5 | 72.2 |

FIG. 4

| Example | Chemical name | Formula M.W. | PAI-1 activity % 50 μM | PAI-1 activity % 20 μM |
|---|---|---|---|---|
| 36 | 5-Chloro-2-(([(2-(ethyl[5-(furan-3-yl)-2-methylphenyl]amino)-2-oxoethyl)sulfanyl]acetyl)amino)benzoic acid | C24H23ClN2O5S 486.97 | 37.3 | 78.2 |
| 37 | 5-Chloro-2-[(5-(ethyl[5-(furan-3-yl)-2-methylphenyl]amino)-5-oxopentanoyl)amino]benzoic acid | C25H25ClN2O5 468.93 | 37.7 | 78.9 |
| 38 | 5-Chloro-2-[((2-[(2'-methoxy-4-methylbiphenyl-3-yl)amino]-2-oxoethoxy)acetyl)amino]benzoic acid | C25H23ClN2NaO6 482.91 | 11.3 | 73.7 |
| 39 | 5-Chloro-2-[((2-[(3'-methoxy-4-methylbiphenyl-3-yl)amino]-2-oxoethoxy)acetyl)amino]benzoic acid | C25H23ClN2O6 482.91 | 6.9 | 64.3 |
| 40 | 5-Chloro-2-[((2-[(4'-methoxy-4-methylbiphenyl-3-yl)amino]-2-oxoethoxy)acetyl)amino]benzoic acid | C25H23ClN2O6 482.91 | 11.2 | 61.5 |
| 41 | 2-([(2-[(5-(1,3-Benzodioxol-5-yl)-2-methylphenyl]amino)-2-oxoethoxy)acetyl]amino)-5-chlorobenzoic acid | C25H21ClN2O7 496.90 | 9.5 | 87.5 |
| 42 | 5-Chloro-2-([(2-[[2-methyl-5-(quinolin-8-yl)phenyl]amino]-2-oxoethoxy)acetyl]amino)benzoic acid hydrochloride | C27H23Cl2N3O5 540.39 | 7.2 | 54.2 |
| 43 | 2-([[(2-[[3'-(Acctylamino)-4-methylbiphenyl-3-yl]amino]-2-oxoethoxy)acetyl]amino)-5-chlorobenzoic acid | C26H24ClN3O6 509.94 | 31.6 | 88.9 |
| 44 | 2-([(2-[[4'-(Acetylamino)-4-methylbiphenyl-3-yl]amino]-2-oxoethoxy)acetyl]amino)-5-chlorobenzoic acid | C26H24ClN3O6 509.94 | 6.7 | 41.4 |
| 45 | 5-Chloro-2-((([3-(furan-3-yl)phenyl]amino)(oxo)acetyl)amino)benzoic acid | C19H13ClN2O5 384.77 | 8.4 | 47.8 |
| 46 | 5-Chloro-2-((([2-[3-(furan-3-yl)phenyl]sulfanyl]acetyl)amino)benzoic acid | C21H17ClN2O5S 444.89 | 47.3 | 83.9 |
| 47 | 5-Chloro-2-([(2-[[3-(2,6-dimethoxypyridin-3-yl)phenyl]amino)-2-oxoethoxy)acetyl]amino)benzoic acid | C24H22ClN3O7 499.90 | 11.0 | 76.5 |

FIG. 5

| Example | Chemical name | Formula M.W. | PAI-1 activity % 50 µM | PAI-1 activity % 20 µM |
|---|---|---|---|---|
| 48 | 5-Chloro-2-([[(2-oxo-2-([3-(1H-pyrrol-1-yl)phenyl]amino)ethoxy)acetyl]amino)benzoic acid sodium salt | C21H17ClN3NaO5 449.82 | 14.5 | 64.0 |
| 49 | 5-Chloro-2-([[(2-([2-fluoro-5-(furan-3-yl)phenyl]amino)-2-oxoethoxy)acetyl]amino)benzoic acid | C21H16ClFN2O6 446.81 | 15.9 | 61.7 |
| 50 | 5-Chloro-2-([[(2-([4-fluoro-3-(furan-3-yl)phenyl]amino)-2-oxoethoxy)acetyl]amino)benzoic acid | C21H16ClFN2O6 446.81 | 9.4 | 60.8 |
| 51 | 2-([[(2-([3-(1-Benzofuran-2-yl)phenyl]amino)-2-oxoethoxy)acetyl]amino)-5-chlorobenzoic acid | C25H19ClN2O6 478.88 | 5.7 | 44.9 |
| 52 | 5-Chloro-2-[(3-([3-(furan-3-yl)phenyl]amino)-3-oxopropanoyl)amino]benzoic acid | C20H15ClN2O5 398.80 | 25.4 | 72.3 |
| 53 | 5-Chloro-2-({{[3-(furan-3-yl)benzyl]amino}(oxo)acetyl}amino)benzoic acid | C20H15ClN2O5 398.80 | 8.6 | 46.9 |
| 54 | 5-Chloro-2-([[(2-([3-(furan-2-ylmethyl)phenyl]amino)-2-oxoethoxy)acetyl]amino)benzoic acid | C22H19ClN2O6 442.85 | 21.4 | 72.0 |
| 55 | 5-Chloro-2-([[(2-([3-(furan-3-ylmethyl)phenyl]amino)-2-oxoethoxy)acetyl]amino)benzoic acid | C22H19ClN2O6 442.85 | 13.6 | 60.2 |
| 56 | 5-Chloro-2-[([(2-oxo-2-[(2-phenoxyphenyl)amino]ethoxy)acetyl]amino)]benzoic acid | C23H19ClN2O6 454.86 | 31.5 | 74.7 |
| 57 | 5-Chloro-2-([[(2-oxo-2-[(2-phenoxyphenyl)amino]ethyl)sulfanyl)acetyl]amino)benzoic acid | C23H19ClN2O5S 470.93 | 26.9 | 64.6 |
| 58 | 5-Chloro-2-([[(2-([3-(furan-3-yl)phenyl]amino)-2-oxoethoxy)acetyl]amino)benzoic acid | C21H17ClN2O6 428.82 | 6.4 | 16.2 |
| 59 | 5-Chloro-2-([[(2-oxo-2-([3-(thiophene-3-yl)phenyl]amino)ethoxy)acetyl]amino)benzoic acid | C21H17ClN2O5S 444.89 | 10.2 | 63.8 |

FIG. 6

| Example | Chemical name | Formula M.W. | PAI-1 activity % 50 μM | PAI-1 activity % 20 μM |
|---|---|---|---|---|
| 60 | 5-Chloro-2-([[2-([3-(1-methyl-1H-pyrazol-4-yl)phenyl]amino)-2-oxoethoxy]acetyl]amino)benzoic acid | C21H19ClN4O5 442.85 | 19.6 | 96.1 |
| 61 | 5-Chloro-2-([[2-([3-(furan-2-yl)phenyl]amino)-2-oxoethoxy]acetyl]amino)benzoic acid | C21H17ClN2O6 428.82 | 13.7 | 69.9 |
| 62 | 5-Chloro-2-([[2-([3-(3,5-dimethylisoxazol-4-yl)phenyl]amino)-2-oxoethoxy]acetyl]amino)benzoic acid sodium salt | C22H19ClN3NaO6 479.85 | 35.8 | 75.8 |
| 63 | 5-Chloro-2-([[2-oxo-2-([3-(thiophen-2-yl)phenyl]amino)ethoxy]acetyl]amino)benzoic acid | C21H17ClN2O5S 444.89 | 10.6 | 64.3 |
| 64 | 5-Chloro-2-([[2-([4-(furan-3-yl)phenyl]amino)-2-oxoethoxy]acetyl]amino)benzoic acid | C21H17ClN2O6 428.82 | 19.2 | 71.6 |
| 65 | 5-Chloro-2-([[2-([3-(furan-2-ylmethoxy)phenyl]amino)-2-oxoethoxy]acetyl]amino)benzoic acid | C22H19ClN2O7 458.85 | 25.4 | 86.0 |
| 66 | 5-Chloro-2-([[2-([3-(furan-3-yl)benzyl]amino)-2-oxoethoxy]acetyl]amino)benzoic acid | C22H19ClN2O6 442.85 | 17.7 | 59.2 |
| 67 | 5-Chloro-2-([[2-([3-(furan-2-yl)benzyl]amino)-2-oxoethoxy]acetyl]amino)benzoic acid | C22H19ClN2O6 442.85 | 8.1 | 57.6 |
| 68 | 5-Chloro-2-([[2-oxo-2-([3-(1H-pyrazol-4-yl)phenyl]amino)ethoxy]acetyl]amino)benzoic acid | C20H17ClN4O5 428.83 | 9.4 | 20.7 |
| 69 | 5-Chloro-2-[((2-oxo-2-[3-(1-[(phosphonatoxy)methyl]-1H-pyrazol-4-yl)phenyl]amino]ethoxy)acetyl]amino]benzoic acid trisodium salt | C21H17ClN4Na3O9P 604.78 | 98.6 | 99.4 |
| 70 | 5-chloro-2-([[2-([3-(1,3-oxazol-5-yl)phenyl]amino)-2-oxoethoxy]acetyl]amino)benzoic acid | C20H16ClN3O6 429.81 | 63.3 | 94.2 |
| 71 | 5-chloro-2-([[2-([3-(isoxazol-5-yl)phenyl]amino)-2-oxoethoxy]acetyl]amino)benzoic acid | C20H16ClN3O6 429.81 | 36.6 | 77.9 |

FIG. 7

| Example | Chemical name | Formula M.W. | PAI-1 activity % 50 µM | PAI-1 activity % 20 µM |
|---|---|---|---|---|
| 72 | 5-Chloro-2-([[(2-oxo-2-([3-(thiophene-3-yl)benzyl]amino)ethoxy)acetyl]amino)benzoic acid | C22H19ClN2O5S 458.91 | 19.9 | 72.1 |
| 73 | 5-Chloro-2-([[(2-oxo-2-([3-(thiophen-2-yl)benzyl]amino)ethoxy)acetyl]amino)benzoic acid | C22H19ClN2O5S 458.91 | 18.5 | 67.6 |
| 74 | 5-Chloro-2-([[[3-(furan-2-yl)benzyl]amino](oxo)acetyl]amino)benzoic acid | C20H15ClN2O5 398.80 | 12.3 | 38.9 |
| 75 | 5-Chloro-2-([(2-([3-(5-chlorothiophen-2-yl)benzyl]amino)-2-oxoethoxy)acetyl]amino)benzoic acid | C22H18Cl2N2O5S 493.36 | 7.4 | 46.1 |
| 76 | 5-Chloro-2-([[(2-([3-(5-methyl thiophen-2-yl)benzyl]amino)-2-oxoethoxy)acetyl]amino)benzoic acid | C23H21ClN2O5S 472.94 | 12.1 | 67.9 |
| 77 | 5-Chloro-2-([[(2-([3-(furan-3-yl)phenyl]amino)benzoic acid N-methyl-D-glucamine salt | C28H34ClN3O11 624.04 | 16.3 | 63.5 |

FIG. 9
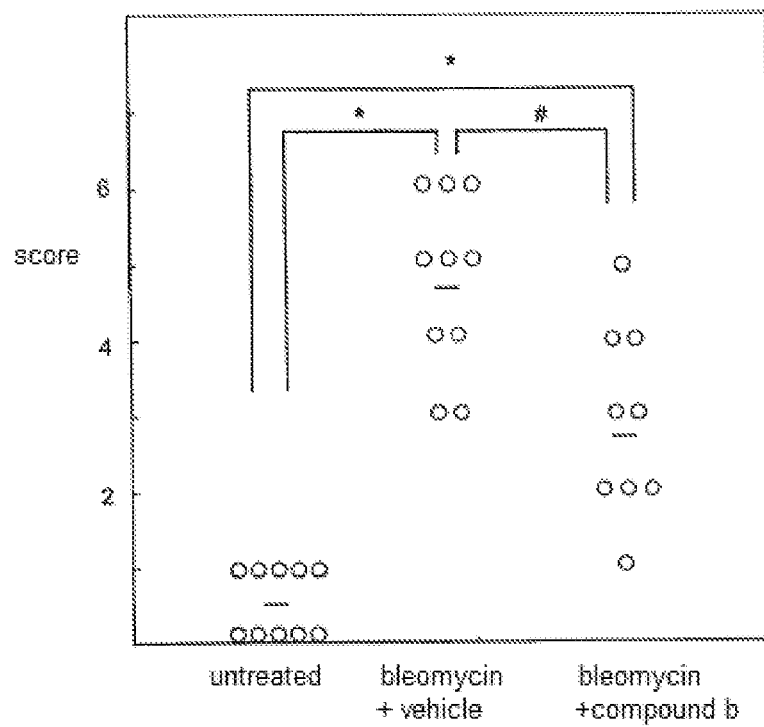
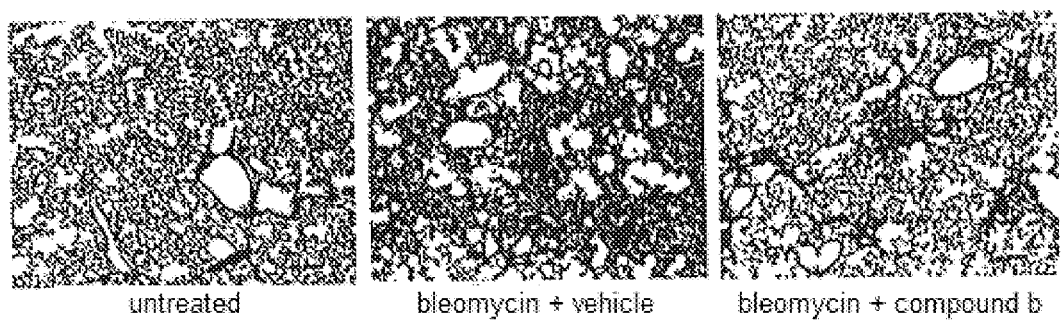

INHIBITOR OF PLASMINOGEN ACTIVATOR INHIBITOR-1

TECHNICAL FIELD

The present invention relates to a novel compound having plasminogen activator inhibitor-1 (hereinafter referred to as "PAI-1") inhibitory activity, and an inhibitor of PAI-1 comprising the compound as an active ingredient. The present invention further relates to a pharmaceutical composition having an inhibitory action on PAI-1 activity and being efficacious in the prevention and treatment of various diseases whose onset is associated with PAI-1 activity.

BACKGROUND ART

Atrial thrombus caused by atrial fibrillation and thrombi formed by the disruption of atheroma (atherosclerotic vessels) in the aorta or carotid artery may cause ischemic cerebrovascular diseases such as cerebral embolism, cerebral infarction, transient ischemic attack, etc., and ischemic heart diseases such as angina pectoris, myocardial infarction, atrial thrombus caused by atrial fibrillation, cardiac insufficiency, etc. While blood circulation must have good fluidity to deliver oxygen and nutrients to body tissues and remove waste (from the circulatory system), it is required to be coagulative to stop bleeding for the prevention of blood loss due to injury. When the balance between such opposed functions of fluidity and coagulation is lost and shifts to coagulation, an intravascular thrombus is formed, which is thought to cause ischemic cerebrovascular disorders and heart diseases.

The fibrinolytic system plays important roles in thrombolysis, tissue destruction and repair, cell migration, etc. The fibrinolytic system is activated when plasminogen activator (hereinafter referred to as "PA") converts plasminogen to plasmin, whereas plasminogen activator inhibitor-1 (PAI-1) inhibits PA.

Tissue plasminogen activator (hereinafter referred to as "t-PA") converts plasminogen, i.e., the precursor of plasmin, to plasmin. Plasmin converts fibrin to a fibrin degradation product by breaking it down.

PAI-1 is a serine protease inhibitor that specifically inhibits t-PA and urokinase plasminogen activator (hereinafter referred to as "u-PA"), suppresses plasmin generation, and as a result inhibits fibrin degradation.

Based on tertiary structural differences, PAI-1 is present in an active form that shows PA inhibitory activity and in a latent form that shows no PA inhibitory activity. In plasma, PAI-1 is known to be typically present in a concentration of 20 ng/mL, and produced in hepatocytes, megakaryocytes and lipocytes in addition to the vascular endothelial cells, which are the primary PAI-1 producing cells.

PAI-1 is an acute phase protein, and is thought to be one of the factors that cause ischemic organ dysfunctions in sepsis and disseminated intravascular coagulation syndrome (DIC) through accelerated production due to various cytokines and growth factors. Further, genetic polymorphism due to single base substitutions in the PAI-1 gene promoter is known, and it has been revealed that plasma PAI-1 concentration increases as a result of such genetic polymorphism.

Furthermore, in diabetes mellitus, accelerating arteriosclerosis and microvascular complications are presumed to be factors in ischemic heart disease, diabetic retinopathy and renal damage, i.e., all are critical complications of diabetes mellitus. For example, in diabetic nephropathy, increased extracellular matrix in the glomerulus and fibrous stroma are observed characteristics, and PAI-1 expression is increased in the glomerulus and renal tubules. In proximal renal tubule incubation, increased PAI-1 production is evident under hyperglycemic conditions. Further, a correlation between PAI-1 expression in renal tissues and macrophage infiltration is confirmed in experiments using a model mouse with renal interstitial fibrosis (non-patent document 1).

Furthermore, PAI-1 concentrations in urine are documented as being high in nephrotic syndrome patients based on the measurement results of PAI-1 levels in urine collected over a 24-hour period from nephrotic syndrome patients (see non-patent document 2).

As a result of administrating an inactive PAI-1 mutant (non-patent document 3) or t-PA (non-patent document 4) as a PAI-1 antagonist to a Thy-1 nephritis model, it is reported that the alleviation of inflammation (cellular infiltration), TGF-β suppression, and a decrease in mesangial matrix are observed, whereby Thy-1 nephritis is alleviated.

Reduced fibrinolytic activity due to an increased PAI-1 concentration in plasma is associated with ischemic heart diseases such as angina pectoris, myocardial infarction, cardiac insufficiency; deep-vein thrombosis and pulmonary embolism originated therefrom; and diabetic angiopathy. In addition to reduced fibrinolytic activity, some other thrombogenic abnormalities including hypercoagulation and platelet hyper-aggregation are also seen in diabetic patients. They are caused by microthrombus formation, and play important roles in the progress of diabetic microangiopathy and diabetic macroangiopathy.

As described above, PAI-1 is presumably involved in the various pathologic formations and the progress of thromboses, cancers, diabetes mellitus, arteriosclerosis, etc. For this reason, a compound that inhibits PAI-1 activity is useful as a preventive and treatment agent for diseases associated with reduced fibrinolytic activity such as thromboses, cancers, diabetic complications, arteriosclerosis, etc. (non-patent document 5).

Tissue fibril formation occurs in many tissues and organs such as the lungs, heart, blood vessels, liver, kidneys, etc. A report has disclosed that the progress of pulmonary fibrosis can be suppressed by the administration of a PA or PAI-1 inhibitor to activate the fibrinolysis system (non-patent document 6). Therefore, a PAI-1 inhibitor is known to be effective for treating tissue fibrosis, in particular pulmonary fibrosis. However, there is no drug available to treat them radically. In reality, adrenocorticotropic hormones such as predonisolone, corticosteroid, etc., and cytotoxic drugs such as cyclophosphamide (alkylating agent) and azathioprine (antimetabolites, immunosuppressants) have been used as palliative therapy based on experience.

It is believed that the onset of Alzheimer's disease is triggered by the accumulation of amyloid β peptide (Aβ) in the brain. Therefore, current research and development of drugs for preventing or treating Alzheimer's disease has been conducted with a focus on suppressing the production of Aβ or promoting decomposition of Aβ. It was recently discovered that the decomposition of Aβ can be promoted by inhibiting PAI-1; this finding suggests that a PAI-1 inhibitor may be usable as a drug for treating Alzheimer's disease (non-patent document 7).

Non-patent document 1: Aya N. et al., J. Pathol., 166, 289-295, 1992

Non-patent document 2: Yoshida Y. et al., Nephron, 88, 24-29, 2001

Non-patent document 3: W. A. Border et al., J. Clin. Invest., 112, 379, 2003

Non-patent document 4: W. A. Border et al., Kidney Int, 59, 246, 2001

Non-patent document 5: Egelund R. et al., J. Biol. Chem., 276, 13077-13086, 2001

Non-patent document 6: D T Eitzman, et al., J. Clin. Invest. 97, 232-237, 1996

Non-patent document 7: Jacobsen J S et al., Proc Natl Acad Sci USA, 105(25), 8754-9, 2008 Jun. 16

Patent document 1: WO 2009/013915 A1

DISCLOSURE OF THE INVENTION

Problems to be Solved by the Invention

Urokinase, i.e., u-PA, is known as a fibrinolytic-system-promoting drug. This drug is obtained by the purification of human urine, and is not considered to be highly productive or safe. Moreover, urokinase is a high molecular weight compound having a molecular weight of about 54000. Other known fibrinolytic-system-promoting drugs include tisokinase, alteplase (gene recombinant), nasaruplase (cell culture), nateplase (gene recombinant), monteplase (gene recombinant), pamiteplase (gene recombinant), and batroxobin; however, they are all high molecular weight compounds. Considering this fact, a highly safe low-molecular-weight compound drug that can be synthesized in large amounts is in demand as a fibrinolytic-system-promoting drug. Also expected is the development of drugs efficacious in radically treating fibrous tissue and the alleviation thereof.

In view of the foregoing problems, an object of the present invention is to provide a pharmaceutical composition that can be mass synthesized, has an active component of a low molecular weight compound with an inhibitory action on PAI-1 activity and is very safe; in particular, to provide a pharmaceutical composition that is useful as a fibrinolysis promoter, an anti-fibrosis agent, or an anti-Alzheimer's agent. Another object of the present invention is to provide a novel compound effective as an active component for a pharmaceutical composition such as a fibrinolysis promoter, an anti-fibrosis agent, or an anti-Alzheimer's agent, or the like.

Means for Solving the Problem

The present inventors have conducted extensive studies to solve the above problems, and found that a compound represented by the following formula (I) or a salt thereof, or a solvate thereof (hereinafter collectively referred to as "compound (I) of the present invention" or simply referred to as "compound (I)"), as well as compounds described a international publication (patent document 1), has high inhibitory activity on plasminogen activator inhibitor-1 (PAI-1). It is known that PAI-1 inhibitor has effects of a fibrinolysis promoter, and an anti-fibrosis agent for inhibiting fibrosis such as fibroid lung. Further, Current studies suggest that PAI-1 inhibitor is useful as a therapeutic medicine for Alzheimer's disease, which is considered to be caused by Aβ deposition in the brain.

The compound (I) of the present invention is effective as a fibrinolysis promoter, and also effective as an anti-fibrosis agent for preventing or treating various kinds of diseases associated with tissue fibrosis, particularly pulmonary fibrosis. Further, the compound (I) of the present invention is effective for preventing and treating Alzheimer's disease as an anti-Alzheimer's agent.

The present invention has been accomplished based on these findings.

More specifically, the present invention encompasses the following embodiments.

(1) Novel Compound (I) and Salt Thereof (1-1) A compound of Formula (I) or a salt thereof:

[Chem. 1]

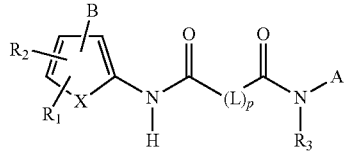

(I)

wherein $R_1$ and $R_2$ are the same or different, and each represents hydrogen, halogen, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic-alkyl, heterocyclic-alkyloxy; aryl optionally having one or two substituents; 5- to 6-membered ring heteroaryl optionally having one or two substituents, or benzo-fused heteroaryl optionally having one or two substituents; amino or carbamoyl, each of which is optionally substituted with one or two substituents; or cyano, carboxy, or alkoxycarbonyl; and $R_1$ and $R_2$ are optionally adjoined with each other to form a ring;

$R_3$ is hydrogen, alkyl, cycloalkyl, or aryl optionally having one or two substituents;

X is oxygen, sulfur, —N($R_4$)—, —C($R_5$)=C($R_6$)—, —C($R_7$)=N—, or —N=C($R_8$)—, wherein $R_4$ represents hydrogen, or alkyl optionally having one or two substituents, and $R_5$, $R_6$, $R_7$ and $R_8$ each represents hydrogen, halogen, alkyl optionally having one or two substituents, or alkoxy;

L is alkylene (some carbon atoms in the alkylene optionally form a cycloalkyl ring), alkenylene, alkynylene, cycloalkylene, alkyleneoxyalkylene, alkylenethioalkylene, alkylene-SO-alkylene, or alkylene-SO$_2$-alkylene, each of which is optionally substituted with one or two substituents; or alkylene-N($R_9$)-alkylene optionally substituted with one or two substituents, wherein $R_9$ represents hydrogen, or alkyl optionally having one or two substituents;

p represents an integer of 0 or 1;

A is a group represented by any one of the following Formulae (a), (b) or (c):

[Chem. 2]

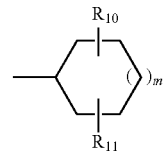

(a)

wherein $R_{10}$ and $R_{11}$ are the same or different, and each represents hydrogen or alkyl; and m represents an integer of 0 to 10,

[Chem. 3]

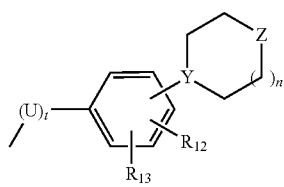

wherein
$R_{12}$ and $R_{13}$ are the same or different, and each represents hydrogen; halogen; or alkyl optionally having one or two substituents, cycloalkyl optionally having one or two substituents, or alkoxy optionally having one or two substituents;
Y represents CH or nitrogen;
Z represents $CH_2$, oxygen, or N-alkyl;
n represents an integer of 0 to 3;
U represents alkylene; and
t represents an integer of 0 or 1,

[Chem. 4]

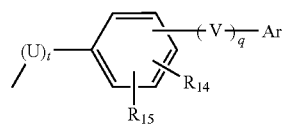

wherein
$R_{14}$ and $R_{15}$ are the same or different, and each represents hydrogen; halogen; or alkyl optionally having one or two substituents, cycloalkyl optionally having one or two substituents, or alkoxy optionally having one or two substituents;
V is alkylene, alkyleneoxyalkylene, oxyalkylene, alkyleneoxy, or oxygen;
q represents an integer of 0 or 1;
U and t are as defined above; and
Ar represents aryl having one or two substituents (the one or two substituents optionally form a ring with a part of carbon atoms in the aryl group), 5- to 6-membered ring heteroaryl optionally having one or two substituents, or benzo-fused heteroaryl optionally having one to three substituents; and
B represents $COOR_{16}$, wherein $R_{16}$ represents hydrogen; alkyl, aryl or aralkyl; a group represented by $CH(R_{17})$—O—$COR_{18}$ or —$CH(R_{17})$—O—CO—$OR_{18}$, wherein $R_{17}$ is hydrogen or alkyl, and $R_{18}$ is alkyl or cycloalkyl; a (5-alkyl-2-oxo-1,3-dioxolen-4-yl)methyl group represented by the following formula:

[Chem. 5]

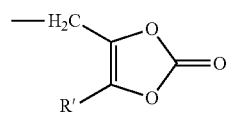

wherein R' represents alkyl; or
a heterocyclic group: a 1H-tetrazol-5-yl group; a 4,5-dihydro-5-oxo-4H-1,2,4-oxadiazol-3-yl group; a 4,5-dihydro-5-thioxo-4H-1,2,4-oxadiazol-3-yl group; or a 4,5-dihydro-5-oxo-1,2,4-thiadiazol-3-yl group, represented by the following formulae (sequentially from the left).

[Chem. 6]

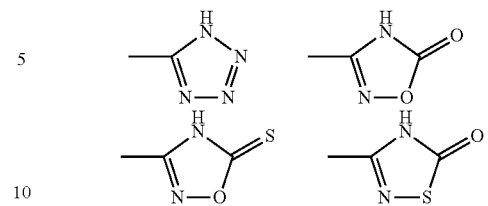

(1-2) The compound according to (1-1), or a salt thereof, wherein the X is vinylene.
(1-3) The compound according to (1-1), or a salt thereof, Wherein the compound represented by Formula (I) is a compound represented by Formula (II-1):

[Chem. 7]

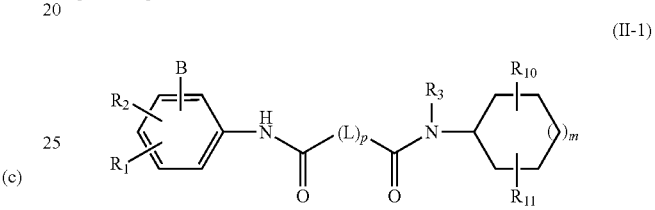

wherein
$R_1$ and $R_2$ are the same or different, and each represents hydrogen, halogen, alkyl, or aryl optionally having one or two substituents;
$R_3$ represents hydrogen, cycloalkyl, or aryl optionally having one or two substituents;
$R_{10}$ and $R_{11}$ represent hydrogen;
L represents alkylene, alkyleneoxyalkylene, or alkylenethioalkylene; and
m, p and B are as defined above.
(1-4) The compound according to (1-1), or a salt thereof, wherein the compound represented by Formula (I) is a compound represented by Formula (II-2):

[Chem. 8]

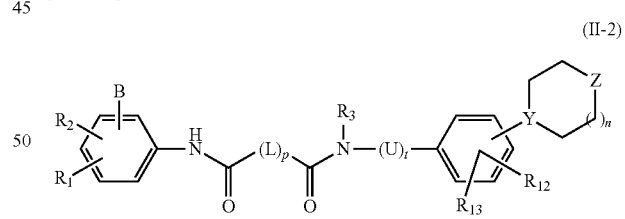

wherein
$R_1$ and $R_2$ are the same or different, and each represents hydrogen, halogen, alkyl, or aryl optionally having one or two substituents;
$R_3$, $R_{12}$ and $R_{13}$ are hydrogen;
Y is CH;
Z is $CH_2$;
L is alkylene, alkyleneoxyalkylene, or alkylenethioalkylene; and
n, p, U, t and B are as defined above.
(1-5) The compound according to (1-1), or a salt thereof, wherein the compound represented by Formula (I) is a compound represented by Formula (II-3):

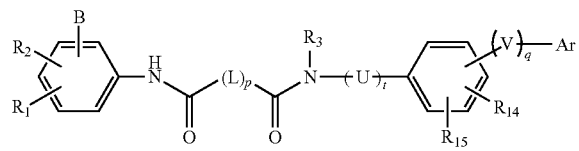
(II-3)

wherein
$R_1$ and $R_2$ are the same or different, and each represents hydrogen, halogen, alkyl, or aryl optionally having one or two substituents;
$R_3$ is hydrogen or alkyl;
$R_{14}$ and $R_{15}$ are the same or different, and each represents hydrogen, alkyl, or halogen;
V is alkylene, oxyalkylene, or oxygen;
Ar is aryl optionally having one or two substituents, heteroaryl optionally having one or two substituents, or benzo-fused heteroaryl optionally having one or three substituents;
L is alkylene, alkyleneoxyalkylene, alkylenethioalkylene, alkylene-SO-alkylene, alkylene-$SO_2$-alkylene; and
q, U, t, p, and B are as defined above.

(1-6) The compound according to (1-1) or (1-2), or a salt thereof, wherein the compound (I) is at least one member selected from the group consisting of compounds (1) to (80) below:

(1)  5-chloro-2-{[(2-oxo-2-{[4-(pyridin-4-yl)phenyl]amino}ethoxy)acetyl]amino}benzoic acid,
(2)  5-chloro-2-{[(2-oxo-2-{[3-(pyridin-4-yl)phenyl]amino}ethoxy)acetyl]amino}benzoic acid,
(3)  5-chloro-2-[({2-[(4'-fluorobiphenyl-2-yl)amino]-2-oxoethoxy}acetyl)amino]benzoic acid,
(4)  5-chloro-2-{[(2-oxo-2-{[2-(pyridin-4-yl)phenyl]amino}ethoxy)acetyl]amino}benzoic acid hydrochloride,
(5)  5-chloro-2-[({2-[(4'-fluoro-4-methylbiphenyl-3-yl)amino]-2-oxoethoxy}acetyl)amino]benzoic acid
(6)  5-chloro-2-[({2-oxo-2-[(3',4,5'-trimethylbiphenyl-3-yl)amino]ethoxy}acetyl)amino]benzoic acid,
(7)  5-chloro-2-[({2-[(4'-fluorobiphenyl-4-yl)amino]-2-oxoethoxy}acetyl)amino]benzoic acid,
(8)  5-chloro-2-[({2-[(4'-fluorobiphenyl-3-yl)amino]-2-oxoethoxy}acetyl)amino]benzoic acid,
(9)  5-chloro-2-({[2-(dicyclohexylamino)-2-oxoethoxy]acetyl}amino)benzoic acid,
(10) 5-chloro-2-[({2-[(4-cyclohexylphenyl)amino]-2-oxoethoxy}acetyl)amino]benzoic acid,
(11) 5-chloro-2-({[2-(cyclododecylamino)-2-oxoethoxy]acetyl}amino)benzoic acid,
(12) 5-chloro-2-{[({2-[(4'-fluorobiphenyl-3-yl)amino]-2-oxoethyl}sulfanyl)acetyl]amino}benzoic acid,
(13) 5-chloro-2-{[({2-[(4'-fluorobiphenyl-3-yl)amino]-2-oxoethyl}sulfinyl)acetyl]amino}benzoic acid,
(14) 5-chloro-2-{[({2-[(4'-fluorobiphenyl-3-yl)amino]-2-oxoethyl}sulfonyl)acetyl]amino}benzoic acid,
(15) 5-chloro-2-[({2-[cyclohexyl(phenyl)amino]-2-oxoethoxy}acetyl)amino]benzoic acid,
(16) 5-chloro-2-{[(2-oxo-2-{[3-(pyridin-4-yl)phenyl]amino}ethoxy)acetyl]amino}benzoic acid [(2,2-dimethylpropanoyl)oxy]methyl ester,
(17) 5-chloro-2-{[(2-oxo-2-{[3-(pyridin-4-yl)phenyl]amino}ethoxy)acetyl]amino}benzoic acid 1-{[(cyclohexyloxy)carbonyl]oxy}ethyl ester,
(18) 5-chloro-2-{[(2-oxo-2-{[3-(pyridin-4-yl)phenyl]amino}ethoxy)acetyl]amino}benzoic acid (5-methyl-2-oxo-1,3-dioxol-4-yl)methyl ester,
(19) 5-chloro-2-{[(2-oxo-2-{[3-(pyridin-3-yl)phenyl]amino}ethoxy)acetyl]amino}benzoic acid,
(20) 5-chloro-2-({[[(4'-fluoro-4-methylbiphenyl-3-yl)amino](oxo)acetyl]amino)benzoic acid
(21) 5-chloro-2-{[(2-oxo-2-{[3-(pyridin-2-yl)phenyl]amino}ethoxy)acetyl]amino}benzoic acid,
(22) 5-chloro-2-[({2-[(4'-fluoro-4-methylbiphenyl-3-yl)(2-methylpropyl)amino]-2-oxoethoxy}acetyl)amino]benzoic acid,
(23) 4'-fluoro-4-[({2-[(4'-fluoro-4-methylbiphenyl-3-yl)amino]-2-oxoethoxy}acetyl)amino]biphenyl-3-carboxylic acid,
(24) 5-chloro-2-{[({2-oxo-2-[(3',4,5'-trimethylbiphenyl-3-yl)amino]ethyl}sulfanyl)acetyl]amino}benzoic acid,
(25) 5-chloro-2-({[(2-oxo-2-{[3-(pyridin-4-yl)phenyl]amino}ethyl)sulfanyl]acetyl}amino)benzoic acid,
(26) 5-chloro-2-[({2-[(3-cyclohexylphenyl)amino]-2-oxoethoxy}acetyl)amino]benzoic acid,
(27) 5-chloro-2-{[({2-[(4-cyclohexylphenyl)amino]-2-oxoethyl}sulfanyl)acetyl]amino}benzoic acid,
(28) 5-chloro-2-[({[2-(cyclododecylamino)-2-oxoethyl]sulfanyl}acetyl)amino]benzoic acid,
(29) 5-chloro-2-[({2-[ethyl(4'-fluoro-4-methylbiphenyl-3-yl)amino]-2-oxoethoxy}acetyl)amino]benzoic acid,
(30) 5-chloro-2-{[({2-[ethyl(4'-fluoro-4-methylbiphenyl-3-yl)amino]-2-oxoethyl}sulfanyl)acetyl]amino}benzoic acid,
(31) 5-chloro-2-({5-[ethyl(4'-fluoro-4-methylbiphenyl-3-yl)amino]-5-oxopentanoyl}amino)benzoic acid,
(32) 5-chloro-2-{[(2-{[5-(furan-3-yl)-2-methylphenyl]amino}-2-oxoethoxy)acetyl]amino}benzoic acid,
(33) 5-chloro-2-({[(2-{[5-(furan-3-yl)-2-methylphenyl]amino}-2-oxoethyl)sulfanyl]acetyl}amino)benzoic acid,
(34) 5-chloro-2-[(5-{[5-(furan-3-yl)-2-methylphenyl]amino}-5-oxopentanoyl)amino]benzoic acid,
(35) 5-chloro-2-{[(2-{ethyl[5-(furan-3-yl)-2-methylphenyl]amino}-2-oxoethoxy)acetyl]amino}benzoic acid,
(36) 5-chloro-2-({[(2-{ethyl[5-(furan-3-yl)-2-methylphenyl]amino}-2-oxoethyl)sulfanyl]acetyl}amino)benzoic acid,
(37) 5-chloro-2-[(5-{ethyl[5-(furan-3-yl)-2-methylphenyl]amino}-5-oxopentanoyl)amino]benzoic acid,
(38) 5-chloro-2-[({2-[(2'-methoxy-4-methylbiphenyl-3-yl)amino]-2-oxoethoxy}acetyl)amino]benzoic acid,
(39) 5-chloro-2-[({2-[(3'-methoxy-4-methylbiphenyl-3-yl)amino]-2-oxoethoxy}acetyl)amino]benzoic acid,
(40) 5-chloro-2-[({2-[(4'-methoxy-4-methylbiphenyl-3-yl)amino]-2-oxoethoxy}acetyl)amino]benzoic acid,
(41) 2-{[(2-{[5-(1,3-benzodioxol-5-yl)-2-methylphenyl]amino}-2-oxoethoxy)acetyl]amino}-5-chlorobenzoic acid,
(42) 5-chloro-2-{[(2-{[2-methyl-5-(quinolin-8-yl)phenyl]amino}-2-oxoethoxy)acetyl]amino}benzoic acid,
(43) 2-{[(2-{[3'-(acetylamino)-4-methylbiphenyl-3-yl]amino}-2-oxoethoxy)acetyl]amino}-5-chlorobenzoic acid,
(44) 2-{[(2-{[4'-(acetylamino)-4-methylbiphenyl-3-yl]amino}-2-oxoethoxy)acetyl]amino}-5-chlorobenzoic acid,
(45) 5-chloro-2-{[{[3-(furan-3-yl)phenyl]amino}(oxo)acetyl]amino}benzoic acid,
(46) 5-chloro-2-({[(2-{[3-(furan-3-yl)phenyl]amino}-2-oxoethyl)sulfanyl]acetyl}amino)benzoic acid,

(47) 5-chloro-2-{[(2-{[3-(2,6-dimethoxypyridin-3-yl)phenyl]amino}-2-oxoethoxy)acetyl]amino}benzoic acid,
(48) 5-chloro-2-{[(2-oxo-2-{[3-(1H-pyrrol-1-yl)phenyl]amino}ethoxy)acetyl]amino}benzoic acid,
(49) 5-chloro-2-{[(2-{[2-fluoro-5-(furan-3-yl)phenyl]amino}-2-oxoethoxy)acetyl]amino}benzoic acid,
(50) 5-chloro-2-{[(2-{[4-fluoro-3-(furan-3-yl)phenyl]amino}-2-oxoethoxy)acetyl]amino}benzoic acid,
(51) 2-{[(2-{[3-(1-benzofuran-2-yl)phenyl]amino}-2-oxoethoxy)acetyl]amino}-5-chlorobenzoic acid,
(52) 5-chloro-2-[(3-{[3-(furan-3-yl)phenyl]amino}-3-oxopropanoyl)amino]benzoic acid,
(53) 5-chloro-2-{[{[3-(furan-3-yl)benzyl]amino}(oxo)acetyl]amino}benzoic acid,
(54) 5-chloro-2-{[(2-{[3-(furan-2-ylmethyl)phenyl]amino}-2-oxoethoxy)acetyl]amino}benzoic acid,
(55) 5-chloro-2-{[(2-{[3-(furan-3-ylmethyl)phenyl]amino}-2-oxoethoxy)acetyl]amino}benzoic acid,
(56) 5-chloro-2-[({2-oxo-2-[(2-phenoxyphenyl)amino]ethoxy}acetyl)amino]benzoic acid,
(57) 5-chloro-2-{[({2-oxo-2-[(2-phenoxyphenyl)amino]ethyl}sulfanyl)acetyl]amino}benzoic acid,
(58) 5-chloro-2-{[(2-{[3-(furan-3-yl)phenyl]amino}-2-oxoethoxy)acetyl]amino}benzoic acid,
(59) 5-chloro-2-{[(2-oxo-2-{[3-(thiophen-3-yl)phenyl]amino}ethoxy)acetyl]amino}benzoic acid,
(60) 5-chloro-2-{[(2-{[3-(1-methyl-1H-pyrazol-4-yl)phenyl]amino}-2-oxoethoxy)acetyl]amino}benzoic acid,
(61) 5-chloro-2-{[(2-{[3-(furan-2-yl)phenyl]amino}-2-oxoethoxy)acetyl]amino}benzoic acid,
(62) 5-chloro-2-{[(2-{[3-(3,5-dimethylisoxazol-4-yl)phenyl]amino}-2-oxoethoxy)acetyl]amino}benzoic acid,
(63) 5-chloro-2-{[(2-oxo-2-{[3-(thiophen-2-yl)phenyl]amino}ethoxy)acetyl]amino}benzoic acid,
(64) 5-chloro-2-{[(2-{[4-(furan-3-yl)phenyl]amino}-2-oxoethoxy)acetyl]amino}benzoic acid,
(65) 5-chloro-2-{[(2-{[3-(furan-2-ylmethoxy)phenyl]amino}-2-oxoethoxy)acetyl]amino}benzoic acid,
(66) 5-chloro-2-{[(2-{[3-(furan-3-yl)benzyl]amino}-2-oxoethoxy)acetyl]amino}benzoic acid,
(67) 5-chloro-2-{[(2-{[3-(furan-2-yl)benzyl]amino}-2-oxoethoxy)acetyl]amino}benzoic acid,
(68) 5-chloro-2-{[(2-oxo-2-{[3-(1H-pyrazol-4-yl)phenyl]amino}ethoxy)acetyl]amino}benzoic acid,
(69) 5-chloro-2-[({2-oxo-2-[(3-{1-[(phosphonateoxy)methyl]-1H-pyrazol-4-yl}phenyl)amino]ethoxy}acetyl)amino]benzoic acid,
(70) 5-chloro-2-{[(2-{[3-(1,3-oxazol-5-yl)phenyl]amino}-2-oxoethoxy)acetyl]amino}benzoic acid,
(71) 5-chloro-2-{[(2-{[3-(isoxazol-5-yl)phenyl]amino}-2-oxoethoxy)acetyl]amino}benzoic acid,
(72) 5-chloro-2-{[(2-oxo-2-{[3-(thiophen-3-yl)benzyl]amino}ethoxy)acetyl]amino}benzoic acid,
(73) 5-chloro-2-{[(2-oxo-2-{[3-(thiophen-2-yl)benzyl]amino}ethoxy)acetyl]amino}benzoic acid,
(74) 5-chloro-2-{[{[3-(furan-2-yl)benzyl]amino}(oxo)acetyl]amino}benzoic acid,
(75) 5-chloro-2-{[(2-{[3-(5-chlorothiophen-2-yl)benzyl]amino}-2-oxoethoxy)acetyl]amino}benzoic acid,
(76) 5-chloro-2-{[(2-{[3-(5-methylthiophen-2-yl)benzyl]amino}-2-oxoethoxy)acetyl]amino}benzoic acid,
(77) 5-chloro-2-{[(2-{[3-(furan-3-yl)phenyl]amino}-2-oxoethoxy)acetyl]amino}benzoic acid,
(78) 5-chloro-2-{[(2-{[3-(furan-3-yl)phenyl]amino}-2-oxoethoxy)acetyl]amino}benzoic acid,
(79) 5-chloro-2-{[(2-{[3-(isoxazol-3-yl)phenyl]amino}-2-oxoethoxy)acetyl]amino}benzoic acid, and
(80) 5-chloro-2-{[(2-{[3-(5-methylfuran-3-yl)phenyl]amino}-2-oxoethoxy)acetyl]amino}benzoic acid.

(1-7) The compound according to (1-3), or a salt thereof, wherein the compound (I) is at least one member selected from the group consisting of the compounds (9), (11), (15) and (28) listed in (1-6).

(1-8) The compound according to (1-4), or a salt thereof, wherein the compound (I) is at least one member selected from the group consisting of the compounds (10), (26) and (27) listed in (1-6).

(1-9) The compound according to (1-5), or a salt thereof, wherein the compound (I) is at least one member selected from the group consisting of the compounds (1) to (8), (12) to (14), (16) to (25), and (29) to (80) listed in (1-6).

(2) Method for Producing Compound (I)

(2-1) A method for producing a compound represented by Formula (I-1), comprising the step (a):

(a) a step of condensing a compound (1) and a compound (2) to form an ester compound (I-1), the compounds being represented by the formulae below:

[Chem. 10]

wherein $R_1$ to $R_3$, X, L, p and A are as defined above, and $R_{16a}$ is alkyl, aryl, or aralkyl.

(2-2) A method for producing a compound represented by Formula (I-1), comprising the steps (b), (c) and (d):

(b) a step of reacting a compound (1) and a compound (3) to produce a compound (4), the compounds being represented by the formulae below;

(c) a step of selectively removing the $R_{19}$ of the compound (4) produced in the step (b) above to produce a compound (5); and (d) a step of reacting the compound (5) produced in the step (C) above and a compound (6) to form an ester compound (I-1),

[Chem. 11]

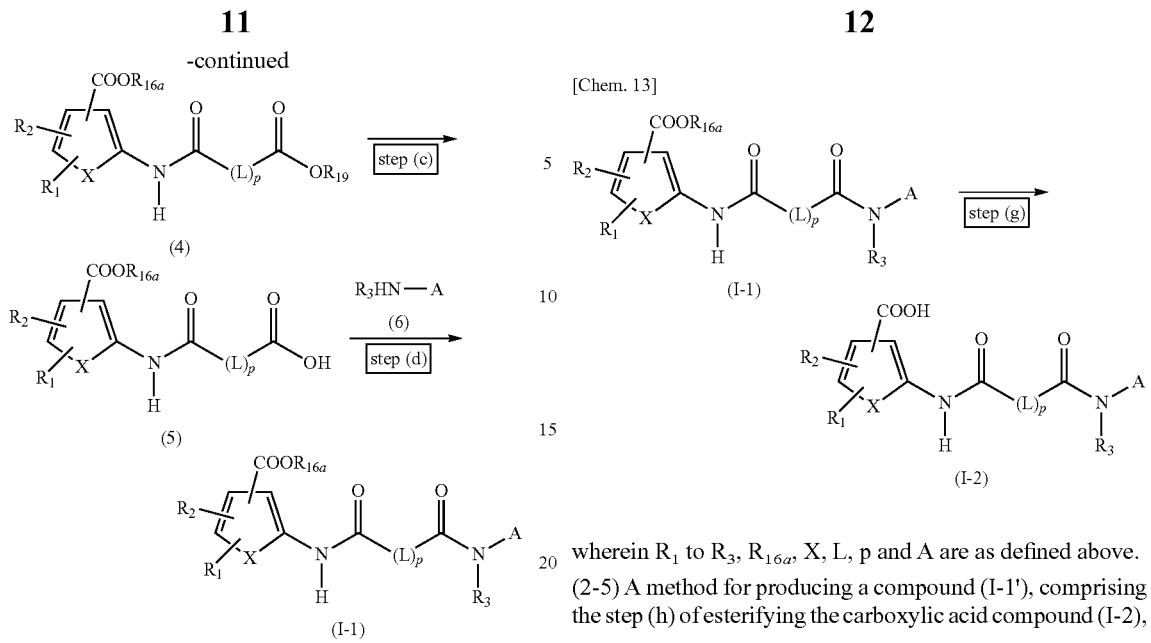

wherein $R_1$ to $R_3$, X, L, A, p and $R_{16a}$ are as defined above, and $R_{19}$ is alkyl, aryl or aralkyl.

(2-3) A method for producing a compound represented by Formula (I-1), comprising the steps (e) and (f):

(e) a step of reacting a compound (1) and an intramolecular anhydride (7) of a dicarboxylic acid to form an ester carboxylic acid compound (5), the compounds being represented by the formulae below; and (f) a step of reacting the ester carboxylic acid (5) formed in the step (e) above and a compound (6) to form an ester compound (I-1),

[Chem. 12]

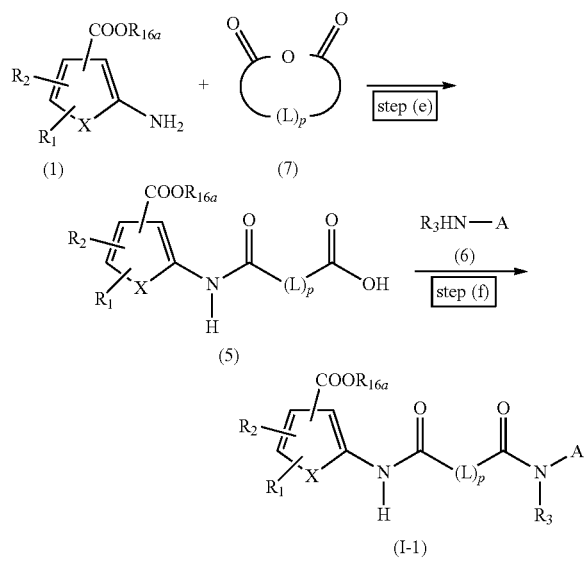

wherein $R_1$ to $R_3$, $R_{16a}$, X, L and A are as defined above, and p is 1.

(2-4) A method for producing a carboxylic acid compound (I-2), comprising the step (g) of removing the $R_{16a}$ of the ester compound (I-1) formed in any of the methods (2-1) to (2-3), wherein $R_1$ to $R_3$, $R_{16a}$, X, L, p and A are as defined above.

(2-5) A method for producing a compound (I-1'), comprising the step (h) of esterifying the carboxylic acid compound (I-2),

[Chem. 14]

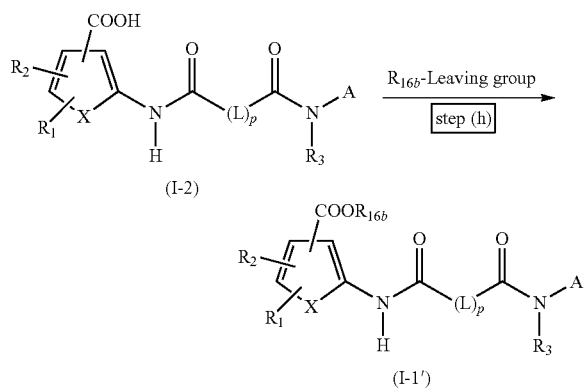

wherein $R_1$ to $R_3$, X, L, p, and A are as defined above, $R_{16b}$ is alkyl, phenyl, benzyl, a (5-alkyl-2-oxo-1,3-dioxolen-4-yl) methyl group, or a group represented by —$CH(R_{17})$—O—$COR_{18}$ or —$CH(R_{17})$—O—CO—$OR_{18}$, wherein $R_{17}$ is hydrogen or alkyl, and $R_{18}$ is alkyl or cycloalkyl.

(2-6) A method for producing a compound represented by Formula (I-3), comprising the steps (a') and (i):

(a') a step of condensing a compound (9) and a compound (2) to produce a nitrile compound (10), the compounds being represented by the formulae below; and (i) a step of producing a tetrazole compound (I-3) from the nitrile compound (10) obtained in the above step (a') and an azide (11),

[Chem. 15]

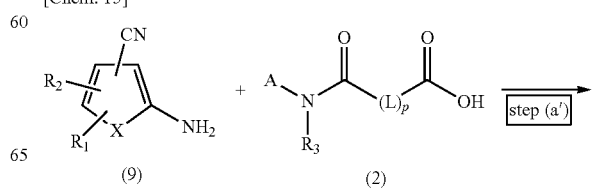

-continued

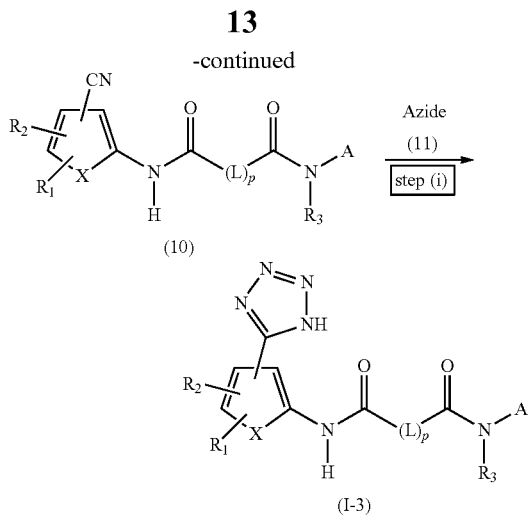

wherein $R_1$ to $R_3$, X, L, p and A are as defined above.

(2-7) A method for producing a compound represented by Formula (I-3), comprising the steps (b'), (c'), (d') and (i):
(b') a step of reacting a compound (9) and a compound (3) to produce a compound (4'), the compounds being represented by the formulae below;
(c') a step of selectively removing the $R_{19}$ of the compound (4') produced in the above step (b') to produce a compound (5');
(d') a step of reacting the compound (5') produced above in the step (c') and a compound (6) to produce a nitrile compound (10); and
(i) a step of producing a tetrazole compound (I-3) from the nitrile compound (10) obtained in the step (d') and an azide (11),

[Chem. 16]

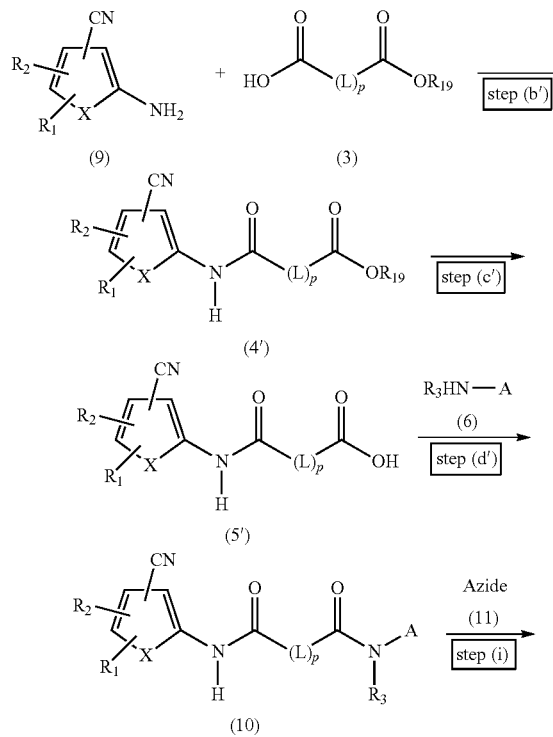

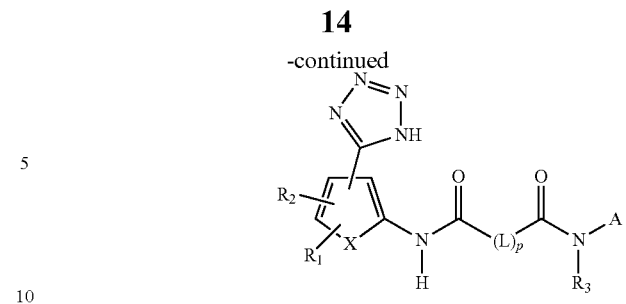

wherein $R_1$ to $R_3$, X, L, A, p and $R_{19}$ are as defined above.

(2-8) A method for producing a compound of Formula (I-3), comprising the steps (e'), (f') and (i):
(e') a step of reacting a compound (9) and an intramolecular anhydride (7) of a dicarboxylic acid to produce a compound (5'), the compounds being represented by the following Formulae;
(f') a step of reacting the compound (5') produced in the step (e') above and a compound (6) to produce a nitrile compound (10); and
(i) a step of producing a tetrazole compound (I-3) from the nitrile compound (10) produced in the step (f') above and an azide (11),

[Chem. 17]

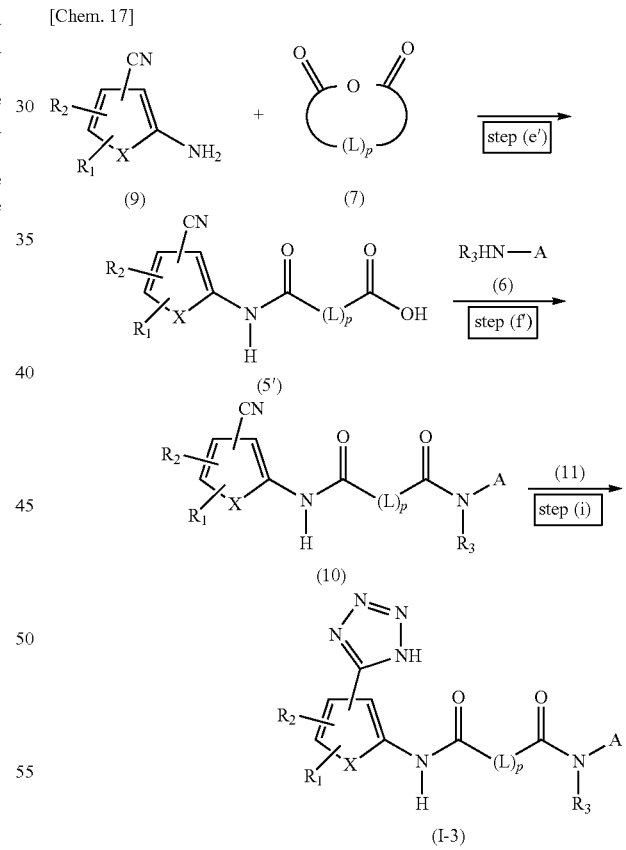

wherein $R_1$ to $R_3$, X, L and A are as defined above; and p represents 1.

(2-9) A method for producing a compound represented by Formula (I-4), comprising the steps (j) and (k):
(j) a step of reacting a compound (10) and hydroxylamine hydrochloride (12) to form an amide oxime compound (13), the compounds being represented by the following formulae; and (k) a step of reacting the amide oxime compound (13) formed in the step (j) above and an active carbonyl compound (14) to form a 1,2,4-oxadiazol-5-on compound (I-4),

[Chem. 18]

(10) → NH₂OH·HCl (12) / step (j) →

(13) → Active carbonyl compound (14) / step (k) →

(I-4)

wherein R₁ to R₃, X, L, p and A are as defined above.

(2-10) A method for producing a 1,2,4-oxadiazol-5-thione compound represented by Formula (I-5), comprising the step (l):

(l) a step of reacting an amide oxime compound (13) and 1,1'-thiocarbonyldiimidazole (15) to produce a 1,2,4-oxadiazol-5-thione compound (I-5), the compounds being represented by the following formulae,

[Chem. 19]

(13) → (15) / step (l) →

(I-5)

wherein R₁ to R₃, X, L, p and A are as defined above.

(2-11) A method for producing a 1,2,4-thiadiazol-5-on compound represented by Formula (i-6), comprising the step (m):

(m) a step of reacting an amide oxime compound (13) and 1,1'-thiocarbonyldiimidazole (15) in the absence of a base, followed by a reaction with an acid, to produce a 1,2,4-thiadiazol-5-on compound (I-6),

[Chem. 20]

(13) → 1) (15); 2) BF₃·OEt₂ or silica gel / step (m) →

(I-6)

wherein R₁ to R₃, X, L, p and A are as defined above.

(2-12) A method for producing a compound represented by Formula (I-8), comprising the step (n):

(n) a step of oxidizing a compound (I-7) to produce a compound (I-8),

[Chem. 21]

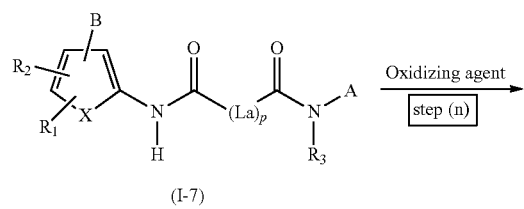

(I-7)

[Chem. 22]

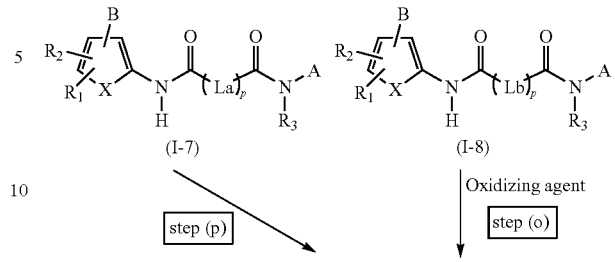

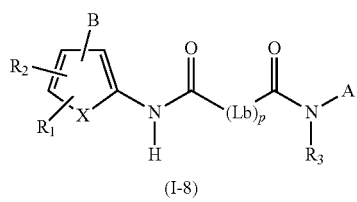

(I-8)

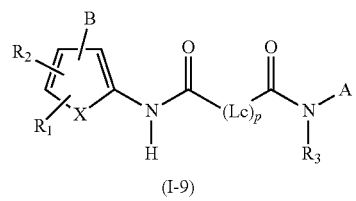

(I-9)

wherein B, $R_1$ to $R_3$, X and A are as defined above, La represents alkylenethioalkylene, Lb represents alkylene-SO-alkylene, and p represents 1.

(2-13) A method for producing a compound represented by Formula (I-9), comprising the step (o) or (p):

(o) a step of further oxidizing the compound (I-8) obtained in accordance with the method of (2-12) to produce a compound (I-9); or (p) a step of reacting an excessive amount of an oxidizing agent with a compound (I-7) to produce a compound (I-9), wherein B, $R_1$ to $R_3$, X, A, La and Lb are as defined above, Lc represents alkylene-$SO_2$-alkylene, and p represents 1.

(2-14) A method for producing a compound represented by Formula (I-1) or (10), comprising the step (q) and (r):

(q) a step of subjecting the compound (5) or (5'), obtained in accordance with the method of (2-2), (2-3), (2-7), or (2-8), to a reaction under the same reaction conditions employed in the step (f), (f'), (d), or (d') to produce a compound (16) or (16'), which has halogen or trifluoromethanesulfonyloxy as a substituent; and (r) a step of reacting the compound (16) or (16') obtained in the above step (q) and a compound (17) to produce a compound (I-1) or (10),

[Chem. 23]

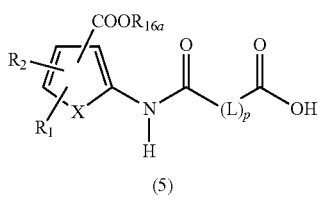

(5)

or

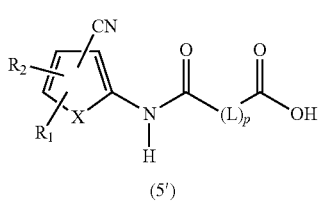

(5')

step (q) →

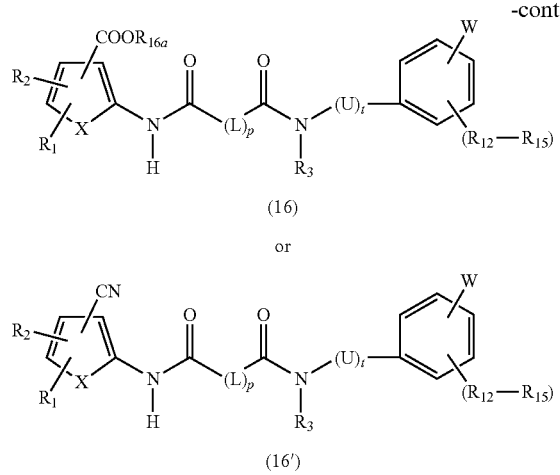

(16)

or

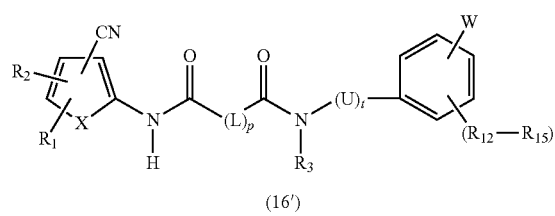

(16')

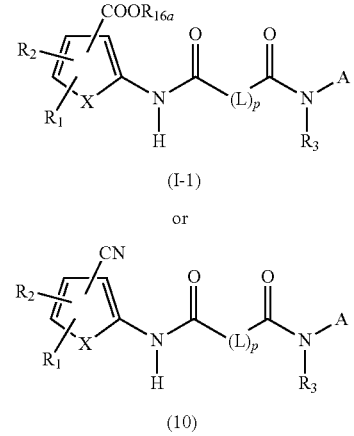

$R_{20}$—Q/Catalyst
(17)
step (r)

(I-1)

or (10)

wherein $R_1$ to $R_3$, $R_{12}$ to $R_{15}$, X, L, p, U, t, and A are as defined above; W represents halogen or trifluoromethanesulfonyloxy; $R_{20}$ represents cycloalkyl, cycloalkoxy, aryl, aryloxy, aralkyl, aralkyloxy, heterocyclic group, heterocyclic-alkyl, or heterocyclic-alkyloxy; Q is —B(OR$_{21}$)OR$_{21}$, wherein $R_{21}$ represents hydrogen or alkyl, and when $R_{21}$ is alkyl, both alkyl groups are optionally joined to form a ring, or —ZnW, wherein Zn represents zinc, and W represents halogen; or $R_{20}$-Q together represent $R_{20}$—OH or a cyclic amine having a structure represented by the following formula:

[Chem. 24]

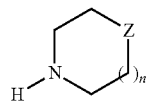

wherein Z and n are as defined above.

(3) PAI-1 Inhibitor (3-1) A PAI-1 inhibitor comprising a compound according to any of (1-1) to (1-9), a salt thereof, or a solvate thereof as an active ingredient.

(4) Pharmaceutical Composition (4-1) A pharmaceutical composition comprising a compound according to any of (1-1) to (1-9), a salt thereof, or a solvate thereof, and a pharmacologically acceptable carrier or additive.

(4-2) The pharmaceutical composition according to (4-1), the composition being a prophylactic or therapeutic agent for a disease whose development is influenced by PAI-1 activity.

(4-3) The pharmaceutical composition according to (4-1) or (4-2), the composition being a fibrinolysis promoter, an anti-fibrosis agent, or an anti-Alzheimer's agent.

(4-4) The pharmaceutical composition according to (4-2) or (4-3), wherein the disease whose development is influenced by PAI-1 activity is thrombosis in arteries, thrombosis in veins, deep vein thrombosis (DVT) during surgical operations, disseminated intravascular coagulation syndrome (DIC), diabetic complications such as angiopathy, neuropathy, retinopathy or nephropathia, or restenosis after percutaneous transluminal coronary angioplasty (PTCA).

(4-5) The pharmaceutical composition according to (4-4), wherein the thrombosis in arteries is thrombosis in the brain (cerebral thrombosis, cerebral embolism or transient ischemic attack), thrombosis in the heart (angina pectoris or cardiac infarction), thrombosis in the lower extremities (acute lower extremity arterial thrombosis), and thrombosis in the upper intestinal tract (upper intestinal tract arterial thrombosis) and the thrombosis in veins is thrombosis occurring in the limbs (deep vein thrombosis) or thrombosis occurring when a blood clot travels to the lung (pulmonary embolism).

(4-6) The pharmaceutical composition according to (4-2) or (4-3), wherein the disease whose development is influenced by PAI-1 activity is a disease accompanied by fibrosis.

(4-7) The pharmaceutical composition according to (4-7), wherein the disease accompanied by fibrosis is pulmonary fibrosis.

(4-8) The pharmaceutical composition according to any of (4-1) to (4-7), the composition being orally administered.

Effects of the Invention

The present invention can provide a novel low molecular weight compound having a highly inhibitory effect on PAI-1. Such a compound is useful as an active ingredient of a pharmaceutical composition such as a prophylactic or therapeutic agent for various kinds of diseases whose development is influenced by PAI-1 activity.

The present invention provides pharmaceutical compositions that can be mass-synthesized and that comprise a low molecular weight compound as an active ingredient. As described above, the pharmaceutical composition comprises, as an active ingredient, a compound (PAI-1 inhibitor) that has a highly inhibitory effect on PAI-1, and that can thus be effectively used as a prophylactic or therapeutic agent for various diseases whose development is influenced by PAI-1 activity. Specifically, the pharmaceutical composition of the present invention is effective as a fibrinolysis promoter for preventing or treating thrombosis in arteries, thrombosis in veins, deep vein thrombosis (DVT) during surgical operations, disseminated intravascular coagulation syndrome (DIC); diabetic complications such as angiopathy, neuropathy, retinopathy or nephropathia; restenosis after percutaneous transluminal coronary angioplasty (PTCA); etc. The pharmaceutical composition of the present invention is also effective as an anti-fibrosis agent for preventing or treating various kinds of diseases associated with tissue fibrosis, particularly pulmonary fibrosis. Further, the pharmaceutical composition of the present invention is effective, based on the Aβ decomposition-promoting effect achieved by the PAI-1 inhibition, for preventing and treating Alzheimer's disease, which is considered to be caused by Aβ deposition in the brain.

BRIEF DESCRIPTION OF THE DRAWINGS

FIG. 1 is a table summarizing the PAI-1 activities (%) of the compounds of Examples 1 to 12.

FIG. 2 is a table summarizing the PAI-1 activities (%) of the compounds of Examples 13 to 23.

FIG. 3 is a table summarizing the PAI-1 activities (%) of the compounds of Examples 24 to 35.

FIG. 4 is a table summarizing the PAI-1 activities (%) of the compounds of Examples 36 to 47.

FIG. 5 is a table summarizing the PAI-1 activities (%) of the compounds of Examples 48 to 59.

FIG. 6 is a table summarizing the PAI-1 activities (%) of the compounds of Examples 60 to 71.

FIG. 7 is a table summarizing the PAI-1 activities (%) of the compounds of Examples 72 to 77.

FIG. 9 shows the anti-fibrotic effects of N,N'-bis[3,3'-carboxy-4,4'-(2,2'-thienyl)-2,2'-thienyl]hexanedicarboxyamide (compound b) on bleomycin-induced pulmonary fibrosis, wherein a shows fibrosis scores, and b shows images of histological stains (see Reference Test Example (3)).

Figure 8:
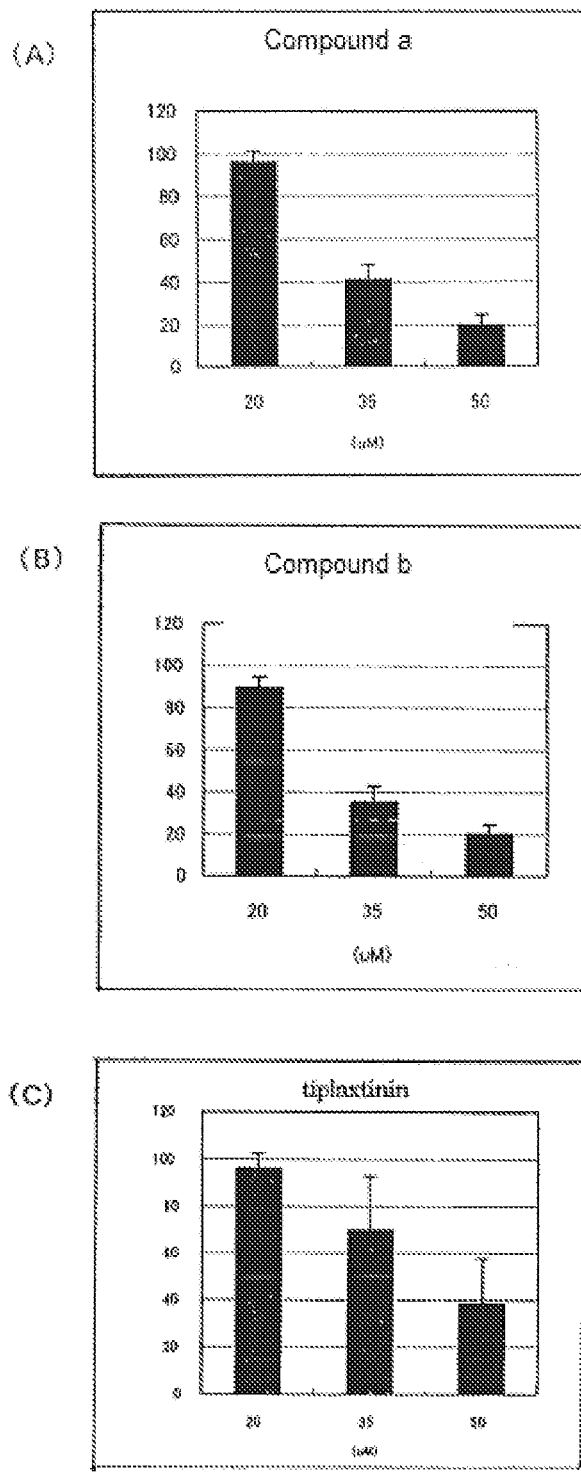
FIG. 8 is a graph showing PAI-1 inhibitory activities of (A) N,N'-bis[3,3'-carboxy-4,4'-phenyl-2,2'-thienyl]hexanedicarboxyamide (compound a), (B) N,N'-bis[3,3'-carboxy-4,4'-(2,2'-thienyl)-2,2'-thienyl]hexanedicarboxyamide (compound b), and (C) tiplaxtinin. The longitudinal axis indicates PAI-1 activity (%) (see Reference Test Example (1)).

BEST MODE FOR CARRYING OUT THE INVENTION (1) Compound of the Present Invention

The compounds of the present invention are represented by Formula (I) below.

[Chem. 25]

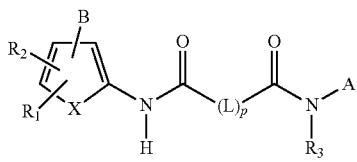

(I)

In the above formula, $R_1$ and $R_2$ are the same or different, and each represents hydrogen, halogen, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic-alkyl, heterocyclic-alkyloxy; aryl optionally having one or two substituents; 5- to 6-membered ring heteroaryl optionally having one or two substituents, or benzo-fused heteroaryl thereof optionally having one or two substituents; amino optionally substituted with one or two substituents, carbamoyl, cyano, carboxy, or alkoxycarbonyl. $R_1$ and $R_2$ optionally join to form a ring. $R_1$ and $R_2$ are preferably hydrogen, halogen, or aryl (in particular phenyl) optionally having one or two substituents.

$R_3$ is hydrogen, alkyl, cycloalkyl, or aryl optionally having one or two substituents. $R_3$ is preferably hydrogen, $C_{3-6}$ cycloalkyl, $C_{1-6}$ alkyl, or aryl (in particular phenyl).

X is oxygen, sulfur, —N($R_4$)—, —C($R_5$)=C($R_6$)—, —C($R_7$)=N—, or —N=C($R_8$)—, wherein $R_4$ represents hydrogen, or alkyl optionally having one or two substituents, and $R_5$, $R_6$, $R_7$ and $R_8$ are the same or different, and each represents hydrogen, halogen, alkyl optionally having one or two substituents, or alkoxy. X is preferably —C($R_5$)=C($R_6$)—, and among the compounds represented thereby, a vinylene group (—CH=CH—), in which $R_5$ and $R_6$ are both hydrogen, is preferable.

L is alkylene (some carbon atoms in the alkylene optionally form a cycloalkyl ring), alkenylene, alkynylene, cycloalkylene, alkyleneoxyalkylene, alkylenethioalkylene, alkylene-SO-alkylene, alkylene-$SO_2$-alkylene, each of which optionally having one or two substituents; or alkylene-N($R_9$)-alkylene optionally having one or two substituents, wherein $R_9$ represents hydrogen, or alkyl optionally having one or two substituents. L is preferably alkylene, alkyleneoxyalkylene, alkylenethioalkylene, alkylene-SO-alkylene, or alkylene-$SO_2$-alkylene, each of which optionally having one or two substituents.

p represents an integer of 0 or 1. p is preferably 1 when L is alkyleneoxyalkylene, alkylenethioalkylene, alkylene-SO-alkylene, or alkylene-$SO_2$-alkylene group, each of which optionally having one or two substituents; or alkylene-N($R_9$)-alkylene optionally having one or two substituents.

A is a group represented by any one of the following Formulae (a), (b) or (c).

[Chem. 26]

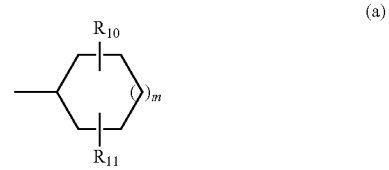

(a)

In Formula (a), $R_{10}$ and $R_{11}$ are the same or different, and each represents hydrogen or alkyl, and m represents an integer of 0 to 10. Of these, groups represented by Formula (a), wherein $R_{10}$ and $R_{11}$ are both hydrogen, and m is 1 to 10, are preferable.

[Chem. 27]

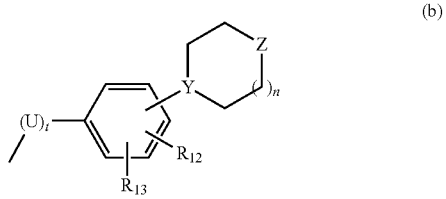

(b)

In Formula (b), each symbol represents the following groups.

$R_{12}$ and $R_{13}$ are the same or different, and each represents hydrogen; halogen; or alkyl optionally having one or two substituents, cycloalkyl optionally having one or two substituents, or alkoxy optionally having one or two substituents. $R_{12}$ is preferably hydrogen.

Y represents CH or nitrogen, preferably CH.

Z represents $CH_2$, oxygen, or N-alkyl, preferably $CH_2$.

n represents an integer of 0 to 3, preferably 1.

U represents alkylene.

t represents an integer of 0 or 1.

[Chem. 28]

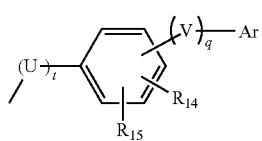

(c)

In Formula (c), each symbol represents the following groups.

$R_{14}$ and $R_{15}$ are the same or different, and each represents hydrogen; halogen; or alkyl optionally having one or two substituents, cycloalkyl optionally having one or two substituents, or alkoxy optionally having one or two substituents. $R_{14}$ and $R_{15}$ are preferably hydrogen, halogen, or alkyl optionally having one or two substituents.

V represents alkylene, alkyleneoxyalkylene, oxyalkylene, alkyleneoxy, or oxygen. V is preferably alkylene, oxyalkylene, or oxygen.

q represents an integer of 0 or 1.

U and t are as defined above.

Ar represents aryl having one or two substituents (the one or two substituents optionally form a ring with a part of carbon atoms in the aryl group), 5- to 6-membered ring heteroaryl optionally having one or two substituents, or benzo-fused heteroaryl optionally having one to three substituents. Ar is preferably phenyl having one or two substituents, heteroaryl optionally having one or two substituents, or benzo-fused heteroaryl optionally having one or two substituents. Examples of heteroatoms include at least one member selected from the group consisting of nitrogen, oxygen, and sulfur. Preferable examples of substituents of Ar include halogen, alkyl, alkoxy, and phosphonooxymethyl. When Ar is aryl having an alkyl or alkoxy group as a substituent, the substituent may form a ring with a part of carbon atoms of the aryl group.

In Formula (I), B represents $COOR_{16}$, or a 1H-tetrazol-5-yl group, a 4,5-dihydro-5-oxo-4H-1,2,4-oxadiazol-3-yl group, a 4,5-dihydro-5-thioxo-4H-1,2,4-oxadiazol-3-yl group, or a 4,5-dihydro-5-oxo-1,2,4-thiadiazol-3-yl group represented by the following formulae (sequentially from the left).

[Chem. 29]

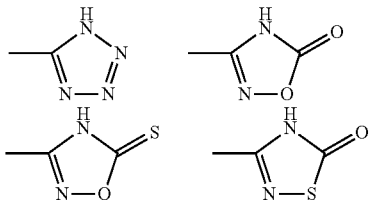

$R_{16}$ in $COOR_{16}$ represents hydrogen; alkyl, aryl or aralkyl; a (5-alkyl-2-oxo-1,3-dioxolen-4-yl)methyl group represented by the following formula:

[Chem. 30]

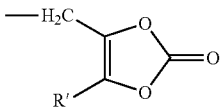

wherein R' represents alkyl;

or a group represented by $CH(R_{17})$—O—$COR_{18}$ or —CH$(R_{17})$—O—CO—$OR_{18}$, wherein $R_{17}$ is hydrogen or alkyl, and $R_{18}$ is alkyl or cycloalkyl. B is preferably carboxy (when the $R_{16}$ in $COOR_{16}$ is hydrogen), alkoxycarbonyl (when the $R_{16}$ in $COOR_{16}$ is alkyl), aralkyloxycarbonyl (when $R_{16}$ in $COOR_{16}$ is benzyl), a (5-alkyl-2-oxo-1,3-dioxolen-4-yl)methyl group, or a group represented by $CH(R_{17})$—O—$COR_{18}$ or —CH$(R_{17})$—O—CO—$OR_{18}$, wherein $R_{17}$ and $R_{18}$ are as defined above.

The designation of each group represented by these characters and specific examples thereof are described below.

Examples of the "alkyl" represented by $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, or R', and the "alkyl" represented by Z as "N-alkyl", in the compound of the present invention, include typically $C_{1-12}$, preferably $C_{1-10}$, more preferably $C_{1-8}$, further preferably $C_{1-6}$, and particularly preferably $C_{1-4}$ straight- or branched-chain alkyl groups. Examples of such alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, heptyl, 1-methylpentyl, 2-methylpentyl, n-heptyl, isoheptyl, sec-heptyl, tert-heptyl, n-octyl, tert-octyl, 2-methylhexyl, 2-ethylhexyl, etc. Preferable groups are $C_{1-4}$ lower alkyl groups such as methyl, ethyl, propyl, isopropyl, butyl and isobutyl; more preferable are methyl and ethyl; and particularly preferable is methyl.

Among these, the "alkyl" represented by $R_4$, $R_5$, $R_6$, $R_7$, $R_8$, $R_9$, $R_{12}$, $R_{13}$, $R_{14}$, or $R_{15}$ optionally has one or two substituents. Examples of such substituents include halogen, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, etc.

Examples of the "cycloalkyl" represented by $R_1$, $R_2$, $R_3$, $R_{12}$, $R_{13}$, $R_{14}$, $R_{15}$, or $R_{18}$ in the compound of the present invention include typically $C_{3-7}$, and preferably $C_5$ or $C_6$ cyclic alkyl groups. Examples of such cycloalkyl groups include cyclopropyl, cyclobutyl, cyclopentyl, cyclohexyl, cycloheptyl, etc. Among these, the "cycloalkyl" represented by $R_{12}$, $R_{13}$, $R_{14}$, or $R_{15}$ optionally has one or two substituents at arbitrary position(s). Examples of such substituents include halogen, $C_{1-6}$ alkyl, halogen-substituted $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, and alkoxycarbonyl having $C_{1-6}$ alkoxy. Preferred are unsubstituted cycloalkyl groups.

Examples of the "cycloalkylalkyl" represented by $R_1$ or $R_2$ in the compound of the present invention include typically $C_{3-7}$, and preferably $C_5$ or $C_6$ cyclic alkyl (cycloalkyl) groups, having a $C_{1-6}$ alkyl substituent. Examples of such cycloalkylalkyl groups include cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, etc.

Examples of the "alkoxy" represented by $R_1$, $R_2$, $R_5$, $R_6$, $R_7$, $R_8$, $R_{12}$, $R_{13}$, $R_{14}$, or $R_{15}$ in the compound of the present invention include hydroxyl groups substituted with the above-mentioned $C_{1-12}$, preferably $C_{1-10}$, more preferably $C_{1-8}$, further preferably $C_{1-6}$, and particularly preferably $C_{1-4}$ alkyl groups. Examples of such alkoxy groups include methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable. Of these, the "alkoxy" represented by $R_{12}$, $R_{13}$, $R_{14}$, or $R_{15}$ optionally has one or two substituents. Examples of the substituents include halogen, $C_{1-6}$ alkyl, halogen-substituted $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, etc.

Examples of the "cycloalkoxy" represented by $R_1$ or $R_2$ in the compound of the present invention include $C_{2-8}$, preferably $C_{4-5}$ cyclic alkoxy groups. Such cycloalkoxy groups include cyclopropyloxy, cyclobutyloxy, cyclopentyloxy, cyclohexyloxy, cycloheptyloxy, etc.

Examples of the "alkenyl" represented by $R_1$ or $R_2$ in the compound of the present invention include $C_{2-6}$ straight- or branched-chain alkenyl groups having 1 to 3 double bonds. Examples of such alkenyl groups include vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl.

Examples of the "alkenyloxy" represented by $R_1$ or $R_2$ in the compound of the present invention include hydroxyl groups substituted with the above-mentioned $C_{2-6}$ straight- or branched-chain alkenyl groups having 1 to 3 double bonds. Specific examples of such alkenyloxy groups include vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, and 1,4-hexadienyloxy.

Examples of the "cycloalkenyl" represented by $R_1$ or $R_2$ in the compound of the present invention include $C_{2-6}$ cyclic alkenyl groups having 1 to 3 double bonds.

Examples of the "cycloalkenyloxy" represented by $R_1$ or $R_2$ in the compound of the present invention include $C_{2-6}$ cyclic alkenyloxy groups having 1 to 3 double bonds.

Examples of the "alkynyl" represented by $R_1$ or $R_2$ in the compound of the present invention include $C_{2-6}$ straight- or branched-chain alkynyl groups having a triple bond. Specific examples of such alkynyl groups include ethynyl, 2-propynyl, 2-butynyl, 3-butynyl, 1-methyl-2-propynyl, 2-pentynyl, 2-hexynyl, etc.

Preferable examples of the "aryl" represented by $R_1$, $R_2$, $R_3$, $R_{16}$, or Ar in the compound of the present invention include $C_{6-14}$ aromatic hydrocarbon groups. Examples of such aryl groups include phenyl, naphthyl, anthryl, phenanthryl, acenaphthylenyl, etc. Preferred among these are phenyl and naphthyl, and more preferred is phenyl.

Of these, the "aryl" represented by $R_1$, $R_2$, or $R_3$ optionally has one or two substituents at arbitrary position(s), preferably meta or para position(s). Further, the "aryl" represented by Ar has one or two substituents at arbitrary position(s). Examples of substituents as used herein include halogen, acetylamino, $C_{1-6}$ alkylamino, hydroxyl, $C_{1-6}$ alkyl (preferably $C_{1-4}$ alkyl), $C_{1-6}$ cycloalkyl, $C_{1-6}$ alkoxy (preferably $C_{1-4}$ alkoxy), and $C_{1-6}$ cycloalkoxy. The substituents of the "aryl" represented by $R_1$, $R_2$, or $R_3$ are preferably halogen or $C_{1-6}$ alkyl, and particularly preferably halogen. The substituents of the "aryl" represented by Ar are preferably halogen, $C_{1-6}$ alkyl, $C_{1-6}$ alkoxy, or acetylamino. When the "aryl" represented by Ar, which is preferably phenyl, has two adjacent substituents, the adjacent substituents may together form a ring. Examples of such "aryl" include (methylenedioxy)phenyl, (ethylenedioxy)phenyl, dihydrobenzofuranyl, dihydroisobenzofuranyl, chromanyl, chromenyl, isochromanyl, isochromenyl, indanyl, indenyl, tetrahydronaphthyl, dihydronaphthyl, indolinyl, etc.

The substituents of the aryl groups, in particular cycloalkyl and cycloalkoxy, may further have a substituent. Examples of such substituents include halogen, $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, benzoyl, phenyl, etc.

Examples of the "heteroaryl" represented by $R_1$, $R_2$ or Ar in the compound of the present invention include 5- to 6-membered ring aryl groups having one or more identical or different heteroatoms selected from the group consisting of nitrogen, oxygen and sulfur. Specific examples thereof include pyrrolyl, furyl, thienyl, pyrazolyl, imidazolyl, oxazolyl, isoxazolyl, thiazolyl, isothiazolyl, oxadiazolyl, thiadiazolyl, triazolyl, tetrazolyl, pyridyl, pyridazinyl, pyrimidinyl, imidazolyl, pyrazinyl, and like unsaturated heterocyclic groups.

Preferable examples of the heteroaryl groups represented by $R_1$ or $R_2$ include pyrazolyl (e.g., pyrazol-4-yl), pyridyl (e.g., pyridin-3-yl, pyridin-4-yl), 2-methylpyrazolyl, quinolyl (quinolin-3-yl), and thiazolyl (e.g., thiazol-5-yl).

Preferable examples of the heteroaryl groups represented by Ar include pyrrolyl (e.g., pyrrol-1-yl, pyrrol-3-yl), furyl (e.g., furan-2-yl, furan-3-yl), oxazolyl (e.g., oxazol-5-yl), isoxazolyl (e.g., isoxazol-5-yl, isoxazol-4-yl), thienyl (e.g., thiophene-3-yl, thiophene-2-yl), pyrazolyl (e.g., pyrazole-4-yl), and pyridyl (e.g., pyridin-2-yl, pyridin-3-yl, pyridin-4-yl).

These groups may have one or two substituents at arbitrary position(s). Examples of substituents of the heteroaryl groups represented by Ar include halogen, $C_{1-6}$ alkyl (preferably $C_{1-4}$ alkyl), $C_{1-6}$ cycloalkyl, $C_{1-6}$ alkoxy (preferably $C_{1-4}$ alkoxy), $C_{1-6}$ cycloalkoxy, and phosphonooxymethyl. A phosphonooxymethyl group is a substituent of "heteroaryl" at the 1-position when the heteroaryl represented by Ar is pyrazolyl or pyrrolyl; the phosphonooxymethyl substituent is removed in vivo, which converts the phosphonooxymethyl-substituted pyrazolyl or pyrrolyl group to a pyrazolyl or pyrrolyl group unsubstituted at the 1-position, allowing the pyrazolyl or pyrrolyl group to show PAI-1 inhibition activity. In other words, phosphonooxymethyl is a water-soluble substituent that serves as a so-called prodrug.

When a substituent of Ar is cycloalkyl or cycloalkoxy, they may also have a substituent. Examples of such substituents include halogen, $C_{1-6}$ alkyl, $C_{1-6}$ alkoxy, halogen-substituted alkoxy having $C_{1-6}$ alkoxy, hydroxyl, $CF_3$, $CF_3O$, $CHF_2O$, $CF_3CH_2O$, cyano, carboxy, alkoxycarbonyl, benzoyl, and phenyl.

Examples of the "benzo-fused heteroaryl" represented by $R_1$, $R_2$, or Ar in the compound of the present invention include groups in which the benzene ring is fused with the above-mentioned heteroaryl. Specific examples thereof include indolyl, isoindolyl, benzofuranyl, benzothienyl, benzimidazolyl, benzisoxazolyl, benzothiazolyl, benzisothiazolyl, quinolyl, isoquinolyl, quinazolinyl, quinoxalinyl, benzoxadiazolyl, benzothiadiazolyl, etc. Preferable examples of the "benzo-fused heteroaryl" represented by Ar include quinolyl (e.g., quinolin-8-yl) and benzofuranyl (benzofuran-2-yl).

The above benzo-fused heteroaryl may have one to three substituents at arbitrary position(s). Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc.

Examples of the "aryloxy" represented by $R_1$ or $R_2$ in the compound of the present invention include hydroxyl groups substituted with $C_{6-14}$ aromatic hydrocarbon groups. Examples of such aryloxy groups include phenyloxy, naphthyloxy, anthryloxy, phenanthryloxy, acenaphthylenyloxy, etc.

Examples of the "aralkyl" represented by $R_1$, $R_2$, or $R_{16}$ in the compound of the present invention include aralkyl groups substituted with one or more aryl groups mentioned above such as phenyl, naphthyl, etc. Examples of these aralkyl groups include benzyl (phenylmethyl); monophenylalkyl groups such as 1-phenylethyl, 2-phenylethyl, 3-phenylpropyl, 4-phenylbutyl, etc.; diphenylakyl groups such as diphenylmethyl, diphenylethyl, etc.; and mononaphthyl alkyl groups such as 1-naphthyl methyl, 1-naphthyl ethyl, 2-naphtyl methyl, 2-naphthyl ethyl, etc. Among these, benzyl is preferable.

Examples of the "aralkyloxy" represented by $R_1$ or $R_2$ in the compound of the present invention include hydroxyl groups substituted with the above-mentioned aralkyl groups. Preferred among these is benzyloxy.

Examples of the "heterocyclic-alkyl" represented by $R_1$ or $R_2$ in the compound of the present invention include groups formed by bonding a bonding hand of the heterocyclic group mentioned below to either of the bonding hands of an alkylene group. Examples of the "heterocyclic-alkoxy" represented by $R_1$ or $R_2$ include groups formed by bonding a bonding hand of the heterocyclic group mentioned below to a bonding hand of the alkylene group of an alkyleneoxy group. Examples of the "alkyl" and "alkoxy" as used herein include those mentioned earlier. Examples of the heterocyclic rings include saturated and unsaturated 4- to 10-membered ring heterocyclic groups containing 1 to 3 identical or different heteroatoms selected from the group consisting of nitrogen, oxygen and sulfur. Specific examples thereof include unsaturated heterocyclic groups, such as pyrrolyl, furyl, thienyl, pyrazolyl, imidazolyl, oxazolyl, isoxazolyl, thiazolyl, isothiazolyl, oxadiazolyl, thiadiazolyl, triazolyl, tetrazolyl, pyranyl, pyridyl, pyridazinyl, pyrimidinyl, pyrazinyl, azepinyl, azocinyl, etc.; groups in which the above-mentioned unsaturated heterocyclic groups are partially or completely reduced, such as azetidinyl, pyrrolidinyl, pyrrolinyl, imidazolidinyl, imidazolinyl, pyrazolidinyl, pyrazolinyl, piperidyl, piperazinyl, morpholinyl, thiomorpholinyl, perhydroazepinyl, perhydroazocinyl, 1,4,5,6-tetrahydropyrimidinyl, 1,2,3, 6-tetrahydropyridyl, etc.; and groups in which the above-mentioned unsaturated heterocyclic rings are condensed with each other, or groups in which a benzene ring is condensed with the above-mentioned unsaturated heterocyclic ring, such as indolyl, isoindolyl, indolinyl, benzofuranyl, benzothienyl, benzimidazolyl, benzisoxazolyl, benzothiazolyl, benzisothiazolyl, benzthiophenyl, quinolyl, isoquinolyl, quinazolinyl, quinoxalinyl, benzoxadiazolyl, benzothiadiazolyl, pyrrolopyrrolyl, pyrrolooxazolyl, pyrrolothiazolyl, pyrrolopyridyl, furopyrrolyl, furopyridyl, thienopyrrolyl, thienopyridyl, imidazopyrrolyl, imidazoimidazolyl, imidazooxazolyl, imidazothiazolyl, imidazoisothiazolyl, imidazopyridyl, imidazopyridazinyl, imidazopyrimidinyl, imidazopyrazinyl, oxazooxazolyl, oxazoisoxazolyl, oxazothiazolyl, oxazoisothiazolyl, oxazopyridyl, thiazolooxazolyl, thiazoloisoxazolyl, thiazolothiazolyl, thiazoloisothiazolyl, thiazolopyridyl, etc. Preferable examples of heterocyclic groups include azetidinyl, pyrrolidinyl, piperidinyl, morpholinyl, piperazinyl, homopiperazinyl, tetrahydrofuryl, tetrahydrothienyl, tetrahydropyranyl, pyrrolyl, furyl, thienyl, oxazolyl, isoxazolyl, thiazolyl, isothiazolyl, pyrazolyl, pyridyl, pyrimidinyl, indolyl, isoindolyl, benzofuranyl, benzoxazolyl, benzothiazolyl, benzothiophenyl, and quinolyl.

Examples of the "halogen atom" in the compound of the present invention include fluorine, chlorine, bromine, and iodine. Preferred are fluorine and chlorine.

Examples of the "alkylene" represented by L, U or V in Formula (I) includes typically $C_{1-12}$, preferably $C_{1-10}$, more preferably $C_{1-8}$, further preferably $C_{1-6}$, and particularly preferably $C_{1-4}$ straight- or branched-chain alkylene groups. Examples of such alkylene groups include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, hexamethylene, heptamethylene, and octamethylene. Examples of the "alkylene" in the "cycloalkylene", "alkyleneoxyalkylene", "alkylenethioalkylene", "alkylene-SO-alkylene", "alkylene-$SO_2$-alkylene", and "alkylene-N($R_9$)-alkylene" represented by L include the same as exemplified above; and examples of the "alkylene" in the "alkyleneoxyalkylene", "oxyalkylene", and "alkyleneoxy" represented by V also include the same as exemplified above.

Specific examples of the "alkylene" represented by L include methylene, ethylene, propylene (trimethylene), tetramethylene, pentamethylene, and hexamethylene, with trimethylene and tetramethylene being preferable. These alkylene groups may be those in which some of the carbon atoms in the alkylene combine to form a cycloalkane ring. Examples of such cycloalkane rings include cyclopropane, cyclobutane, cyclopentane, and cyclohexane.

Specific examples of the "alkylene" represented by U or V include methylene, ethylene, propylene (trimethylene), tetramethylene, pentamethylene, and hexamethylene. Among these, preferable as an alkylene group represented by U is methylene, and preferable as alkylene groups represented by V are methylene, ethylene, and trimethylene.

The "alkylene" in the "alkyleneoxyalkylene", "oxyalkylene", or "alkyleneoxy" represented by V is preferably methylene or ethylene.

Preferable examples of the "cycloalkylene" include cyclopropylene, cyclobutylene, cyclopentylene, cyclohexylene, cyclooctylene, etc.; preferable examples of the "alkyleneoxyalkylene" include methyleneoxymethylene, ethyleneoxymethylene, methyleneoxyethylene, ethyleneoxyethylene, etc.; preferable examples of the "alkylenethioalkylene" include methylenethiomethylene, ethylenethiomethylene, methylenethioethylene, and ethylenethioethylene; preferable examples of the "alkylene-SO-alkylene" include methylene-SO-methylene, ethylene-SO-methylene, methylene-SO-ethylene, and ethylene-SO-ethylene; and preferable examples of the "alkylene-$SO_2$-alkylene" include methylene-$SO_2$-methylene, ethylene-$SO_2$-methylene, methylene-$SO_2$-ethylene, and ethylene-SO$_2$-ethylene. Examples of the "alkylene-N(R$_9$)-alkylene group" include lower alkylene-lower alkylamino-lower alkylene. Examples of the lower alkylene used herein include C$_{1-6}$ alkylene, and preferable examples thereof include methylene, ethylene, propylene, and trimethylene; examples of the lower alkylamino include C$_{1-6}$ alkylamino, and preferable examples thereof include methylamino, ethylamino, propylamino, isopropylamino, and butylamino. Preferred are methylene-methylamino-methylene, ethylene-methylamino-methylene, methylene-methylamino-ethylene, and ethylene-methylamino-ethylene.

Examples of the "alkenylene" represented by L in Formula (I) includes C$_{2-6}$ straight- or branched-chain alkenylene groups having 1 to 3 double bonds. Examples of such alkenylene groups include vinylene, 1-methylvinylene, propenylene, 1-butenylene, 2-butenylene, 1-pentenylene, 2-pentenylene, etc.

Examples of the "alkynylene" represented by L in Formula (I) include C$_{2-6}$ straight- or branched-chain alkynylene groups having one triple bond. Examples of such alkynylene groups include ethynylene, propynylene, 1-methylpropynylene, 1-butynylene, 2-butynylene, 1-methylbutynylene, 2-methylbutynylene, 1-pentynylene, and 2-pentynylene.

The above-mentioned "alkylene", "cycloalkylene", "alkyleneoxyalkylene", "alkylenethioalkylene", "alkylene-SO-alkylene", "alkylene-SO$_2$-alkylene", "alkylene-N(R$_9$)-alkylene", "alkenylene" and "alkynylene" may have one or two substitutes. Examples of such substituents include halogen, C$_{1-4}$ lower alkyl, C$_{1-4}$ halogenated alkyl, C$_{1-4}$ alkoxy, C$_{1-4}$ halogenated alkoxy, hydroxyl, CF$_3$, CF$_3$O, CHF$_2$O, CF$_3$CH$_2$O, cyano, carboxy, alkoxycarbonyl having C$_{1-4}$ alkoxy, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, butoxypropoxycarbonylamino), acyl, etc.

Examples of the groups represented by B in Formula (I) include, in addition to carboxyl (COOH), (1) alkoxycarbonyl, aryloxycarbonyl, and aralkyloxycarbonyl, which can be converted to a carboxyl group when absorbed in vivo; (2) groups that can be easily converted to a carboxyl group when absorbed in vivo; and (3) groups that have been designated as a group that is biologically equivalent to a carboxyl group. Here, examples of the alkoxycarbonyl, aryloxycarbonyl and aralkyloxycarbonyl in (1) above include groups that are each represented by COOR$_{16}$, wherein R$_{16}$ is respectively C$_{1-6}$ alkyl, aryl (preferably phenyl) or aralkyl (preferably benzyl).

Specific examples of the groups in (2) above include groups represented by COOR$_{16}$, wherein R$_{16}$ is a (5-alkyl-2-oxo-1,3-dioxolen-4-yl)methyl group represented by the following formula:

[Chem. 31]

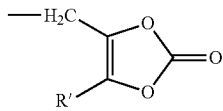

wherein R' is alkyl;
or groups represented by —CH(R$_{17}$)—O—COR$_{18}$ or —CH(R$_{17}$)—O—OR$_{18}$, wherein R$_{17}$ is hydrogen or C$_{1-6}$ alkyl, and R$_{18}$ is C$_{1-6}$ alkyl or cycloalkyl.

Examples of the groups in (3) above include heterocyclic groups such as 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, 4,5-dihydro-5-oxo-1,2,4-thiadiazol-3-yl, represented by the following formulae in order from the left (see, for example, Kohara et al. J. Med. Chem., 1996, 39, 5228-5235).

[Chem. 32]

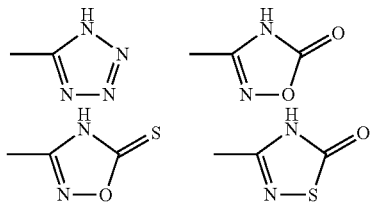

In the present invention, the groups of (1) to (3) mentioned above may each be called "a group that is biologically equivalent to a carboxyl group", and a compound (I) having the above group may be called a bioisostere of the carboxylic acid.

Specific examples of the "alkoxycarbonyl" represented by R$_1$, R$_2$, or B (when B represents —COOR$_{16}$, wherein R$_{16}$ is alkyl) in Formula (I) include t-butoxycarbonyl, methoxycarbonyl, ethoxycarbonyl, propoxycarbonyl, isopropoxycarbonyl, butoxycarbonyl, etc.

The compound (I) targeted by the present invention preferably includes benzene carboxylic acids represented by Formula (II) below, wherein X in Formula (I) is vinylene, and bioisosteres thereof:

[Chem. 33]

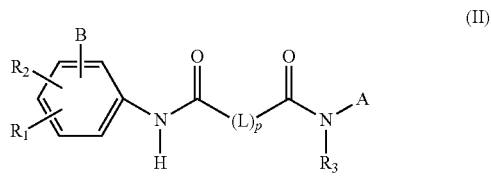

(II)

wherein R$_1$, R$_2$, R$_3$, L, B, A, and p are as defined above.

Benzene carboxylic acids, and bioisosteres thereof (II) herein refer to a compound having a structure in which a single hydrogen atom (at the ortho, meta, or para position) of the benzene is substituted with a carboxyl group represented by substituent B, or with a group that is biologically equivalent to a carboxyl group (e.g., groups that are converted in vivo to a carboxyl group; or 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl).

(1-1) Benzene Carboxylic Acid or Bioisostere of the Carboxylic Acid (II)

The above-mentioned benzene carboxylic acids or bioisosteres of the carboxylic acids (II) preferably include the following compounds.

(II-1) Benzene carboxylic acids represented by Formula (II), wherein A is a group represented by Formula (a), or bioisosteres of the benzene carboxylic acids.

(II-2) Benzene carboxylic acids represented by Formula (II), wherein A is a group represented by Formula (b), or bioisosteres of the benzene carboxylic acids.

(II-3) Benzene carboxylic acids represented by Formula (II), wherein A is a group represented by Formula (c), or bioisosteres of the benzene carboxylic acids.

(II-1) Benzene Carboxylic Acid or Bioisostere of the Benzene Carboxylic Acid

Preferable examples of benzene carboxylic acids, or bioisosteres of the benzene carboxylic acids (II-1) include compounds represented by the following formula.

[Chem. 34]

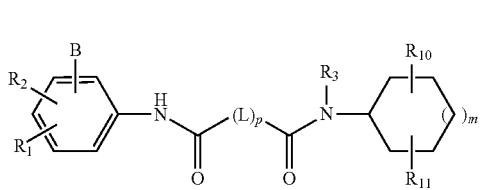

(II-1)

In the above formula, B represents a carboxyl group or a group that is biologically equivalent to a carboxyl group. Of these, a carboxyl group is preferable. B, $R_1$ and $R_2$ may be located at any of the ortho, meta or para positions of the benzene ring to which imino is bound. It is preferable, but not required, that B be located at the ortho position, and $R_2$ and $R_1$ be respectively located at the meta and para position, within the benzene ring.

The $R_1$ and $R_2$ herein are as defined above, and are preferably the same or different; and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen or halogen; and more preferably, either of them (e.g., $R_2$) is hydrogen, and the other (e.g., $R_1$) is halogen.

$R_3$ is as defined above, and is preferably hydrogen, $C_{3-8}$ (preferably $C_6$) cycloalkyl, unsubstituted aryl (preferably phenyl), or aryl (preferably phenyl) having one or two substituents.

$R_{10}$ and $R_{11}$ are as defined above, and are preferably hydrogen.

m is an integer of 1 to 10, preferably 1 to 9, and more preferably 1 to 7.

L is as defined above, and is preferably, for example, alkylene, alkyleneoxyalkylene, or alkylenethioalkylene. Among these, L is more preferably alkyleneoxyalkylene or alkylenethioalkylene. Preferable examples of alkylene include methylene.

p is as defined above, and is preferably an integer of 1.

Specific examples of the benzene carboxylic acids represented by the above formula, or bioisosteres of the benzene carboxylic acid (II-1), of the present invention, include the following compounds:

5-chloro-2-({[2-(dicyclohexylamino)-2-oxoethoxy]acetyl}amino)benzoic acid (desalted product of Example 9)

5-chloro-2-[({2-(cyclododecylamino)-2-oxoethoxy]acetyl}amino)benzoic acid (Example 11)

5-chloro-2-[({2-[cyclohexyl(phenyl)amino]-2-oxoethoxy}acetyl)amino]benzoic acid (desalted product of Example 15)

5-chloro-2-[({[2-(cyclododecylamino)-2-oxoethyl]sulfanyl}acetyl)amino]benzoic acid (Example 28)

(II-2) Benzene Carboxylic Acid or Bioisostere of the Benzene Carboxylic Acid

Preferable examples of the benzene carboxylic acids or bioisosteres of the benzene carboxylic acids (II-2) include compounds represented by the following formula.

[Chem. 35]

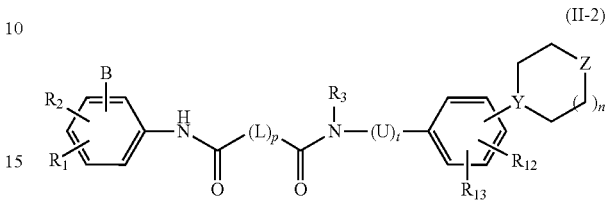

(II-2)

In the above formula, B represents a carboxyl group or a group that is biologically equivalent to a carboxyl group. Of these, a carboxyl group is preferable. B, $R_1$ and $R_2$ may be located at any of the ortho, meta or para positions of the benzene ring to which imino is bound. It is preferable, but not required, that B be located at the ortho position, and $R_2$ and $R_1$ be respectively located at the meta and para position, within the benzene ring.

The $R_1$ and $R_2$ herein are as defined above, and are preferably the same or different; and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen or halogen; and more preferably, either of them (e.g., $R_2$) is hydrogen, and the other (e.g., $R_1$) is halogen.

$R_3$, $R_{12}$ and $R_{13}$ are as defined above, and are preferably hydrogen.

Y and Z are as defined above. Y is preferably CH, and Z is preferably $CH_2$.

n is an integer of 0 to 3, preferably 1.

L is as defined above, and is preferably, for example, alkylene, alkyleneoxyalkylene, or alkylenethioalkylene. Among these, L is more preferably alkyleneoxyalkylene or alkylenethioalkylene. Preferable examples of alkylene include methylene.

p is as defined above, and is preferably an integer of 1.

U and t are as defined above. t is preferably 0.

Specific examples of the benzene carboxylic acids represented by the formula above, or bioisosteres of the benzene carboxylic acid (II-2), of the present invention, include the following compounds:

5-chloro-2-[({2-[(4-cyclohexylphenyl)amino]-2-oxoethoxy}acetyl)amino]benzoic acid (desalted product of Example 10)

5-chloro-2-[({2-[(3-cyclohexylphenyl)amino]-2-oxoethoxy}acetyl)amino]benzoic acid (Example 26)

5-chloro-2-{[({2-[(4-cyclohexylphenyl)amino]-2-oxoethyl}sulfanyl)acetyl]amino}benzoic acid (Example 27)

(II-3) Benzene Carboxylic Acid or Bioisostere of the Benzene Carboxylic Acid

Preferable examples of the benzene carboxylic acids or bioisosteres of the benzene carboxylic acids (II-3) include compounds represented by the following formula.

[Chem. 36]

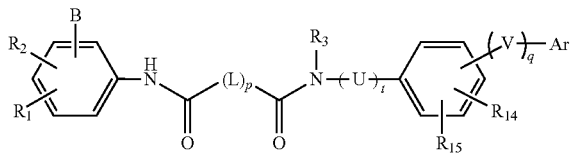

(II-3)

In the above formula, B represents a carboxyl group or a group that is biologically equivalent to a carboxyl group. Of these, a carboxyl group is preferable. Preferable examples of groups that are biologically equivalent to a carboxyl group include groups represented by —CH($R_{17}$)—O—CO$R_{18}$ or —CH($R_{17}$)—O—CO—O$R_{18}$, wherein $R_{17}$ is hydrogen or alkyl, and $R_{18}$ is alkyl or cycloalkyl; and (5-alkyl-2-oxo-1,3-dioxolen-4-yl)methyl. B, $R_1$ and $R_2$ may be located at any of the ortho, meta or para positions of the benzene ring to which imino is bound. It is preferable, but not required, that B be located at the ortho position, and $R_2$ and $R_1$ be respectively located at the meta and para positions, within the above benzene ring.

$R_1$ and $R_2$ herein are as defined above, and are preferably the same or different; and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen, halogen or aryl substituted with one or two substituents; and more preferably, either of them (e.g., $R_2$) is hydrogen, and the other (e.g., $R_1$) is halogen, unsubstituted phenyl, or phenyl having one halogen as a substituent.

$R_3$ is as defined above, and is preferably hydrogen or $C_{1-6}$ alkyl.

U and t are as defined above. U is preferably $C_1$ alkylene (methylene).

$R_{14}$ and $R_{15}$ are as defined above, and are preferably the same or different; and each represents hydrogen, $C_{1-6}$ alkyl, or halogen. $R_{14}$ and $R_{15}$ may be located at any of the ortho, meta or para positions of the benzene ring. It is preferable, but not required, that $R_{15}$ be located at the ortho position, and $R_{14}$ at the para position, within the above benzene ring. More preferably, when either $R_{14}$ or $R_{15}$ is $C_{1-6}$ alkyl or halogen, the other one is hydrogen.

V and q are as defined above, and V is preferably $C_1$ alkylene (methylene), oxyalkylene (oxymethylene), or oxygen.

Ar is as defined above, and is preferably aryl having one or two substituents; 5- to 6-membered ring heteroaryl having one or two substituents or unsubstituted 5- to 6-membered ring heteroaryl; or benzo-fused heteroaryl having one or two substituents or unsubstituted benzo-fused heteroaryl. The aryl is preferably phenyl.

Specific examples of heteroaryl groups include pyridyl (e.g., pyridin-4-yl, pyridin-3-yl, pyridin-2-yl), furyl (e.g., furan-3-yl, furan-2-yl), pyrrolyl (e.g., pyrrol-1-yl), thienyl (e.g., thiophen-3-yl, thiophen-2-yl), pyrazolyl (e.g., pyrazol-4-yl), isoxazolyl (e.g., isoxazol-3-yl, isoxazol-4-yl, isoxazol-5-yl), and oxazolyl (e.g., oxazol-5-yl). Specific examples of benzo-fused heteroaryl include quinolyl (e.g., quinolin-8-yl), which is a fused group of a 6-membered ring heteroaryl having nitrogen and a benzene ring; and benzofuranyl, which is a fused group of a 5-membered ring heteroaryl (e.g., benzofuran-2-yl) having oxygen and a benzene ring.

The substituents of the aryl, heteroaryl and benzo-fused heteroaryl are also as defined above, and are preferably $C_{1-4}$ alkyl, $C_{1-4}$ alkoxy, halogen, acetylamino, or phosphonooxymethyl. When Ar is phenyl, the substituent thereof may form a ring with some carbon atoms of the phenyl, and may form a benzo-fused heterocyclic ring with Ar. Examples of such benzo-fused heterocyclic rings include 1,3-benzodioxolyl (1,3-benzodioxol-5-yl), which is a fused product in which a 5-membered ring cycloalkyl having two oxygens is fused with a benzene ring.

Ar may be located at any of the ortho, meta or para positions of the benzene ring.

L is as defined above, and is preferably alkylene, alkyleneoxyalkylene, alkylenethioalkylene, alkylene-SO-alkylene, or alkylene-$SO_2$-alkylene. Preferable examples of the alkylene as used herein include $C_{1-3}$ alkylene (methylene, ethylene or trimethylene). Preferable examples of the alkylene in "alkyleneoxyalkylene", "alkylenethioalkylene", "alkylene-SO-alkylene", and "alkylene-$SO_2$-alkylene" include methylene.

p is as defined above, and is an integer of 0 or 1.

Specific examples of the benzene carboxylic acids represented by the above formula, or bioisosteres of the benzene carboxylic acid (II-3), of the present invention, include the following compounds:

Compounds of Formula (II-3), Wherein Ar is Aryl Having a Substituent 5-chloro-2-[({2-[(4'-fluorobiphenyl-2-yl)amino]-2-oxoethoxy}acetyl)amino]benzoic acid (Example 3)

5-chloro-2-[({2-[(4'-fluoro-4-methylbiphenyl-3-yl)amino]-2-oxoethoxy}acetyl)amino]benzoic acid (Example 5)

5-chloro-2-[({2-oxo-2-[(3',4,5'-trimethylbiphenyl-3-yl)amino]ethoxy}acetyl)amino]benzoic acid (Example 6)

5-chloro-2-[({2-[(4'-fluorobiphenyl-4-yl)amino]-2-oxoethoxy}acetyl)amino]benzoic acid (desalted product of Example 7)

5-chloro-2-[({2-[(4'-fluorobiphenyl-3-yl)amino]-2-oxoethoxy}acetyl)amino]benzoic acid (desalted product of Example 8)

5-chloro-2-{[({2-[(4'-fluorobiphenyl-3-yl)amino]-2-oxoethyl}sulfanyl)acetyl]amino}benzoic acid (desalted product of Example 12)

5-chloro-2-{[({2-[(4'-fluorobiphenyl-3-yl)amino]-2-oxoethyl}sulfinyl)acetyl]amino}benzoic acid (Example 13)

5-chloro-2-{[({2-[(4'-fluorobiphenyl-3-yl)amino]-2-oxoethyl}sulfonyl)acetyl]amino}benzoic acid (Example 14)

5-chloro-2-({[(4'-fluoro-4-methylbiphenyl-3-yl)amino](oxo)acetyl}amino)benzoic acid (desalted product of Example 20)

5-chloro-2-[({2-[(4'-fluoro-4-methylbiphenyl-3-yl)(2-methylpropyl)amino]-2-oxoethoxy}acetyl)amino]benzoic acid (desalted product of Example 22)

4'-fluoro-4-[({2-[(4'-fluoro-4-methylbiphenyl-3-yl)amino]-2-oxoethoxy}acetyl)amino]biphenyl-3-carboxylic acid (desalted product of Example 23)

5-chloro-2-{[({2-oxo-2-[(3',4,5'-trimethylbiphenyl-3-yl)amino]ethyl}sulfanyl)acetyl]amino}benzoic acid (Example 24)

5-chloro-2-[({2-[ethyl(4'-fluoro-4-methylbiphenyl-3-yl)amino]-2-oxoethoxy}acetyl)amino]benzoic acid (Example 29)

5-chloro-2-{[({2-[ethyl(4'-fluoro-4-methylbiphenyl-3-yl)amino]-2-oxoethyl}sulfanyl)acetyl]amino}benzoic acid (Example 30)

5-chloro-2-({5-[ethyl(4'-fluoro-4-methylbiphenyl-3-yl)amino]-5-oxopentanoyl}amino)benzoic acid (Example 31)

5-chloro-2-[({2-[(2'-methoxy-4-methylbiphenyl-3-yl)amino]-2-oxoethoxy}acetyl)amino]benzoic acid (Example 38)

5-chloro-2-[({2-[(3'-methoxy-4-methylbiphenyl-3-yl)amino]-2-oxoethoxy}acetyl)amino]benzoic acid (Example 39)

5-chloro-2-[({2-[(4'-methoxy-4-methylbiphenyl-3-yl)amino]-2-oxoethoxy}acetyl)amino]benzoic acid (Example 40)

2-{[(2-{[5-(1,3-benzodioxol-5-yl)-2-methylphenyl]amino}-2-oxoethoxy)acetyl]amino}-5-chlorobenzoic acid (Example 41)

2-{[(2-{[3'-(acetylamino)-4-methylbiphenyl-3-yl]amino}-2-oxoethoxy)acetyl]amino}-5-chlorobenzoic acid (Example 43)

2-{[(2-{[4'-(acetylamino)-4-methylbiphenyl-3-yl]amino}-2-oxoethoxy)acetyl]amino}-5-chlorobenzoic acid (Example 44)

5-chloro-2-[({2-oxo-2-[(2-phenoxyphenyl)amino]ethoxy}acetyl)amino]benzoic acid (Example 56)

5-chloro-2-{[({2-oxo-2-[(2-phenoxyphenyl)amino]ethyl}sulfanyl)acetyl]amino}benzoic acid (Example 57).

Compounds Represented by Formula (II-3), Wherein Ar is Heteroaryl Optionally Having a Substituent 5-chloro-2-{[(2-oxo-2-{[4-(pyridin-4-yl)phenyl]amino}ethoxy)acetyl]amino}benzoic acid (Example 1)

5-chloro-2-{[(2-oxo-2-{[3-(pyridin-4-yl)phenyl]amino}ethoxy)acetyl]amino}benzoic acid (Example 2)

5-chloro-2-{[(2-oxo-2-{[2-(pyridin-4-yl)phenyl]amino}ethoxy)acetyl]amino}benzoic acid (desalted product of Example 4)

5-chloro-2-{[(2-oxo-2-{[3-(pyridin-4-yl)phenyl]amino}ethoxy)acetyl]amino}benzoic acid [(2,2-dimethylpropanoyl)oxy]methyl ester (Example 16)

5-chloro-2-{[(2-oxo-2-{[3-(pyridin-4-yl)phenyl]amino}ethoxy)acetyl]amino}benzoic acid 1-{[(cyclohexyloxy)carbonyl]oxy}ethyl ester (Example 17)

5-chloro-2-{[(2-oxo-2-{[3-(pyridin-4-yl)phenyl]amino}ethoxy)acetyl]amino}benzoic acid (5-methyl-2-oxo-1,3-dioxol-4-yl)methyl ester (Example 18)

5-chloro-2-{[(2-oxo-2-{[3-(pyridin-3-yl)phenyl]amino}ethoxy)acetyl]amino}benzoic acid (desalted product of Example 19)

5-chloro-2-{[(2-oxo-2-{[3-(pyridin-2-yl)phenyl]amino}ethoxy)acetyl]amino}benzoic acid (desalted product of Example 21)

5-chloro-2-({[(2-oxo-2-{[3-(pyridin-4-yl)phenyl]amino}ethyl)sulfanyl]acetyl}amino)benzoic acid (Example 25)

5-chloro-2-{[(2-{[5-(furan-3-yl)-2-methylphenyl]amino}-2-oxoethoxy)acetyl]amino}benzoic acid (Example 32)

5-chloro-2-({[(2-{[5-(furan-3-yl)-2-methylphenyl]amino}-2-oxoethyl)sulfanyl]acetyl}amino)benzoic acid (Example 33)

5-chloro-2-[(5-{[5-(furan-3-yl)-2-methylphenyl]amino}-5-oxopentanoyl)amino]benzoic acid (Example 34)

5-chloro-2-{[(2-{ethyl[5-(furan-3-yl)-2-methylphenyl]amino}-2-oxoethoxy)acetyl]amino}benzoic acid (Example 35)

5-chloro-2-({[(2-{ethyl[5-(furan-3-yl)-2-methylphenyl]amino}-2-oxoethyl)sulfanyl]acetyl}amino)benzoic acid (Example 36)

5-chloro-2-[(5-{ethyl[5-(furan-3-yl)-2-methylphenyl]amino}-5-oxopentanoyl)amino]benzoic acid (Example 37)

5-chloro-2-{[{[3-(furan-3-yl)phenyl]amino}(oxo)acetyl]amino}benzoic acid (Example 45)

5-chloro-2-({[(2-{[3-(furan-3-yl)phenyl]amino}-2-oxoethyl)sulfanyl]acetyl}amino)benzoic acid (Example 46)

5-chloro-2-{[(2-{[3-(2,6-dimethoxypyridin-3-yl)phenyl]amino}-2-oxoethoxy)acetyl]amino}benzoic acid (Example 47)

5-chloro-2-{[(2-oxo-2-{[3-(1H-pyrrol-1-yl)phenyl]amino}ethoxy)acetyl]amino}benzoic acid (desalted product of Example 48)

5-chloro-2-{[(2-{[2-fluoro-5-(furan-3-yl)phenyl]amino}-2-oxoethoxy)acetyl]amino}benzoic acid (Example 49)

5-chloro-2-{[(2-{[4-fluoro-3-(furan-3-yl)phenyl]amino}-2-oxoethoxy)acetyl]amino}benzoic acid (Example 50)

5-chloro-2-[(3-{[3-(furan-3-yl)phenyl]amino}-3-oxopropanoyl)amino]benzoic acid (Example 52)

5-chloro-2-{[{[3-(furan-3-yl)benzyl]amino}(oxo)acetyl]amino}benzoic acid (Example 53)

5-chloro-2-{[(2-{[3-(furan-2-ylmethyl)phenyl]amino}-2-oxoethoxy)acetyl]amino}benzoic acid (Example 54)

5-chloro-2-{[(2-{[3-(furan-3-ylmethyl)phenyl]amino}-2-oxoethoxy)acetyl]amino}benzoic acid (Example 55)

5-chloro-2-{[(2-{[3-(furan-3-yl)phenyl]amino}-2-oxoethoxy)acetyl]amino}benzoic acid (Example 58)

5-chloro-2-{[(2-oxo-2-{[3-(thiophen-3-yl)phenyl]amino}ethoxy)acetyl]amino}benzoic acid (Example 59)

5-chloro-2-{[(2-{[3-(1-methyl-1H-pyrazol-4-yl)phenyl]amino}-2-oxoethoxy)acetyl]amino}benzoic acid (Example 60)

5-chloro-2-{[(2-{[3-(furan-2-yl)phenyl]amino}-2-oxoethoxy)acetyl]amino}benzoic acid (Example 61)

5-chloro-2-{[(2-{[3-(3,5-dimethylisoxazol-4-yl)phenyl]amino}-2-oxoethoxy)acetyl]amino}benzoic acid (desalted product of Example 62)

5-chloro-2-{[(2-oxo-2-{[3-(thiophen-2-yl)phenyl]amino}ethoxy)acetyl]amino}benzoic acid (Example 63)

5-chloro-2-{[(2-{[4-(furan-3-yl)phenyl]amino}-2-oxoethoxy)acetyl]amino}benzoic acid (Example 64)

5-chloro-2-{[(2-{[3-(furan-2-ylmethoxy)phenyl]amino}-2-oxoethoxy)acetyl]amino}benzoic acid (Example 65)

5-chloro-2-{[(2-{[3-(furan-3-yl)benzyl]amino}-2-oxoethoxy)acetyl]amino}benzoic acid (Example 66)

5-chloro-2-{[(2-{[3-(furan-2-yl)benzyl]amino}-2-oxoethoxy)acetyl]amino}benzoic acid (Example 67)

5-chloro-2-{[(2-oxo-2-{[3-(1H-pyrazol-4-yl)phenyl]amino}ethoxy)acetyl]amino}benzoic acid (Example 68)

5-chloro-2-[({2-oxo-2-[(3-{1-[(phosphonateoxy)methyl]-1H-pyrazol-4-yl}phenyl)amino]ethoxy}acetyl)amino]benzoic acid (desalted product of Example 69)

5-chloro-2-{[(2-{[3-(1,3-oxazol-5-yl)phenyl]amino}-2-oxoethoxy)acetyl]amino}benzoic acid (Example 70)

5-chloro-2-{[(2-{[3-(isoxazol-5-yl)phenyl]amino}-2-oxoethoxy)acetyl]amino}benzoic acid (Example 71)

5-chloro-2-{[(2-oxo-2-{[3-(thiophen-3-yl)benzyl]amino}ethoxy)acetyl]amino}benzoic acid (Example 72)

5-chloro-2-{[(2-oxo-2-{[3-(thiophen-2-yl)benzyl]amino}ethoxy)acetyl]amino}benzoic acid (Example 73)

5-chloro-2-{[{[3-(furan-2-yl)benzyl]amino}(oxo)acetyl]amino}benzoic acid (Example 74)

5-chloro-2-{[(2-{[3-(5-chlorothiophen-2-yl)benzyl]amino}-2-oxoethoxy)acetyl]amino}benzoic acid (Example 75)

5-chloro-2-{[(2-{[3-(5-methylthiophen-2-yl)benzyl]amino}-2-oxoethoxy)acetyl]amino}benzoic acid (Example 76)

5-chloro-2-{[(2-{[3-(furan-3-yl)phenyl]amino}-2-oxoethoxy)acetyl]amino}benzoic acid (desalted product of Example 77)

5-chloro-2-{[(2-{[3-(furan-3-yl)phenyl]amino}-2-oxoethoxy)acetyl]amino}benzoic acid (desalted product of Example 78)

5-chloro-2-{[(2-{[3-(isoxazol-3-yl)phenyl]amino}-2-oxoethoxy)acetyl]amino}benzoic acid (Example 79)

5-chloro-2-{[(2-{[3-(5-methylfuran-3-yl)phenyl]amino}-2-oxoethoxy)acetyl]amino}benzoic acid (Example 80)

Compounds Represented by Formula (II-3), Wherein Ar is Benzo-Fused Heteroaryl Optionally Having a Substituent 5-chloro-2-{[(2-{[2-methyl-5-(quinolin-8-yl)phenyl]amino}-2-oxoethoxy)acetyl]amino}benzoic acid (desalted product of Example 42)

2-{[(2-{[3-(1-benzofuran-2-yl)phenyl]amino}-2-oxoethoxy)acetyl]amino}-5-chlorobenzoic acid (Example 51)

The compounds of Examples 16 to 18 mentioned above are all converted in vivo to the compound of Example 2, and the compounds of Example 69 are converted in vivo to the compound of Example 68. Specifically, these compounds show PAI-1 activity as a compound of Example 2 or 68 when metabolized in vivo, and are thus so-called prodrugs of the compounds of Example 2 or 68.

Each of the compounds (I) targeted by the present invention may be in free or salt form.

Examples of salts as used herein typically include pharmaceutically acceptable salts, e.g., a salt formed with an inorganic base or organic base, a salt formed with a basic amino acid, and other salts. Examples of inorganic bases include alkali metals such as sodium, potassium, etc.; alkaline earth metals such as calcium, magnesium, etc.; and aluminium, ammonium, etc. Examples of organic bases include primary amines such as ethanolamine, tromethamine (2-amino-2-hydroxymethyl-1,3-propanediol), ethylenediamine, etc.; secondary amines such as dimethylamine, diethylamine, diethanolamine, meglumine (N-methyl-D-glucamine), dicyclohexylamine, N,N'-dibenzylethylenediamine, etc.; and tertiary amines such as trimethylamine, triethylamine, pyridine, picoline, triethanolamine, etc. Examples of basic amino acids include arginine, lysine, ornithine, histidine, etc. Further, the compound of the present invention may form a salt with an inorganic acid, or organic acid. Examples of inorganic acids include hydrochloric acid, hydrobromic acid, sulfuric acid, phosphoric acid, etc. Examples of organic acids include formic acid, acetic acid, trifluoroacetic acid, maleic acid, tartaric acid, fumaric acid, citric acid, lactic acid, methanesulfonic acid, benzenesulfonic acid, toluenesulfonic acid, etc.

Further, when the carboxylic acid represented by Formula (I), a salt thereof, or a bioisostere of the carboxylic acid form a solvate (e.g., hydrate, alcohol), such a solvate is also encompassed in the present invention. Furthermore, the present invention encompasses all of the compounds (e.g., a so-called prodrug) that are converted, when metabolized in vivo, to a carboxylic acid represented by Formula (I), a bioisostere thereof, or a pharmaceutically acceptable salt.

(2) Production Method of Compound of the Present Invention

The following describes in detail the methods of producing the aromatic or heterocyclic carboxylic acids represented by Formula (I) of the present invention or bioisosteres thereof, and salts thereof.

Needless to say, however, the present invention is not limited thereto. Further, for the production of the compound, the order of the production steps is not limited to those described below, and can be suitably adjusted in accordance with the practice of the industry of interest. Furthermore, whenever a reaction functional group is found in any step, the group can be suitably protected and deprotected unless otherwise specified. Reagents in addition to those listed below can be suitably used to promote reaction progress.

(2-1) Production Method 1

Compounds (1) and (2) are condensed to produce a compound (I-1) equivalent to an ester moiety of the aromatic or heterocyclic carboxylic acid of the present invention [step (a)].

[Chem. 37]

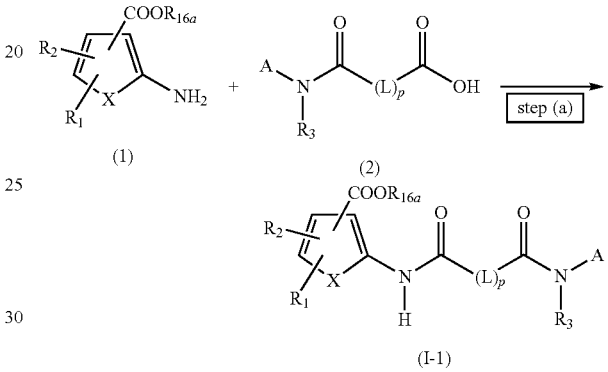

wherein $R_1$ to $R_3$, X, L, p, and A are defined as above; and $R_{16a}$ represents alkyl, aryl or aralkyl.

The condensation reaction may be carried out between the compounds (1) and (2) in the presence of a known condensing agent, or by converting the compound (2) to a reactive derivative before further reacting with the compound (1).

Examples of condensing agents include known agents, such as dicyclohexylcarbodiimide (DCC), water-soluble carbodiimide (WSC) (e.g., 1-ethyl-3-(3-dimethylaminopropyl) carbodiimide hydrochloride), carbonyldiimidazole (CDI), benzotriazol-1-yloxy-tris (pyrrolidino)phosphonium hexafluorophosphate (PyBOP), and the like. Examples of additives include N-hydroxysuccinimide (HOSu), 1-hydroxybenzotriazole (HOBT), and the like.

Further, examples of reactive derivatives of the compound (2) include acid chlorides (e.g., chloride, bromide), active esters (e.g., p-nitrophenyl ester, pentachlorophenyl ester, esters reacted with N-hydroxysuccinimide, and esters reacted with 1-hydroxybenzotriazole), imidazolide, and mixed acid anhydrides (e.g., mixed acid anhydride formed with methoxy formic acid, ethoxy formic acid, propoxy formic acid, butoxy formic acid, isobutoxy formic acid, tert-butoxy formic acid, phenoxy formic acid, 2,2-dimethylpropionate, methanesulfonic acid, benzenesulfonic acid, and toluenesulfonic acid). These reactive derivatives may be reacted with the compound (1) after being formed or as they are formed within a reaction system, or may be isolated from the reaction system before reacting with the compound (1).

The reaction of the compounds (1) and (2) with the reactive derivative is generally carried out in a solvent, and, if necessary, in the presence of a base. An inert organic solvent is commonly used as a solvent; however, water can sometimes be used as a solvent, or a mixture thereof can also be used. Examples of usable organic solvents include halogenated alkyls (e.g., methylene chloride and chloroform); aromatic hydrocarbons (e.g., benzene, toluene, xylene, and anisole); ethers (e.g., diethyl ether, diisopropyl ether, methyl isobutyl ether, methyl cyclopentyl ether, tetrahydrofuran (THF), and dioxane); esters (e.g., methyl acetate, ethyl acetate, isopropyl acetate, and butyl acetate); ketones (e.g., acetone, methyl ethyl ketone, and methyl isobutyl ketone); acetonitrile, N,N-dimethylformamide (DMF), N,N-dimethylacetamide (DMA), N-methylpiperidone, dimethyl sulfoxide (DMSO); etc. Examples of usable bases include inorganic bases (e.g., sodium hydrogencarbonate, potassium hydrogencarbonate, sodium carbonate, potassium carbonate, sodium hydroxide, potassium hydroxide, and lithium hydroxide); and organic bases (e.g., pyridine, triethyl amine, N,N-diisopropylethylamine, N-methyl morpholine, and N-methylpiperidine). The reaction temperature varies depending on the condensing agent used or the kind of reactive derivative of the compound (2), but typically ranges from about −30° C. to about 120° C., and preferably from about −10° C. to about 100° C. The amount of the condensing agent and base used is typically about 1 to about 5 equivalent weight, and preferably about 1 to about 3 equivalent weight, per mol of the compound (2). The amount of the compound (2), when used in the form of a reactive derivative, is about 1 to about 5 equivalent weight, and preferably about 1 to about 2 equivalent weight, per mol of the compound (1).

The thus-prepared ester moiety (I-1) can be made into the compound (I-2) of the present invention in the form of a free radical carboxylic acid by removing the ester linkage $R_{16a}$ therefrom [step (g)].

[Chem. 38]

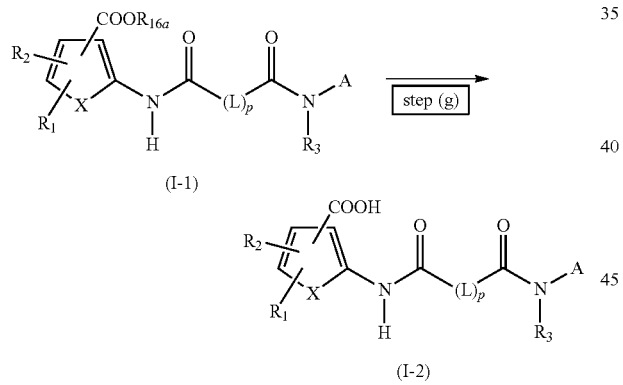

(I-1)

(I-2)

wherein $R_1$ to $R_3$, $R_{16a}$, X, L, p, and A are defined as above.

The conditions to perform such a removal vary depending on the kind of $R_{16a}$, but preferably used acids include hydrogen chloride, hydrogen bromide, methanesulfonic acid, benzenesulfonic acid, p-toluenesulfonic acid, trifluoroacetic acid, etc., when $R_{16a}$ is a t-butyl group. In this case, the removal reaction is typically carried out in an inactive solvent (e.g., benzene, toluene, ethyl ether, isopropyl ether, THF, ethyl acetate, dichloromethane, and chloroform) at about 0° C. to about 60° C. The amount of acid used varies depending on the kind thereof, but is typically about 1 to about 10 equivalent weight per mol of the compound (I-1). Further, when trifluoroacetic acid is used as the acid, it can also be used as a solvent.

When $R_{16a}$ is alkyl, aryl or aralkyl, an alkali hydrolysis reaction can be employed. In this case, suitably usable alkalis include lithium hydroxide, sodium hydroxide, potassium hydroxide, barium hydroxide, etc.; and suitably usable solvents include methanol, ethanol, dioxane, THF, or mixtures thereof, etc. The amount of alkali used is typically about 1 to about 3 equivalent weight per mole of the compound (I-1), and the reaction temperature ranges from about 0° C. to about 80° C. In an alkali hydrolysis reaction, a salt is first formed from the alkali used. Thus, $R_{16a}$ can be isolated as a salt thereof, or can be isolated as a free radical carboxylic acid by neutralization using a suitable acid (e.g., acetic acid, hydrochloric acid, and sulfuric acid). Alternatively, a free radical carboxylic acid is first isolated and then converted into an alkali metal salt or alkaline earth metal salt by a known method. Further, when the compound (I) of the present invention contains a basic nitrogen functional group in molecules, $R_{16a}$ can be isolated as an acid chloride of the compound (I) by treating with an equivalent or excessive weight of an acid.

When $R_{16a}$ is aralkyl (e.g., benzyl), the compound (I-1) can be converted to a free radical carboxylic acid (I-2) by being subjected to catalytic reduction by a known method using hydrogen gas in the presence of a catalyst such as palladium carbon, palladium black, etc.

(2-2) Production Method 2

[Chem. 39]

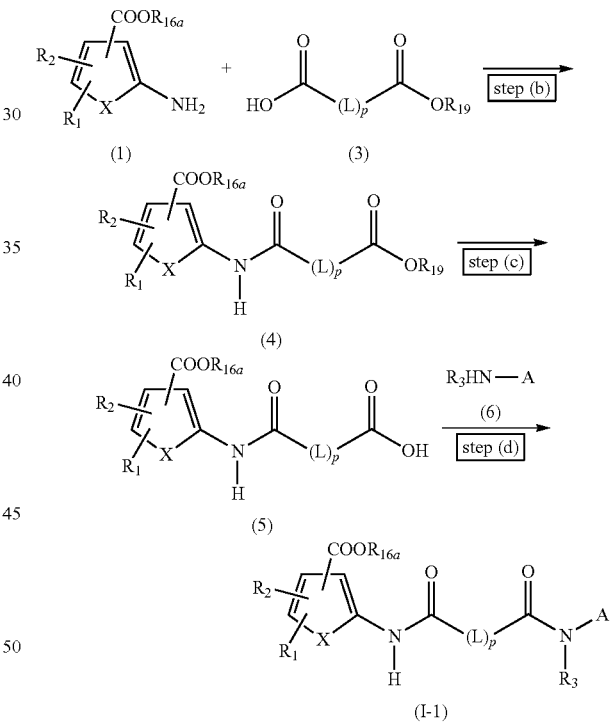

wherein $R_1$ to $R_3$, X, L, A, p, and $R_{16a}$ are defined as above; and $R_{19}$ represents alkyl, aryl or aralkyl.

In place of the compound (2) used in the production method 1, a dicarboxylic acid monoester (3) is reacted with the compound (1) to produce an ester moiety (4) [step (b)]. The compound (4) is converted to a compound (5) by selectively removing only $R_{19}$ from the compound (4) [step (c)]. The compound (5) is then condensed with amine (6) [step (d)], thereby producing an ester moiety (I-1). If necessary, the step (g) described above is subsequently carried out to produce a carboxylic acid (I-2). The reactions of the steps (b) and (d) can be carried out under the same reaction conditions as in the step (a) of the production method 1.

(2-3) Production Method 3

[Chem. 40]

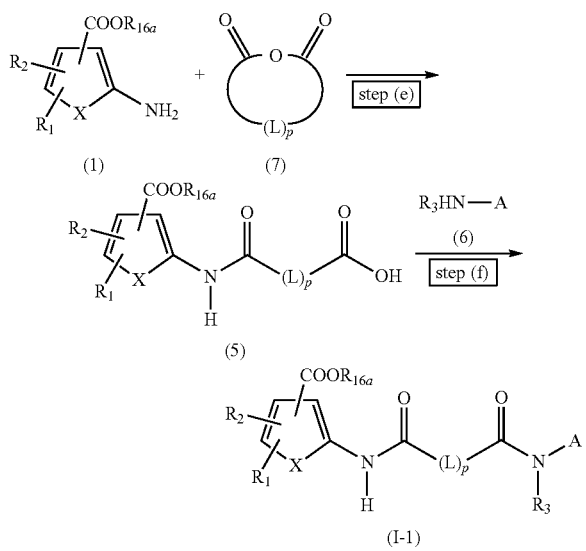

wherein $R_1$ to $R_3$, $R_{16a}$, X, L, and A are defined as above; and p represents 1.

The ester-carboxylic acid (5) obtained in the production method 2 can be easily produced using an intramolecular anhydride of dicarboxylic acid (7) as the reactive derivative of the dicarboxylic acid monoester (3) used in the production method 2 [step (e)].

The reaction between the compounds (1) and (7) is typically carried out in a solvent at about 30° C. to about 100° C., and preferably about 50° C. to about 80° C. The solvent employable is any of those inactive in the reaction, and examples include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), ketones (e.g., acetone, methyl ethyl ketone, and methyl isobutyl ketone), dioxane, THF, acetonitrile, pyridine, DMF, DMA, DMSO, etc. The amount of the compound (7) used is about 1 to about 2 equivalent weight, and preferably about 1 to about 1.5 equivalent weight, per mole of the compound (1).

The reaction may be carried out in the presence of a base, as necessary; and, for example, pyridine, picoline, 4-dimethylaminopyridine, triethylamine, N-methylpiperidine, N-methyl morpholine, etc., can be used in an amount of about 1 to about 3 equivalent weight, and preferably about 1 to about 2 equivalent weight, per mol of the compound (1).

The obtained ester-carboxylic acid (5) is then condensed with the amine (6) in the same manner as in the production method 2 to produce an ester moiety (I-1) [step (f)]. If necessary, the step (g) described above is subsequently carried out to produce a carboxylic acid (I-2).

(2-4) Production Method 4

The compound (I-2) produced by the production method 1, 2, or 3 can be converted to an ester compound (I-1'), if necessary [step (h)].

[Chem. 41]

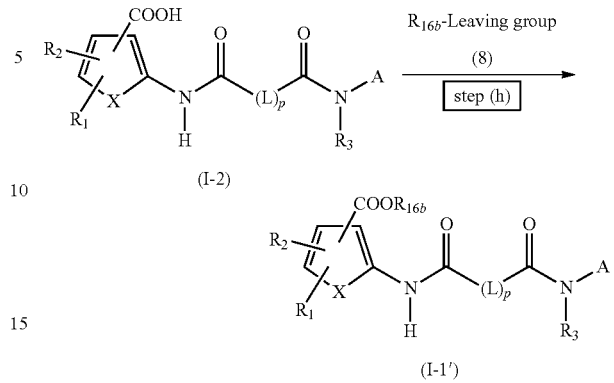

wherein $R_1$ to $R_3$, X, L, p, and A are defined as above; and $R_{16b}$ is alkyl, phenyl, benzyl, (5-alkyl-2-oxo-1,3-dioxolen-4-yl)methyl, or a group represented by —CH($R_{17}$)—O—COR$_{18}$ or —CH($R_{17}$)—O—CO—OR$_{18}$, wherein $R_{17}$ represents hydrogen or alkyl, and $R_{18}$ represents alkyl or cycloalkyl.

In this reaction, the compound (I-1') is generally synthesized by reacting the carboxylic acid (I-2) or an alkali metal salt thereof with the corresponding compound (8). Examples of the leaving group in the compound (8) include halogen (e.g., chlorine, bromine, and iodine), sulfonyloxy groups (e.g., mesyloxy, besyloxy, and tosyloxy), and the like. The reaction is typically carried out in a solvent and, if necessary, in the presence of a base. The solvent employable is any of those inactive in the reaction, and examples include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), dioxane, THF, ketones (e.g., acetone, methyl ethyl ketone, and methyl isobutyl ketone), acetonitrile, pyridine, DMF, DMA, DMSO, etc. The amount of the compound (8) used is about 1 to about 2 equivalent weight, and preferably about 1 to about 1.5 equivalent weight, per mole of the compound (I-2).

Examples of bases usable in the reaction include inorganic bases, such as sodium hydrogencarbonate, potassium hydrogencarbonate, sodium carbonate, potassium carbonate, sodium hydroxide, potassium hydroxide, lithium hydroxide, and cesium hydroxide; and organic bases, such as pyridine, picoline, 4-dimethylaminopyridine, triethylamine, N-methylpiperidine, and N-methyl morpholine. The amount of such a base used is about 1 to about 3 equivalent weight, and preferably about 1 to about 2 equivalent weight, per mole of the compound (I-2).

The reaction temperature typically ranges from about −10° C. to about 100° C., and preferably from about 0° C. to about 60° C.

(2-5) Production Method 5

A cyano-amide compound (10) can easily be produced by the reaction of a cyano compound (9), in place of the compound (1), in the same manner as in the production method 1, 2, or 3 [(i) step (a'), (ii) step (b')+step (c')+step (d'), or (iii) step (e')+step (f')]. The obtained cyano-amide compound (10) is then reacted with an azide (11) to produce a compound having a 1H-tetrazol-5-yl group (I-3) [step (i)].

[Chem. 42]

(i)
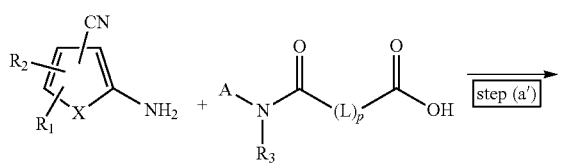

(ii)
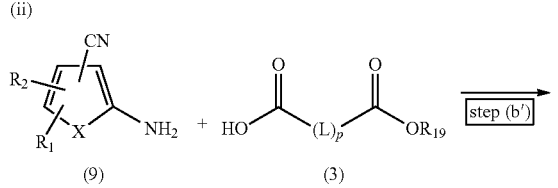

(iii)
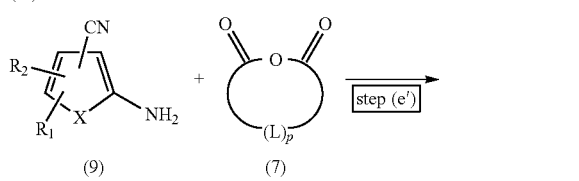

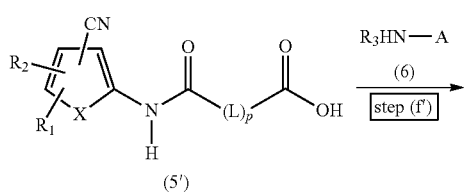

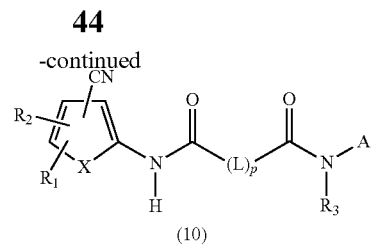

[Chem. 43]

(iv)
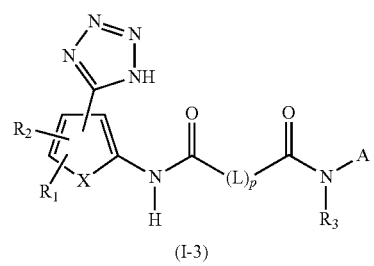

wherein $R_1$ to $R_3$, $R_{19}$, X, L, p, and A are defined as above; however, in the compounds (7), (5'), and (10) of the process (iii), p is 1.

The reaction between the compound (10) and azide (11) (e.g., sodium azide and trimethylsilyl azide) is typically carried out in a solvent (e.g., chloroform, toluene, xylene, diethyl ether, THF, dioxane, ethyl acetate, methyl ethyl ketone, acetonitrile, DMF, DMA, DMSO, ethanol, water, or a mixture thereof), preferably in the presence of a tin compound (e.g., n-tributyltinchloride and di-n-butyltinoxide) or Lewis acid (e.g., zinc bromide and copper iodide). The reaction temperature typically ranges from about 20° C. to about 120° C., and preferably from about 50° C. to about 100° C. The amount of the azide compound used is typically about 1 to about 10 equivalent weight, and preferably about 1 to about 5 equivalent weight, per mol of the compound (10). The amount of the tin compound used is typically about 0.1 to about 5 equivalent weight, and preferably about 0.1 to about 1.5 equivalent weight, per mol of the compound (10). The amount of the Lewis acid used is typically about 0.1 to about 5 equivalent weight, and preferably about 0.1 to about 1.5 equivalent weight, per mol of the compound (10).

(2-6) Production Method 6

The compound (10) produced by the production method 5 is reacted with hydroxylamine hydrochloride (12) to produce an amide oxime compound (13) [step (j)]. The amide oxime compound is then reacted with an active carbonyl compound (14) to produce a compound (I-4) [step (k)].

[Chem. 44]

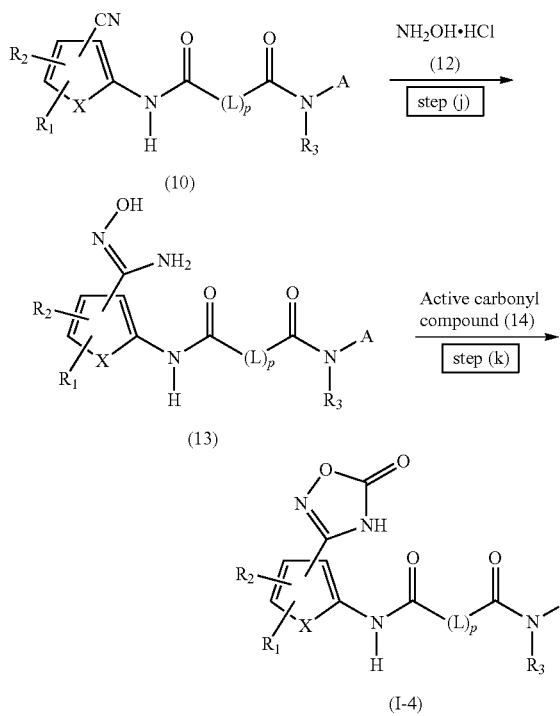

wherein $R_1$ to $R_3$, X, L, p, and A are defined as above.

The reaction between the compound (10) and hydroxylamine hydrochloride (12) (step (j)) is typically carried out in a solvent (e.g., chloroform, toluene, xylene, diethyl ether, THF, dioxane, ethyl acetate, methyl ethyl ketone, acetonitrile, DMF, DMA, DMSO, ethanol, water, or a mixture thereof) preferably in the presence of a base (e.g., pyridine, triethylamine, N,N-diisopropylethylamine, N-methylmorpholine, N-methylpyridine, potassium carbonate, and sodium hydroxide). The reaction temperature typically ranges from about −30° C. to about 120° C., and preferably from about 20° C. to about 100° C. The amount of hydroxylamine hydrochloride and base used is typically about 1 to about 2 equivalent weight, and preferably about 1 to about 1.5 equivalent weight, per mol of the compound (10).

For the production of the compound (I-4) having a 4,5-dihydro-5-oxo-4H-1,2,4-oxadiazol-3-yl group (step (k)), the compound (13) is reacted with an active carbonyl compound, such as chlorocarbonic acid monoesters (e.g., methyl chlorocarbonate, ethyl chlorocarbonate, isopropyl chlorocarbonate, butyl chlorocarbonate, isobutyl chlorocarbonate, phenyl chlorocarbonate, and 2-ethylhexyl chlorocarbonate) in a solvent (e.g., chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (e.g., triethylamine, N-methylmorpholine, pyridine, 1,8-diazabicyclo[5.4.0]undeca-7-ene (DBU), 1,5-diazabicyclo[4.3.0]non-5-ene (DBN), and sodium hydride), subjected to suitable aftertreatment, and cyclized with heat. Alternatively, the compound (13) is reacted with N,N′-carbonyldiimidazole (CDI) in a solvent (e.g., chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (e.g., triethylamine, N-methylmorpholine, pyridine, DBU, DBN, and sodium hydride). The reaction temperature of the compound (13) and chlorocarbonic acid monoester typically ranges from about −30° C. to about 100° C., and preferably from about −10° C. to about 50° C. The reaction temperature during the cyclization reaction typically ranges from about 40° C. to about 180° C., and preferably from about 80° C. to about 150° C. The temperature of the reaction between the compound (13) and CDI typically ranges from about 20° C. to about 100° C., and preferably from about 40° C. to about 100° C. The amount of chlorocarbonic acid monoester and base is typically about 1 to about 2 equivalent weight, and preferably about 1 to about 1.5 equivalent weight, per mol of the compound (13).

(2-7) Production Method 7

The compound (13) is reacted with 1,1′-thiocarbonyldiimidazole (TCDI) (15) in a solvent (e.g., chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (e.g., triethylamine, N-methylmorpholine, pyridine, DBU, DBN, and sodium hydride) to form a compound (I-5) having a 4,5-dihydro-5-thioxo-4H-1,2,4-oxadiazol-3-yl group [step (l)].

[Chem. 45]

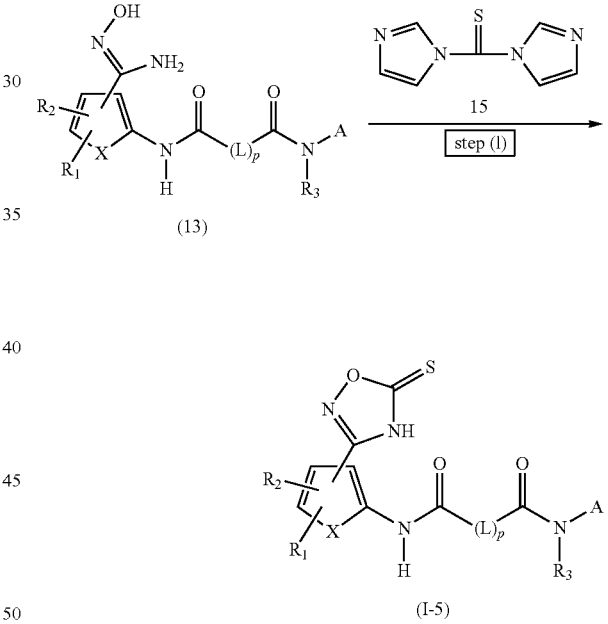

wherein $R_1$ to $R_3$, X, L, p, and A are defined as above.

The reaction temperature typically ranges from about −30° C. to about 100° C., and preferably from about −10° C. to about 50° C. The amount of TCDI and base used is typically about 1 to about 10 equivalent weight, and preferably about 1 to about 1.5 equivalent weight, per mol of the compound (13).

Alternatively, the compound (13) is reacted with TCDI (15) in a solvent (e.g., chloroform, toluene, xylene, diethyl ether, THF, dioxane, ethyl acetate, methyl ethyl ketone, acetonitrile, DMF, DMA, DMSO, methanol, ethanol, or a mixture thereof) in the absence of a base, subjected to suitable aftertreatment, and further reacted in a solvent in the presence of a boron trifluoride diethyl ether complex or silica gel to form a compound (I-6) having a 4,5-dihydro-5-oxo-1,2,4-thiadiazol-3-yl group.

[Chem. 46]

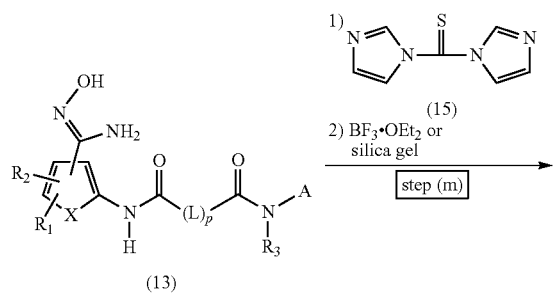

The amount of silica gel used is typically about 1 to about 50 times the weight, and preferably about 5 to about 20 times the weight of the compound (13). The reaction temperature typically ranges from about −30° C. to about 100° C., and preferably from about −10° C. to about 50° C.

(2-8) Production Method 8

When L in the compound (I-2) produced by the production method 1, 2, or 3 is alkylenethioalkylene, namely, a compound represented by Formula (I-7), the compound (I-7) can be converted to a sulfoxide compound (I-8) [step (n)] or a sulfone compound (I-9) [step (p)] by the action of an oxidizing agent. Alternatively, the sulfone compound (I-9) can be obtained from the compound (I-7) via the compound (I-8) stepwise [step (o)].

[Chem. 47]

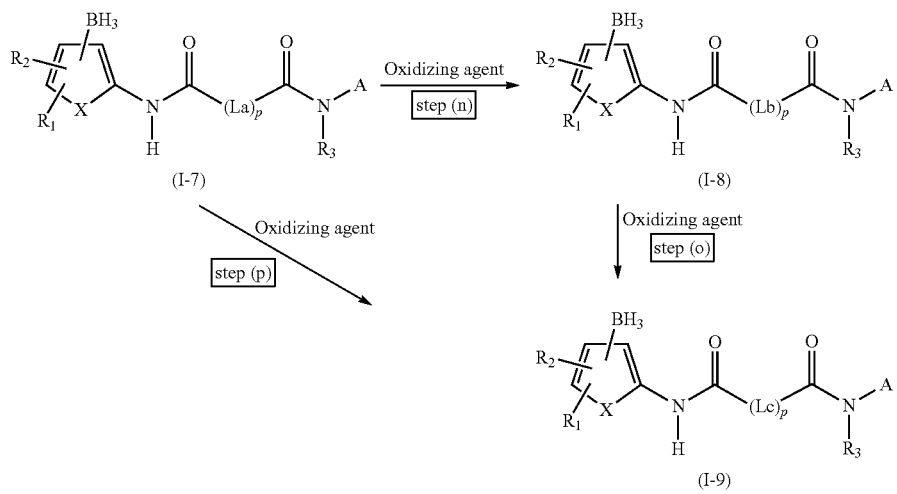

-continued

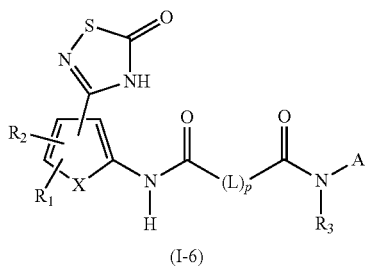

wherein $R_1$ to $R_3$, X, L, p, and A are defined as above.

The reaction temperature typically ranges from about −30° C. to about 100° C., and preferably from about −10° C. to about 50° C. The amount of TCDI used is typically about 1 to about 3 equivalent weight, and preferably about 1 to about 1.5 equivalent weight, per mol of the compound (13). The amount of boron trifluoride diethyl ether complex used is typically about 1 to about 10 equivalent weight, and preferably about 3 to about 6 equivalent weight, per mol of the compound (13).

wherein B, $R_1$ to $R_2$, X, and A are defined as above; La represents alkylenethioalkylene; Lb represents alkylene-SO-alkylene; Lc represents alkylene-$SO_2$-alkylene; and p is 1.

Examples of the oxidizing agent used to produce the sulfoxide compound (I-8) include hydrogen peroxide, peracetic acid, meta-chloro perbenzoic acid, etc. Any solvents inactive in the reaction are usable, and examples thereof include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), ketones (e.g., acetone, methyl ethyl ketone, and methyl isobutyl ketone), dioxane, THF, DMF, DMA, acetate, ethanol, water, or mixtures thereof, etc. The reaction temperature typically ranges from about −30° C. to about 80° C., and preferably from about −20° C. to about 40° C. The amount of oxidizing agent used is typically about 0.5 to about 2 equivalent weight, and preferably about 0.8 to about 1.2 equivalent weight, per mol of the compound (I-7).

Furthermore, an optically active sulfoxide compound (I-8) can also be produced by the use of a resolving agent, or by asymmetric synthesis by the combination of an oxidizing agent, a transitional metal such as titanium, and an asymmetric ligand. Examples of the transition metal include ortho-tetraisopropyl titanate, etc.; examples of the asymmetric ligand include diethyl ester tartrate, etc.; and examples of the resolving agent include 10-camphorsulfonic acid, 1-phenylethylamine, etc. Any reaction solvents inactive in the reaction are usable, and examples thereof include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), ketones (e.g., acetone, methyl ethyl ketone, and methyl isobutyl ketone), dioxane, THF, DMF, DMA, acetate, ethanol, water, or mixtures thereof, etc. The reaction temperature typically ranges from about −40° C. to about 80° C., and preferably from about −20° C. to about 40° C. The amount of oxidizing agent used is typically about 0.5 to about 2 equivalent weight, and preferably about 0.8 to about 1.2 equivalent weight, per mol of the compound (I-7). The amount of transitional metal and asymmetric ligand used is about 0.1 to about 3 equivalent weight, and preferably about 0.5 to about 2 equivalent weight, per mol of the compound (I-7). The amount of resolving agent used is about 0.5 to about 2 equivalent weight, and preferably about 0.8 to about 1.2 equivalent weight, per mol of the compound (I-8).

Examples of the oxidizing agent used to produce the sulfone compound (I-9) include hydrogen peroxide, peracetic acid, meta-chloro perbenzoic acid, etc.; any solvents inactive in the reaction are usable, and examples thereof include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), ketones (e.g., acetone, methyl ethyl ketone, and methyl isobutyl ketone), dioxane, THF, DMF, DMA, acetate, ethanol, water, or mixtures thereof, etc. The reaction temperature typically ranges from about 0° C. to about 100° C., and preferably from about 20° C. to about 50° C. The amount of oxidizing agent used is typically about 2 to about 20 equivalent weight, and preferably about 3 to about 10 equivalent weight, per mol of the compound (I-7), and about 1 to about 10 equivalent weight, and preferably about 2 to about 5 equivalent weight, per mol of the compound (I-8).

(2-9) Production Method 9

The compound (5) or (5') produced by the production methods 2, 3, 5 (ii), or 5 (iii) is reacted with, for example, halogenated aniline that may have a substituent, under the same reaction conditions as in the step (f), step (f'), step (d), or step (d') [step (q)] to easily produce a compound (16) or (16'). The halogen or trifluoromethanesulfonyloxy (W) of the compound (16) or (16') can easily be substituted by other functional groups [step (r)] to produce a compound (I-1) or (10) having a structure represented by A.

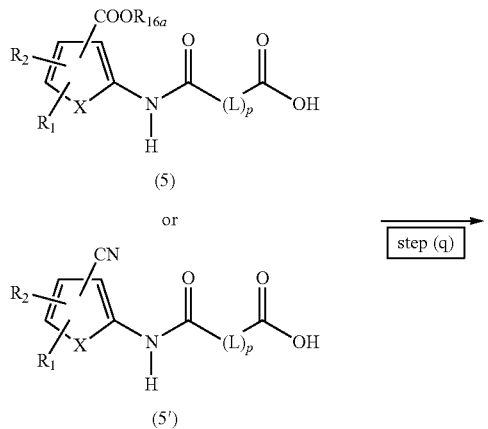

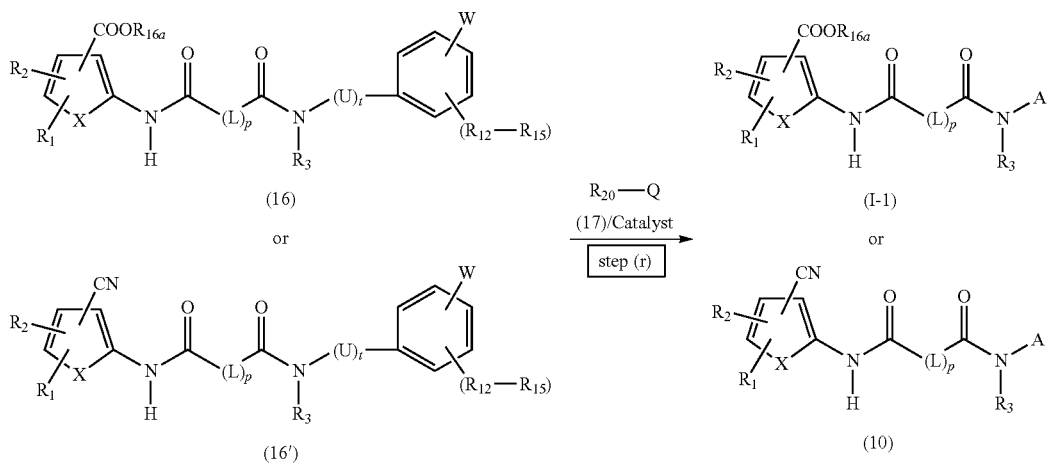

wherein $R_1$ to $R_3$, $R_{12}$ to $R_{15}$, X, L, p, U, t, and A are defined as above; W is halogen or trifluoromethanesulfonyloxy; $R_{20}$ is cycloalkyl, cycloalkoxy, aryl, aryloxy, aralkyl, aralkyloxy, heterocyclic group, heterocyclic-alkyl, or heterocyclic-alkyloxy; Q is a group represented by —B(OR$_{21}$)OR$_{21}$ (wherein $R_{21}$ is hydrogen or alkyl; when $R_{21}$ is alkyl, $R_{21}$ may join together to form a ring) or a group represented by —ZnW (wherein Zn is zinc, and W is halogen); or $R_{20}$-Q together represent $R_{20}$—OH or cyclic amine having a structure shown by the following formula:

[Chem. 49]

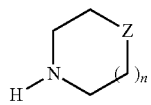

wherein Z and n are defined as above.

In the present process, the compound (16) or (16') and the compound (17) represented by $R_{20}$-Q are reacted in the presence of a catalyst, as necessary. The reaction conditions vary depending on the kind of halogen atom, $R_{12}$ to $R_{15}$, and Q; however, when Q is —B(OR$_{21}$)OR$_{21}$, that is, when the compound (16) that is boric acid or (cyclic) boric acid ester residue is used, preferable examples of the catalyst include palladium catalysts (e.g., tetrakis(triphenylphosphine)palladium (0), bis(dibenzylideneacetone)palladium (0), and palladium acetate); and preferable examples of the halogen atom represented by W include a chlorine atom, bromine atom, and iodine atom, with a bromine and iodine atom being particularly preferable.

The reaction is typically carried out in a solvent (e.g., DMF, 1,4-dioxane, toluene, and THF) in the presence of, if necessary, a base (e.g., sodium carbonate, potassium carbonate, potassium phosphate, and cesium carbonate). The reaction temperature is about 20° C. to about 120° C., and preferably about 30° C. to about 100° C. The amount of the compound (17) used is about 1 to about 5 equivalent weight, and preferably about 1.5 to about 2 equivalent weight, per mol of the compound (16) or (16'). The amount of catalyst used is about 0.05 to about 0.5 equivalent weight, and preferably about 0.1 to about 0.2 equivalent weight, per mol of the compound (16) or (16').

Further, when a so-called zinc reagent represented by Q=—ZnW (wherein Zn is zinc, and W is halogen) is used as the compound (17), palladium catalysts (e.g., tetrakis(triphenylphosphine))palladium (0), bis(dibenzylideneacetone) palladium (0), and palladium acetate) are preferably used, in a manner similar to the above. The amount of the zinc reagent (17) used is about 1 to about 3 equivalent weight, and preferably about 1.5 to about 2 equivalent weight, per mol of the compound (16) or (16').

For the compound (17) wherein $R_{20}$-Q together represent $R_{20}$—OH or cyclic amine having a structure shown by the following formula (oxygen or like hetero atoms may be contained in the circle), palladium catalysts (e.g., tetrakis(triphenylphosphine))palladium (0), bis(dibenzylideneacetone) palladium (0), and palladium acetate) are preferably used, in a manner similar to the above. The reaction is typically carried out in a solvent (e.g., DMF, 1,4-dioxane, toluene, and THF) in the presence of, if necessary, a base (e.g., sodium carbonate, potassium carbonate, potassium phosphate, and cesium carbonate). The reaction temperature is about 20° C. to about 120° C., and preferably about 30° C. to about 100° C. The amount of the alcohol or cyclic amine (17) used is about 1 to about 3 equivalent weight, and preferably about 1.5 to about 2 equivalent weight, per mol of the compound (16) or (16').

[Chem. 50]

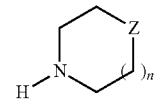

wherein Z and n are defined as above.

The step (r) can be used not only in the reaction with (16) or (16'), but also in the preparation of the compound (6) by reacting the compound (17) with, for example, a halogenated aniline derivative that may have a substituent.

The thus-obtained compound (6) can be used in the production method 2, 3, 5 (ii), or 5 (iii).

(3) PAI-1 Inhibitor

The present invention provides an application of the compound (I) as a PAI-1 inhibitor. More specifically, the present invention provides a PAI-1 inhibitor comprising the compound (I) as an active ingredient. In other words, the PAI-1 inhibitor of the invention comprises the compound (I) as an active ingredient.

The PAI-1 inhibitory action of the compound (I) can be evaluated using an in vitro assay system. For example, mentioned as such an in vitro assay system is a method for examining change in PAI-1 activity to a tissue plasminogen activator (t-PA) in the presence of the compound (I). The change in PAI-1 activity can be examined by setting, as an index, a reaction product produced by the action of t-PA on a substrate. For example, the test example described later shows an in vitro assay system for examining change in the PAI-1 activity by setting, as an index, a quantity of p-nitroaniline (reaction product) produced by the action of t-PA on a coloring substrate (S-2288). It can be judged that when the amount of reaction product is larger, the PAI-1 inhibitory action is higher.

The evaluation of PAI-1 inhibitory action of the compound (I) can also be carried out by examining the change in formation of a complex of PAI-1 and t-PA (PAI-1/t-PA complex) in the presence of the compound (I) using, for example, western blotting. In the invention, it can be judged that when the amount of formation of PAI-1/t-PA complex is smaller (PAI-1/t-PA complex formation inhibition), the PAI-1 inhibitory action is higher.

The compound (I) has an inhibitory action on PAI-1 activity. Among examples of the compounds (I), compounds (1)-(80), particularly compounds (1), (2), (5)-(9), (11), (15), (20), (22)-(26), (28)-(33), (38)-(42), (44), (45), (47)-(51), (53), (55), (58)-(61), (63), (64), (66)-(68), and (72)-(77) have an excellent inhibitory action on PAI-1 activity, as shown in the test example described later. The compounds (1), (2), (5), (22), (23), (25), (26), (29), (33), (39), (41), (42), (44), (45), (50), (51), (53), (58), (67), (68), and (75) are preferred; and the compounds (1), (2), (25), (26), (58), and (68) are more preferred.

The action can increase plasmin-dependent degradation of fibrin and fibrinogen, thereby promoting in vivo fibrinolysis and also improving depression of in vivo fibrinolysis.

It has been proved that one of the causes of tissue fibrosis is PAI-1. It is also known that the development of pulmonary fibrosis can be inhibited by PAI-1 inhibitors (see Non-Patent Document 6). Therefore, the use of the compound (I) makes it possible to prevent or improve tissue fibrosis and diseases associated with tissue fibrosis (e.g., pulmonary fibrosis) based on inhibitory action on PAI-1 activity.

Additionally, it is also reported that PAI-1 inhibitors have a stimulatory effect on the degradation of Aβ, which is regarded as a cause of the development of Alzheimer's disease, as a result of being accumulated in the brain (see Non-Patent Document 7). Therefore, the compound (I) is expected to be able to promote Aβ degradation based on the PAI-1 inhibitory activity to prevent the onset of Alzheimer's disease or to improve the disease.

The PAI-1 inhibitor of the invention comprises the compound (I) as an active ingredient. In the PAI-1 inhibitor of the invention, the proportion of the compound (I) may be 100%; conversely, the PAI-1 inhibitor of the invention may comprise an effective amount of the compound (I) for demonstrating PAI-1 inhibitory action. The proportion of the compound (I) is not limited, and is usually 0.1 to 99% by weight, and preferably 1 to 80% by weight.

(4) Pharmaceutical Composition

The present invention provides a pharmaceutical composition comprising the PAI-1 inhibitor described above as an active ingredient. In other words, the pharmaceutical composition of the invention comprises the compound (I) described above as an active ingredient. The pharmaceutical composition of the invention is imparted with PAI-1 inhibitory action by including an effective amount of the compound (I). As a result, the pharmaceutical composition of the invention increases the plasmin-dependent degradation of fibrin and fibrinogen, to thereby demonstrate the actions of promoting in vivo fibrinolysis or improving depression of in vivo fibrinolysis.

Therefore, the pharmaceutical composition of the invention can be used as a fibrinolysis promoter. To be specific, the pharmaceutical composition of the invention is useful as a prophylactic and therapeutic agent for thrombotic diseases and pathologies whose development is influenced by PAI-1 activity, or diseases and pathologies whose development is influenced by depression of the fibrinolytic system. Mentioned as such diseases or pathologies are various diseases or pathologies caused by thrombus formation, such as thrombosis in arteries, thrombosis in veins, deep vein thrombosis (DVT) during surgical operations, disseminated intravascular coagulation syndrome (DIC), diabetic complications, such as angiopathy, neuropathy, retinopathy, and nephropathy, or restenosis after percutaneous transluminal coronary angioplasty (PTCA). Examples of thrombosis in arteries include thrombosis in the brain (cerebral thrombosis, cerebral embolism, and transient ischemic attack), thrombosis in the heart (angina pectoris and myocardial infarction), thrombosis in the lower extremities (lower extremity acute arterial thrombosis), and thrombosis in the upper intestinal tract (upper intestinal tract arterial thrombosis). Examples of thrombosis in veins include thrombosis in the extremities (deep-vein thrombosis) and thrombosis occurring when a blood clot travels to the lung (pulmonary embolism).

The pharmaceutical composition of the invention has an effective amount of the compound (I), and is thus imparted with a PAI-1 inhibitory action. Therefore, the pharmaceutical composition of the invention prevents or alleviates tissue or organ fibrosis. Accordingly, the pharmaceutical composition of the invention is useful as an agent for preventing or treating diseases and/or pathologies related to tissue or organ fibrosis whose development is influenced by PAI-1 activity. Examples of such diseases or pathologies include tissue fibrosis associated with pulmonary fibrosis and myocardial infarction, and organ fibrosis associated with nephropathy, etc.

Moreover, since the pharmaceutical composition of the invention has an effective amount of the compound (I), and thus is imparted with a PAI-1 inhibitory action, the pharmaceutical composition of the invention is useful as an anti-Alzheimer's drug, as described above. Therefore, the pharmaceutical composition of the invention is useful as an agent for preventing or treating Alzheimer's disease.

The pharmaceutical composition of the invention generally comprises a pharmaceutically acceptable carrier or additive in addition to the compound (I) in an amount effective for promoting (or alleviating) fibrinolysis or anti-fibrosis. The proportion of the compound (I) in the pharmaceutical composition of the invention is suitably determined according to the kind of target diseases and/or pathologies or manner of administrating the pharmaceutical composition, and is usually in the range of from 0.001 to 50% by weight, and particularly from 0.01 to 10% by weight, based on the total weight of the pharmaceutical composition (100% by weight).

The pharmaceutical composition of the invention can be administered orally or parenterally, such as intravenously, intramuscularly, subcutaneously, transmucosally, transdermally, intrarectally, etc. Among these, preferable are oral administration and intravenous administration, and more preferable is oral administration. The pharmaceutical composition of the invention can be provided in various forms of preparations (dosage forms) depending on the above-mentioned administration manners. Various preparations (dosage forms) are described below; however, the dosage forms employed in the invention are not limited thereto. Any dosage forms that are usually used in the field of pharmaceutical preparation can be employed.

In the case of oral administration, the dosage form of the pharmaceutical composition of the invention is suitably selected from powders, granules, capsules, pills, tablets, elixirs, suspensions, emulsions, and syrups. Such preparations can be imparted with sustained-release properties, stabilization, easy-degradation, difficult-degradation, enteric properties, easy adsorption properties, etc.

In the case of intravenous administration, intramuscular administration, or subcutaneous administration, the dosage form can be suitably selected from injections or drops (including dried products that are prepared upon use), and the like.

In the case of transmucosal administration, transdermal administration, or intrarectal administration, the dosage form can be suitably selected from masticatories, sublingual agents, buccal tablets, trochisci, ointments, patch agents, liquid agents, etc., according to the applied portion. Such preparations can be imparted with sustained-release properties, stabilization, easy-degradation, difficult-degradation, easy adsorption properties, etc.

The pharmaceutical composition of the invention can contain a pharmaceutically acceptable carrier and additive according to the dosage form (oral administration or various parenteral administrations). Examples of pharmaceutically acceptable carriers and additives include solvents, excipients, coating agents, bases, binders, lubricants, disintegrators, solubilizers, suspending agents, thickening agents, emulsifiers, stabilizers, buffers, isotonizing agents, soothing agents, preservatives, corrigents, flavors, and coloring agents. Specific examples of pharmaceutically acceptable carriers and additives are mentioned below; however, the invention is not limited thereto.

Examples of solvents include purified water, sterile purified water, water for injection, physiologic saline, peanut oil, ethanol, glycerol, etc. Examples of excipients include starches (e.g., potato starch, wheat starch, and corn starch), lactose, dextrose, saccharose, crystalline cellulose, calcium sulfate, calcium carbonate, sodium hydrogencarbonate, sodium chloride, talc, titanium oxide, trehalose, xylitol, etc.

Examples of binders include starch and starch derivatives, cellulose and cellulose derivatives (e.g., methylcellulose, ethylcellulose, hydroxypropylcellulose, and carboxymethylcellulose), natural high molecular weight compounds, such as gelatin, sodium arginine, tragacanth, gum arabic, etc., synthetic high molecular weight compounds, such as polyvinyl pyrrolidone, polyvinyl alcohol, etc., dextrin, hydroxypropyl starch, and the like.

Examples of lubricants include light anhydrous silicic acid, stearin acid and salts thereof (e.g., magnesium stearate), talc, waxes, wheat starch, macrogol, hydrogenated vegetable oil, sucrose fatty acid ester, polyethylene glycol, silicone oil, etc.

Examples of disintegrators include starch and starch derivatives, agar, gelatin powder, sodium hydrogencarbonate, calcium carbonate, cellulose and cellulose derivatives, hydroxypropyl starch, carboxymethylcellulose, salts thereof, and bridging materials thereof, low-substituted hydroxypropylcellulose, etc.

Examples of solubilizers include cyclodextrin, ethanol, propylene glycol, polyethylene glycol, etc. Examples of suspending agents include sodium carboxymethylcellulose, polyvinylpyrrolidone, gum arabic, tragacanth, sodium arginine, aluminum monostearate, citric acid, various surfactants, etc.

Examples of thickening agents include sodium carboxymethylcellulose, polyvinylpyrrolidone, methylcellulose, hydroxypropyl methylcellulose, polyvinyl alcohol, tragacanth, gum arabic, sodium arginine, etc.

Examples of emulsifiers include gum arabic, cholesterol, tragacanth, methylcellulose, lecithin, various surfactants (e.g., polyoxyl 40 stearate, sorbitan sesquioleate, polysorbate 80, and sodium lauryl sulfate), etc.

Examples of stabilizers include tocopherol, chelating agents (e.g., EDTA and thioglycolic acid), inert gases (e.g., nitrogen and carbon dioxide), reducing substances (e.g., sodium hydrogen sulfite, sodium thiosulfate, ascorbic acid, and rongalite), etc.

Examples of buffers include sodium hydrogenphosphate, sodium acetate, sodium citrate, boric acid, etc.

Examples of isotonizing agents include sodium chloride, glucose, etc. Examples of soothing agents include local anesthetics (e.g., procaine hydrochloride and lidocaine), benzyl alcohol, glucose, sorbitol, amino acid, etc.

Examples of corrigents include saccharose, saccharin, Glycyrrhiza extract, sorbitol, xylitol, glycerol, etc. Examples of flavoring agents include orange peel tincture, rose oil, etc. Examples of coloring agents include water-soluble food colors, lake pigment, etc.

Examples of preservatives include benzoic acid and salts thereof, p-hydroxybenzoate esters, chlorobutanol, invert soap, benzyl alcohol, phenol, thimerosal, dehydroacetic acid, boric acid, etc.

Examples of coating agents include saccharose, hydroxypropylcellulose (HPC), shellac, gelatin, glycerol, sorbitol, hydroxypropyl methylcellulose (HPMC), ethylcellulose, polyvinyl pyrrolidone (PVP), hydroxypropylmethylcellulose phthalate (HPMCP), cellulose acetate phthalate (CAP), methyl methacrylate-methacrylic acid copolymer and polymers described above, etc.

Examples of bases include Vaseline, liquid paraffin, carnauba wax, beef tallow, hardened oil, paraffin, yellow beeswax, vegetable oil, macrogol, macrogol fatty acid ester, stearic acid, sodium carboxymethylcellulose, bentonite, cacao butter, Witepsol, gelatin, stearyl-alcohol, hydrous lanolin, cetanol, light liquid paraffin, hydrophilic petrolatum, simple ointment, white ointment, hydrophilic ointment, macrogol ointment, hard fat, oil-in-water emulsion bases, water-in-oil emulsion bases, etc.

Known drug delivery systems (DDS) can be applied for the dosage forms given above. The term DDS preparation as used in the present specification refers to slow-release preparations, locally applied preparations (troches, buccal tablets, sublingual tablets, etc.), drug control-release preparations, enteric coated preparations and gastric soluble preparations, etc., that are all prepared in the best form considering the administration route, bioavailability, side effects, etc.

When the pharmaceutical composition of the invention is used as a prophylactic or therapeutic agent for pathologies associated with depression of the fibrinolytic system (thrombosis), the oral dose is preferably in the range of from 0.03 to 300 mg/kg of body weight, and is more preferably in the range of from 0.1 to 50 mg/kg of body weight as calculated in terms of the amount of the compound (I). In the case of intravenous administration, the administration amount can be determined in such a manner that the effective blood concentration of the compound (I) is preferably 0.2 to 50 µg/mL, and more preferably 0.5 to 20 µg/mL.

When the pharmaceutical composition of the invention is used as an agent for preventing or treating pathologies associated with tissue fibrosis, the oral dose is preferably in the range of from 0.03 to 300 mg/kg of body weight, and is more preferably in the range of from 0.1 to 50 mg/kg weight as calculated in terms of the amount of the compound (I). In the case of intravenous administration, the administration amount can be determined in such a manner that the effective blood concentration of the compound (I) is preferably 0.2 to 50 µg/mL, and more preferably 0.5 to 20 µg/mL. These dosage amounts may vary according to the age, gender, body type, etc. of a patient.

Additionally, when the pharmaceutical composition of the invention is used as an anti-Alzheimer's drug, the dosage amount thereof may be determined as described above.

EXAMPLES

Hereinbelow, the present invention is described in more detail with reference to Examples and Experimental Examples. However, the present invention is not limited to such examples. All of the compounds used in Examples 1 to 80 as starting materials are known compounds. In the Examples, nuclear magnetic resonance spectra ($^1$H-NMR) were measured using a Varian Gemini 200. Chemical shift is shown as a δ value (ppm) using tetramethylsilane (TMS) or 3-(trimethylsilyl)propion-2,2,3,3-$d_4$ acid sodium salt as an internal standard. Each column chromatography elution was completed under observation using TLC (Thin Layer Chromatography). For TLC observation, silica gel 60F$_{254}$ produced by Merck Co. was used as the TLC plate. Silica gel 60 (70 to 230 meshes) produced by Merck Co., Inc. was used as the silica gel for each column.

Example 1

Production of 5-chloro-2-([(2-oxo-2-([4-(pyridin-4-yl)phenyl]amino)ethoxy)acetyl]amino)benzoic acid (1)

The target compound (1) was synthesized according to the following Steps (i) to (iii).

(i) (2-([4-Chloro-2-(methoxycarbonyl)phenyl]amino)-2-oxoethoxy)acetic acid 10 g (53.9 mmol) of 2-amino-5-chlorobenzoic acid methyl, and 6.88 g (59.3 mmol) of diglycolic anhydride were heated under reflux in 135 mL of THF for 3 hours. After cooling, the reaction mixture was condensed. The residue was collected by filtration, washed with IPE, and dried to give 15.7 g of (2-([4-chloro-2-(methoxycarbonyl)phenyl]amino)-2-oxoethoxy)acetic acid (yield: 97%).

$^1$H-NMR (DMSO-$d_6$) δ: 3.90 (3H, s), 4.22 (2H, s), 4.28 (2H, s), 7.71 (1H, dd, J=9.0, 2.7 Hz), 7.93 (1H, d, J=2.7 Hz), 8.62 (1H, d, J=8.8 Hz), 11.4 (1H, s) 12.9 (1H, br).

(ii) 5-Chloro-2-([(2-oxo-2-([4-(pyridin-4-yl)phenyl]amino)ethoxy)acetyl]amino)benzoic acid.methyl ester 0.75 g (2.5 mmol) of (2-([4-chloro-2-(methoxycarbonyl)phenyl]amino)-2-oxoethoxy)acetic acid, 0.43 g (2.5 mmol) of 4-(pyridin-4-yl)aniline, 0.58 g (3.0 mmol) of 1-ethyl-3-(3-dimethylaminopropyl)carbodiimide hydrochloride, 0.41 g (3.0 mmol) of 1-hydroxybenzotriazole were stirred in 5.3 mL of DMA for 2 hours. After completion of the reaction, the reaction solution was introduced into an aqueous sodium bicarbonate solution. The solid was separated by filtration, and washed with water to give 0.96 g of 5-chloro-2-([(2-oxo-2-([4-(pyridin-4-yl)phenyl]amino)ethoxy)acetyl]amino)benzoic acid.methyl ester (yield: 85%).

$^1$H-NMR (CDCl$_3$) δ: 3.89 (3H, s), 4.28 (2H, s), 4.30 (2H, s), 7.48-7.69 (5H, m), 7.86-7.92 (2H, m), 8.06 (1H, d, J=2.5 Hz), 8.60-8.73 (2H, m), 8.79 (1H, d, J=9.0 Hz), 8.93 (1H, s), 11.9 (1H, s).

(iii) 5-Chloro-2-([(2-oxo-2-([4-(pyridin-4-yl)phenyl]amino)ethoxy)acetyl]amino)benzoic acid 0.95 g (2.1 mmol) of 5-chloro-2-([(2-oxo-2-([4-(pyridin-4-yl)phenyl]amino)ethoxy)acetyl]amino)benzoic acid.methyl ester was dissolved in 9.5 mL of THF. Subsequently, 1N sodium hydroxide was added thereto and stirred at 50° C. for 1 hour. After cooling, THF was distilled off under reduced pressure, and 1N hydrochloric acid was added to neutralize the residue. Water was added to wash the residue. The resulting residue was then washed with IPE, thereby giving the target 5-chloro-2-([(2-oxo-2-([4-(pyridin-4-yl)phenyl]amino)ethoxy)acetyl]amino)benzoic acid (yield: 28%).

$^1$H-NMR (DMSO-$d_6$) δ: 4.27 (2H, s), 4.32 (2H, s), 7.60-8.00 (8H, m), 8.60-8.67 (3H, m), 10.0 (1H, s), 12.5 (1H, s).

Example 2

Production of 5-chloro-2-([(2-oxo-2-([3-(pyridin-4-yl)phenyl]amino)ethoxy)acetyl]amino)benzoic acid (2)

The target compound (2) was synthesized according to the following Steps (i) to (ii).

(i) 5-Chloro-2-([(2-oxo-2-([3-(pyridin-4-yl)phenyl]amino)ethoxy)acetyl]amino)benzoic acid.methyl ester Using the same method as in Example 1-(ii), 4-(3-aminophenyl)pyridine was reacted with the (2-([4-chloro-2-(methoxycarbonyl)phenyl]amino)-2-oxoethoxy)acetic acid obtained in Example 1-(i) to give 5-chloro-2-([(2-oxo-2-([3-(pyridin-4-yl)phenyl]amino)ethoxy)acetyl]amino)benzoic acid.methyl ester (yield: 82%).

$^1$H-NMR (CDCl$_3$) δ: 3.71 (3H, s), 4.28 (2H, s), 4.31 (2H, s), 7.41-7.79 (6H, m), 8.03 (1H, d, J=2.5 Hz), 8.11 (1H, s), 8.65-8.69 (2H, m), 8.78 (1H, d, J=9.2 Hz), 8.94 (1H, s), 11.9 (1H, s).

(ii) 5-Chloro-2-([(2-oxo-2-([3-(pyridin-4-yl)phenyl]amino)ethoxy)acetyl]amino)benzoic acid Using the same method as in Example 1-(iii), the target 5-chloro-2-([(2-oxo-2-([3-(pyridin-4-yl)phenyl]amino)ethoxy)acetyl]amino)benzoic acid was obtained from 5-chloro-2-([(2-oxo-2-([3-(pyridin-4-yl)phenyl]amino)ethoxy)acetyl]amino)benzoic acid.methyl ester (yield: 94%).

$^1$H-NMR (DMSO-$d_6$) δ: 4.31 (2H, s), 4.34 (2H, s), 7.45-7.85 (6H, m), 7.98 (1H, d, J=2.6 Hz), 8.18 (1H, d, J=1.7 Hz), 8.66-8.70 (3H, m), 9.99 (1H, s), 12.2 (1H, s).

Example 3

Production of 5-chloro-2-[((2-[(4'-fluorobiphenyl-2-yl)amino]-2-oxoethoxy)acetyl)amino]benzoic acid (3)

The target compound (3) was synthesized according to the following Steps (i) to (ii).

(i) 5-Chloro-2-[((2-[(4'-fluorobiphenyl-2-yl)amino]-2-oxoethoxy)acetyl)amino]benzoic acid.methyl ester Using the same method as in Example 1-(ii), 4'-fluoro-(1,1'-biphenyl)-2-amine was reacted with the (2-([4-chloro-2-(methoxycarbonyl)phenyl]amino)-2-oxoethoxy)acetic acid obtained in Example 1-(i) to give 5-chloro-2-[((2-[(4'-fluorobiphenyl-2-yl)amino]-2-oxoethoxy)acetyl)amino]benzoic acid.methyl ester (yield: 60%).

$^1$H-NMR (CDCl$_3$) δ: 3.69 (3H, s), 4.09 (2H, s), 4.20 (2H, s), 6.92-7.02 (2H, m), 7.20-7.45 (5H, m), 7.54 (1H, dd, J=9.2, 2.5 Hz), 8.01 (1H, d, J=2.5 Hz), 8.18 (1H, d, J=8.0 Hz), 8.61 (1H, s), 8.70 (1H, d, J=9.2 Hz), 11.6 (1H, s).

(ii) 5-Chloro-2-[((2-[(4'-fluorobiphenyl-2-yl)amino]-2-oxoethoxy)acetyl)amino]benzoic acid Using the same method as in Example 1-(iii), the target 5-chloro-2-[((2-[(4'-fluorobiphenyl-2-yl)amino]-2-oxoethoxy)acetyl)amino]benzoic acid was obtained from 5-chloro-2-[((2-[(4'-fluorobiphenyl-2-yl)amino]-2-oxoethoxy)acetyl)amino]benzoic acid.methyl ester (yield: 88%).

$^1$H-NMR (DMSO-$d_6$) δ: 4.18 (2H, s), 4.20 (2H, s), 7.04-7.49 (7H, m), 7.70 (1H, dd, J=9.0, 2.7 Hz), 7.89-7.95 (2H, m), 8.65 (1H, d, J=9.0 Hz), 9.05 (1H, s), 11.7 (1H, s), 13.9 (1H, br).

Example 4

Production of 5-chloro-2-([(2-oxo-2-([2-(pyridin-4-yl)phenyl]amino)ethoxy)acetyl]amino)benzoic acid.hydrochloride (4)

The target compound (4) was synthesized according to the following Steps (i) to (ii).

(i) 5-Chloro-2-([[(2-oxo-2-([2-(pyridin-4-yl)phenyl]amino)ethoxy)acetyl]amino)benzoic acid.methyl ester Using the same method as in Example 1-(ii), 2-pyridin-4-yl-phenylamine was reacted with the (2-([4-chloro-2-(methoxycarbonyl)phenyl]amino)-2-oxoethoxy)acetic acid obtained in Example 1-(i) to give 5-chloro-2-([(2-oxo-2-([2-(pyridin-4-yl)phenyl]amino)ethoxy)acetyl]amino)benzoic acid.methyl ester (yield: 22%).

$^1$H-NMR (CDCl$_3$) δ: 3.66 (3H, s), 4.14 (2H, s), 4.19 (2H, s), 7.28-7.50 (6H, m), 7.54 (1H, dd, J=9.0, 2.2 Hz), 8.00 (1H, d, J=2.2 Hz), 8.56-8.74 (4H, m), 11.7 (1H, s). s

(ii) 5-Chloro-2-([[(2-oxo-2-([2-(pyridin-4-yl)phenyl]amino)ethoxy)acetyl]amino)benzoic acid.hydrochloride Using the same method as in Example 1-(iii), the target 5-chloro-2-([[(2-oxo-2-([2-(pyridin-4-yl)phenyl]amino)ethoxy)acetyl]amino)benzoic acid hydrochloride was obtained from 5-chloro-2-([[(2-oxo-2-([2-(pyridin-4-yl)phenyl]amino)ethoxy)acetyl]amino)benzoic acid.methyl ester (yield: 67%). Note that, after completion of the reaction, THF was distilled off under reduced pressure, 1N hydrochloric acid was added to acidify the residue, and water was added to wash the residue.

$^1$H-NMR (DMSO-d$_6$) δ: 4.18 (4H, s), 7.38-7.80 (7H, m), 7.94 (1H, d, J=2.4 Hz), 8.52 (2H, d, J=5.8 Hz), 8.64 (1H, d, J=9.1 Hz), 9.38 (1H, s), 11.9 (1H, s).

Example 5

Production of 5-chloro-2-[((2-[(4'-fluoro-4-methylbiphenyl-3-yl)amino]-2-oxoethoxy)acetyl)amino]benzoic acid (5)

The target compound (5) was synthesized according to the following Steps (i) to (iii).

(i) 4'-Fluoro-4-methylbiphenyl-3-amine 5.0 g (22.5 mmol) of 4-(4,4,5,5-tetramethyl-1,3,2-dioxaborolan-2-yl)-fluorobenzene, 1.87 mL (15 mmol) of 5-bromo-2-methylaniline, 1.73 g (1.5 mmol) of tetrakis(triphenyl phosphine)palladium (0), and 7.33 g (15 mmol) of cesium carbonate were heated under reflux for 8 hours in 150 mL of THF. After completion of the reaction, THF was distilled off under reduced pressure, and ethyl acetate was added to separate the solid by filtration. The organic layer was then washed with a saturated sodium chloride solution, and dried over anhydrous sodium sulfate. Thereafter, the solvent was distilled off under reduced pressure. The resulting crude product was separated and purified using silica gel column chromatography, thereby giving 4'-fluoro-4-methylbiphenyl-3-amine (yield: 43%).

$^1$H-NMR (CDCl$_3$) δ: 2.19 (3H, s), 3.66 (2H, br), 6.83-6.90 (2H, m), 7.03-7.13 (3H, m), 7.43-7.53 (2H, m).

(ii) 5-Chloro-2-[((2-[(4'-fluoro-4-methylbiphenyl-3-yl)amino]-2-oxoethoxy)acetyl)amino]benzoic acid.methyl ester Using the same method as in Example 1-(ii), 4'-fluoro-4-methylbiphenyl-3-amine was reacted with the (2-([4-chloro-2-(methoxycarbonyl)phenyl]amino)-2-oxoethoxy)acetic acid obtained in Example 1-(i) to give 5-chloro-2-[((2-[(4'-fluoro-4-methylbiphenyl-3-yl)amino]-2-oxoethoxy)acetyl)amino]benzoic acid.methyl ester (yield: 96%).

$^1$H-NMR (CDCl$_3$) δ: 2.36 (3H, s), 3.55 (3H, s), 4.29 (2H, s), 4.34 (2H, s), 7.03-7.57 (7H, m), 7.85 (1H, d, J=1.6 Hz), 7.99 (1H, d, J=2.5 Hz), 8.77 (1H, d, J=9.2 Hz), 8.78 (1H, s), 12.0 (1H, s).

(iii) 5-Chloro-2-[((2-[(4'-fluoro-4-methylbiphenyl-3-yl)amino]-2-oxoethoxy)acetyl)amino]benzoic acid Using the same method as in Example 1-(iii), the target 5-chloro-2-[((2-[(4'-fluoro-4-methylbiphenyl-3-yl)amino]-2-oxoethoxy)acetyl)amino]benzoic acid was obtained from 5-chloro-2-[((2-[(4'-fluoro-4-methylbiphenyl-3-yl)amino]-2-oxoethoxy)acetyl)amino]benzoic acid.methyl ester (yield: 87%).

$^1$H-NMR (DMSO-d$_6$) δ: 2.26 (3H, s), 4.34 (2H, s), 4.36 (2H, s), 7.23-7.43 (4H, m), 7.43-7.82 (4H, m), 7.96 (1H, d, J=2.7 Hz), 8.68 (1H, d, J=9.1 Hz), 9.34 (1H, s), 12.0 (1H, s).

Example 6

Production of 5-chloro-2-[((2-oxo-2-[(3',4,5'-trimethylbiphenyl-3-yl)amino]ethoxy)acetyl)amino]benzoic acid (6)

The target compound (6) was synthesized according to the following Steps (i) to (iii).

(i) 3',4,5'-Trimethylbiphenyl-3-amine

Using the same method as in Example 5-(i), 5-bromo-2-methylaniline was reacted with 3,5-dimethylphenyl boronic acid to give 3',4,5'-trimethylbiphenyl-3-amine (yield: 94%).

$^1$H-NMR (CDCl$_3$) δ: 2.18 (3H, s), 2.35 (3H, s), 2.35 (3H, s), 3.63 (2H, br), 6.87-7.16 (6H, m).

(ii) 5-Chloro-2-[((2-oxo-2-[(3',4,5'-trimethylbiphenyl-3-yl)amino]ethoxy)acetyl)amino]benzoic acid.methyl ester Using the same method as in Example 1-(ii), 3',4,5'-trimethylbiphenyl-3-amine was reacted with the (2-([4-chloro-2-(methoxycarbonyl)phenyl]amino)-2-oxoethoxy)acetic acid obtained in Example 1-(i) to give 5-chloro-2-[((2-oxo-2-[(3',4,5'-trimethylbiphenyl-3-yl)amino]ethoxy)acetyl)amino]benzoic acid.methyl ester (yield: 91%).

$^1$H-NMR (CDCl$_3$) δ: 2.35 (3H, s), 2.36 (6H, s), 3.53 (3H, s), 4.29 (2H, s), 4.34 (2H, s), 6.97 (1H, s), 7.16-7.41 (4H, m), 7.52 (1H, dd, J=9.0, 2.6 Hz), 7.85 (1H, d, J=1.6 Hz), 7.98 (1H, d, J=2.6 Hz), 8.77 (1H, d, J=9.0 Hz), 8.77 (1H, s), 12.0 (1H, s).

(iii) 5-Chloro-2-[((2-oxo-2-[(3',4,5'-trimethylbiphenyl-3-yl)amino]ethoxy)acetyl)amino]benzoic acid Using the same method as in Example 1-(iii), the target 5-chloro-2-[((2-oxo-2-[(3',4,5'-trimethylbiphenyl-3-yl)

amino]ethoxy)acetyl)amino]benzoic acid was obtained from 5-chloro-2-[((2-oxo-2-[(3',4,5'-trimethylbiphenyl-3-yl) amino]ethoxy)acetyl)amino]benzoic acid.methyl ester (yield: 85%).

$^1$H-NMR (DMSO-$d_6$) δ: 2.25 (3H, s), 2.33 (6H, s), 4.33 (2H, s), 4.35 (2H, s), 6.98 (1H, s), 7.22-7.42 (4H, m), 7.70 (1H, dd, J=9.0, 2.7 Hz), 7.77 (1H, d, J=1.7 Hz), 7.96 (1H, d, J=2.7 Hz), 8.67 (1H, d, J=9.0 Hz), 9.31 (1H, s), 11.9 (1H, s).

Example 7

Production of 5-chloro-2-[((2-[(4'-fluorobiphenyl-4-yl)amino]-2-oxoethoxy)acetyl)amino]benzoic acid-.sodium salt (7)

The target compound (7) was synthesized according to the following Steps (i) to (ii).

(i) 5-Chloro-2-[((2-[(4'-fluorobiphenyl-4-yl)amino]-2-oxoethoxy)acetyl)amino]benzoic acid.methyl ester Using the same method as in Example 1-(ii), 4'-fluorobiphenyl-4-yl amine was reacted with the (2-([4-chloro-2-(methoxycarbonyl)phenyl]amino)-2-oxoethoxy)acetic acid obtained in Example 1-(i) to give 5-chloro-2-[((2-[(4'-fluorobiphenyl-4-yl)amino]-2-oxoethoxy)acetyl)amino]benzoic acid.methyl ester (yield: 86%).

$^1$H-NMR (CDCl$_3$) δ: 3.88 (3H, s), 4.28 (2H, s), 4.30 (2H, s), 7.06-7.18 (2H, m), 7.48-7.59 (5H, m), 7.77-7.84 (2H, m), 8.06 (1H, d, J=2.5 Hz), 8.79 (1H, d, J=9.0 Hz), 8.86 (1H, s), 11.9 (1H, s).

(ii) 5-Chloro-2-[((2-[(4'-fluorobiphenyl-4-yl)amino]-2-oxoethoxy)acetyl)amino]benzoic acid.sodium salt 1.90 g (4.03 mmol) of 5-chloro-2-[((2-[(4'-fluorobiphenyl-4-yl)amino]-2-oxoethoxy)acetyl)amino]benzoic acid.methyl ester was dissolved in 19 mL of THF. Subsequently, 1N sodium hydroxide was added thereto and the mixture was stirred at 50° C. for 1 hour. After cooling, THF was distilled off under reduced pressure, and water was added to wash the residue. The resulting residue was washed with IPE, thereby giving the target 5-chloro-2-[((2-[(4'-fluorobiphenyl-4-yl) amino]-2-oxoethoxy)acetyl)amino]benzoic acid.sodium salt (yield: 96%).

$^1$H-NMR (DMSO-$d_6$) δ: 4.18 (2H, s), 4.25 (2H, s), 7.23-7.75 (7H, m), 8.00 (1H, d, J=2.6 Hz), 8.28 (2H, d, J=8.8 Hz), 8.51 (1H, d, J=8.8 Hz), 10.4 (1H, s), 15.1 (1H, s).

Example 8

Production of 5-chloro-2-[((2-[(4'-fluorobiphenyl-3-yl)amino]-2-oxoethoxy)acetyl)amino]benzoic acid-.sodium salt (8)

The target compound (8) was synthesized according to the following Steps (i) to (ii).

(i) 5-Chloro-2-[((2-[(4'-fluorobiphenyl-3-yl)amino]-2-oxoethoxy)acetyl)amino]benzoic acid.methyl ester Using the same method as in Example 1-(ii), 4'-fluorobiphenyl-3-amine was reacted with the (2-([4-chloro-2-(methoxycarbonyl)phenyl]amino)-2-oxoethoxy)acetic acid obtained in Example 1-(i) to give 5-chloro-2-[((2-[(4'-fluorobiphenyl-3-yl)amino]-2-oxoethoxy)acetyl)amino]benzoic acid.methyl ester (yield: 82%).

$^1$H-NMR (CDCl$_3$) δ: 3.67 (3H, s), 4.27 (2H, s), 4.30 (2H, s), 7.07-7.72 (8H, m), 7.92-7.94 (1H, m), 8.02 (1H, d, J=2.7 Hz), 8.78 (1H, d, J=9.0 Hz), 8.87 (1H, s), 11.9 (1H, s).

(ii) 5-Chloro-2-[((2-[(4'-fluorobiphenyl-3-yl)amino]-2-oxoethoxy)acetyl)amino]benzoic acid.sodium salt Using the same method as in Example 7-(ii), the target 5-chloro-2-[((2-[(4'-fluorobiphenyl-3-yl)amino]-2-oxoethoxy)acetyl)amino]benzoic acid.sodium salt was obtained from 5-chloro-2-[((2-[(4'-fluorobiphenyl-3-yl)amino]-2-oxoethoxy)acetyl)amino]benzoic acid.methyl ester (yield: 85%).

$^1$H-NMR (DMSO-$d_6$) δ: 4.18 (2H, s), 4.25 (2H, s), 7.23-7.41 (5H, m), 7.91-8.22 (4H, m), 8.50-8.55 (2H, m), 10.4 (1H, s), 15.1 (1H, s).

Example 9

Production of 5-chloro-2-(([2-(dicyclohexylamino)-2-oxoethoxy]acetyl)amino)benzoic acid.sodium salt (9)

The target compound (9) was synthesized according to the following Steps (i) to (ii).

(i) 5-Chloro-2-(([2-(dicyclohexylamino)-2-oxoethoxy]acetyl)amino)benzoic acid.methyl ester 1.0 g (3.3 mmol) of (2-([4-chloro-2-(methoxycarbonyl) phenyl]amino)-2-oxoethoxy)acetic acid, a catalytic quantity of DMF, and 505 mg (3.98 mmol) of oxalyl chloride were stirred at 0° C. for 1.5 hours in 10 mL of THF. After completion of the reaction, the solvent was distilled off under reduced pressure. 0.66 g (3.6 mmol) of dicyclohexylamine, and 10 mL of DMA were added to this residue, and stirred at room temperature for 2 hours. After completion of the reaction, water was added, and the precipitated crystals were collected by filtration and dried to give the crude product of 5-chloro-2-(([2-(dicyclohexylamino)-2-oxoethoxy]acetyl) amino)benzoic acid.methyl ester. The crude product was then used in the subsequent stage without being purified.

$^1$H-NMR (CDCl$_3$) δ: 1.00-1.90 (18H, m), 2.30-2.60 (2H, m), 2.80-3.10 (1H, m), 3.20-3.44 (1H, m), 3.94 (3H, s), 4.25 (2H, s), 4.32 (2H, s), 7.50 (1H, dd, J=9.0, 2.7 Hz), 8.01 (1H, d, J=2.7 Hz), 8.75 (1H, d, J=9.0 Hz), 11.7 (1H, s).

(ii) 5-Chloro-2-(([2-(dicyclohexylamino)-2-oxoethoxy]acetyl)amino)benzoic acid.sodium salt Using the same method as in Example 7-(ii), the target 5-chloro-2-(([2-(dicyclohexylamino)-2-oxoethoxy]acetyl) amino)benzoic acid.sodium salt was obtained from the crude product of 5-chloro-2-(([2-(dicyclohexylamino)-2-oxoethoxy]acetyl)amino)benzoic acid.methyl ester (yield from Step (i): 27%).

$^1$H-NMR (DMSO-$d_6$) δ: 0.90-1.80 (18H, m), 2.20-2.50 (2H, m), 2.84-3.10 (1H, m), 3.20-3.50 (1H, m), 4.07 (2H, s), 4.26 (2H, s), 7.32 (1H, dd, J=8.8, 2.7 Hz), 7.94 (1H, d, J=2.7 Hz), 8.54 (1H, d, J=8.8 Hz), 14.3 (1H, s).

Example 10

Production of 5-chloro-2-[((2-[(4-cyclohexylphenyl) amino]-2-oxoethoxy)acetyl)amino]benzoic acid.sodium salt (10)

The target compound (10) was synthesized according to the following Steps (i) to (ii).

(i) 5-Chloro-2-[((2-[(4-cyclohexylphenyl)amino]-2-oxoethoxy)acetyl)amino]benzoic acid.methyl ester Using the same method as in Example 1-(ii), 4-cyclohexylaniline was reacted with the (2-([4-chloro-2-(methoxycarbonyl)phenyl]amino)-2-oxoethoxy)acetic acid obtained in Example 1-(i) to give 5-chloro-2-[((2-[(4-cyclohexylphenyl)amino]-2-oxoethoxy)acetyl)amino]benzoic acid.methyl ester (yield: 89%).

$^1$H-NMR (CDCl$_3$) δ: 1.20-1.93 (10H, m), 2.55-2.60 (1H, m), 3.84 (3H, s), 4.25 (2H, s), 4.26 (2H, s), 7.12-7.23 (2H, m), 7.54 (1H, dd, J=9.2, 2.6 Hz), 7.57-7.66 (2H, m), 8.05 (1H, d, J=2.6 Hz), 8.74 (1H, s), 8.78 (1H, d, J=9.2 Hz), 11.9 (1H, s).

(ii) 5-Chloro-2-[((2-[(4-cyclohexylphenyl)amino]-2-oxoethoxy)acetyl)amino]benzoic acid.sodium salt Using the same method as in Example 7-(ii), the target 5-chloro-2-[((2-[(4-cyclohexylphenyl)amino]-2-oxoethoxy)acetyl)amino]benzoic acid.sodium salt was obtained from 5-chloro-2-[((2-[(4-cyclohexylphenyl)amino]-2-oxoethoxy)acetyl)amino]benzoic acid.methyl ester (yield: 93%).

$^1$H-NMR (DMSO-d$_6$) δ: 1.10-1.90 (10H, m), 2.35-2.54 (1H, m), 4.15 (2H, s), 4.19 (2H, s), 7.09-7.19 (2H, m), 7.35 (1H, dd, J=8.8, 2.7 Hz), 7.97 (1H, d, J=2.7 Hz), 7.98-8.06 (2H, m), 8.50 (1H, d, J=8.8 Hz), 10.2 (1H, s), 15.0 (1H, s).

Example 11

Production of 5-chloro-2-(([2-(cyclododecylamino)-2-oxoethoxy]acetyl)amino)benzoic acid (11)

The target compound (11) was synthesized according to the following Steps (i) to (ii).

(i) 5-Chloro-2-(([2-(cyclododecylamino)-2-oxoethoxy]acetyl)amino)benzoic acid.methyl ester Using the same method as in Example 1-(ii), cyclododecylamine was reacted with the (2-([4-chloro-2-(methoxycarbonyl)phenyl]amino)-2-oxoethoxy)acetic acid obtained in Example 1-(i) to give 5-chloro-2-(([2-(cyclododecylamino)-2-oxoethoxy]acetyl)amino)benzoic acid.methyl ester (yield: 92%).

$^1$H-NMR (CDCl$_3$) δ: 1.10-1.85 (22H, m), 3.95 (3H, s), 4.13 (2H, s), 4.17 (2H, s), 4.15-4.35 (1H, m), 6.83 (1H, d, J=9.2 Hz), 7.53 (1H, dd, J=9.0, 2.6 Hz), 8.05 (1H, d, J=2.6 Hz), 8.77 (1H, d, J=9.0 Hz), 11.7 (1H, s).

(ii) 5-Chloro-2-(([2-(cyclododecylamino)-2-oxoethoxy]acetyl)amino)benzoic acid Using the same method as in Example 1-(iii), the target 5-chloro-2-(([2-(cyclododecylamino)-2-oxoethoxy]acetyl)amino)benzoic acid was obtained from 5-chloro-2-(([2-(cyclododecylamino)-2-oxoethoxy]acetyl)amino)benzoic acid.methyl ester (yield: 83%).

$^1$H-NMR (DMSO-d$_6$) δ: 1.00-1.75 (22H, m), 3.85-4.10 (1H, m), 4.07 (2H, s), 4.18 (2H, s), 7.50 (1H, d, J=8.8 Hz), 7.69 (1H, dd, J=9.0, 2.6 Hz), 7.98 (1H, d, J=2.6 Hz), 8.68 (1H, d, J=9.0 Hz), 11.9 (1H, s).

Example 12

Production of 5-chloro-2-([((2-[(4'-fluorobiphenyl-3-yl)amino]-2-oxoethyl)sulfanyl)acetyl]amino)benzoic acid.sodium salt (12)

The target compound (12) was synthesized according to the following Steps (i) to (iii).

(i) [(2-([4-Chloro-2-(methoxycarbonyl)phenyl]amino)-2-oxoethyl)sulfanyl]acetic acid The mixture containing 5.0 g (33.3 mmol) of 2,2'-thiodiglycolic acid and 30 mL of acetic anhydride were heated under reflux for 1.5 hours. The reaction solution was condensed, thereby quantitatively giving 2,2'-thiodiglycolic anhydride 3.78 g (28.8 mmol) of the 2,2'-thiodiglycolic anhydride and 5.35 g (28.8 mmol) of 2-amino-5-chlorobenzoic acid methyl were heated under reflux in 50 mL of THF for 4 hours. The reaction mixture was condensed, and IPE was added to the resulting crystals. The mixture was then filtered, thereby giving 8.57 g of [(2-([4-chloro-2-(methoxycarbonyl)phenyl]amino)-2-oxoethyl)sulfanyl]acetic acid (yield: 93%).

$^1$H-NMR (DMSO-d$_6$) δ: 3.38 (2H, s), 3.56 (2H, s), 3.88 (3H, s), 7.68 (1H, dd, J=9.0, 2.7 Hz), 7.87 (1H, d, J=2.7 Hz), 8.33 (1H, d, J=9.0 Hz), 11.1 (1H, s), 12.7 (1H, br).

(ii) 5-Chloro-2-([((2-[(4'-fluorobiphenyl-3-yl)amino]-2-oxoethyl)sulfanyl)acetyl]amino)benzoic acid.methyl ester Using the same method as in Example 1-(ii), 4'-fluorobiphenyl-3-amine was reacted with the [(2-([4-chloro-2-(methoxycarbonyl)phenyl]amino)-2-oxoethyl)sulfanyl]acetic acid to give 5-chloro-2-([((2-[(4'-fluorobiphenyl-3-yl)amino]-2-oxoethyl)sulfanyl)acetyl]amino)benzoic acid.methyl ester (yield: 78%).

$^1$H-NMR (CDCl$_3$) δ: 3.51 (2H, s), 3.53 (2H, s), 3.90 (3H, s), 7.10-7.55 (7H, m), 7.39 (1H, dd, J=9.2, 2.4 Hz), 7.69-7.75 (1H, m), 7.93 (1H, d, J=2.4 Hz), 8.60 (1H, d, J=9.2 Hz), 8.93 (1H, s), 11.5 (1H, s).

(iii) 5-Chloro-2-([((2-[(4'-fluorobiphenyl-3-yl)amino]-2-oxoethyl)sulfanyl)acetyl]amino)benzoic acid.sodium salt Using the same method as in Example 7-(ii), the target 5-chloro-2-([((2-[(4'-fluorobiphenyl-3-yl)amino]-2-oxoethyl)sulfanyl)acetyl]amino)benzoic acid.sodium salt was obtained from 5-chloro-2-([((2-[(4'-fluorobiphenyl-3-yl)amino]-2-oxoethyl)sulfanyl)acetyl]amino)benzoic acid.methyl ester (yield: 95%).

$^1$H-NMR (DMSO-d$_6$) δ: 3.53 (2H, s), 3.54 (2H, s), 7.23-7.45 (5H, m), 7.62-7.76 (3H, m), 7.97 (1H, d, J=2.7 Hz), 8.01-8.07 (1H, m), 8.49 (1H, d, J=8.8 Hz), 10.9 (1H, s), 14.5 (1H, s).

Example 13

Production of 5-chloro-2-([((2-[(4'-fluorobiphenyl-3-yl)amino]-2-oxoethyl)sulfinyl)acetyl]amino)benzoic acid (13)

The target compound (13) was synthesized according to the following step.

6 mL of acetic acid, 18 mg of sulfuric acid, and 686 mg of a 30% hydrogen peroxide solution were added to 300 mg (0.61 mmol) of the 5-chloro-2-([((2-[(4'-fluorobiphenyl-3-yl)amino]-2-oxoethyl)sulfanyl)acetyl]amino)benzoic acid.sodium salt obtained in Example 12-(iii), and the mixture was stirred at room temperature for 2.5 hours. Thereafter, the reaction solution was diluted with water, and filtered. The resulting crystals were dried, thereby obtaining the target 5-chloro-2-([((2-[(4'-fluorobiphenyl-3-yl)amino]-2-oxoethyl)sulfinyl)acetyl]amino)benzoic acid (yield: 88%).

$^1$H-NMR (DMSO-$d_6$) δ: 4.00 (1H, d, J=13.7 Hz), 4.05 (1H, d, J=13.7 Hz), 4.18 (1H, d, J=13.7 Hz), 4.28 (1H, d, J=13.7 Hz), 7.22-7.48 (4H, m), 7.52-7.70 (3H, m), 7.70 (1H, dd, J=9.0, 2.7 Hz), 7.89-7.93 (1H, m), 7.93 (1H, d, J=2.7 Hz), 8.45 (1H, d, J=9.0 Hz), 10.5 (1H, s), 11.2 (1H, s), 14.0 (1H, br).

Example 14

Production of 5-chloro-2-([((2-[(4'-fluorobiphenyl-3-yl)amino]-2-oxoethyl)sulfonyl)acetyl]amino)benzoic acid (14)

The target compound (14) was synthesized according to the following step.

5 mL of DMF was added to 500 mg (0.61 mmol) of the 5-chloro-2-([((2-[(4'-fluorobiphenyl-3-yl)amino]-2-oxoethyl)sulfanyl)acetyl]amino)benzoic acid.sodium salt obtained in Example 12-(iii), and 805 mg (3.3 mmol) of m-chloroperbenzoic acid (65%) were added thereto at room temperature, and stirred for 2 hours. Thereafter, water was added to the reaction solution, and the mixture was stirred at 0° C., followed by filtration. The resulting crystals were washed with IPE, and dried to give the target 5-chloro-2-([((2-[(4'-fluorobiphenyl-3-yl)amino]-2-oxoethyl)sulfonyl)acetyl] amino)benzoic acid (yield: 96%).

$^1$H-NMR (DMSO-$d_6$) δ: 4.52 (2H, s), 4.70 (2H, s), 7.25-7.58 (5H, m), 7.59-7.75 (2H, m), 7.70 (1H, dd, J=9.0, 2.7 Hz), 7.90-7.93 (1H, m), 7.93 (1H, d, J=2.7 Hz), 8.37 (1H, d, J=9.0 Hz), 10.6 (1H, s), 11.3 (1H, s), 14.0 (1H, br).

Example 15

Production of 5-chloro-2-[((2-[cyclohexyl(phenyl)amino]-2-oxoethoxy)acetyl)amino]benzoic acid.sodium salt (15)

The target compound (15) was synthesized according to the following Steps (i) to (ii).

(i) 5-Chloro-2-[((2-[cyclohexyl(phenyl)amino]-2-oxoethoxy)acetyl)amino]benzoic acid.methyl ester 1.21 g (4.0 mmol) of (2-([4-chloro-2-(methoxycarbonyl) phenyl]amino)-2-oxoethoxy)acetic acid obtained in Example 1-(i), 32 mg (0.44 mmol) of DMF, and 0.41 mL (4.8 mmol) of oxalyl chloride were added to 12 mL of THF, and stirring was conducted at 0° C. for 30 minutes. After completion of the reaction, the solvent was distilled off under reduced pressure and dried. 0.84 g (4.8 mmol) of N-cyclohexylaniline and 8.4 mL of DMA were added to this residue and stirred at room temperature overnight. After completion of the reaction, an aqueous sodium bicarbonate solution was added, extraction was carried out using ethyl acetate, and washing was conducted with a saturated sodium chloride solution. The resulting organic layer was dried over anhydrous sodium sulfate, and the solvent was distilled off under reduced pressure. The resulting crude product was separated and purified using silica gel column chromatography, thereby giving 1.77 g of 5-chloro-2-[((2-[cyclohexyl(phenyl)amino]-2-oxoethoxy)acetyl)amino]benzoic acid.methyl ester (yield: 96%).

$^1$H-NMR (CDCl$_3$) δ: 0.80-1.92 (10H, m), 3.85 (1H, s), 3.87 (2H, s), 3.92 (3H, s), 4.16 (2H, s), 7.11-7.50 (6H, m), 7.99 (1H, d, J=2.6 Hz), 8.70 (1H, d, J=8.9 Hz), 11.6 (1H, s).

(ii) 5-Chloro-2-[((2-[cyclohexyl(phenyl)amino]-2-oxoethoxy)acetyl)amino]benzoic acid.sodium salt Using the same method as in Example 7-(ii), the target 5-chloro-2-[((2-[cyclohexyl(phenyl)amino]-2-oxoethoxy)acetyl)amino]benzoic acid.sodium salt was obtained from 5-chloro-2-[((2-[cyclohexyl(phenyl)amino]-2-oxoethoxy)acetyl)amino]benzoic acid.methyl ester (yield: 75%).

$^1$H-NMR (DMSO-$d_6$) δ: 0.74-1.83 (10H, m), 3.76 (2H, s), 4.03 (2H, s), 4.36-4.48 (1H, m), 7.25-7.48 (6H, m), 7.90 (1H, d, J=2.7 Hz), 8.49 (1H, d, J=8.8 Hz), 14.6 (1H, s).

Example 16

Production of 5-chloro-2-([(2-oxo-2-([3-(pyridin-4-yl)phenyl]amino)ethoxy)acetyl]amino)benzoic acid. [(2,2-dimethylpropanoyl)oxy]methyl ester (16)

The target compound (16) was synthesized according to the following step.

1N sodium hydroxide was added to the 5-chloro-2-([(2-oxo-2-([3-(pyridin-4-yl)phenyl]amino)ethoxy)acetyl] amino)benzoic acid obtained in Example 2-(ii) to yield 5-chloro-2-([(2-oxo-2-([3-(pyridin-4-yl)phenyl]amino) ethoxy)acetyl]amino)benzoic acid.sodium salt. The resulting product was used in the following reaction.

0.51 g (1.1 mmol) of 5-chloro-2-([(2-oxo-2-([3-(pyridin-4-yl)phenyl]amino)ethoxy)acetyl]amino)benzoic acid.sodium salt, 0.19 mL (1.32 mmol) of chloromethyl pivalate, and 0.18 g (1.21 mmol) of sodium iodide were stirred in DMF (5 mL) at 30° C. for 2 hours. After completion of the reaction, ethyl acetate was added to the mixture, and the mixture was washed with a saturated sodium chloride solution and water, and dried over anhydrous sodium sulfate. The solvent was distilled off under reduced pressure. The resulting crude product was separated and purified using silica gel column chromatography to give the target 5-chloro-2-([(2-oxo-2-([3-(pyridin-4-yl)phenyl]amino)ethoxy)acetyl]amino)benzoic acid.[(2,2-dimethylpropanoyl)oxy]methyl ester (yield: 48%).

$^1$H-NMR (CDCl$_3$) δ: 1.18 (9H, s), 4.30 (2H, s), 4.32 (2H, s), 5.79 (2H, s), 7.41-7.67 (6H, m), 8.02 (1H, d, J=2.4 Hz), 8.18-8.20 (1H, m), 8.65-8.68 (2H, m), 8.80 (1H, d, J=9.2 Hz), 8.83 (1H, s), 11.7 (1H, br).

Example 17

Production of 5-chloro-2-([(2-oxo-2-([3-(pyridin-4-yl)phenyl]amino)ethoxy)acetyl]amino)benzoic acid.1-([(cyclohexyloxy)carbonyl]oxy)ethyl ester (17)

The target compound (17) was synthesized according to the following step.

0.69 g (1.5 mmol) of 5-chloro-2-([(2-oxo-2-([3-(pyridin-4-yl)phenyl]amino)ethoxy)acetyl]amino)benzoic acid.sodium salt, 0.37 g (1.8 mmol) of carbonic acid-1-chloro-ethylcyclohexyl, and 0.25 g (1.65 mmol) of sodium iodide were stirred in DMF (7 mL) at 60° C. for 2 hours. After completion of the reaction, ethyl acetate was added thereto, and the mixture was washed with a sodium chloride solution and water, and dried over anhydrous sodium sulfate. The solvent was distilled off under reduced pressure. The resulting crude product was separated and purified using silica gel column chromatography to give the target 5-chloro-2-([(2-oxo-2-([3-(pyridin-4-yl)phenyl]amino)ethoxy)acetyl]amino)benzoic acid.1-([[(cyclohexyloxy)carbonyl]oxy)ethyl ester (yield: 28%).

$^1$H-NMR (CDCl$_3$) δ: 1.38 (3H, d, J=5.5 Hz), 1.25-1.86 (10H, m), 4.28 (2H, s), 4.31 (2H, s), 4.51-4.60 (1H, m), 6.73 (1H, q, J=5.5 Hz), 7.42-7.68 (6H, m), 8.00 (1H, d, J=2.4 Hz), 8.11-8.12 (1H, m), 8.64-8.67 (2H, m), 8.79 (1H, d, J=9.2 Hz), 8.85 (1H, s), 11.7 (1H, br).

Example 18

Production of 5-chloro-2-([(2-oxo-2-([3-(pyridin-4-yl)phenyl]amino)ethoxy)acetyl]amino)benzoic acid. (5-methyl-2-oxo-1,3-dioxol-4-yl)methyl ester (18)

The target compound (18) was synthesized according to the following step.

0.69 g (1.5 mmol) of 5-chloro-2-([(2-oxo-2-([3-(pyridin-4-yl)phenyl]amino)ethoxy)acetyl]amino)benzoic acid.sodium salt, 0.35 g (1.8 mmol) of 4-(chloromethyl)-5-methyl-1,3-dioxole-2-one, and 0.25 g (1.65 mmol) of sodium iodide were stirred in DMF (7 mL) at 30° C. for 3 hours. After completion of the reaction, ethyl acetate was added to the mixture, and the mixture was washed with a sodium chloride solution and water, and dried over anhydrous sodium sulfate. The solvent was distilled off under reduced pressure. The resulting crude product was separated and purified using silica gel column chromatography to give the target 5-chloro-2-([[(2-oxo-2-([3-(pyridin-4-yl)phenyl]amino)ethoxy)acetyl]amino)benzoic acid.(5-methyl-2-oxo-1,3-dioxol-4-yl)methyl ester (yield: 19%).

$^1$H-NMR (CDCl$_3$) δ: 1.96 (3H, s), 4.32 (2H, s), 4.33 (2H, s), 4.82 (2H, s), 7.41-7.72 (6H, m), 8.01 (1H, d, J=2.6 Hz), 8.06-8.07 (1H, m), 8.66-8.67 (2H, m), 8.80 (1H, d, J=9.0 Hz), 8.82 (1H, s), 11.6 (1H, br).

Example 19

Production of 5-chloro-2-([(2-oxo-2-([3-(pyridin-3-yl)phenyl]amino)ethoxy)acetyl]amino)benzoic acid-.sodium salt (19)

The target compound (19) was synthesized according to the following steps (i) to (iii).

(i) 2-[((2-[(3-Bromophenyl)amino]-2-oxoethoxy) acetyl)amino]-5-chlorobenzoic acid.methyl ester Using the same method as in Example 1-(ii), 3-bromoaniline was reacted with the (2-([4-chloro-2-(methoxycarbonyl)phenyl]amino)-2-oxoethoxy)acetic acid obtained in Example 1-(i) to give 2-[((2-[(3-bromophenyl)amino]-2-oxoethoxy)acetyl)amino]-5-chlorobenzoic acid.methyl ester (yield: 81%)

$^1$H-NMR (CDCl$_3$) δ: 3.93 (3H, s), 4.26 (2H, s), 4.27 (2H, s), 7.18-7.32 (2H, m), 7.56 (1H, dd, J=9.2, 2.6 Hz), 7.80-7.90 (2H, m), 8.07 (1H, d, J=2.6 Hz), 8.79 (1H, d, J=9.2 Hz), 8.82 (1H, s), 11.9 (1H, s).

(ii) 5-Chloro-2-([(2-oxo-2-([3-(pyridin-3-yl)phenyl] amino)ethoxy)acetyl]amino)benzoic acid.methyl ester 0.48 g (3.88 mmol) of 3-pyridineboronic acid, 1.3 g (2.85 mmol) of 2-[((2-[(3-bromophenyl)amino]-2-oxoethoxy) acetyl)amino]-5-chlorobenzoic acid.methyl ester, 95.9 mg (0.08 mmol) of tetrakis(triphenyl phosphine)palladium (0), and 0.41 g (3.88 mmol) of 2N sodium carbonate were heated under reflux for 8 hours in 9.2 mL of toluene and 2.6 mL of methanol. After completion of the reaction, the solvent was distilled off under reduced pressure, and ethyl acetate was added to separate the solid by filtration. Thereafter, the organic layer was washed with a saturated sodium chloride solution, and dried over anhydrous sodium sulfate. The solvent was distilled off under reduced pressure. The resulting crude product was separated and purified using silica gel column chromatography to give 5-chloro-2-([(2-oxo-2-([3-(pyridin-3-yl)phenyl]amino)ethoxy)acetyl]amino)benzoic acid.methyl ester (yield: 62%).

$^1$H-NMR (CDCl$_3$) δ: 3.71 (3H, s), 4.29 (2H, s), 4.31 (2H, s), 7.32-7.50 (3H, m), 7.55 (1H, dd, J=9.0, 2.6 Hz), 7.72-7.78 (1H, m), 7.85-7.95 (1H, m), 8.00-8.06 (1H, m), 8.03 (1H, d, J=2.6 Hz), 8.61 (1H, dd, J=4.8, 1.6 Hz), 8.79 (1H, d, J=9.0 Hz), 8.80-8.90 (1H, m), 8.95 (1H, s), 11.9 (1H, s).

(iii) 5-Chloro-2-([(2-oxo-2-([3-(pyridin-3-yl)phenyl] amino)ethoxy)acetyl]amino)benzoic acid.sodium salt Using the same method as in Example 7-(ii), the target 5-chloro-2-([(2-oxo-2-([3-(pyridin-3-yl)phenyl]amino) ethoxy)acetyl]amino)benzoic acid.sodium salt was obtained from 5-chloro-2-([(2-oxo-2-([3-(pyridin-3-yl)phenyl]amino) ethoxy)acetyl]amino)benzoic acid.methyl ester (yield: 76%).

$^1$H-NMR (DMSO-d$_6$) δ: 4.18 (2H, s), 4.26 (2H, s), 7.38 (1H, dd, J=8.7, 2.7 Hz), 7.40-7.55 (2H, m), 8.03 (1H, d, J=2.7 Hz), 8.20-8.30 (1H, m), 8.35-8.45 (1H, m), 8.50-8.65 (2H, m), 8.52 (1H, d, J=8.7 Hz), 9.06 (1H, d, J=1.8 Hz), 10.5 (1H, s), 15.2 (1H, s).

Example 20

Production of 5-chloro-2-(([(4'-fluoro-4-methylbiphenyl-3-yl)amino](oxo)acetyl)amino)benzoic acid-.sodium salt (20)

The target compound (20) was synthesized according to the following Steps (i) to (iv).

(i) [(4'-Fluoro-4-methylbiphenyl-3-yl)amino] (oxo) acetic acid.ethyl ester 2.0 g (9.9 mmol) of 4'-fluoro-4-methylbiphenyl-3-amine and 1.64 g (11.9 mmol) of potassium carbonate were suspended in THF, and 1.49 g (10.9 mmol) of chloroglyoxylic acid ethyl were added thereto at 0° C., and stirred at room temperature for 4 hours. After completion of the reaction, ethyl acetate was added to the mixture, and the mixture was washed with an aqueous sodium bicarbonate solution and a sodium chloride solution in this order. The resulting organic layer was dried over anhydrous sodium sulfate, and the solvent was distilled off under reduced pressure to give 2.76 g of [(4'-fluoro-4-methylbiphenyl-3-yl)amino] (oxo)acetic acid-.ethyl ester (yield: 93%).

$^1$H-NMR (CDCl$_3$) δ: 1.45 (3H, t, J=7.1 Hz), 2.36 (3H, s), 4.44 (2H, q, J=7.1 Hz), 7.02-7.18 (2H, m), 7.22-7.36 (2H, m), 7.48-7.60 (2H, m), 8.28 (1H, d, J=1.5 Hz), 8.89 (1H, s).

(ii) [(4'-Fluoro-4-methylbiphenyl-3-yl)amino](oxo) acetic acid

Using the same method as in Example 1-(iii), 2.08 g of [(4'-fluoro-4-methylbiphenyl-3-yl)amino](oxo)acetic acid was obtained from [(4'-fluoro-4-methylbiphenyl-3-yl) amino](oxo)acetic acid.ethyl ester (yield: 83%).

$^1$H-NMR (DMSO-$d_6$) δ: 2.24 (3H, s), 7.20-7.40 (3H, m), 7.40-7.50 (1H, m), 7.60-7.72 (3H, m), 10.3 (1H, s).

(iii) 5-Chloro-2-(([(4'-fluoro-4-methylbiphenyl-3-yl) amino](oxo)acetyl)amino)benzoic acid.methyl ester 1.41 g (7.6 mmol) of 2-amino-5 chlorobenzoic acid methyl, 3.47 g (9.12 mmol) of O-(7-azabenzotriazol-1-yl)-N, N,N',N'-tetramethyl uranium.hexa fluorophosphoric acid (HATU), and 3.17 mL (18.2 mmol) of N,N-diisopropylethyl amine were added at 0° C. to a DMF solution of 2.08 g (7.6 mmol) of [(4'-fluoro-4-methylbiphenyl-3-yl)amino](oxo) acetic acid, and stirred at room temperature for 66 hours. Thereafter, the mixture was diluted with ethyl acetate, and washed with 1N hydrochloric acid, a saturated aqueous sodium bicarbonate solution, and a saturated sodium chloride solution. The resulting organic layer was dried over anhydrous sodium sulfate, and the solvent was distilled off under reduced pressure. The resulting residue was washed with IPE and methanol, followed by filtration and drying, thereby giving 0.40 g of 5-chloro-2-(([(4'-fluoro-4-methylbiphenyl-3-yl) amino](oxo)acetyl)amino)benzoic acid.methyl ester (yield: 12%).

$^1$H-NMR (CDCl$_3$) δ: 2.42 (3H, s), 4.01 (3H, s), 7.00-7.20 (2H, m), 7.22-7.35 (2H, m), 7.52-7.62 (3H, m), 8.10 (1H, d, J=2.3 Hz), 8.51 (1H, s), 8.75 (1H, d, J=9.0 Hz), 9.37 (1H, s), 12.9 (1H, s).

(iv) 5-Chloro-2-(([(4'-fluoro-4-methylbiphenyl-3-yl) amino](oxo)acetyl)amino)benzoic acid.sodium salt Using the same method as in Example 7-(ii), 0.13 g of 5-chloro-2-(([(4'-fluoro-4-methylbiphenyl-3-yl)amino] (oxo)acetyl)amino)benzoic acid.sodium salt was obtained from 5-chloro-2-(([(4'-fluoro-4-methylbiphenyl-3-yl)amino] (oxo)acetyl)amino)benzoic acid.methyl ester (yield: 33%).

$^1$H-NMR (DMSO-$d_6$) δ: 2.30 (3H, s), 7.20-7.50 (4H, m), 7.60-7.76 (1H, m), 8.00 (1H, d, J=2.6 Hz), 8.62 (1H, d, J=8.9 Hz), 10.2 (1H, s), 15.4 (1H, s).

Example 21

Production of 5-chloro-2-([(2-oxo-2-([3-(pyridin-2-yl)phenyl]amino)ethoxy)acetyl]amino)benzoic acid-.sodium salt (21)

The target compound (21) was synthesized according to the following Steps (i) to (iii).

(i) 3-(Pyridin-2-yl)aniline 3.72 g (20.0 mmol) of 3-aminophenyl boronic acid-.hemisulphate salt, 3.16 g (20.0 mmol) of 2-bromopyridine, 1.16 g (1.0 mmol) of tetrakis(triphenyl phosphine)palladium (0), and 11.2 g (106 mmol) of sodium carbonate were heated under reflux for 5 hours in a mixed solvent of 100 mL of DME and 34 mL of water. After completion of the reaction, extraction with ethyl acetate, and drying over anhydrous sodium sulfate were carried out. The solvent was distilled off under reduced pressure. The resulting crude product was separated and purified using silica gel column chromatography to give 1.27 g of 3-(pyridin-2-yl)aniline (yield: 37%).

$^1$H-NMR (CDCl$_3$) δ: 3.76 (2H, br), 6.65-6.78 (1H, m), 7.10-7.40 (4H, m), 7.60-7.78 (2H, m), 8.60-8.70 (1H, m).

(ii) 5-Chloro-2-([[(2-oxo-2-([3-(pyridin-2-yl)phenyl] amino)ethoxy)acetyl]amino)benzoic acid.methyl ester Using the same method as in Example 1-(ii), 3-(pyridin-2-yl)aniline was reacted with the (2-([4-chloro-2-(methoxycarbonyl)phenyl]amino)-2-oxoethoxy)acetic acid obtained in Example 1-(i) to give 5-chloro-2-([(2-oxo-2-([3-(pyridin-2-yl)phenyl]amino)ethoxy)acetyl]amino)benzoic acid.methyl ester (yield: 79%).

$^1$H-NMR (CDCl$_3$) δ: 3.74 (3H, s), 4.27 (2H, s), 4.30 (2H, s), 7.20-7.30 (1H, m), 7.40-7.53 (1H, m), 7.54 (1H, dd, J=9.0, 2.6 Hz), 7.70-7.80 (3H, m), 7.85-7.95 (1H, m), 8.03 (1H, d, J=2.6 Hz), 8.25-8.30 (1H, m), 8.26-8.70 (1H, m), 8.79 (1H, d, J=9.0 Hz), 8.95 (1H, s), 12.0 (1H, s).

(iii) 5-Chloro-2-([[(2-oxo-2-([3-(pyridin-2-yl)phenyl] amino)ethoxy)acetyl]amino)benzoic acid.sodium salt Using the same method as in Example 7-(ii), the target 5-chloro-2-([(2-oxo-2-([3-(pyridin-2-yl)phenyl]amino) ethoxy)acetyl]amino)benzoic acid.sodium salt was obtained from 5-chloro-2-([(2-oxo-2-([3-(pyridin-2-yl)phenyl]amino) ethoxy)acetyl]amino)benzoic acid.methyl ester (yield: 91%).

$^1$H-NMR (DMSO-$d_6$) δ: 4.19 (2H, s), 4.26 (2H, s), 7.30-7.50 (3H, m), 7.80-8.00 (2H, m), 8.04 (1H, d, J=2.7 Hz), 8.20-8.32 (1H, m), 8.32-8.45 (1H, m), 8.54 (1H, d, J=8.9 Hz), 8.60-8.70 (1H, m), 8.85-8.95 (1H, m), 10.4 (1H, s), 15.1 (1H, s).

Example 22

Production of 5-chloro-2-[((2-[(4'-fluoro-4-methylbiphenyl-3-yl)(2-methylpropyl)amino]-2-oxoethoxy) acetyl)amino]benzoic acid (22)

The target compound (22) was synthesized according to the following Steps (i) to (iv).

(i) 5-Bromo-2-methyl-N-(2-methylpropyl)aniline 7.44 g (40.0 mmol) of 5-bromo-2-methylaniline, 8.22 g (60.0 mmol) of 1-bromo-2-methyl propane, 8.99 g (60.0 mmol) of sodium iodide and 8.29 g (60.0 mmol) of potassium carbonate were stirred in a DMF solvent at 70° C. for 22 hours. To the reaction mixture was added water and extracted with ethyl acetate. The organic layer was separated, washed with a saturated sodium chloride solution, dried over anhydrous sodium sulfate, and concentrated under reduced pressure. The resulting crude product was separated and purified using silica gel column chromatography to give 5.92 g of 5-bromo-2-methyl-N-(2-methylpropyl)aniline (yield: 61%).

$^1$H-NMR (CDCl$_3$) δ: 1.00 (6H, d, J=6.8 Hz), 1.80-2.05 (1H, m), 2.07 (3H, s), 2.94 (2H, dd, J=6.8, 5.7 Hz), 3.58 (1H, br), 6.65-6.75 (2H, m), 6.83-6.93 (1H, m).

(ii) 4'-Fluoro-4-methyl-N-(2-methylpropyl)biphenyl-3-amine

Using the same method as in Example 19-(ii), 4-fluorobenzene boronic acid was reacted with 5-bromo-2-methyl-N-(2-methylpropyl)aniline to give 4'-fluoro-4-methyl-N-(2-methylpropyl)biphenyl-3-amine (yield: 83%).

$^1$H-NMR (CDCl$_3$) δ: 1.03 (6H, d, J=6.8 Hz), 1.82-2.10 (1H, m), 2.18 (3H, s), 3.04 (2H, d, J=6.8 Hz), 3.62 (1H, br), 6.73 (1H, d, J=1.7 Hz), 6.80 (1H, dd, J=7.6, 1.7 Hz), 7.02-7.16 (3H, m), 7.46-7.60 (2H, m).

(iii) 5-Chloro-2-[((2-[(4'-fluoro-4-methylbiphenyl-3-yl)(2-methylpropyl)amino]-2-oxoethoxy)acetyl)amino]benzoic acid.methyl ester Using the same method as in Example 15-(i), 4'-fluoro-4-methyl-N-(2-methylpropyl)biphenyl-3-amine was reacted with the (2-([4-chloro-2-(methoxycarbonyl)phenyl]amino)-2-oxoethoxy)acetic acid obtained in Example 1-(i) to quantitatively give 5-chloro-2-[((2-[(4'-fluoro-4-methylbiphenyl-3-yl)(2-methylpropyl)amino]-2-oxoethoxy)acetyl)amino]benzoic acid.methyl ester.

A mixture of two rotamers in the ratio ca.1:1

$^1$H-NMR (CDCl$_3$) δ: 0.94 (½×6H for one rotamer, d, J=6.8 Hz), 1.05 (½×6H for another rotamer, d, J=6.6 Hz), 1.78 (½×1H×2, for two rotamers, m), 2.29 (3H, s), 2.88 (½×2H for one rotamer, dd, J=13.3, 5.6 Hz), 3.80 (1H, d, J=15.3 Hz), 3.88 (3H, s), 4.10 (1H, d, J=15.6 Hz), 4.11 (1H, d, J=15.3 Hz), 4.15 (½×2H for another rotamer, dd, J=13.2, 9.2 Hz), 4.22 (1H, d, J=15.6 Hz), 7.02-7.18 (2H, m), 7.30-7.55 (6H, m), 7.97 (1H, d, J=2.6 Hz), 8.69 (1H, d, J=9.0 Hz), 11.6 (1H, s).

(iv) 5-Chloro-2-[((2-[(4'-fluoro-4-methylbiphenyl-3-yl)(2-methylpropyl)amino]-2-oxoethoxy)acetyl)amino]benzoic acid Using the same method as in Example 1-(iii), the target 5-chloro-2-[((2-[(4'-fluoro-4-methylbiphenyl-3-yl)(2-methylpropyl)amino]-2-oxoethoxy)acetyl)amino]benzoic acid was obtained from 5-chloro-2-[((2-[(4'-fluoro-4-methylbiphenyl-3-yl)(2-methylpropyl)amino]-2-oxoethoxy)acetyl)amino]benzoic acid.methyl ester (yield: 85%).

A mixture of two rotamers in the ratio ca.1:1

$^1$H-NMR (DMSO-d$_6$) δ: 0.87 (½×6H for one rotamer, d, J=6.6 Hz), 0.96 (½×6H, d, for another rotamer, d, J=6.3 Hz), 1.60-1.85 (½×1H×2, for two rotamers, m), 2.23 (3H, s), 2.87 (½×2H for one rotamer, dd, J=13.2, 5.7 Hz), 3.75 (1H, d, J=15.6 Hz), 3.95 (½×2H for another rotamer, dd, J=13.2, 8.8 Hz), 4.12 (2H, s), 4.18 (1H, d, J=15.6 Hz), 7.20-7.80 (8H, m), 7.91 (1H, d, J=2.4 Hz), 8.63 (1H, d, J=8.8 Hz), 11.7 (1H, s).

Example 23

Production of 4'-fluoro-4-[((2-[(4'-fluoro-4-methylbiphenyl-3-yl)amino]-2-oxoethoxy)acetyl)amino]biphenyl-3-carboxylic acid.sodium salt (23)

The target compound (23) was synthesized according to the following Steps (i) to (iv).

(i) 4-Amino-4'-fluorobiphenyl-3-carboxylic acid.methyl ester

Using the same method as in Example 19-(ii), 4-fluorobenzene boronic acid was reacted with the 2-amino-5-bromobenzoic acid methyl to give 4-amino-4'-fluorobiphenyl-3-carboxylic acid.methyl ester (yield: 69%).

$^1$H-NMR (CDCl$_3$) δ: 3.90 (3H, s), 5.78 (2H, br), 6.73 (1H, d, J=8.4 Hz), 7.00-7.15 (2H, m), 7.40-7.50 (3H, m), 8.05 (1H, d, J=2.2 Hz).

(ii) (2-([4'-Fluoro-3-(methoxycarbonyl)biphenyl-4-yl]amino)-2-oxoethoxy)acetic acid Using the same method as in Example 1-(i), diglycolic anhydride was reacted with the 4-amino-4'-fluorobiphenyl-3-carboxylic acid.methyl ester to quantitatively give (2-([4'-fluoro-3-(methoxycarbonyl)biphenyl-4-yl]amino)-2-oxoethoxy)acetic acid.

$^1$H-NMR (DMSO-d$_6$) δ: 3.92 (3H, s), 4.29 (2H, s), 4.23 (2H, s), 7.22-7.40 (2H, m), 7.65-7.80 (2H, m), 8.95 (1H, dd, J=8.8, 2.2 Hz), 8.21 (1H, d, J=2.2 Hz), 8.69 (1H, d, J=8.8 Hz), 11.4 (1H, s), 12.8 (1H, br).

(iii) 4'-Fluoro-4-[((2-[(4'-fluoro-4-methylbiphenyl-3-yl)amino]-2-oxoethoxy)acetyl)amino]biphenyl-3-carboxylic acid.methyl ester Using the same method as in Example 1-(ii), 4'-fluoro-4-methylbiphenyl-3-amine was reacted with the (2-([4'-fluoro-3-(methoxycarbonyl)biphenyl-4-yl]amino)-2-oxoethoxy)acetic acid to quantitatively give 4'-fluoro-4-[((2-[(4'-fluoro-4-methylbiphenyl-3-yl)amino]-2-oxoethoxy)acetyl)amino]biphenyl-3-carboxylic acid.methyl ester.

$^1$H-NMR (CDCl$_3$) δ: 2.37 (3H, s), 3.57 (3H, s), 4.33 (2H, s), 4.36 (2H, s), 7.03-7.20 (4H, m), 7.25-7.40 (2H, m), 7.45-7.60 (4H, m), 7.77 (1H, dd, J=8.8, 2.2 Hz), 7.88 (1H, d, J=1.6 Hz), 8.20 (1H, d, J=2.2 Hz), 8.84 (1H, s), 8.86 (1H, d, J=8.8 Hz), 12.1 (1H, s).

(iv) 4'-Fluoro-4-[((2-[(4'-fluoro-4-methylbiphenyl-3-yl)amino]-2-oxoethoxy)acetyl)amino]biphenyl-3-carboxylic acid.sodium salt Using the same method as in Example 7-(ii), the target 4'-fluoro-4-[((2-[(4'-fluoro-4-methylbiphenyl-3-yl)amino]-2-oxoethoxy)acetyl)amino]biphenyl-3-carboxylic acid.sodium salt was obtained from 4'-fluoro-4-[((2-[(4'-fluoro-4-methylbiphenyl-3-yl)amino]-2-oxoethoxy)acetyl)amino]biphenyl-3-carboxylic acid.methyl ester (yield: 50%).

$^1$H-NMR (DMSO-d$_6$) δ: 2.32 (3H, s), 4.29 (2H, s), 4.23 (2H, s), 7.20-7.50 (6H, m), 7.55-7.80 (6H, m), 8.29 (1H, d, J=2.3 Hz), 8.59 (1H, d, J=8.5 Hz), 10.1 (1H, s), 15.1 (1H, s).

Example 24

Production of 5-chloro-2-([((2-oxo-2-[(3',4,5'-trimethylbiphenyl-3-yl)amino]ethyl)sulfanyl)acetyl]amino)benzoic acid (24)

The target compound (24) was synthesized according to the following Steps (i) to (ii).

(i) 5-Chloro-2-([((2-oxo-2-[(3',4,5'-trimethylbiphenyl-3-yl)amino]ethyl)sulfanyl)acetyl]amino)benzoic acid.methyl ester Using the same method as in Example 1-(ii), 3',4,5'-trimethylbiphenyl-3-amine was reacted with the [(2-([4-chloro-2-(methoxycarbonyl)phenyl]amino)-2-oxoethyl)sulfanyl]acetic acid obtained in Example 12-(i) to give 5-chloro-2-([((2-oxo-2-[(3',4,5'-trimethylbiphenyl-3-yl)amino]ethyl)sulfanyl)acetyl]amino)benzoic acid.methyl ester (yield: 87%).

$^1$H-NMR (CDCl$_3$) δ: 2.33 (3H, s), 2.36 (6H, s), 3.54 (2H, s), 3.57 (2H, s), 3.89 (3H, s), 6.97 (1H, s), 7.17 (2H, s), 7.19 (1H, d, J=7.9), 7.28 (1H, dd, J=7.9, 1.6 Hz), 7.38 (1H, dd, J=9.1, 2.6 Hz), 7.94 (1H, d, J=2.6 Hz), 8.06 (1H, d, J=1.5 Hz), 8.59 (1H, d, J=9.1 Hz), 8.60 (1H, br), 11.6 (1H, br).

(ii) 5-Chloro-2-([((2-oxo-2-[(3',4,5'-trimethylbiphenyl-3-yl)amino]ethyl)sulfanyl)acetyl]amino)benzoic acid Using the same method as in Example 1-(iii), the target 5-chloro-2-([((2-oxo-2-[(3',4,5'-trimethylbiphenyl-3-yl)

amino]ethyl)sulfanyl)acetyl]amino)benzoic acid was obtained from 5-chloro-2-([((2-oxo-2-[(3',4,5'-trimethylbiphenyl-3-yl)amino]ethyl)sulfanyl)acetyl]amino)benzoic acid.methyl ester (yield: 97%).

$^1$H-NMR (DMSO-d$_6$) δ: 2.22 (3H, s), 2.32 (6H, s), 3.53 (2H, s), 3.67 (2H, s), 6.97 (1H, s), 7.14 (2H, s), 7.24 (1H, d, J=8.0 Hz), 7.32 (1H, dd, J=8.0, 1.6 Hz), 7.54 (1H, dd, J=9.0, 2.7 Hz), 7.67 (1H, d, J=1.6 Hz), 7.87 (1H, d, J=2.7 Hz), 8.50 (1H, d, J=9.0 Hz), 9.49 (1H, s), 11.7 (1H, s).

Example 25

Production of 5-chloro-2-(([(2-oxo-2-([3-(pyridin-4-yl)phenyl]amino)ethyl)sulfanyl]acetyl)amino)benzoic acid (25)

The target compound (25) was synthesized according to the following Steps (i) to (ii).

(i) 5-Chloro-2-(([(2-oxo-2-([3-(pyridin-4-yl)phenyl]amino)ethyl)sulfanyl]acetyl)amino)benzoic acid.methyl ester Using the same method as in Example 1-(ii), 3-(pyridin-4-yl)aniline was reacted with the [(2-([4-chloro-2-(methoxycarbonyl)phenyl]amino)-2-oxoethyl)sulfanyl]acetic acid obtained in Example 12-(i) to give 5-chloro-2-(([(2-oxo-2-([3-(pyridin-4-yl)phenyl]amino)ethyl)sulfanyl]acetyl)amino)benzoic acid.methyl ester (yield: 74%).

$^1$H-NMR (CDCl$_3$) δ: 3.52 (2H, s), 3.54 (2H, s), 3.91 (3H, s), 7.31-7.51 (5H, m), 7.53-7.61 (1H, m), 7.89 (1H, s), 7.92 (1H, d, J=2.6 Hz), 8.59 (1H, d, J=9.1 Hz), 8.62-8.69 (2H, m), 9.16 (1H, br), 11.5 (1H, br).

(ii) 5-Chloro-2-(([(2-oxo-2-([3-(pyridin-4-yl)phenyl]amino)ethyl)sulfanyl]acetyl)amino)benzoic acid Using the same method as in Example 1-(iii), the target 5-chloro-2-(([(2-oxo-2-([3-(pyridin-4-yl)phenyl]amino)ethyl)sulfanyl]acetyl)amino)benzoic acid was obtained from 5-chloro-2-(([(2-oxo-2-([3-(pyridin-4-yl)phenyl]amino)ethyl)sulfanyl]acetyl)amino)benzoic acid.methyl ester (yield: 70%).

$^1$H-NMR (DMSO-d$_6$) δ: 3.47 (2H, s), 3.67 (2H, s), 7.33-7.62 (6H, m), 7.82 (1H, d, J=2.6 Hz), 7.95 (1H, s), 8.50 (1H, d, J=9.0 Hz), 8.60-8.69 (2H, m), 10.3 (1H, s), 11.8 (1H, s).

Example 26

Production of 5-chloro-2-[((2-[(3-cyclohexylphenyl)amino]-2-oxoethoxy)acetyl)amino]benzoic acid (26)

The target compound (26) was synthesized according to the following Steps (i) to (iii).

(i) 5-Chloro-2-[((2-[(3-iodophenyl)amino]-2-oxoethoxy)acetyl)amino]benzoic acid.methyl ester Using the same method as in Example 1-(ii), 3-iode aniline was reacted with the (2-([4-chloro-2-(methoxycarbonyl)phenyl]amino)-2-oxoethoxy)acetic acid obtained in Example 1-(i) to give 5-chloro-2-[((2-[(3-iodophenyl)amino]-2-oxoethoxy)acetyl)amino]benzoic acid.methyl ester (yield: 92%).

$^1$H-NMR (CDCl$_3$) δ: 3.93 (3H, s), 4.25 (2H, s), 4.27 (2H, s), 7.09 (1H, t, J=8.1 Hz), 7.49 (1H, ddd, J=8.1, 1.8, 1.0 Hz), 7.56 (1H, dd, J=9.0, 2.6 Hz), 7.88 (1H, ddd, J=8.1, 1.8, 1.0 Hz), 7.98 (1H, t, J=1.8 Hz), 8.07 (1H, d, J=2.6 Hz), 8.78 (1H, d, J=9.0 Hz), 8.80 (1H, s), 11.9 (1H, s).

(ii) 5-Chloro-2-[((2-[(3-cyclohexylphenyl)amino]-2-oxoethoxy)acetyl)amino]benzoic acid.methyl ester 503 mg (1.0 mmol) of 5-chloro-2-[((2-[(3-iodophenyl)amino]-2-oxoethoxy)acetyl)amino]benzoic acid.methyl ester, and 116 mg (0.1 mmol) of tetrakis(triphenyl phosphine) palladium(0) were dissolved in THF. Subsequently, a THF solution of 9 mL (4.5 mmol) of 0.5 M cyclohexylzinc bromide was added in an argon atmosphere at room temperature and stirred for 5 hours. Thereafter, the reaction solution was diluted with ethyl acetate, and washed with saturated aqueous sodium bicarbonate solution and a saturated aqueous sodium chloride solution. The organic layer was dried over anhydrous sodium sulfate, and the solvent was distilled off under reduced pressure. The resulting crude product was separated and purified using silica gel column chromatography, thereby giving 184 mg of 5-chloro-2-[((2-[(3-cyclohexylphenyl)amino]-2-oxoethoxy)acetyl)amino]benzoic acid.methyl ester (yield: 40%).

$^1$H-NMR (CDCl$_3$) δ: 1.08-1.57 (5H, m), 1.62-1.96 (5H, m), 2.38-2.59 (1H, m), 3.81 (3H, s), 4.23 (2H, s), 4.25 (2H, s), 6.97-7.05 (1H, m), 7.24 (1H, t, J=7.9 Hz), 7.41-7.49 (1H, m), 7.51 (1H, dd, J=9.1, 2.5 Hz), 7.57-7.63 (1H, m), 8.01 (1H, d, J=2.5 Hz), 8.73 (1H, s), 8.76 (1H, d, J=9.1 Hz), 11.9 (1H, s).

(iii) 5-Chloro-2-[((2-[(3-cyclohexylphenyl)amino]-2-oxoethoxy)acetyl)amino]benzoic acid Using the same method as in Example 1-(iii), the target 5-chloro-2-[((2-[(3-cyclohexylphenyl)amino]-2-oxoethoxy)acetyl)amino]benzoic acid was obtained from 5-chloro-2-[((2-[(3-cyclohexylphenyl)amino]-2-oxoethoxy)acetyl)amino]benzoic acid.methyl ester (yield: 91%).

$^1$H-NMR (DMSO-d$_6$) δ: 1.08-1.52 (5H, m), 1.60-1.90 (5H, m), 2.36-2.53 (1H, m), 4.28 (4H, s), 6.94 (1H, d, J=7.8 Hz), 7.22 (1H, t, J=7.8 Hz), 7.46 (1H, d, J=7.8 Hz), 7.54 (1H, s), 7.71 (1H, dd, J=9.0, 2.7 Hz), 7.97 (1H, d, J=2.7 Hz), 8.69 (1H, d, J=9.0 Hz), 9.69 (1H, s), 11.9 (1H, s).

Example 27

Production of 5-chloro-2-([((2-[(4-cyclohexylphenyl)amino]-2-oxoethyl)sulfanyl)acetyl]amino)benzoic acid (27)

The target compound (27) was synthesized according to the following Steps (i) to (ii).

(i) 5-Chloro-2-([((2-[(4-cyclohexylphenyl)amino]-2-oxoethyl)sulfanyl)acetyl]amino)benzoic acid.methyl ester Using the same method as in Example 1-(ii), 4-cyclohexylaniline was reacted with the [(2-([4-chloro-2-(methoxycarbonyl)phenyl]amino)-2-oxoethyl)sulfanyl]acetic acid obtained in Example 12-(i) to give 5-chloro-2-([((2-[(4-cyclohexylphenyl)amino]-2-oxoethyl)sulfanyl)acetyl]amino)benzoic acid.methyl ester (yield: 68%).

$^1$H-NMR (CDCl$_3$) δ: 1.15-1.54 (5H, m), 1.64-1.97 (5H, m), 2.36-2.54 (1H, m), 3.47 (2H, s), 3.51 (2H, s), 3.93 (3H, s), 7.06-7.14 (2H, m), 7.36-7.45 (2H, m), 7.44 (1H, dd, J=9.1, 2.6 Hz), 7.96 (1H, d, J=2.6 Hz), 8.61 (1H, d, J=9.1 Hz), 8.70 (1H, s), 11.5 (1H, s).

(ii) 5-Chloro-2-([(((2-[(4-cyclohexylphenyl)amino]-2-oxoethyl)sulfanyl)acetyl]amino)benzoic acid Using the same method as in Example 1-(iii), the target 5-chloro-2-([(((2-[(4-cyclohexylphenyl)amino]-2-oxoethyl)sulfanyl)acetyl]amino)benzoic acid was obtained from 5-chloro-2-([(((2-[(4-cyclohexylphenyl)amino]-2-oxoethyl)sulfanyl)acetyl]amino)benzoic acid.methyl ester (yield: 82%
$^1$H-NMR (DMSO-d$_6$) δ: 1.07-1.50 (5H, m), 1.59-1.90 (5H, m), 2.27-2.48 (1H, m), 3.41 (2H, s), 3.63 (2H, s), 7.00-7.10 (2H, m), 7.33-7.42 (2H, m), 7.61 (1H, dd, J=9.0, 2.7 Hz), 7.88 (1H, d, J=2.7 Hz), 8.50 (1H, d, J=9.0 Hz), 9.98 (1H, s), 11.6 (1H, s).

Example 28

Production of 5-chloro-2-[(([2-(cyclododecylamino)-2-oxoethyl]sulfanyl)acetyl)amino]benzoic acid (28)

The target compound (28) was synthesized according to the following Steps (i) to (ii).

(i) 5-Chloro-2-[(([2-(cyclododecylamino)-2-oxoethyl]sulfanyl)acetyl)amino]benzoic acid.methyl ester Using the same method as in Example 1-(ii), cyclododecylamine was reacted with the [(2-([4-chloro-2-(methoxycarbonyl)phenyl]amino)-2-oxoethyl)sulfanyl]acetic acid obtained in Example 12-(i) to give 5-chloro-2-[(([2-(cyclododecylamino)-2-oxoethyl]sulfanyl)acetyl)amino]benzoic acid.methyl ester (yield: 95%).
$^1$H-NMR (CDCl$_3$) δ: 1.08-1.76 (22H, m), 3.33 (2H, s), 3.45 (2H, s), 3.90-4.12 (1H, m), 3.96 (3H, s), 6.60 (1H, d, J=8.4 Hz), 7.51 (1H, dd, J=9.1, 2.6 Hz), 8.02 (1H, d, J=2.6 Hz), 8.68 (1H, d, J=9.1 Hz), 11.5 (1H, s).

(ii) 5-Chloro-2-[(([2-(cyclododecylamino)-2-oxoethyl]sulfanyl)acetyl)amino]benzoic acid Using the same method as in Example 1-(iii), the target 5-chloro-2-[(([2-(cyclododecylamino)-2-oxoethyl]sulfanyl)acetyl)amino]benzoic acid was obtained from 5-chloro-2-[(([2-(cyclododecylamino)-2-oxoethyl]sulfanyl)acetyl)amino]benzoic acid.methyl ester (yield: 94%).
$^1$H-NMR (DMSO-d$_6$) δ: 1.00-1.60 (22H, m), 3.19 (2H, s), 3.57 (2H, s), 3.68-3.88 (1H, m), 7.67 (1H, dd, J=9.0, 2.6 Hz), 7.74 (1H, d, J=8.2 Hz), 7.93 (1H, d, J=2.6 Hz), 8.56 (1H, d, J=9.0 Hz), 11.6 (1H, s).

Example 29

Production of 5-chloro-2-[((2-[ethyl(4'-fluoro-4-methylbiphenyl-3-yl)amino]-2-oxoethoxy)acetyl)amino]benzoic acid (29)

The target compound (29) was synthesized according to the following Steps (i) to (iv).

(i) 5-Bromo-N-ethyl-2-methylaniline

Using the same method as in Example 22-(i), bromoethane was reacted with the 5-bromo-2-methylaniline to give 5-bromo-N-ethyl-2-methylaniline (yield: 71%).
$^1$H-NMR (CDCl$_3$) δ: 1.29 (3H, t, J=7.1 Hz), 2.06 (3H, s), 3.15 (2H, q, 7.1 Hz), 3.41 (1H, br), 6.69 (1H, d, J=1.9 Hz), 6.74 (1H, dd, J=7.8, 1.9 Hz), 6.87 (1H, d, J=7.8 Hz).

(ii) N-Ethyl-4'-fluoro-4-methylbiphenyl-3-amine

Using the same method as in Example 19-(ii), 4-fluorobenzene boronic acid was reacted with 5-bromo-N-ethyl-2-methylaniline to quantitatively give N-ethyl-4'-fluoro-4-methylbiphenyl-3-amine.
$^1$H-NMR (CDCl$_3$) δ: 1.33 (3H, t, J=7.1 Hz), 2.16 (3H, s), 3.26 (2H, q, J=7.1 Hz), 3.45 (1H, br), 6.75 (1H, d, J=1.8 Hz), 6.81 (1H, dd, J=7.6, 1.8 Hz), 7.01-7.30 (2H, m), 7.47-7.59 (2H, m).

(iii) 5-Chloro-2-[((2-[ethyl(4'-fluoro-4-methylbiphenyl-3-yl)amino]-2-oxoethoxy)acetyl)amino]benzoic acid.methyl ester Using the same method as in Example 15-(i), N-ethyl-4'-fluoro-4-methylbiphenyl-3-amine was reacted with the (2-([4-chloro-2-(methoxycarbonyl)phenyl]amino)-2-oxoethoxy)acetic acid obtained in Example 1-(i) to give 5-chloro-2-[((2-[ethyl(4'-fluoro-4-methylbiphenyl-3-yl)amino]-2-oxoethoxy)acetyl)amino]benzoic acid.methyl ester (yield: 79%).
A mixture of two rotamers in the ratio ca.1:1
$^1$H-NMR (CDCl$_3$) δ: 1.21 (3H, t, J=7.1 Hz), 2.29 (3H, s), 3.30 (½×2H for one rotamer, dq, J=13.3, 7.1 Hz), 3.82 (1H, d, J=15.1 Hz), 3.89 (3H, s), 4.07 (1H, d, J=15.1 Hz), 4.13 (1H, d, J=15.4 Hz), 4.20 (½×2H, for another rotamer, dq, J=14.9, 7.1 Hz), 4.21 (1H, d, J=15.4 Hz), 7.04-7.17 (2H, m), 7.29 (1H, d, J=1.8 Hz), 7.38 (1H, d, J=7.9 Hz), 7.42-7.55 (4H, m), 7.97 (1H, d, J=2.6), 8.69 (1H, d, J=9.1 Hz), 11.6 (1H, s).

(iv) 5-Chloro-2-[((2-[ethyl(4'-fluoro-4-methylbiphenyl-3-yl)amino]-2-oxoethoxy)acetyl)amino]benzoic acid Using the same method as in Example 1-(iii), the target 5-chloro-2-[((2-[ethyl(4'-fluoro-4-methylbiphenyl-3-yl)amino]-2-oxoethoxy)acetyl)amino]benzoic acid was obtained from 5-chloro-2-[((2-[ethyl(4'-fluoro-4-methylbiphenyl-3-yl)amino]-2-oxoethoxy)acetyl)amino]benzoic acid.methyl ester (yield: 79%).
A mixture of two rotamers in the ratio ca.1:1
$^1$H-NMR (DMSO-d$_6$) δ: 1.08 (3H, t, J=7.1), 2.24 (3H, s), 3.24 (½×2H dq, for one rotamer, J=13.6, 7.1 Hz), 3.78 (1H, d, J=15.2 Hz), 3.92-4.13 (½×2H for another rotamer, m), 4.09 (1H, d, J=15.2), 4.12 (2H, s), 7.19-7.31 (2H, m), 7.45 (1H, d, J=7.9 Hz), 7.53-7.79 (5H, m), 7.91 (1H, d, J=2.6 Hz), 8.63 (1H, d, J=9.0 Hz), 11.7 (1H, s).

Example 30

Production of 5-chloro-2-([(((2-[ethyl(4'-fluoro-4-methylbiphenyl-3-yl)amino]-2-oxoethyl)sulfanyl)acetyl]amino)benzoic acid (30)

The target compound (30) was synthesized according to the following Steps (i) to (ii).

(i) 5-Chloro-2-([(((2-[ethyl(4'-fluoro-4-methylbiphenyl-3-yl)amino]-2-oxoethyl)sulfanyl)acetyl]amino) benzoic acid.methyl ester Using the same method as in Example 15-(i), N-ethyl-4'-fluoro-4-methylbiphenyl-3-amine was reacted with the [(2-([4-chloro-2-(methoxycarbonyl)phenyl]amino)-2-oxoethyl)sulfanyl]acetic acid obtained in Example 12-(i) to give 5-chloro-2-([((2-[ethyl(4'-fluoro-4-methylbiphenyl-3-yl)amino]-2-oxoethyl)sulfanyl)acetyl]amino)benzoic acid.methyl ester (yield: 28%).

A mixture of two rotamers in the ratio ca.1:1

$^1$H-NMR (CDCl$_3$) δ: 1.14 (3H, t, J=7.1 Hz), 2.25 (3H, s), 3.13 (2H, s), 3.27 (½×2H for one rotamer, dq, J=13.4, 7.1 Hz), 3.56 (1H, d, J=15.9 Hz), 3.59 (1H, d, J=15.9 Hz), 3.88 (3H, s), 4.13 (½×2H for another rotamer, dq, J=13.4, 7.1 Hz), 7.04-7.18 (2H, m), 7.33 (1H, d, J=7.8 Hz), 7.36-7.57 (5H, m), 7.96 (1H, d, J=2.6 Hz), 8.62 (1H, d, J=9.0 Hz), 11.4 (1H, s).

(ii) 5-Chloro-2-([((2-[ethyl(4'-fluoro-4-methylbiphenyl-3-yl)amino]-2-oxoethyl)sulfanyl)acetyl]amino)benzoic acid Using the same method as in Example 1-(iii), the target 5-chloro-2-([((2-[ethyl(4'-fluoro-4-methylbiphenyl-3-yl)amino]-2-oxoethyl)sulfanyl)acetyl]amino)benzoic acid was obtained from 5-chloro-2-([((2-[ethyl(4'-fluoro-4-methylbiphenyl-3-yl)amino]-2-oxoethyl)sulfanyl)acetyl]amino)benzoic acid.methyl ester (yield: 74%).

A mixture of two rotamers in the ratio ca.1:1

$^1$H-NMR (DMSO-d$_6$) δ: 1.03 (3H, t, J=7.1 Hz), 2.18 (3H, s), 3.09 (1H, d, J=14.8 Hz), 3.14-3.32 (½×2H for one rotamer, m), 3.21 (1H, d, J=14.8 Hz), 3.49 (2H, s), 3.95 (½×2H for another rotamer, dq, 13.3, 7.1 Hz), 7.17-7.32 (2H, m), 7.38 (1H, d, J=8.0 Hz), 7.44-7.74 (4H, m), 7.59 (1H, dd, J=8.9, 2.6 Hz), 7.87 (1H, d, J=2.6 Hz), 8.42 (1H, d, J=8.9 Hz), 11.4 (1H, s).

Example 31

Production of 5-chloro-2-((5-[ethyl(4'-fluoro-4-methylbiphenyl-3-yl)amino]-5-oxopentanoyl)amino)benzoic acid (31)

The target compound (31) was synthesized according to the following Steps (i) to (iii).

(i) 5-([4-Chloro-2-(methoxycarbonyl)phenyl]amino)-5-oxopentanoic acid

Using the same method as in Example 1-(i), glutaric anhydride was reacted with 2-amino-5-chlorobenzoic acid methyl to give 5-([4-chloro-2-(methoxycarbonyl)phenyl]amino)-5-oxopentanoic acid (yield: 61%).

$^1$H-NMR (CDCl$_3$) δ: 1.73-1.92 (2H, m), 2.31 (2H, t, J=7.4 Hz), 2.43 (2H, t, J=7.4), 3.85 (3H, s), 7.66 (1H, dd, J=8.9, 2.6 Hz), 7.83 (1H, d, J=2.6 Hz), 8.20 (1H, d, J=8.9 Hz), 10.5 (1H, s), 12.1 (1H, s).

(ii) 5-Chloro-2-((5-[ethyl(4'-fluoro-4-methylbiphenyl-3-yl)amino]-5-oxopentanoyl)amino)benzoic acid.methyl ester Using the same method as in Example 15-(i), N-ethyl-4'-fluoro-4-methylbiphenyl-3-amine was reacted with the 5-([4-chloro-2-(methoxycarbonyl)phenyl]amino)-5-oxopentanoic acid to give 5-chloro-2-((5-[ethyl(4'-fluoro-4-methylbiphenyl-3-yl)amino]-5-oxopentanoyl)amino)benzoic acid.methyl ester (yield: 62%).

A mixture of two rotamers in the ratio ca.1:1

$^1$H-NMR (CDCl$_3$) δ: 1.16 (3H, t, J=7.1 Hz), 1.90-2.20 (4H, m), 2.23 (3H, s), 2.38-2.50 (2H, m), 3.29 (½×2H for one rotamer, J=13.5, 7.1 Hz), 3.91 (3H, s), 4.14 (½×2H for another rotamer, J=13.5, 7.1 Hz), 7.03-7.17 (2H, m), 7.20-7.55 (6H, m), 7.95 (1H, d, J=2.6 Hz), 8.60 (1H, d, J=9.1), 10.9 (1H, s).

(iii) 5-Chloro-2-((5-[ethyl(4'-fluoro-4-methylbiphenyl-3-yl)amino]-5-oxopentanoyl)amino)benzoic acid Using the same method as in Example 1-(iii), the target 5-chloro-2-((5-[ethyl(4'-fluoro-4-methylbiphenyl-3-yl)amino]-5-oxopentanoyl)amino)benzoic acid was obtained from 5-chloro-2-((5-[ethyl(4'-fluoro-4-methylbiphenyl-3-yl)amino]-5-oxopentanoyl)amino)benzoic acid.methyl ester (yield: 78%).

A mixture of two rotamers in the ratio ca.1:1

$^1$H-NMR (DMSO-d$_6$) δ: 1.06 (3H, t, J=7.1 Hz), 1.70-2.20 (4H, m), 2.18 (3H, s), 2.30-2.42 (2H, m), 3.24 (½×2H for one rotamer, J=13.5, 7.1 Hz), 3.98 (½×2H for another rotamer, J=13.5, 7.1 Hz), 7.16-7.32 (2H, m), 7.35-7.47 (2H, m), 7.50-7.75 (4H, m), 7.87 (1H, d, J=2.7 Hz), 8.40 (1H, d, J=8.9 Hz), 10.9 (1H, s), 13.9 (1H, br).

Example 32

Production of 5-chloro-2-([(2-([5-(furan-3-yl)-2-methylphenyl]amino)-2-oxoethoxy)acetyl]amino)benzoic acid (32)

The target compound (32) was synthesized according to the following Steps (i) to (iii).

(i) 5-(Furan-3-yl)-2-methylaniline

Using the same method as in Example 5-(i), 3-(4,4,5,5-tetramethyl-1,3,2-dioxaborolan-2-yl)furan was reacted with the 5-bromo-2-methylaniline to give 5-(furan-3-yl)-2-methylaniline (yield: 98%).

$^1$H-NMR (CDCl$_3$) δ: 2.17 (3H, s), 3.63 (2H, br), 6.64 (1H, dd, J=1.8, 0.8 Hz), 6.80 (1H, m), 6.84 (1H, dd, J=7.6, 1.7 Hz), 7.04 (1H, d, J=7.6 Hz), 7.43 (1H, t, J=1.7 Hz), 7.63-7.68 (1H, m).

(ii) 5-Chloro-2-([(2-([5-(furan-3-yl)-2-methylphenyl]amino)-2-oxoethoxy)acetyl]amino)benzoic acid.methyl ester Using the same method as in Example 15-(i), 5-(furan-3-yl)-2-methylaniline was reacted with the (2-([4-chloro-2-(methoxycarbonyl)phenyl]amino)-2-oxoethoxy)acetic acid obtained in Example 1-(i) to give 5-chloro-2-([(2-([5-(furan-3-yl)-2-methylphenyl]amino)-2-oxoethoxy)acetyl]amino)benzoic acid.methyl ester (yield: 87%).

$^1$H-NMR (CDCl$_3$) δ: 2.32 (3H, s), 3.57 (3H, s), 4.30 (2H, s), 4.34 (2H, s), 6.68 (1H, dd, J=1.8, 0.8 Hz), 7.23 (1H, d, J=7.8 Hz), 7.28 (1H, dd, J=7.8, 1.7 Hz), 7.46 (1H, t, J=1.7 Hz), 7.53 (1H, dd, J=9.1, 2.6 Hz), 7.69-7.75 (1H, m), 7.76-7.81 (1H, m), 7.99 (1H, d, J=2.6 Hz), 8.77 (1H, d, J=9.1 Hz), 8.77 (1H, br), 12.0 (1H, s).

(iii) 5-Chloro-2-([(2-([5-(furan-3-yl)-2-methylphenyl]amino)-2-oxoethoxy)acetyl]amino)benzoic acid Using the same method as in Example 1-(iii), the target 5-chloro-2-([(2-([5-(furan-3-yl)-2-methylphenyl]amino)-2-oxoethoxy)acetyl]amino)benzoic acid was obtained from 5-chloro-2-([(2-([5-(furan-3-yl)-2-methylphenyl]amino)-2-oxoethoxy)acetyl]amino)benzoic acid.methyl ester (yield: 67%).

¹H-NMR (DMSO-d₆) δ: 2.22 (3H, s), 4.33 (2H, s), 4.43 (2H, s), 6.86-6.92 (1H, m), 7.26 (1H, d, J=7.9 Hz), 7.38 (1H, dd, J=7.9, 1.7 Hz), 7.60-7.78 (3H, m), 7.97 (1H, d, J=2.6 Hz), 8.12 (1H, s), 8.68 (1H, d, J=9.0 Hz), 9.31 (1H, s), 11.9 (1H, s).

Example 33

Production of 5-chloro-2-(([(2-([5-(furan-3-yl)-2-methylphenyl]amino)-2-oxoethyl)sulfanyl]acetyl)amino)benzoic acid (33)

The target compound (33) was synthesized according to the following Steps (i) to (ii).

(i) 5-Chloro-2-(([(2-([5-(furan-3-yl)-2-methylphenyl]amino)-2-oxoethyl)sulfanyl]acetyl)amino)benzoic acid.methyl ester Using the same method as in Example 15-(i), 5-(furan-3-yl)-2-methylaniline was reacted with the [(2-([4-chloro-2-(methoxycarbonyl)phenyl]amino)-2-oxoethyl)sulfanyl]acetic acid obtained in Example 12-(i) to give 5-chloro-2-(([(2-([5-(furan-3-yl)-2-methylphenyl]amino)-2-oxoethyl)sulfanyl]acetyl)amino)benzoic acid.methyl ester (yield: 74%).
¹H-NMR (CDCl₃) δ: 2.29 (3H, s), 3.54 (2H, s), 3.56 (2H, s), 3.90 (3H, s), 6.60-6.68 (1H, m), 7.09-7.22 (2H, m), 7.39 (1H, dd, J=9.0, 2.6 Hz), 7.43-7.46 (1H, m), 7.66-7.70 (1H, m), 7.93 (1H, d, J=2.6 Hz), 7.96 (1H, s), 8.57 (1H, s), 8.58 (1H, d), 11.5 (1H, s).

(ii) 5-Chloro-2-(([(2-([5-(furan-3-yl)-2-methylphenyl]amino)-2-oxoethyl)sulfanyl]acetyl)amino)benzoic acid Using the same method as in Example 1-(iii), the target 5-chloro-2-(([(2-([5-(furan-3-yl)-2-methylphenyl]amino)-2-oxoethyl)sulfanyl]acetyl)amino)benzoic acid was obtained from 5-chloro-2-(([(2-([5-(furan-3-yl)-2-methylphenyl]amino)-2-oxoethyl)sulfanyl]acetyl)amino)benzoic acid.methyl ester (yield: 58%).
¹H-NMR (DMSO-d₆) δ: 2.19 (3H, s), 3.51 (2H, s), 3.67 (2H, s), 6.75-6.85 (1H, m), 7.20 (1H, d, J=7.9 Hz), 7.32 (1H, dd, J=7.9, 1.7 Hz), 7.57 (1H, d, J=1.7 Hz), 7.62 (1H, dd, J=9.0, 2.6 Hz), 7.71 (1H, t, J=1.7 Hz), 7.91 (1H, d, J=2.6 Hz), 8.04 (1H, s), 8.54 (1H, d, J=9.0 Hz), 9.49 (1H, s), 11.6 (1H, s).

Example 34

Production of 5-chloro-2-[(5-([5-(furan-3-yl)-2-methylphenyl]amino)-5-oxopentanoyl)amino]benzoic acid (34)

The target compound (34) was synthesized according to the following Steps (i) to (ii).

(i) 5-Chloro-2-[(5-([5-(furan-3-yl)-2-methylphenyl]amino)-5-oxopentanoyl)amino]benzoic acid.methyl ester Using the same method as in Example 15-(i), 5-(furan-3-yl)-2-methylaniline was reacted with the 5-([4-chloro-2-(methoxycarbonyl)phenyl]amino)-5oxopentanoic acid obtained in Example 31-(i) to give 5-chloro-2-[(5-([5-(furan-3-yl)-2-methylphenyl]amino)-5-oxopentanoyl)amino]benzoic acid.methyl ester (yield: 73%).

¹H-NMR (CDCl₃) δ: 2.10-2.30 (2H, m), 2.26 (3H, s), 2.46-2.68 (4H, m), 3.91 (3H, m), 6.64-6.72 (1H, m), 7.11-7.23 (2H, m), 7.37-7.49 (2H, m), 7.47 (1H, dd, J=9.1, 2.6 Hz), 7.71 (1H, s), 7.99 (1H, d, J=2.6 Hz), 8.01 (1H, s), 8.69 (1H, d, J=9.1 Hz), 11.0 (1H, s).

(ii) 5-Chloro-2-[(5-([5-(furan-3-yl)-2-methylphenyl]amino)-5-oxopentanoyl)amino]benzoic acid Using the same method as in Example 1-(iii), the target 5-chloro-2-[(5-([5-(furan-3-yl)-2-methylphenyl]amino)-5-oxopentanoyl)amino]benzoic acid was obtained from 5-chloro-2-[(5-([5-(furan-3-yl)-2-methylphenyl]amino)-5-oxopentanoyl)amino]benzoic acid.methyl ester (yield: 69%).
¹H-NMR (DMSO-d₆) δ: 1.85-2.10 (2H, m), 2.19 (3H, s), 2.36-2.62 (4H, m), 6.87 (1H, dd, J=1.8, 0.8 Hz), 7.21 (1H, d, J=7.8 Hz), 7.33 (1H, dd, J=7.8, 1.7 Hz), 7.53-7.60 (1H, m), 7.65 (1H, dd, J=9.0, 2.7 Hz), 7.72 (1H, t, J=1.8 Hz), 7.92 (1H, d, J=2.7 Hz), 8.08-8.12 (1H, m), 8.53 (1H, d, J=9.0 Hz), 9.34 (1H, s), 11.1 (1H, s).

Example 35

Production of 5-chloro-2-([(2-(ethyl[5-(furan-3-yl)-2-methylphenyl]amino)-2-oxoethoxy)acetyl]amino)benzoic acid (35)

The target compound (35) was synthesized according to the following Steps (i) to (iii).

(i) N-Ethyl-5-(furan-3-yl)-2-methylaniline 0.69 g (3.20 mmol) of 5-bromo-N-ethyl-2-methylaniline and 0.93 g (4.80 mmol) of 3-furan boronic acid pinacol ester were dissolved in 7 mL of THF. 1.56 g (4.80 mmol) of cesium carbonate and 370 mg (0.32 mmol) of tetrakis(triphenyl phosphine)palladium(0) were added thereto and heated under reflux for 22 hours. After completion of the reaction, filtration was conducted, and the filtrate was condensed. The resulting crude product was separated and purified using silica gel column chromatography to give N-ethyl-5-(furan-3-yl)-2-methylaniline (yield: 98%).
¹H-NMR (CDCl₃) δ: 1.33 (3H, t, J=7.0 Hz), 2.14 (3H, s), 3.24 (2H, q, J=7.0 Hz), 3.40 (1H, br), 6.67-6.71 (2H, m), 6.78 (1H, dd, J=7.6, 1.8 Hz), 7.04 (1H, d, J=7.6 Hz), 7.44-7.45 (1H, m), 7.67-7.69 (1H, m).

(ii) 5-Chloro-2-([(2-(ethyl[5-(furan-3-yl)-2-methylphenyl]amino)-2-oxoethoxy)acetyl]amino)benzoic acid.methyl ester Using the same method as in Example 15-(i), N-ethyl-5-(furan-3-yl)-2-methylaniline was reacted with the (2-([4-chloro-2-(methoxycarbonyl)phenyl]amino)-2-oxoethoxy)acetic acid obtained in Example 1-(i) to give 5-chloro-2-([(2-(ethyl[5-(furan-3-yl)-2-methylphenyl]amino)-2-oxoethoxy)acetyl]amino)benzoic acid.methyl ester (yield: 73%).
A mixture of two rotamers in the ratio ca.1:1
¹H-NMR (CDCl₃) δ: 1.19 (3H, t, J=7.2 Hz), 2.26 (3H, s), 3.32 (½×2H for one rotamer, dq, J=13.6, 7.2 Hz), 3.80 (1H, d, J=15.3 Hz), 3.90 (3H, s), 4.05-4.24 (½×2H for another rotamer, m), 4.06 (1H, d, J=15.3 Hz), 4.14 (1H, d, J=15.4 Hz), 4.21 (1H, d, J=15.4 Hz), 6.64 (1H, dd, J=1.8, 0.9 Hz), 7.21 (1H, d, J=1.7 Hz), 7.31 (1H, d, J=8.0 Hz), 7.36-7.51 (3H, m), 7.68-7.75 (1H, m), 7.98 (1H, d, J=2.6 Hz), 8.69 (1H, d, J=9.0 Hz), 11.6 (1H, s).

(iii) 5-Chloro-2-([[2-(ethyl[5-(furan-3-yl)-2-methylphenyl]amino)-2-oxoethoxy)acetyl]amino)benzoic acid Using the same method as in Example 1-(iii), the target 5-chloro-2-([[2-(ethyl[5-(furan-3-yl)-2-methylphenyl]amino)-2-oxoethoxy)acetyl]amino)benzoic acid was obtained from 5-chloro-2-([[2-(ethyl[5-(furan-3-yl)-2-methylphenyl]amino)-2-oxoethoxy)acetyl]amino)benzoic acid.methyl ester (yield: 86%).

A mixture of two rotamers in the ratio ca.1:1

$^1$H-NMR (DMSO-d$_6$) δ: 1.07 (3H, t, J=7.1 Hz), 2.20 (3H, s), 3.24 (½×2H for one rotamer, dq, J=13.5, 7.1 Hz), 3.76 (1H, d, J=15.4 Hz), 3.98 (½×2H for another rotamer, dq, J=13.6, 7.2 Hz), 4.06 (1H, d, J=15.4 Hz), 4.13 (2H, s), 6.96-7.03 (1H, m), 7.38 (1H, d, J=7.8 Hz), 7.49-7.62 (2H, m), 7.66 (1H, dd, J=9.0, 2.6 Hz), 7.70-7.75 (1H, m), 7.91 (1H, d, J=2.6 Hz), 8.21 (1H, s), 8.64 (1H, d, J=9.0 Hz), 11.7 (1H, s), 13.9 (1H, br).

Example 36

Production of 5-chloro-2-(([[2-(ethyl[5-(furan-3-yl)-2-methylphenyl]amino)-2-oxoethyl)sulfanyl]acetyl)amino)benzoic acid (36)

The target compound (36) was synthesized according to the following Steps (i) to (ii).

(i) 5-Chloro-2-(([[2-(ethyl[5-(furan-3-yl)-2-methylphenyl]amino)-2-oxoethyl)sulfanyl]acetyl)amino)benzoic acid.methyl ester Using the same method as in Example 15-(i), N-ethyl-5-(furan-3-yl)-2-methylaniline was reacted with the [(2-([4-chloro-2-(methoxycarbonyl)phenyl]amino)-2-oxoethyl)sulfanyl]acetic acid obtained in Example 12-(i) to give 5-chloro-2-(([[2-(ethyl[5-(furan-3-yl)-2-methylphenyl]amino)-2-oxoethyl)sulfanyl]acetyl)amino)benzoic acid.methyl ester (yield: 62%).

A mixture of two rotamers in the ratio ca.1:1

$^1$H-NMR (CDCl$_3$) δ: 1.12 (3H, t, J=7.1 Hz), 2.22 (3H, s), 3.10 (1H, d, J=14.4 Hz), 3.15 (1H, d, J=14.4 Hz), 3.27 (½×2H for one rotamer, dq, J=13.4, 7.1 Hz), 3.57 (2H, s), 3.89 (3H, s), 4.08 (½×2H for another rotamer, dq, J=13.4, 7.1 Hz), 6.67 (1H, dd, J=1.9 Hz, 0.9 Hz), 7.20-7.40 (3H, m), 7.42 (1H, dd, J=9.1 Hz, 2.6 Hz), 7.47 (1H, dd, J=1.9, 1.8 Hz), 7.74 (1H, dd, J=1.8, 0.9 Hz), 7.94 (1H, d, J=2.6 Hz), 8.61 (1H, d, J=9.1 Hz), 11.4 (1H, s).

(ii) 5-Chloro-2-(([[2-(ethyl[5-(furan-3-yl)-2-methylphenyl]amino)-2-oxoethyl)sulfanyl]acetyl)amino)benzoic acid Using the same method as in Example 1-(iii), the target 5-chloro-2-(([[2-(ethyl[5-(furan-3-yl)-2-methylphenyl]amino)-2-oxoethyl)sulfanyl]acetyl)amino)benzoic acid was obtained from 5-chloro-2-(([[2-(ethyl[5-(furan-3-yl)-2-methylphenyl]amino)-2-oxoethyl)sulfanyl]acetyl)amino)benzoic acid.methyl ester (yield: 92%).

A mixture of two rotamers in the ratio ca.1:1

$^1$H-NMR (DMSO-d$_6$) δ: 1.02 (3H, t, J=7.1 Hz), 2.14 (3H, s), 3.08 (1H, d, J=14.9 Hz), 3.12-3.34 (½×2H for one rotamer, m), 3.19 (1H, d, J=14.9 Hz), 3.50 (2H, s), 3.91 (½×2H for another rotamer, dq, J=13.5, 7.0 Hz), 6.94 (1H, s), 7.30 (1H, d, J=7.8 Hz), 7.43-7.56 (2H, m), 7.61 (1H, dd, J=9.0, 2.4 Hz), 7.72 (1H, s), 7.89 (1H, d, J=2.4 Hz), 8.15 (1H, s), 8.44 (1H, d, J=9.0 Hz), 11.4 (1H, s).

Example 37

Production of 5-chloro-2-[(5-(ethyl[5-(furan-3-yl)-2-methylphenyl]amino)-5-oxopentanoyl)amino]benzoic acid (37)

The target compound (37) was synthesized according to the following Steps (i) to (ii).

(i) 5-Chloro-2-[(5-(ethyl[5-(furan-3-yl)-2-methylphenyl]amino)-5-oxopentanoyl)amino]benzoic acid.methyl ester Using the same method as in Example 15-(i), N-ethyl-5-(furan-3-yl)-2-methylaniline was reacted with the 5-([4-chloro-2-(methoxycarbonyl)phenyl]amino)-5-oxopentanoic acid obtained in Example 31-(i) to give 5-chloro-2-[(5-(ethyl[5-(furan-3-yl)-2-methylphenyl]amino)-5-oxopentanoyl)amino]benzoic acid.methyl ester (yield: 58%).

A mixture of two rotamers in the ratio ca.1:1

$^1$H-NMR (CDCl$_3$) δ: 1.15 (3H, t, J=7.2 Hz), 1.85-2.22 (4H, m), 2.20 (3H, s), 2.38-2.50 (2H, m), 3.31 (½×2H for one rotamer, dq, J=13.3, 7.2 Hz), 3.91 (3H, s), 4.09 (½×2H for another rotamer, dq, J=13.3, 7.2 Hz), 6.63 (1H, dd, J=1.9, 0.9 Hz), 7.17 (1H, d, J=1.8 Hz), 7.26 (1H, d, J=7.9 Hz), 7.34 (1H, dd, J=7.9, 1.8 Hz), 7.40 (1H, dd, J=9.1, 2.6 Hz), 7.46 (1H, dd, J=1.9, 1.7 Hz), 7.67 (1H, dd, J=1.5, 0.9 Hz), 7.94 (1H, d, J=2.6 Hz), 8.60 (1H, d, J=9.1 Hz), 10.9 (1H, s).

(ii) 5-Chloro-2-[(5-(ethyl[5-(furan-3-yl)-2-methylphenyl]amino)-5-oxopentanoyl)amino]benzoic acid Using the same method as in Example 1-(iii), the target 5-chloro-2-[(5-(ethyl[5-(furan-3-yl)-2-methylphenyl]amino)-5-oxopentanoyl)amino]benzoic acid was obtained from 5-chloro-2-[(5-(ethyl[5-(furan-3-yl)-2-methylphenyl]amino)-5-oxopentanoyl)amino]benzoic acid.methyl ester (yield: 85%).

A mixture of two rotamers in the ratio ca.1:1

$^1$H-NMR (DMSO-d$_6$) δ: 1.04 (3H, t, J=7.1 Hz), 1.70-2.22 (4H, m), 2.14 (3H, s), 2.26-2.41 (2H, m), 3.25 (½×2H for one rotamer, dq, J=13.5, 7.1 Hz), 3.93 (½×2H for another rotamer, dq, J=13.5, 7.1 Hz), 6.95 (1H, s), 7.33 (1H, d, J=7.9 Hz), 7.43 (1H, s), 7.51 (1H, d, J=7.9 Hz), 7.59 (1H, dd, J=9.0, 2.4 Hz), 7.71 (1H, s), 7.88 (1H, d, J=2.4 Hz), 8.17 (1H, s), 8.40 (1H, d, J=9.0 Hz), 10.9 (1H, s).

Example 38

Production of 5-chloro-2-[((2-[(2'-methoxy-4-methylbiphenyl-3-yl)amino]-2-oxoethoxy)acetyl)amino]benzoic acid (38)

The target compound (38) was synthesized according to the following Steps (i) to (iii).

(i) 2-[((2-[(5-Bromo-2-methylphenyl)amino]-2-oxoethoxy)acetyl)amino]-5-chlorobenzoic acid.methyl ester Using the same method as in Example 15-(i), 5-bromo-2-methylaniline was reacted with the (2-([4-chloro-2-(methoxycarbonyl)phenyl]amino)-2-oxoethoxy)acetic acid obtained in Example 1-(i) to give 2-[((2-[(5-bromo-2-methylphenyl)amino]-2-oxoethoxy)acetyl)amino]-5-chlorobenzoic acid.methyl ester (yield: 92%).

$^1$H-NMR (CDCl$_3$) δ: 2.27 (3H, s), 3.67 (3H, s), 4.28 (2H, s), 4.31 (2H, s), 7.10 (1H, d, J=8.2 Hz), 7.27 (1H, dd, J=8.2, 2.0 Hz), 7.54 (1H, dd, J=9.1, 2.6 Hz), 7.84 (1H, d, J=2.0 Hz), 8.01 (1H, d, J=2.6 Hz), 8.73 (1H, br), 8.77 (1H, d, J=9.1 Hz), 11.9 (1H, br).

(ii) 5-Chloro-2-[((2-[(2'-methoxy-4-methylbiphenyl-3-yl)amino]-2-oxoethoxy)acetyl)amino]benzoic acid.methyl ester Using the same method as in Example 19-(ii), 2-methoxybenzene boronic acid was reacted with the 2-[((2-[(5-bromo-2-methylphenyl)amino]-2-oxoethoxy)acetyl)amino]-5-chlorobenzoic acid.methyl ester to give 5-chloro-2-[((2-[(2'-methoxy-4-methylbiphenyl-3-yl)amino]-2-oxoethoxy) acetyl)amino]benzoic acid.methyl ester (yield: 87%).

$^1$H-NMR (CDCl$_3$) δ: 2.35 (3H, s), 3.55 (3H, s), 3.79 (3H, s), 4.29 (2H, s), 4.33 (2H, s), 6.91-7.06 (2H, m), 7.20-7.38 (4H, m), 7.53 (1H, dd, J=9.0, 2.5 Hz), 7.77 (1H, d, J=1.3 Hz), 7.98 (1H, d, J=2.5 Hz), 8.75 (1H, s), 8.77 (1H, d, J=9.0 Hz), 12.0 (1H, s).

(iii) 5-Chloro-2-[((2-[(2'-methoxy-4-methylbiphenyl-3-yl)amino]-2-oxoethoxy)acetyl)amino]benzoic acid Using the same method as in Example 1-(iii), the target 5-chloro-2-[((2-[(2'-methoxy-4-methylbiphenyl-3-yl)amino]-2-oxoethoxy)acetyl)amino]benzoic acid was obtained from 5-chloro-2-[((2-[(2'-methoxy-4-methylbiphenyl-3-yl)amino]-2-oxoethoxy)acetyl)amino]benzoic acid.methyl ester (yield: 81%).

$^1$H-NMR (DMSO-d$_6$) δ: 2.25 (3H, s), 3.76 (3H, s), 4.33 (2H, s), 4.34 (2H, s), 6.95-7.16 (2H, m), 7.18-7.39 (4H, m), 7.62 (1H, s), 7.70 (1H, dd, J=9.0, 2.6 Hz), 7.97 (1H, d, J=2.6 Hz), 8.68 (1H, d, J=9.0 Hz), 9.25 (1H, s), 11.9 (1H, s).

Example 39

Production of 5-chloro-2-[((2-[(3'-methoxy-4-methylbiphenyl-3-yl)amino]-2-oxoethoxy)acetyl)amino]benzoic acid (39)

The target compound (39) was synthesized according to the following Steps (i) to (ii).

(i) 5-Chloro-2-[((2-[(3'-methoxy-4-methylbiphenyl-3-yl)amino]-2-oxoethoxy)acetyl)amino]benzoic acid.methyl ester Using the same method as in Example 19-(ii), 3-methoxybenzene boronic acid was reacted with the 2-[((2-[(5-bromo-2-methylphenyl)amino]-2-oxoethoxy)acetyl)amino]-5-chlorobenzoic acid.methyl ester obtained in Example 38-(i) to give 5-chloro-2-[((2-[(3'-methoxy-4-methylbiphenyl-3-yl)amino]-2-oxoethoxy)acetyl)amino]benzoic acid.methyl ester (yield: 63%).

$^1$H-NMR (CDCl$_3$) δ: 2.35 (3H, s), 3.54 (3H, s), 3.85 (3H, s), 4.30 (2H, s), 4.34 (2H, s), 6.88 (1H, ddd, J=8.1, 2.5, 0.9 Hz), 7.08-7.20 (2H, m), 7.27-7.43 (3H, m), 7.53 (1H, d, J=9.0, 2.6 Hz), 7.86 (1H, d, J=1.7 Hz), 7.99 (1H, d, J=2.6 Hz), 8.78 (1H, d, J=9.0 Hz), 8.79 (1H, s), 12.0 (1H, s).

(ii) 5-Chloro-2-[((2-[(3'-methoxy-4-methylbiphenyl-3-yl)amino]-2-oxoethoxy)acetyl)amino]benzoic acid Using the same method as in Example 1-(iii), the target 5-chloro-2-[((2-[(3'-methoxy-4-methylbiphenyl-3-yl)amino]-2-oxoethoxy)acetyl)amino]benzoic acid was obtained from 5-chloro-2-[((2-[(3'-methoxy-4-methylbiphenyl-3-yl)amino]-2-oxoethoxy)acetyl)amino]benzoic acid.methyl ester (yield: 67%).

$^1$H-NMR (DMSO-d$_6$) δ: 2.26 (3H, s), 3.82 (3H, s), 4.34 (2H, s), 4.36 (2H, s), 6.93 (1H, m), 7.10-7.23 (2H, m), 7.28-7.48 (3H, m), 7.70 (1H, dd, J=9.0, 2.6 Hz), 7.80 (1H, d, J=1.6 Hz), 7.97 (1H, d, J=2.6 Hz), 8.68 (1H, d, J=9.0 Hz), 9.32 (1H, s), 11.9 (1H, s).

Example 40

Production of 5-chloro-2-[((2-[(4'-methoxy-4-methylbiphenyl-3-yl)amino]-2-oxoethoxy)acetyl)amino] benzoic acid (40)

The target compound (40) was synthesized according to the following Steps (i) to (ii).

(i) 5-Chloro-2-[((2-[(4'-methoxy-4-methylbiphenyl-3-yl)amino]-2-oxoethoxy)acetyl)amino]benzoic acid.methyl ester Using the same method as in Example 19-(ii), 4-methoxybenzene boronic acid was reacted with the 2-[((2-[(5-bromo-2-methylphenyl)amino]-2-oxoethoxy)acetyl)amino]-5-chlorobenzoic acid.methyl ester obtained in Example 38-(i) to give 5-chloro-2-[((2-[(4'-methoxy-4-methylbiphenyl-3-yl)amino]-2-oxoethoxy)acetyl)amino]benzoic acid.methyl ester (yield: 84%).

$^1$H-NMR (CDCl$_3$) δ: 2.34 (3H, s), 3.54 (3H, s), 3.84 (3H, s), 4.30 (2H, s), 4.34 (2H, s), 6.90-7.00 (2H, m), 7.27 (1H, d, J=7.9 Hz), 7.35 (1H, dd, J=7.9, 1.8 Hz), 7.47-7.56 (2H, m), 7.54 (1H, dd, J=9.0, 2.6 Hz), 7.83 (1H, d, J=1.8 Hz), 7.99 (1H, d, J=2.6 Hz), 8.77 (1H, s), 8.78 (1H, d, J=9.0 Hz), 12.0 (1H, s).

(ii) 5-Chloro-2-[((2-[(4'-methoxy-4-methylbiphenyl-3-yl)amino]-2-oxoethoxy)acetyl)amino]benzoic acid Using the same method as in Example 1-(iii), the target 5-chloro-2-[((2-[(4'-methoxy-4-methylbiphenyl-3-yl)amino]-2-oxoethoxy)acetyl)amino]benzoic acid was obtained from 5-chloro-2-[((2-[(4'-methoxy-4-methylbiphenyl-3-yl)amino]-2-oxoethoxy)acetyl)amino]benzoic acid.methyl ester (yield: 89%).

$^1$H-NMR (DMSO-d$_6$) δ: 2.24 (3H, s), 3.79 (3H, s), 4.34 (2H, s), 4.35 (2H, s), 6.96-7.07 (2H, m), 7.29 (1H, d, J=8.0 Hz), 7.37 (1H, dd, J=8.0, 1.7 Hz), 7.50-7.60 (2H, m), 7.70 (1H, dd, J=9.0, 2.6 Hz), 7.75 (1H, d, J=1.7 Hz), 7.97 (1H, d, J=2.6 Hz), 8.68 (1H, d, J=9.0 Hz), 9.29 (1H, s), 11.9 (1H, s).

Example 41

Production of 2-([(2-([5-(1,3-benzodioxol-5-yl)-2-methylphenyl]amino)-2-oxoethoxy)acetyl]amino)-5-chlorobenzoic acid (41)

The target compound (41) was synthesized according to the following step.

Using the same method as in Example 19-(ii), 3,4-(methylenedioxy)phenyl boronic acid was reacted with the 2-[((2-

[(5-bromo-2-methylphenyl)amino]-2-oxoethoxy)acetyl)amino]-5-chlorobenzoic acid.methyl ester obtained in Example 38-(i) to give 2-([(2-([5-(1,3-benzodioxol-5-yl)-2-methylphenyl]amino)-2-oxoethoxy)acetyl]amino)-5-chlorobenzoic acid.methyl ester. Thereafter, using the same method as in Example 1-(iii), the target 2-([(2-([5-(1,3-benzodioxol-5-yl)-2-methylphenyl]amino)-2-oxoethoxy)acetyl]amino)-5-chlorobenzoic acid was obtained (yield: 58%).

$^1$H-NMR (DMSO-$d_6$) δ: 2.24 (3H, s), 4.34 (2H, s), 4.35 (2H, s), 6.06 (2H, s), 6.99 (1H, d, J=8.1 Hz), 7.09 (1H, dd, J=8.1, 1.8 Hz), 7.17 (1H, d, J=1.8 Hz), 7.28 (1H, d, J=8.0 Hz), 7.36 (1H, dd, J=8.0, 1.8 Hz), 7.70 (1H, dd, J=9.0, 2.7 Hz), 7.73 (1H, s), 7.97 (1H, d, J=2.7 Hz), 8.68 (1H, d, J=9.0 Hz), 9.29 (1H, s), 11.9 (1H, s).

Example 42

Production of 5-chloro-2-([(2-([2-methyl-5-(quinolin-8-yl)phenyl]amino)-2-oxoethoxy)acetyl]amino)benzoic acid.hydrochloride (42)

The target compound (42) was synthesized according to the following Steps (i) to (ii).

(i) 5-Chloro-2-([(2-([2-methyl-5-(quinolin-8-yl)phenyl]amino)-2-oxoethoxy)acetyl]amino)benzoic acid.methyl ester Using the same method as in Example 19-(ii), 8-quinoline boronic acid was reacted with the 2-[((2-[(5-bromo-2-methylphenyl)amino]-2-oxoethoxy)acetyl)amino]-5-chlorobenzoic acid.methyl ester obtained in Example 38-(i) to give 5-chloro-2-([(2-([2-methyl-5-(quinolin-8-yl)phenyl]amino)-2-oxoethoxy)acetyl]amino)benzoic acid.methyl ester (yield: 53%).

$^1$H-NMR (CDCl$_3$) δ: 2.40 (3H, s), 3.56 (3H, s), 4.29 (2H, s), 4.33 (2H, s), 7.35 (1H, d, J=7.9 Hz), 7.40 (1H, dd, J=8.3, 4.2 Hz), 7.47-7.64 (3H, m), 7.76 (1H, dd, J=7.2, 1.6 Hz), 7.80 (1H, dd, J=8.0, 1.6 Hz), 7.95 (1H, d, J=1.7 Hz), 7.97 (1H, d, J=2.6 Hz), 8.19 (1H, dd, J=8.3, 1.9 Hz), 8.76 (1H, d, J=9.0 Hz), 8.76 (1H, s), 8.91 (1H, dd, J=4.2, 1.9 Hz), 12.0 (1H, s).

(ii) 5-Chloro-2-([(2-([2-methyl-5-(quinolin-8-yl)phenyl]amino)-2-oxoethoxy)acetyl]amino)benzoic acid.hydrochloride Using the same method as in Example 4-(ii), the target 5-chloro-2-([(2-([2-methyl-5-(quinolin-8-yl)phenyl]amino)-2-oxoethoxy)acetyl]amino)benzoic acid.hydrochloride was obtained from 5-chloro-2-([(2-([2-methyl-5-(quinolin-8-yl)phenyl]amino)-2-oxoethoxy)acetyl]amino)benzoic acid.methyl ester (yield: 66%).

$^1$H-NMR (DMSO-$d_6$) δ: 2.31 (3H, s), 4.33 (2H, s), 4.35 (2H, s), 7.34 (1H, d, J=7.8 Hz), 7.42 (1H, dd, J=7.8, 1.7 Hz), 7.57 (1H, dd, J=8.3, 4.2 Hz), 7.62-7.78 (3H, m), 7.81 (1H, d, 1.7 Hz), 7.96 (1H, d, J=2.7 Hz), 8.00 (1H, dd, J=8.3, 1.8 Hz), 8.44 (1H, dd, J=8.3, 1.8 Hz), 8.68 (1H, d, J=9.0 Hz), 8.89 (1H, dd, J=4.2, 1.8 Hz), 9.30 (1H, s), 11.9 (1H, s).

Example 43

Production of 2-([(2-([3'-(acetylamino)-4-methylbiphenyl-3-yl]amino)-2-oxoethoxy)acetyl]amino)-5-chlorobenzoic acid (43)

The target compound (43) was synthesized according to the following Steps (i) to (iii).

(i) N-(3'-amino-4'-methylbiphenyl-3-yl)acetamido 0.67 g (3.61 mmol) of 5-bromo-2-methylaniline and 1.14 g (4.37 mmol) of 3-acetamidophenyl boronic acid pinacol ester were dissolved in 15 mL of DME. Subsequently, 5 mL of a 2M aqueous sodium carbonate solution, and then 417 mg (0.36 mmol) of tetrakis(triphenyl phosphine)palladium (0) were added to the mixture, and the mixture was heated under reflux for 7 hours. After completion of the reaction, ethyl acetate and water were added to the reaction mixture. The organic layer was separated, washed with a saturated sodium chloride solution, and dried over anhydrous magnesium sulfate. Filtration was conducted, and the filtrate was condensed. The resulting crude product was separated and purified using silica gel column chromatography to give N-(3'-amino-4'-methylbiphenyl-3-yl)acetamido (yield: 74%).

$^1$H-NMR (CDCl$_3$) δ: 2.19 (3H, s), 2.20 (3H, s), 3.68 (2H, br), 6.88-6.94 (2H, m), 7.10 (1H, d, J=7.4 Hz), 7.30-7.69 (5H, m).

(ii) 2-([(2-([3'-(Acetylamino)-4-methylbiphenyl-3-yl]amino)-2-oxoethoxy)acetyl]amino)-5-chlorobenzoic acid.methyl ester Using the same method as in Example 15-(i), N-(3'-amino-4'-methylbiphenyl-3-yl)acetamido was reacted with the (2-([4-chloro-2-(methoxycarbonyl)phenyl]amino)-2-oxoethoxy)acetic acid obtained in Example 1-(i) to give 2-([(2-([3'-(acetylamino)-4-methylbiphenyl-3-yl]amino)-2-oxoethoxy)acetyl]amino)-5-chlorobenzoic acid.methyl ester (yield: 51%).

$^1$H-NMR (DMSO-$d_6$) δ: 2.06 (3H, s), 2.28 (3H, s), 3.78 (3H, s), 4.34 (2H, s), 4.38 (2H, s), 7.23-7.41 (4H, m), 7.52-7.61 (1H, m), 7.72 (1H, s), 7.73 (1H, dd, J=9.0, 2.6 Hz), 7.87 (1H, s), 7.94 (1H, d, J=2.6 Hz), 8.60 (1H, d, J=8.6 Hz), 9.39 (1H, s), 10.0 (1H, s), 11.4 (1H, s).

(iii) 2-([(2-([3'-(Acetylamino)-4-methylbiphenyl-3-yl]amino)-2-oxoethoxy)acetyl]amino)-5-chlorobenzoic acid Using the same method as in Example 1-(iii), the target 2-([(2-([3'-(acetylamino)-4-methylbiphenyl-3-yl]amino)-2-oxoethoxy)acetyl]amino)-5-chlorobenzoic acid was obtained from 2-([(2-([3'-(acetylamino)-4-methylbiphenyl-3-yl]amino)-2-oxoethoxy)acetyl]amino)-5-chlorobenzoic acid.methyl ester (yield: 82%).

$^1$H-NMR (DMSO-$d_6$) δ: 2.06 (3H, s), 2.26 (3H, s), 4.34 (2H, s), 4.36 (1H, s), 7.23-7.43 (4H, m), 7.53-7.62 (1H, m), 7.71 (1H, dd, J=9.0, 2.7 Hz), 7.77 (1H, s), 7.86 (1H, s), 7.97 (1H, d, J=2.7 Hz), 8.68 (1H, d, J=9.0 Hz), 9.32 (1H, s), 10.0 (1H, s), 11.9 (1H, s).

Example 44

Production of 2-([(2-([4'-(acetylamino)-4-methylbiphenyl-3-yl]amino)-2-oxoethoxy)acetyl]amino)-5-chlorobenzoic acid (44)

The target compound (44) was synthesized according to the following Steps (i) to (iii).

(i) N-(3'-amino-4'-methylbiphenyl-4-yl)acetamido 0.60 g (3.20 mmol) of 5-bromo-2-methylaniline and 1.01 g (4.87 mmol) of 4-acetamidophenylboronic acid pinacol ester were dissolved in 15 mL of DME. Next, 5 mL of a 2M aqueous sodium carbonate solution, and then 369 mg (0.32 mmol) of tetrakis (triphenyl phosphine)palladium (0) were added and heated under reflux for 7 hours. After completion of the reaction, ethyl acetate and water were added to the reaction mixture. The organic layer was separated, washed with a saturated sodium chloride solution, and dried over anhydrous magnesium sulfate. Filtration was then carried out, and the filtrate was condensed. The resulting crude product was separated and purified using silica gel column chromatography to give N-(3'-amino-4'-methylbiphenyl-4-yl)acetamido (yield: 66%).

$^1$H-NMR (CDCl$_3$) δ: 2.19 (3H, s), 2.20 (3H, s), 3.68 (2H, br), 6.88-6.94 (2H, m), 7.10 (1H, d, J=7.4 Hz), 7.29-7.32 (1H, m), 7.48-7.55 (4H, m).

(ii) 2-([(2-([4'-(Acetylamino)-4-methylbiphenyl-3-yl]amino)-2-oxoethoxy)acetyl]amino)-5-chlorobenzoic acid.methyl ester Using the same method as in Example 15-(i), N-(3'-amino-4'-methylbiphenyl-4-yl)acetamido was reacted with the (2-([4-chloro-2-(methoxycarbonyl)phenyl]amino)-2-oxoethoxy)acetic acid obtained in Example 1-(i) to give 2-([(2-([4'-(acetylamino)-4-methylbiphenyl-3-yl]amino)-2-oxoethoxy)acetyl]amino)-5-chlorobenzoic acid.methyl ester (yield: 76%).

$^1$H-NMR (DMSO-d$_6$) δ: 2.07 (3H, s), 2.26 (3H, s), 3.78 (3H, s), 4.34 (2H, s), 4.37 (2H, s), 7.31 (1H, d, J=8.0 Hz), 7.41 (1H, dd, J=8.0, 1.7 Hz), 7.50-7.73 (5H, m), 7.73 (1H, dd, J=9.0, 2.6 Hz), 7.94 (1H, d, J=2.6 Hz), 8.60 (1H, d, J=9.0 Hz), 9.38 (1H, s), 10.0 (1H, s), 11.5 (1H, s).

(iii) 2-([(2-([4'-(Acetylamino)-4-methylbiphenyl-3-yl]amino)-2-oxoethoxy)acetyl]amino)-5-chlorobenzoic acid Using the same method as in Example 1-(iii), the target 2-([(2-([4'-(acetylamino)-4-methylbiphenyl-3-yl]amino)-2-oxoethoxy)acetyl]amino)-5-chlorobenzoic acid was obtained from 2-([(2-([4'-(acetylamino)-4-methylbiphenyl-3-yl]amino)-2-oxoethoxy)acetyl]amino)-5-chlorobenzoic acid.methyl ester (yield: 85%).

$^1$H-NMR (DMSO-d$_6$) δ: 2.07 (3H, s), 2.25 (3H, s), 4.34 (2H, s), 4.36 (2H, s), 7.30 (1H, d, J=8.0 Hz), 7.40 (1H, dd, J=8.0, 1.7 Hz), 7.51-7.80 (6H, m), 7.97 (1H, d, J=2.6 Hz), 8.68 (1H, d, J=9.0 Hz), 9.31 (1H, s), 10.0 (1H s), 11.9 (1H, s).

Example 45

Production of 5-chloro-2-([[(3-(furan-3-yl)phenyl]amino) (oxo)acetyl]amino)benzoic acid (45)

The target compound (45) was synthesized according to the following Steps (i) to (iv).

(i) ([3-(Furan-3-yl)phenyl]amino)(oxo)acetic acid.ethyl ester

Using the same method as in Example 20-(i), 3-(furan-3-yl)aniline was reacted with chloroglyoxylic acid ethyl to give 1.41 g of ([3-(furan-3-yl)phenyl]amino) (oxo)acetic acid.ethyl ester (yield: 98%).

$^1$H-NMR (CDCl$_3$) δ: 1.43 (3H, t, J=7.1 Hz), 4.42 (2H, q, J=7.1 Hz), 6.70 (1H, dd, J=1.8, 1.0 Hz), 7.27-7.42 (2H, m), 7.46-7.54 (2H, m), 7.75 (1H, t, J=1.0 Hz), 7.83 (1H, J=1.8 Hz), 8.91 (1H, s).

(ii) ([3-(Furan-3-yl)phenyl]amino)(oxo)acetic acid

Using the same method as in Example 1-(iii), 0.92 g of ([3-(furan-3-yl)phenyl]amino)(oxo)acetic acid was obtained from ([3-(furan-3-yl)phenyl]amino)(oxo)acetic acid.ethyl ester (yield: 74%).

$^1$H-NMR (DMSO-d$_6$) δ: 6.84-6.89 (1H, m), 7.31-7.43 (2H, m), 7.62-7.73 (1H, m), 7.76 (1H, t, J=1.7 Hz), 7.94-7.99 (1H, m), 8.09-8.14 (1H, m), 10.7 (1H, s).

(iii) 5-Chloro-2-([[(3-(furan-3-yl)phenyl]amino) (oxo)acetyl]amino)benzoic acid.methyl ester Using the same method as in Example 15-(i), 2-amino-5-chlorobenzoic acid methyl was reacted with ([3-(furan-3-yl)phenyl]amino)(oxo)acetic acid to give 5-chloro-2-([[(3-(furan-3-yl)phenyl]amino)(oxo)acetyl]amino)benzoic acid.methyl ester (yield: 89%).

$^1$H-NMR (CDCl$_3$) δ: 4.02 (3H, s), 6.69-6.75 (1H, m), 7.27-7.45 (2H, m), 7.46-7.51 (1H, m), 7.51-7.59 (1H, m), 7.59 (1H, dd, J=9.0, 2.6 Hz), 7.54-7.80 (1H, m), 7.93-7.99 (1H, m), 8.08 (1H, d, J=2.6 Hz), 8.72 (1H, d, J=2.6 Hz), 9.29 (1H, s), 12.8 (1H, s).

(iv) 5-Chloro-2-([[(3-(furan-3-yl)phenyl]amino) (oxo)acetyl]amino)benzoic acid

Using the same method as in Example 1-(iii), the target 5-chloro-2-([[(3-(furan-3-yl)phenyl]amino)(oxo)acetyl]amino)benzoic acid was obtained from 5-chloro-2-([[(3-(furan-3-yl)phenyl]amino)(oxo)acetyl]amino)benzoic acid.methyl ester (yield: 29%).

$^1$H-NMR (DMSO-d$_6$) δ: 6.88-6.92 (1H, m), 7.34-7.47 (2H, m), 7.74-7.84 (3H, m), 8.02 (1H, d, J=2.6 Hz), 8.06-8.11 (1H, m), 8.15 (1H, s), 8.72 (1H, d, J=9.0 Hz), 10.9 (1H, s), 12.7 (1H, s).

Example 46

Production of 5-chloro-2-(([(2-([3-(furan-3-yl)phenyl]amino)-2-oxoethyl)sulfanyl]acetyl)amino)benzoic acid (46)

The target compound (46) was synthesized according to the following Steps (i) to (ii).

(i) 5-Chloro-2-(([(2-([3-(furan-3-yl)phenyl]amino)-2-oxoethyl)sulfanyl]acetyl)amino)benzoic acid.methyl ester Using the same method as in Example 15-(ii), 3-(furan-3-yl)aniline was reacted with the [(2-([4-chloro-2-(methoxycarbonyl)phenyl]amino)-2-oxoethyl)sulfanyl]acetic acid obtained in Example 12-(i) to give 5-chloro-2-(([(2-([3-(furan-3-yl)phenyl]amino)-2-oxoethyl)sulfanyl]acetyl)amino) benzoic acid.methyl ester (yield: 65%).

$^1$H-NMR (CDCl$_3$) δ: 3.50 (2H, s), 3.53 (2H, s), 3.92 (3H, s), 6.65-6.69 (1H, m), 7.17-7.32 (2H, m), 7.36-7.49 (3H, m), 7.65-7.74 (2H, m), 7.93 (1H, J=2.6 Hz), 8.60 (1H, d, J=9.1 Hz), 8.87 (1H, s), 11.5 (1H, s).

(ii) 5-Chloro-2-(([(2-([3-(furan-3-yl)phenyl]amino)-2-oxoethyl)sulfanyl]acetyl)amino)benzoic acid Using the same method as in Example 1-(iii), the target 5-chloro-2-(([(2-([3-(furan-3-yl)phenyl]amino)-2-oxoethyl)sulfanyl]acetyl)amino)benzoic acid was obtained from 5-chloro-2-(([(2-([3-(furan-3-yl)phenyl]amino)-2-oxoethyl) sulfanyl]acetyl)amino)benzoic acid.methyl ester (yield: 82%).

$^1$H-NMR (DMSO-d$_6$) δ: 3.45 (2H, s), 3.65 (2H, s), 6.76-6.82 (1H, m), 7.21-7.43 (3H, m), 7.60 (1H, dd, J=9.0, 2.7 Hz), 7.68 (1H, s), 7.74 (1H, t, J=1.7 Hz), 7.87 (1H, d, J=2.7 Hz), 8.05 (1H, s), 8.51 (1H, d, J=9.0 Hz), 10.1 (1H, s), 11.6 (1H, s).

Example 47

Production of 5-chloro-2-([(2-([3-(2,6-dimethoxypyridin-3-yl)phenyl]amino)-2-oxoethoxy)acetyl]amino) benzoic acid (47)

The target compound (47) was synthesized according to the following Steps (i) to (ii).

(i) 5-Chloro-2-([(2-([3-(2,6-dimethoxypyridin-3-yl) phenyl]amino)-2-oxoethoxy)acetyl]amino)benzoic acid.methyl ester Using the same method as in Example 19-(ii), 2,6-dimethoxy-3-pyridine boronic acid was reacted with the 2-[((2-[(3-bromophenyl)amino]-2-oxoethoxy)acetyl) amino]-5-chlorobenzoic acid.methyl ester obtained in Example 19-(i) to give 5-chloro-2-([(2-([3-(2,6-dimethoxypyridin-3-yl)phenyl]amino)-2-oxoethoxy)acetyl]amino) benzoic acid.methyl ester (yield: 51%).

$^1$H-NMR (CDCl$_3$) δ: 3.69 (3H, s), 3.95 (3H, s), 3.97 (3H, s), 4.27 (2H, s), 4.29 (2H, s), 6.39 (1H, d, J=8.1 Hz), 7.31 (1H, dt, J=7.8, 1.7 Hz), 7.37 (1H, t, J=7.8 Hz), 7.54 (1H, dd, J=9.1, 2.6 Hz), 7.57 (1H, d, J=8.1 Hz), 7.69 (1H, dt, J=7.8, 1.7 Hz), 7.84 (1H, t, J=1.7 Hz), 8.02 (1H, d, J=2.6 Hz), 8.78 (1H, d, J=9.1 Hz), 8.82 (1H, s), 11.9 (1H, s).

(ii) 5-Chloro-2-([(2-([3-(2,6-dimethoxypyridin-3-yl) phenyl]amino)-2-oxoethoxy)acetyl]amino)benzoic acid Using the same method as in Example 1-(iii), the target 5-chloro-2-([(2-([3-(2,6-dimethoxypyridin-3-yl)phenyl] amino)-2-oxoethoxy)acetyl]amino)benzoic acid was obtained from 5-chloro-2-([(2-([3-(2,6-dimethoxypyridin-3-yl)phenyl]amino)-2-oxoethoxy)acetyl]amino)benzoic acid.methyl ester (yield: 91%).

$^1$H-NMR (DMSO-d$_6$) δ: 3.90 (3H, s), 3.91 (3H, s), 4.30 (2H, s), 4.32 (2H, s), 6.49 (1H, d, J=8.1 Hz), 7.22 (1H, dt, J=7.8, 1.6 Hz), 7.35 (1H, t, J=7.8 Hz), 7.59-7.67 (1H, m), 7.67 (1H, d, J=8.1 Hz), 7.70 (1H, dd, J=9.0, 2.7 Hz), 7.81 (1H, t, J=1.6 Hz), 7.97 (1H, d, J=2.7 Hz), 8.69 (1H, d, J=9.0 Hz), 9.82 (1H, s), 11.9 (1H, s).

Example 48

Production of 5-chloro-2-([(2-oxo-2-([3-(1H-pyrrol-1-yl)phenyl]amino)ethoxy)acetyl]amino)benzoic acid.sodium salt (48)

The target compound (48) was synthesized according to the following Steps (i) to (ii).

(i) 5-Chloro-2-([(2-oxo-2-([3-(1H-pyrrol-1-yl)phenyl]amino)ethoxy)acetyl]amino)benzoic acid.methyl ester Using the same method as in Example 15-(i), 3-(1H-pyrrol-1-yl)aniline was reacted with the (2-([4-chloro-2-(methoxycarbonyl)phenyl]amino)-2-oxoethoxy)acetic acid obtained in Example 1-(i) to give 5-chloro-2-([(2-oxo-2-([3-(1H-pyrrol-1-yl)phenyl]amino)ethoxy)acetyl]amino)benzoic acid.methyl ester (yield: 60%).

$^1$H-NMR (CDCl$_3$) δ: 3.71 (3H, s), 4.27 (2H, s), 4.29 (2H, s), 6.34 (2H, t, J=2.2 Hz), 7.08 (2H, t, J=2.2 Hz), 7.19 (1H, ddd, J=8.1, 2.0, 0.9 Hz), 7.38 (1H, t, J=8.1 Hz), 7.55 (1H, dd, J=9.0, 2.6 Hz), 7.55-7.63 (1H, m), 7.90 (1H, t, J=2.0 Hz), 8.04 (1H, d, J=2.6 Hz), 8.79 (1H, d, J=9.0 Hz), 8.89 (1H, s), 11.9 (1H, s).

(ii) 5-Chloro-2-([(2-oxo-2-([3-(1H-pyrrol-1-yl)phenyl]amino)ethoxy)acetyl]amino)benzoic acid.sodium salt Using the same method as in Example 7-(ii), the target 5-chloro-2-([(2-oxo-2-([3-(1H-pyrrol-1-yl)phenyl]amino) ethoxy)acetyl]amino)benzoic acid.sodium salt was obtained from 5-chloro-2-([(2-oxo-2-([3-(1H-pyrrol-1-yl)phenyl] amino)ethoxy)acetyl]amino)benzoic acid.methyl ester (yield: 93%).

$^1$H-NMR (DMSO-d$_6$) δ: 4.17 (2H, s), 4.25 (2H, s), 6.26 (2H, t, J=2.1 Hz), 7.27-7.44 (2H, m), 7.39 (1H, dd, J=8.8, 2.7 Hz), 7.72 (2H, t, J=2.1 Hz), 8.04 (1H, d, J=2.7 Hz), 8.11-8.19 (1H, m), 8.44-8.51 (1H, m), 8.52 (1H, d, J=8.8 Hz), 10.5 (1H, s), 15.1 (1H, s).

Example 49

Production of 5-chloro-2-([(2-([2-fluoro-5-(furan-3-yl)phenyl]amino)-2-oxoethoxy)acetyl]amino)benzoic acid (49)

The target compound (49) was synthesized according to the following Steps (i) to (ii).

(i) 5-Chloro-2-([(2-([2-fluoro-5-(furan-3-yl)phenyl] amino)-2-oxoethoxy)acetyl]amino)benzoic acid.methyl ester Using the same method as in Example 15-(i), 2-fluoro-5-(furan-3-yl)aniline was reacted with the (2-([4-chloro-2-(methoxycarbonyl)phenyl]amino)-2-oxoethoxy)acetic acid obtained in Example 1-(i) to give 5-chloro-2-([(2-([2-fluoro-5-(furan-3-yl)phenyl]amino)-2-oxoethoxy)acetyl]amino) benzoic acid.methyl ester (yield: 87%).

$^1$H-NMR (CDCl$_3$) δ: 3.72 (3H, s), 4.29 (2H, s), 4.34 (2H, s), 6.68 (1H, dd, J=1.8, 0.8 Hz), 7.11 (1H, dd, J=10.2, 8.5 Hz), 7.25 (1H, ddd, J=8.5, 4.9, 2.2 Hz), 7.47 (1H, t, J=1.8 Hz), 7.53 (1H, dd, J=9.0, 2.6 Hz), 7.72 (1H, t, J=0.8 Hz), 8.02 (1H, d, J=2.6 Hz), 8.31 (1H, dd, J=7.4, 2.2 Hz), 8.77 (1H, d, J=9.0 Hz), 8.87 (1H, s), 12.0 (1H, s).

(ii) 5-Chloro-2-([(2-([2-fluoro-5-(furan-3-yl)phenyl] amino)-2-oxoethoxy)acetyl]amino)benzoic acid Using the same method as in Example 1-(iii), the target 5-chloro-2-([(2-([2-fluoro-5-(furan-3-yl)phenyl]amino)-2-oxoethoxy)acetyl]amino)benzoic acid was obtained from 5-chloro-2-([(2-([2-fluoro-5-(furan-3-yl)phenyl]amino)-2-oxoethoxy)acetyl]amino)benzoic acid.methyl ester (yield: 60%).

$^1$H-NMR (DMSO-d$_6$) δ: 4.32 (2H, s), 4.38 (2H, s), 6.91 (1H, dd, J=1.7, 0.6 Hz), 7.31 (1H, dd, J=10.4, 8.6 Hz), 7.46 (1H, ddd, J=8.6, 4.8, 2.3 Hz), 7.71 (1H, dd, J=9.0, 2.6 Hz), 7.76 (1H, t, J=1.7 Hz), 7.97 (1H, d, J=2.6 Hz), 8.01 (1H, dd, J=7.4, 2.3 Hz), 8.15 (1H, t, J=0.6 Hz), 8.69 (1H, d, J=9.0 Hz), 9.70 (1H, s), 11.9 (1H, s).

Example 50

Production of 5-chloro-2-([(2-([4-fluoro-3-(furan-3-yl)phenyl]amino)-2-oxoethoxy)acetyl]amino)benzoic acid (50)

The target compound (50) was synthesized according to the following Steps (i) to (iii).

(i) 4-Fluoro-3-(furan-3-yl)aniline

Using the same method as in Example 19-(ii), 3-furanboronic acid was reacted with the 3-bromo 4-fluoro-aniline to give 4-fluoro-3-(furan-3-yl)aniline (yield: 65%).
$^1$H-NMR (CDCl$_3$) δ: 3.58 (2H, br), 6.52 (1H, ddd, J=8.7, 3.9, 3.0 Hz), 6.69-6.74 (1H, m), 6.80 (1H, dd, J=6.2, 3.0 Hz), 6.92 (1H, dd, J=10.6, 8.7 Hz), 7.48 (1H, t, J=1.7 Hz), 7.82-7.89 (1H, m).

(ii) 5-Chloro-2-([(2-([4-fluoro-3-(furan-3-yl)phenyl]amino)-2-oxoethoxy)acetyl]amino)benzoic acid.methyl ester Using the same method as in Example 15-(i), 4-fluoro-3-(furan-3-yl)aniline was reacted with the (2-([4-chloro-2-(methoxycarbonyl)phenyl]amino)-2-oxoethoxy)acetic acid obtained in Example 1-(i) to give 5-chloro-2-([(2-([4-fluoro-3-(furan-3-yl)phenyl]amino)-2-oxoethoxy)acetyl]amino)benzoic acid.methyl ester (yield: 52%).
$^1$H-NMR (CDCl$_3$) δ: 3.74 (3H, s), 4.27 (2H, s), 4.29 (2H, s), 6.73-6.79 (1H, m), 7.10 (1H, dd, J=10.4, 8.9 Hz), 7.46-7.59 (2H, m), 7.55 (1H, dd, J=9.0, 2.5 Hz), 7.85-7.94 (2H, m), 8.04 (1H, d, J=2.5 Hz), 8.79 (1H, d, J=9.0 Hz), 8.88 (1H, s), 11.9 (1H, s).

(iii) 5-Chloro-2-([(2-([4-fluoro-3-(furan-3-yl)phenyl]amino)-2-oxoethoxy)acetyl]amino)benzoic acid Using the same method as in Example 1-(iii), the target 5-chloro-2-([(2-([4-fluoro-3-(furan-3-yl)phenyl]amino)-2-oxoethoxy)acetyl]amino)benzoic acid was obtained from 5-chloro-2-([(2-([4-fluoro-3-(furan-3-yl)phenyl]amino)-2-oxoethoxy)acetyl]amino)benzoic acid.methyl ester (yield: 96%).
$^1$H-NMR (DMSO-d$_6$) δ: 4.31 (2H, s), 4.32 (2H, s), 6.83-6.90 (1H, m), 7.26 (1H, dd, J=10.8, 8.9 Hz), 7.63 (1H, ddd, J=8.9, 4.5, 2.7 Hz), 7.71 (1H, dd, J=9.0, 2.7 Hz), 7.83 (1H, t, J=1.7 Hz), 7.94 (1H, dd, J=6.9, 2.7 Hz), 7.98 (1H, d, J=2.7 Hz), 8.06-8.12 (1H, m), 8.70 (1H, d, J=9.0 Hz), 9.88 (1H, s), 11.9 (1H, s).

Example 51

Production of 2-([(2-([3-(1-benzofuran-2-yl)phenyl]amino)-2-oxoethoxy)acetyl]amino)-5-chlorobenzoic acid (51)

The target compound (51) was synthesized according to the following Steps (i) to (ii).

(i) 2-([(2-([3-(1-Benzofuran-2-yl)phenyl]amino)-2-oxoethoxy)acetyl]amino)-5-chlorobenzoic acid.methyl ester Using the same method as in Example 19-(ii), 2-benzofuran boronic acid was reacted with the 2-[((2-[(3-bromophenyl)amino]-2-oxoethoxy)acetyl)amino]-5-chlorobenzoic acid.methyl ester obtained in Example 19-(i) to give 2-([(2-([3-(1-benzofuran-2-yl)phenyl]amino)-2-oxoethoxy)acetyl]amino)-5-chlorobenzoic acid.methyl ester (yield: 44%).
$^1$H-NMR (CDCl$_3$) δ: 3.80 (3H, s), 4.26 (2H, s), 4.30 (2H, s), 7.04 (1H, s), 7.18-7.67 (7H, m), 7.76-7.85 (1H, m), 8.03 (1H, d, J=2.6 Hz), 8.16 (1H, t, J=1.8 Hz), 8.79 (1H, d, J=9.0 Hz), 8.92 (1H, s), 11.9 (1H, s).

(ii) 2-([(2-([3-(1-Benzofuran-2-yl)phenyl]amino)-2-oxoethoxy)acetyl]amino)-5-chlorobenzoic acid Using the same method as in Example 1-(iii), the target 2-([(2-([3-(1-benzofuran-2-yl)phenyl]amino)-2-oxoethoxy)acetyl]amino)-5-chlorobenzoic acid was obtained from 2-([(2-([3-(1-benzofuran-2-yl)phenyl]amino)-2-oxoethoxy)acetyl]amino)-5-chlorobenzoic acid.methyl ester (yield: 98%).
$^1$H-NMR (DMSO-d$_6$) δ: 4.33 (2H, s), 4.36 (2H, s), 7.22-7.36 (3H, m), 7.39 (1H, s), 7.47 (1H, t, J=8.0 Hz), 7.59-7.76 (5H, m), 7.99 (1H, d, J=2.6 Hz), 8.30 (1H, t, J=1.6 Hz), 8.71 (1H, d, J=9.0 Hz), 9.97 (1H, s), 11.9 (1H s).

Example 52

Production of 5-chloro-2-[(3-([3-(furan-3-yl)phenyl]amino)-3-oxopropanoyl)amino]benzoic acid (52)

The target compound (52) was synthesized according to the following Steps (i) to (v).

(i) 3-([3-(Furan-3-yl)phenyl]amino)-3-oxopropanoic acid.ethyl ester

Using the same method as in Example 20-(i), ethylmalonyl chloride was reacted with 3-(furan-3-yl)aniline to give 3-([3-(furan-3-yl)phenyl]amino)-3-oxopropanoic acid.ethyl ester (yield: 93%).
$^1$H-NMR (CDCl$_3$) δ: 1.33 (3H, t, J=7.2 Hz), 3.49 (2H, s), 4.26 (2H, q, J=7.2 Hz), 6.70 (1H, dd, J=1.8, 0.8 Hz), 7.24 (1H, dt, J=7.7, 1.5 Hz), 7.33 (1H, t, J=7.7 Hz), 7.41-7.50 (2H, m), 7.68 (2H, m), 9.31 (1H, s).

(ii) 3-([3-(Furan-3-yl)phenyl]amino)-3-oxopropanoic acid

Using the same method as in Example 1-(iii), 3-([3-(furan-3-yl)phenyl]amino)-3-oxopropanoic acid was obtained from 3-([3-(furan-3-yl)phenyl]amino)-3-oxopropanoic acid.ethyl ester (yield: 76%).
$^1$H-NMR (CDCl$_3$) δ: 3.38 (2H, s), 6.86 (1H, dd, J=1.8, 0.8 Hz), 7.28-7.39 (2H, m), 7.43-7.53 (1H, m), 7.73-7.80 (1H, m), 8.09-8.14 (1H m), 10.2 (1H, s), 12.7 (1H, br).

(iii) 2-Amino-5-chlorobenzoic acid.benzylester 1.0 g (5.1 mmol) of 5-chloroisatoic acid was heated under stirring in a mixed solvent of benzyl alcohol (5 mL) and DMF (5 mL) at 100° C. for 5 hours. After cooling, the reaction mixture was diluted with ethyl acetate, and washed with water. The organic layer was dried over anhydrous sodium sulfate, and the solvent was distilled off under reduced pressure. The resulting crude product was separated and purified using silica gel column chromatography to give 0.516 g of 2-amino-5-chlorobenzoic acid.benzylester (yield: 39%).

$^1$H-NMR (CDCl$_3$) δ: 5.31 (2H, s), 5.75 (2H, br), 6.59 (1H, d, J=8.8 Hz), 7.20 (1H, dd, J=8.8, 2.6 Hz), 7.28-7.49 (5H, m), 7.86 (1H, d, J=2.6 Hz).

(iv) 5-Chloro-2-[(3-([3-(furan-3-yl)phenyl]amino)-3-oxopropanoyl)amino]benzoic acid.benzylester Using the same method as in Example 15-(i), 2-amino-5-chlorobenzoic acid.benzylester was reacted with the 3-([3-(furan-3-yl)phenyl]amino)-3-oxopropanoic acid to give 5-chloro-2-[(3-([3-(furan-3-yl)phenyl]amino)-3-oxopropanoyl)amino]benzoic acid.benzylester (yield: 48%).

$^1$H-NMR (CDCl$_3$) δ: 3.59 (2H, s), 5.37 (2H, s), 6.67-6.72 (1H, m), 7.20-7.57 (10H, m), 7.68-7.76 (2H, m), 8.04 (1H, d, J=2.6 Hz), 8.65 (1H, d, J=9.0 Hz), 9.46 (1H, s), 11.4 (1H, s).

(v) 5-Chloro-2-[(3-([3-(furan-3-yl)phenyl]amino)-3-oxopropanoyl)amino]benzoic acid 0.42 g (0.89 mmol) of 5-chloro-2-[(3-([3-(furan-3-yl)phenyl]amino)-3-oxopropanoyl)amino]benzoic acid.benzylester and 40 mg of 5% Pd/C were stirred under hydrogen atmosphere in a mixed solvent of 10 mL of ethanol, 10 mL of THF, and 4 mL of DMF for 18 hours. Thereafter, the reaction solution was filtered through celite, and the filtrate was condensed to give the target 5-chloro-2-[(3-([3-(furan-3-yl)phenyl]amino)-3-oxopropanoyl)amino]benzoic acid (yield: 81%).

$^1$H-NMR (DMSO-d$_6$) δ: 3.61 (2H, s), 6.83-6.89 (1H, m), 7.29-7.41 (2H, m), 7.45-7.56 (1H, m), 7.69 (1H, dd, J=9.0, 2.7 Hz), 7.77 (1H, t, J=1.7 Hz), 7.77-7.83 (1H, m), 7.93 (1H, d, J=2.7 Hz), 8.13 (1H, s), 8.53 (1H, J=9.0 Hz), 10.4 (1H, s), 11.4 (1H, s).

Example 53

Production of 5-chloro-2-([(3-(furan-3-yl)benzyl]amino) (oxo)acetyl]amino)benzoic acid (53)

The target compound (53) was synthesized according to the following Steps (i) to (v).

(i) 1-[3-(Furan-3-yl)phenyl]methanamine

Using the same method as in Example 19-(ii), 3-furanboronic acid was reacted with the 3-bromobenzyl amine to give 1-[3-(furan-3-yl)phenyl]methanamine (yield: 76%).

$^1$H-NMR (CDCl$_3$) δ: 1.58 (2H, br), 3.90 (2H, s), 6.68-6.75 (1H, m), 7.16-7.52 (5H, m), 7.74 (1H, s).

(ii) ([3-(Furan-3-yl)benzyl]amino)(oxo)acetic acid.ethyl ester

Using the same method as in Example 20-(i), chloroglyoxylic acid ethyl was reacted with 3-(furan-3-yl)aniline to give 1.04 g of ([3-(furan-3-yl)benzyl]amino)(oxo)acetic acid.ethyl ester (yield: 50%).

$^1$H-NMR (CDCl$_3$) δ: 1.39 (3H, t, J=7.1 Hz), 4.36 (2H, q, J=7.1 Hz), 4.55 (2H, d, J=6.1 Hz), 6.70 (1H, dd, J=1.8, 0.8 Hz), 7.15-7.24 (1H, m), 7.31-7.51 (5H, m), 7.72-7.76 (1H, m).

(iii) ([3-(Furan-3-yl)benzyl]amino)(oxo)acetic acid

Using the same method as in Example 1-(iii), 0.66 g of ([3-(furan-3-yl)benzyl]amino)(oxo)acetic acid was obtained from ([3-(furan-3-yl)benzyl]amino)(oxo)acetic acid.ethyl ester (yield: 73%).

$^1$H-NMR (DMSO-d$_6$) δ: 4.35 (2H, d, J=6.3 Hz), 6.93 (1H, dd, J=1.8, 0.7 Hz), 7.16 (1H, d, J=7.7 Hz), 7.34 (1H, t, J=7.7 Hz), 7.46-7.55 (2H, m), 7.75 (1H, t, J=1.8 Hz), 8.16 (1H, s), 9.40 (1H, t, J=6.3 Hz).

(iv) 5-Chloro-2-([([3-(furan-3-yl)benzyl]amino) (oxo)acetyl]amino) benzoic acid.methyl ester Using the same method as in Example 15-(i), 2-amino-5-chlorobenzoic acid methyl was reacted with the ([3-(furan-3-yl)benzyl]amino)(oxo)acetic acid to give 5-chloro-2-([([3-(furan-3-yl)benzyl]amino)(oxo)acetyl]amino)benzoic acid.methyl ester (yield: 53%).

$^1$H-NMR (CDCl$_3$) δ: 4.00 (3H, s), 4.60 (2H, d, J=6.2 Hz), 6.70 (1H, dd, J=1.9, 0.9 Hz), 7.19-7.27 (1H, m), 7.31-7.50 (4H, m), 7.54 (1H, dd, J=9.0, 2.5 Hz), 7.74 (1H, dd, J=1.4, 0.9 Hz), 7.80 (1H, t, J=6.2 Hz), 8.07 (1H, d, J=2.5 Hz), 8.67 (1H, d, J=9.0 Hz), 12.7 (1H, s).

(v) 5-Chloro-2-([([3-(furan-3-yl)benzyl]amino) (oxo) acetyl]amino)benzoic acid

Using the same method as in Example 1-(iii), the target 5-chloro-2-([([3-(furan-3-yl)benzyl]amino)(oxo)acetyl] amino)benzoic acid was obtained from 5-chloro-2-([([3-(furan-3-yl)benzyl]amino)(oxo)acetyl]amino)benzoic acid.methyl ester (yield: 55%).

$^1$H-NMR (DMSO-d$_6$) δ: 4.43 (2H, d, J=6.3 Hz), 6.94 (1H, dd, J=1.8, 0.8 Hz), 7.20 (1H, dt, J=7.6, 1.3 Hz), 7.35 (1H, t, J=7.6 Hz), 7.51 (1H, dt, J=7.6, 1.3 Hz), 7.56 (1H, t, J=1.3 Hz), 7.74-7.76 (1H, m), 7.76 (1H, dd, J=9.0, 2.7 Hz), 7.99 (1H, d, J=2.7 Hz), 8.18 (1H, dd, J=1.4, 0.8 Hz), 8.69 (1H, d, J=9.0 Hz), 9.70 (1H, t, J=6.3 Hz), 12.6 (1H, s).

Example 54

Production of 5-chloro-2-([(2-([3-(furan-2-ylmethyl) phenyl]amino)-2-oxoethoxy)acetyl]amino)benzoic acid (54)

The target compound (54) was synthesized according to the following Steps (i) to (iv).

(i) 2-(3-Nitrobenzyl)furan

Using the same method as in Example 19-(ii), 2-furanboronic acid was reacted with the 3-nitrobenzyl bromide to give 2-(3-nitrobenzyl)furan (yield: 92%).

$^1$H-NMR (CDCl$_3$) δ: 4.08 (2H, s), 6.09 (1H, d, J=3.1 Hz), 6.32 (1H, dd, J=3.1, 2.0 Hz), 7.35 (1H, d, J=1.5 Hz), 7.41-7.62 (2H, m), 8.04-8.15 (2H, m).

(ii) 3-(Furan-2-ylmethyl)aniline 0.85 g (4.18 mmol) of 2-(3-nitrobenzyl)furan, 1.21 g (21.8 mmol) of reduced iron, and 1 mL of 1N hydrochloric acid were heated under reflux in 10 mL of ethanol for 3.5 hours. After cooling the reaction solution, an aqueous sodium bicarbonate solution was added to alkalify the reaction solution; and filtration through a glass filter, which was covered by celite, was conducted. The filtrate was condensed, and the resulting product was separated and purified using silica gel column chromatography, thereby giving 0.72 g of 3-(furan-2-ylmethyl)aniline (yield: 99%).

$^1$H-NMR (CDCl$_3$) δ: 3.61 (2H, br), 3.87 (2H, s), 6.01 (1H, d, J=3.2 Hz), 6.28 (1H, dd, J=3.2, 2.0 Hz), 6.50-6.68 (3H, m), 7.02-7.14 (1H, m), 7.32 (1H, d, J=2.0 Hz).

(iii) 5-Chloro-2-([(2-([3-(furan-2-ylmethyl)phenyl]amino)-2-oxoethoxy)acetyl]amino)benzoic acid.methyl ester Using the same method as in Example 15-(i), 3-(furan-2-ylmethyl)aniline was reacted with the (2-([4-chloro-2-(methoxycarbonyl)phenyl]amino)-2-oxoethoxy)acetic acid obtained in Example 1-(i) to give 5-chloro-2-([(2-([3-(furan-2-ylmethyl)phenyl]amino)-2-oxoethoxy)acetyl]amino)benzoic acid.methyl ester (yield: 54%).

$^1$H-NMR (CDCl$_3$) δ: 3.77 (3H, s), 3.96 (2H, s), 4.25 (2H, s), 4.27 (2H, s), 6.01 (1H, dd, J=3.0, 0.6 Hz), 6.29 (1H, dd, J=3.0, 2.0 Hz), 7.04 (1H, d, J=7.7 Hz), 7.23-7.34 (2H, m), 7.54-7.56 (2H, m), 7.55 (1H, dd, J=9.0, 2.6 Hz), 8.04 (1H, d, J=2.6 Hz), 8.78 (1H, d, J=9.0 Hz), 8.78 (1H, s), 11.9 (1H, s).

(iv) 5-Chloro-2-([(2-([3-(furan-2-ylmethyl)phenyl]amino)-2-oxoethoxy)acetyl]amino)benzoic acid Using the same method as in Example 1-(iii), the target 5-chloro-2-([(2-([3-(furan-2-ylmethyl)phenyl]amino)-2-oxoethoxy)acetyl]amino)benzoic acid was obtained from 5-chloro-2-([(2-([3-(furan-2-ylmethyl)phenyl]amino)-2-oxoethoxy)acetyl]amino)benzoic acid.methyl ester (yield: 96%).

$^1$H-NMR (DMSO-d$_6$) δ: 3.94 (2H, s), 4.28 (2H, s), 4.29 (2H, s), 6.14 (1H, dd, J=3.1, 0.5 Hz), 6.36 (1H, dd, J=3.1, 1.9 Hz), 6.95 (1H, d, J=7.7 Hz), 7.26 (1H, t, J=7.7 Hz), 7.48-7.59 (3H, m), 7.71 (1H, dd, J=9.0, 2.6 Hz), 7.97 (1H, d, J=2.6 Hz), 8.69 (1H, d, J=9.0 Hz), 9.77 (1H, s), 11.9 (1H, s).

Example 55

Production of 5-chloro-2-([(2-([3-(furan-3-ylmethyl)phenyl]amino)-2-oxoethoxy)acetyl]amino)benzoic acid (55)

The target compound (55) was synthesized according to the following Steps (i) to (iv).

(i) 3-(3-Nitrobenzyl)furan

Using the same method as in Example 19-(ii), 3-furanboronic acid was reacted with the 3-nitrobenzyl bromide to give 3-(3-nitrobenzyl)furan (yield: 84%).

$^1$H-NMR (CDCl$_3$) δ: 3.88 (2H, s), 6.20-6.26 (1H, m), 7.24-7.29 (1H, m), 7.36-7.61 (3H, m), 8.02-8.12 (2H, m).

(ii) 3-(Furan-3-ylmethyl)aniline

Using the same method as in Example 54-(ii), 3-(3-nitrobenzyl)furan was reacted with reduced iron to give 3-(furan-3-ylmethyl)aniline (yield: 93%).

$^1$H-NMR (CDCl$_3$) δ: 3.60 (2H, br), 3.67 (2H, s), 6.25 (1H, d, J=1.1 Hz), 6.49-6.57 (2H, m), 6.62 (1H, d, J=7.6 Hz), 7.02-7.13 (1H, m), 7.22 (1H, s), 7.35 (1H, t, J=1.6 Hz).

(iii) 5-Chloro-2-([(2-([3-(furan-3-ylmethyl)phenyl]amino)-2-oxoethoxy)acetyl]amino)benzoic acid.methyl ester Using the same method as in Example 15-(i), 3-(furan-3-ylmethyl)aniline was reacted with the (2-([4-chloro-2-(methoxycarbonyl)phenyl]amino)-2-oxoethoxy)acetic acid obtained in Example 1-(i) to give 5-chloro-2-([(2-([3-(furan-3-ylmethyl)phenyl]amino)-2-oxoethoxy)acetyl]amino)benzoic acid.methyl ester (yield: 34%).

$^1$H-NMR (CDCl$_3$) δ: 3.76 (3H, s), 3.77 (2H, s), 4.26 (2H, s), 4.27 (2H, s), 6.24 (1H, d, J=0.6 Hz), 7.02 (1H, d, J=7.6 Hz), 7.20 (1H, s), 7.27 (1H, t, J=7.7 Hz), 7.35 (1H, t, J=1.6 Hz), 7.50-7.59 (1H, m), 7.55 (1H, dd, J=9.0, 2.6 Hz), 7.62 (1H, t, J=1.6 Hz), 8.04 (1H, d, J=2.6 Hz), 8.77 (1H, s), 8.78 (1H, d, J=9.0 Hz), 11.9 (1H, s).

(iv) 5-Chloro-2-([(2-([3-(furan-3-ylmethyl)phenyl]amino)-2-oxoethoxy)acetyl]amino)benzoic acid Using the same method as in Example 1-(iii), the target 5-chloro-2-([(2-([3-(furan-3-ylmethyl)phenyl]amino)-2-oxoethoxy)acetyl]amino)benzoic acid was obtained from 5-chloro-2-([(2-([3-(furan-3-ylmethyl)phenyl]amino)-2-oxoethoxy)acetyl]amino)benzoic acid.methyl ester (yield: 81%).

$^1$H-NMR (DMSO-d$_6$) δ: 3.71 (2H, s), 4.28 (4H, s), 6.32 (1H, d, J=1.6 Hz), 6.96 (1H, d, J=7.6 Hz), 7.18-7.31 (1H, m), 7.47-7.55 (3H, m), 7.57 (1H, t, J=1.6 Hz), 7.71 (1H, dd, J=9.0, 2.6 Hz), 7.97 (1H, d, J=2.6), 8.69 (1H, d, J=9.0 Hz), 9.74 (1H, s), 11.9 (1H, s).

Example 56

Production of 5-chloro-2-[((2-oxo-2-[(2-phenoxyphenyl)amino]ethoxy)acetyl)amino]benzoic acid (56)

The target compound (56) was synthesized according to the following Steps (i) to (ii).

(i) 5-Chloro-2-[((2-oxo-2-[(2-phenoxyphenyl)amino]ethoxy)acetyl)amino]benzoic acid.methyl ester Using the same method as in Example 1-(ii), 2-phenoxyaniline was reacted with the (2-([4-chloro-2-(methoxycarbonyl)phenyl]amino)-2-oxoethoxy)acetic acid obtained in Example 1-(i) to give 5-chloro-2-[((2-oxo-2-[(2-phenoxyphenyl)amino]ethoxy)acetyl)amino]benzoic acid.methyl ester (yield: 89%).

$^1$H-NMR (CDCl$_3$) δ: 3.75 (3H, s), 4.13 (2H, s), 4.25 (2H, s), 6.78-7.24 (8H, m), 7.50 (1H, dd, J=9.0, 2.6 Hz), 7.95 (1H, d, J=2.6 Hz), 8.36 (1H, dd, J=7.8, 2.0 Hz), 8.69 (1H, d, J=9.0 Hz), 8.95 (1H, s), 11.9 (1H, s).

(ii) 5-Chloro-2-[((2-oxo-2-[(2-phenoxyphenyl)amino]ethoxy)acetyl)amino]benzoic acid Using the same method as in Example 1-(iii), the target 5-chloro-2-[((2-oxo-2-[(2-phenoxyphenyl)amino]ethoxy)acetyl)amino]benzoic acid was obtained from 5-chloro-2-[((2-oxo-2-[(2-phenoxyphenyl)amino]ethoxy)acetyl)amino]benzoic acid methyl ester (yield: 60%).

$^1$H-NMR (DMSO-d$_6$) δ: 4.20 (2H, s), 4.29 (2H, s), 6.86-7.37 (8H, m), 7.67 (1H, dd, J=9.0, 2.7 Hz), 7.91 (1H, d, J=2.7 Hz), 8.09-8.20 (1H, m), 8.62 (1H, d, J=9.0 Hz), 9.31 (1H, s), 11.8 (1H, s), 14.0 (1H, br).

Example 57

Production of 5-chloro-2-([((2-oxo-2-[(2-phenoxyphenyl)amino]ethyl)sulfanyl)acetyl]amino)benzoic acid (57)

The target compound (57) was synthesized according to the following Steps (i) to (ii).

(i) 5-Chloro-2-([((2-oxo-2-[(2-phenoxyphenyl) amino]ethyl)sulfanyl)acetyl]amino)benzoic acid.methyl ester Using the same method as in Example 1-(ii), 2-phenoxyaniline was reacted with the [(2-([4-chloro-2-(methoxycarbonyl)phenyl]amino)-2-oxoethyl)sulfanyl]acetic acid obtained in Example 12-(i) to give 5-chloro-2-([((2-oxo-2-[(2-phenoxyphenyl)amino]ethyl)sulfanyl)acetyl]amino)benzoic acid.methyl ester (yield: 72%).
$^1$H-NMR (CDCl$_3$) δ: 3.28 (2H, s), 3.48 (2H, s), 3.92 (3H, s), 6.83-7.17 (6H, m), 7.24-7.37 (2H, m), 7.41 (1H, dd, J=9.1, 2.6 Hz), 7.96 (1H, d, J=2.6 Hz), 8.35 (1H, dd, J=7.8, 2.0 Hz), 8.57 (1H, d, J=9.1 Hz), 9.04 (1H, s), 11.5 (1H, s).

(ii) 5-Chloro-2-([((2-oxo-2-[(2-phenoxyphenyl) amino]ethyl)sulfanyl)acetyl]amino)benzoic acid Using the same method as in Example 1-(iii), the target 5-chloro-2-([((2-oxo-2-[(2-phenoxyphenyl)amino]ethyl) sulfanyl)acetyl]amino)benzoic acid was obtained from 5-chloro-2-([((2-oxo-2-[(2-phenoxyphenyl)amino]ethyl) sulfanyl)acetyl]amino)benzoic acid.methyl ester (yield: 97%).
$^1$H-NMR (DMSO-d$_6$) δ: 3.50 (2H, s), 3.57 (2H, s), 6.77-6.89 (1H, m), 6.93-7.19 (5H, m), 7.31-7.44 (2H, m), 7.63 (1H, dd, J=9.0, 2.6 Hz), 7.91 (1H, d, J=2.6 Hz), 7.91-8.02 (1H, m), 8.50 (1H, d, J=9.0 Hz), 9.69 (1H, s), 11.6 (1H, s).

Example 58

Production of 5-chloro-2-([(2-([3-(furan-3-yl)phenyl]amino)-2-oxoethoxy)acetyl]amino)benzoic acid (58)

The target compound (58) was synthesized according to either the following synthesization steps (i) and (iii), or the steps (ii) and (iii).

(i) 5-Chloro-2-([(2-([3-(furan-3-yl)phenyl]amino)-2-oxoethoxy)acetyl]amino)benzoic acid.methyl ester Using the same method as in Example 1-(ii), 3-(furan-3-yl)aniline was reacted with the (2-([4-chloro-2-(methoxycarbonyl)phenyl]amino)-2-oxoethoxy)acetic acid obtained in Example 1-(i) to give 5-chloro-2-([(2-([3-(furan-3-yl)phenyl]amino)-2-oxoethoxy)acetyl]amino)benzoic acid.methyl ester (yield: 89%).
$^1$H-NMR (CDCl$_3$) δ: 3.75 (3H, s), 4.28 (2H, s), 4.29 (2H, s), 6.69 (1H, dd, J=2.0, 1.0 Hz), 7.24-7.32 (1H, m), 7.35 (1H, dd, J=8.1, 7.6), 7.48 (1H, dd, J=1.7, 1.5 Hz), 7.55 (1H, dd, J=9.0, 2.7 Hz), 7.55-7.63 (1H, m), 7.72-7.76 (1H, m), 7.85-7.90 (1H, m), 8.04 (1H, d, J=2.7 Hz), 8.79 (1H, d, J=9.0 Hz), 8.86 (1H, s), 11.9 (1H, s).

(ii) 5-Chloro-2-([(2-([3-(furan-3-yl)phenyl]amino)-2-oxoethoxy)acetyl]amino)benzoic acid.methyl ester Using the same method as in Example 5-(i), 3-(4,4,5,5-tetramethyl-1,3,2-dioxaborolan-2-yl)furan was reacted with the 2-[((2-[(3-bromophenyl)amino]-2-oxoethoxy)acetyl)amino]-5-chlorobenzoic acid.methyl ester obtained in Example 19-(i) to give 5-chloro-2-([(2-([3-(furan-3-yl)phenyl]amino)-2-oxoethoxy)acetyl]amino)benzoic acid.methyl ester (yield: 75%).

(iii) 5-Chloro-2-([(2-([3-(furan-3-yl)phenyl]amino)-2-oxoethoxy)acetyl]amino)benzoic acid Using the same method as in Example 1-(iii), the target 5-chloro-2-([(2-([3-(furan-3-yl)phenyl]amino)-2-oxoethoxy)acetyl]amino)benzoic acid was obtained from 5-chloro-2-([(2-([3-(furan-3-yl)phenyl]amino)-2-oxoethoxy)acetyl]amino)benzoic acid.methyl ester (yield: 90%).
$^1$H-NMR (DMSO-d$_6$) δ: 4.30 (2H, s), 4.31 (2H, s), 6.87 (1H, dd, J=1.9, 0.9 Hz), 7.30-7.37 (2H, m), 7.52-7.65 (1H, m), 7.70 (1H, dd, J=9.1, 2.6 Hz), 7.75 (1H, dd, J=1.8, 1.6 Hz), 7.84-7.88 (1H, m), 7.98 (1H, d, J=2.6 Hz), 8.11-8.14 (1H, m), 8.69 (1H, d, J=9.1 Hz), 9.80 (1H, s), 12.0 (1H, s).

Example 59

Production of 5-chloro-2-([(2-oxo-2-([3-(thiophene-3-yl)phenyl]amino)ethoxy)acetyl]amino)benzoic acid (59)

The target compound (59) was synthesized according to the following Steps (i) to (ii).

(i) 5-Chloro-2-([(2-([3-(thiophene-3-yl)phenyl] amino)-2-oxoethoxy)acetyl]amino)benzoic acid.methyl ester Using the same method as in Example 19-(ii), 3-thiopheneboronic acid was reacted with the 2-[((2-[(3-bromophenyl)amino]-2-oxoethoxy)acetyl)amino]-5-chlorobenzoic acid.methyl ester obtained in Example 19-(i) to give 5-chloro-2-([(2-([3-(thiophene-3-yl)phenyl]amino)-2-oxoethoxy)acetyl]amino)benzoic acid.methyl ester (yield: 82%).
$^1$H-NMR (CDCl$_3$) δ: 3.70 (3H, s), 4.27 (2H, s), 4.29 (2H, s), 7.21-7.27 (1H, m), 7.30-7.50 (4H, m), 7.54 (1H, dd, J=8.9, 2.5 Hz), 7.60-7.70 (1H, m), 7.91-7.98 (1H, m), 8.03 (1H, d, J=2.5 Hz), 8.78 (1H, d, J=8.9 Hz), 8.85 (1H, s), 11.9 (1H, s).

(ii) 5-Chloro-2-([(2-oxo-2-([3-(thiophene-3-yl)phenyl]amino)ethoxy)acetyl]amino)benzoic acid Using the same method as in Example 1-(iii), the target 5-chloro-2-([(2-oxo-2-([3-(thiophene-3-yl)phenyl]amino) ethoxy)acetyl]amino)benzoic acid was obtained from 5-chloro-2-([(2-oxo-2-([3-(thiophene-3-yl)phenyl]amino) ethoxy)acetyl]amino)benzoic acid.methyl ester (yield: 59%).
$^1$H-NMR (DMSO-d$_6$) δ: 4.29 (2H, s), 4.31 (2H, s), 7.38 (1H, dd, J=7.7, 7.6 Hz), 7.41-7.47 (1H, m), 7.50 (1H, dd, J=5.0, 1.3 Hz), 7.61-7.72 (3H, m), 7.84 (1H, dd, J=2.9, 1.3 Hz), 7.98 (1H, d, J=2.6 Hz), 8.02-8.06 (1H, m), 8.67 (1H, d, J=9.0 Hz), 9.86 (1H, s), 12.2 (1H, s).

Example 60

Production of 5-chloro-2-([(2-([3-(1-methyl-1H-pyrazol-4-yl)phenyl]amino)-2-oxoethoxy)acetyl] amino)benzoic acid (60)

The target compound (60) was synthesized according to the following Steps (i) to (ii).

(i) 5-Chloro-2-([(2-([3-(1-methyl-1H-pyrazol-4-yl) phenyl]amino)-2-oxoethoxy)acetyl]amino) benzoic acid.methyl ester Using the same method as in Example 5-(i), 4-(4,4,5,5-tetramethyl-1,3,2-dioxaborolan-2-yl)-1-methylpyrazole was reacted with the 2-[((2-[(3-bromophenyl)amino]-2-oxoethoxy)acetyl)amino]-5-chlorobenzoic acid.methyl ester obtained in Example 19-(i) to give 5-chloro-2-([(2-([3-(1-methyl-1H-pyrazol-4-yl)phenyl]amino)-2-oxoethoxy)acetyl]amino)benzoic acid.methyl ester (yield: 56%).

$^1$H-NMR (CDCl$_3$) δ: 3.76 (3H, s), 3.94 (3H, s), 4.27 (2H, s), 4.29 (2H, s), 7.20-7.38 (2H, m), 7.45-7.53 (1H, m), 7.55 (1H, dd, J=9.3, 2.5 Hz), 7.63 (1H, s), 7.75 (1H, s), 7.88-7.92 (1H, m), 8.04 (1H, d, J=2.8 Hz), 8.79 (1H, d, J=9.3 Hz), 8.82 (1H, s), 11.9 (1H, s).

(ii) 5-Chloro-2-([(2-([3-(1-methyl-1H-pyrazol-4-yl)phenyl]amino)-2-oxoethoxy)acetyl]amino)benzoic acid Using the same method as in Example 1-(iii), the target 5-chloro-2-([(2-([3-(1-methyl-1H-pyrazol-4-yl)phenyl]amino)-2-oxoethoxy)acetyl]amino)benzoic acid was obtained from 5-chloro-2-([(2-([3-(1-methyl-1H-pyrazol-4-yl)phenyl]amino)-2-oxoethoxy)acetyl]amino)benzoic acid.methyl ester (yield: 70%).

$^1$H-NMR (DMSO-d$_6$) δ: 3.87 (3H, s), 4.30 (2H, s), 4.31 (2H, s), 7.24-7.36 (2H, m), 7.44-7.53 (1H, m), 7.71 (1H, dd, J=9.0, 2.7 Hz), 7.78 (1H, s), 7.85 (1H, s), 7.98 (1H, d, J=2.7 Hz), 8.08 (1H, s), 8.69 (1H, d, J=9.0 Hz), 9.78 (1H, s), 12.0 (1H, s).

Example 61

Production of 5-chloro-2-([(2-([3-(furan-2-yl)phenyl]amino)-2-oxoethoxy)acetyl]amino)benzoic acid (61)

The target compound (61) was synthesized according to the following Steps (i) to (iv).

(i) [3-(Furan-2-yl)phenyl]carbamic acid.tert-butyl

Using the same method as in Example 5-(i), 2-furanboronic acid was reacted with the (3-iodophenyl)carbamic acid.tert-butyl to quantitatively give [3-(furan-2-yl)phenyl]carbamic acid.tert-butyl.

$^1$H-NMR (CDCl$_3$) δ: 1.53 (9H, s), 6.46 (1H, dd, J=3.5, 1.8 Hz), 6.52 (1H, s), 6.65 (1H, dd, J=3.5, 0.7 Hz), 7.19-7.38 (3H, m), 7.45 (1H, dd, J=1.8, 0.7 Hz), 7.72 (1H, s).

(ii) 3-(Furan-2-yl)aniline.hydrochloride 2 mL of ethyl acetate was added to and dissolved in 0.28 g (1.08 mmol) of [3-(furan-2-yl)phenyl]carbamic acid tert-butyl. Under ice-cooling, 2 mL of a 4N hydrochloric acid/ethyl acetate solution was added to the mixture and stirred at room temperature overnight. After condensing the reaction solution, IPE was added to the residue. The precipitate was collected by filtration, washed with IPE, and dried under reduced pressure at room temperature for 5 hours to yield 204 mg of 3-(furan-2-yl)aniline.hydrochloride (yield: 96%).

$^1$H-NMR (DMSO-d$_6$) δ: 3.71 (3H, s), 6.63 (1H, dd, J=3.3, 1.8 Hz), 7.00 (1H, d, J=3.3 Hz), 7.17-7.27 (1H, m), 7.49 (1H, dd, J=8.1, 7.7 Hz), 7.58-7.70 (2H, m), 7.80 (1H, d, J=1.8 Hz).

(iii) 5-Chloro-2-([(2-([3-(furan-2-yl)phenyl]amino)-2-oxoethoxy)acetyl]amino)benzoic acid.methyl ester Using the same method as in Example 1-(ii), 3-(furan-2-yl)aniline.hydrochloride was reacted with the (2-([4-chloro-2-(methoxycarbonyl)phenyl]amino)-2-oxoethoxy)acetic acid obtained in Example 1-(i) to give 5-chloro-2-([(2-([3-(furan-2-yl)phenyl]amino)-2-oxoethoxy)acetyl]amino)benzoic acid.methyl ester (yield: 77%). Note that 3-(furan-2-yl)aniline.hydrochloride was neutralized in DMA by adding an equivalent amount of triethylamine, and then used in the reaction.

$^1$H-NMR (CDCl$_3$) δ: 3.79 (3H, s), 4.27 (2H, s), 4.29 (2H, s), 6.48 (1H, dd, J=3.4, 1.7 Hz), 6.67 (1H, d, J=3.4 Hz), 7.36 (1H, dd, J=8.1, 7.8 Hz), 7.42-7.50 (2H, m), 7.56 (1H, dd, J=8.8, 2.7 Hz), 7.76-7.74 (1H, m), 7.92-7.98 (1H, m), 8.05 (1H, d, J=2.7 Hz), 8.79 (1H, d, J=8.8 Hz), 8.86 (1H, s), 12.0 (1H, s).

(iv) 5-Chloro-2-([(2-([3-(furan-2-yl)phenyl]amino)-2-oxoethoxy)acetyl]amino)benzoic acid Using the same method as in Example 1-(iii), the target 5-chloro-2-([(2-([3-(furan-2-yl)phenyl]amino)-2-oxoethoxy)acetyl]amino)benzoic acid was obtained from 5-chloro-2-([(2-([3-(furan-2-yl)phenyl]amino)-2-oxoethoxy)acetyl]amino)benzoic acid.methyl ester (yield: 97%).

$^1$H-NMR (DMSO-d$_6$) δ: 4.30 (2H, s), 4.32 (2H, s), 6.60 (1H, dd, J=3.4, 1.8 Hz), 6.89 (1H, d, J=3.4 Hz), 7.30-7.48 (2H, m), 7.52-7.61 (1H, m), 7.71 (1H, dd, J=9.0, 2.7 Hz), 7.73-7.79 (1H, m), 7.98 (1H, d, J=2.7 Hz), 8.05-8.10 (1H, m), 8.69 (1H, d, J=9.0 Hz), 9.87 (1H, s), 11.9 (1H, s).

Example 62

Production of 5-chloro-2-([(2-([3-(3,5-dimethylisoxazol-4-yl)phenyl]amino)-2-oxoethoxy)acetyl]amino)benzoic acid.sodium salt (62)

The target compound (62) was synthesized according to the following Steps (i) to (iv).

(i) [3-(3,5-Dimethylisoxazol-4-yl)phenyl]carbamic acid.tert-butyl

Using the same method as in Example 5-(i), 3,5-dimethyl-4-(4,4,5,5-tetramethyl-1,3,2-dioxaborolan-2-yl)isoxazole was reacted with the (3-iodophenyl)carbamic acid.tert-butyl to give [3-(3,5-dimethylisoxazol-4-yl)phenyl]carbamic acid.tert-butyl (yield: 85%).

$^1$H-NMR (CDCl$_3$) δ: 1.52 (9H, s), 2.27 (3H, s), 2.41 (3H, s), 6.52 (1H, s), 6.84-6.95 (1H, m), 7.28-7.41 (3H, m).

(ii) 3-(3,5-Dimethylisoxazol-4-yl)aniline.hydrochloride

Using the same method as in Example 61-(ii), 3-(3,5-dimethylisoxazol-4-yl)aniline.hydrochloride was obtained from [3-(3,5-dimethylisoxazol-4-yl)phenyl]carbamic acid.tert-butyl (yield: 90%).

$^1$H-NMR (DMSO-d$_6$) δ: 2.25 (3H, s), 2.43 (3H, s), 7.31-7.41 (3H, m), 7.51-7.61 (1H, m).

(iii) 5-Chloro-2-([(2-([3-(3,5-dimethylisoxazol-4-yl)phenyl]amino)-2-oxoethoxy)acetyl]amino)benzoic acid.methyl ester Using the same method as in Example 1-(ii), 3-(3,5-dimethylisoxazol-4-yl)aniline.hydrochloride was reacted with the (2-([4-chloro-2-(methoxycarbonyl)phenyl]amino)-2-oxoethoxy)acetic acid obtained in Example 1-(i) to give 5-chloro-2-([(2-([3-(3,5-dimethylisoxazol-4-yl)phenyl]amino)-2-oxoethoxy)acetyl]amino)benzoic acid.methyl ester (yield: 82%). Note that 3-(3,5-dimethylisoxazol-4-yl)aniline.hydrochloride was neutralized in DMA by adding an equivalent amount of triethylamine, and then used in the reaction.

$^1$H-NMR (CDCl$_3$) δ: 2.29 (3H, s), 2.43 (3H, s), 3.78 (3H, s), 4.28 (2H, s), 4.29 (2H, s), 7.01-7.09 (1H, m), 7.40 (1H, dd, J=8.0, 7.8 Hz), 7.55 (1H, dd, J=9.2, 2.5 Hz), 7.57-7.66 (1H, m), 7.81 (1H, dd, J=1.8, 1.7 Hz), 8.05 (1H, d, J=2.5 Hz), 8.78 (1H, d, J=9.2 Hz), 8.87 (1H, s), 11.9 (1H, s).

(iv) 5-Chloro-2-([(2-([3-(3,5-dimethylisoxazol-4-yl)phenyl]amino)-2-oxoethoxy)acetyl]amino)benzoic acid.sodium salt Using the same method as in Example 1-(iii), the target 5-chloro-2-([(2-([3-(3,5-dimethylisoxazol-4-yl)phenyl]amino)-2-oxoethoxy)acetyl]amino)benzoic acid.sodium salt was obtained from 5-chloro-2-([(2-([3-(3,5-dimethylisoxazol-4-yl)phenyl]amino)-2-oxoethoxy)acetyl]amino)benzoic acid.methyl ester (yield: 96%).

$^1$H-NMR (DMSO-d$_6$) δ: 2.26 (3H, s), 2.44 (3H, s), 4.21 (2H, s), 4.26 (2H, s), 7.05-7.14 (1H, m), 7.34-7.54 (2H, m), 7.95 (1H, d, J=2.6 Hz), 7.98-8.08 (2H, m), 8.56 (1H, d, J=8.8 Hz), 10.21 (1H, s), 13.9 (1H, s).

Example 63

Production of 5-chloro-2-([(2-oxo-2-([3-(thiophen-2-yl)phenyl]amino)ethoxy)acetyl]amino)benzoic acid (63)

The target compound (63) was synthesized according to the following Steps (i) to (ii).

(i) 5-Chloro-2-([(2-oxo-2-([3-(thiophen-2-yl)phenyl]amino)ethoxy)acetyl]amino)benzoic acid.methyl ester Using the same method as in Example 1-(ii), 3-(thiophen-2-yl)aniline was reacted with the (2-([4-chloro-2-(methoxycarbonyl)phenyl]amino)-2-oxoethoxy)acetic acid obtained in Example 1-(i) to give 5-chloro-2-([(2-oxo-2-([3-(thiophen-2-yl)phenyl]amino)ethoxy)acetyl]amino)benzoic acid.methyl ester (yield: 69%).

$^1$H-NMR (CDCl$_3$) δ: 3.73 (3H, s), 4.27 (2H, s), 4.29 (2H, s), 7.08 (1H, dd, J=4.8, 3.6 Hz), 7.27-7.45 (4H, m), 7.55 (1H, dd, J=9.0, 2.6 Hz), 7.64-7.72 (1H, m), 7.90-7.95 (1H, m), 8.04 (1H, d, J=2.6 Hz), 8.79 (1H, d, J=9.0 Hz), 8.86 (1H, s), 11.9 (1H, s).

(ii) 5-Chloro-2-([(2-oxo-2-([3-(thiophen-2-yl)phenyl]amino)ethoxy)acetyl]amino)benzoic acid Using the same method as in Example 1-(iii), the target 5-chloro-2-([(2-oxo-2-([3-(thiophen-2-yl)phenyl]amino)ethoxy)acetyl]amino)benzoic acid was obtained from 5-chloro-2-([(2-oxo-2-([3-(thiophen-2-yl)phenyl]amino)ethoxy)acetyl]amino)benzoic acid.methyl ester.

$^1$H-NMR (DMSO-d$_6$) δ: 4.30 (2H, s), 4.32 (2H, s), 7.14 (1H, dd, J=5.0, 3.6 Hz), 7.31-7.50 (3H, m), 7.55 (1H, d, J=5.0 Hz), 7.58-7.65 (1H, m), 7.71 (1H, dd, J=9.0, 2.7 Hz), 7.98 (1H, d, J=2.7 Hz), 7.99-8.04 (1H, m), 8.69 (1H, d, J=9.0 Hz), 9.90 (1H, s), 11.9 (1H, s).

Example 64

Production of 5-chloro-2-([(2-([4-(furan-3-yl)phenyl]amino)-2-oxoethoxy)acetyl]amino)benzoic acid (64)

The target compound (64) was synthesized according to the following Steps (i) to (ii).

(i) 5-Chloro-2-([(2-([4-(furan-3-yl)phenyl]amino)-2-oxoethoxy)acetyl]amino)benzoic acid.methyl ester Using the same method as in Example 1-(ii), 4-(furan-3-yl)aniline was reacted with the (2-([4-chloro-2-(methoxycarbonyl)phenyl]amino)-2-oxoethoxy)acetic acid obtained in Example 1-(i) to give 5-chloro-2-([(2-([4-(furan-3-yl)phenyl]amino)-2-oxoethoxy)acetyl]amino)benzoic acid.methyl ester (yield: 84%).

$^1$H-NMR (CDCl$_3$) δ: 3.87 (3H, s), 4.27 (2H, s), 4.28 (2H, s), 6.66-6.71 (1H, m), 7.41-7.50 (1H, m), 7.47 (2H, d, J=8.4 Hz), 7.55 (1H, dd, J=9.1, 2.5 Hz), 7.74 (2H, d, J=8.4 Hz), 7.69-7.79 (1H, m), 8.06 (1H, d, J=2.5 Hz), 8.79 (1H, d, J=9.1 Hz), 8.83 (1H, s), 11.9 (1H, s).

(ii) 5-Chloro-2-([(2-([4-(furan-3-yl)phenyl]amino)-2-oxoethoxy)acetyl]amino)benzoic acid Using the same method as in Example 1-(iii), the target 5-chloro-2-([(2-([4-(furan-3-yl)phenyl]amino)-2-oxoethoxy)acetyl]amino)benzoic acid was obtained from 5-chloro-2-([(2-([4-(furan-3-yl)phenyl]amino)-2-oxoethoxy)acetyl]amino)benzoic acid.methyl ester (yield: 99%).

$^1$H-NMR (DMSO-d$_6$) δ: 4.29 (2H, s), 4.31 (2H, s), 6.90-6.96 (1H, m), 7.57 (2H, d, J=8.6 Hz), 7.66-7.76 (4H, m), 7.98 (1H, d, J=2.6 Hz), 8.13 (1H, s), 8.69 (1H, d, J=8.9 Hz), 9.81 (1H, s), 12.0 (1H, s).

Example 65

Production of 5-chloro-2-([(2-([3-(furan-2-ylmethoxy)phenyl]amino)-2-oxoethoxy)acetyl]amino)benzoic acid (65)

The target compound (65) was synthesized according to the following Steps (i) to (iv).

(i) 2-[(3-Nitrophenoxy)methyl]furan 20 mL of DMF was blended with 2.0 g (14.4 mmol) of 3-nitrophenol, 3.57 g (30.6 mmol) of 2-(chloromethyl)furan, and 2.0 g (14.4 mmol) of potassium carbonate, and the mixture was stirred at 80° C. for 3 hours. After cooling the reaction solution to room temperature, the reaction solution was extracted with ethyl acetate, and resultant solid material was washed with water 3 times and with a saturated sodium chloride solution, and dried over magnesium sulfate. Thereafter, filtration was conducted and the filtrate was condensed. The resulting crude product was separated and purified using silica gel column chromatography to give 2-[(3-nitrophenoxy)methyl]furan (yield: 91%).

$^1$H-NMR (CDCl$_3$) δ: 5.09 (2H, s), 6.40 (1H, dd, J=3.3, 1.8 Hz), 6.49 (1H, dd, J=3.3, 0.7 Hz), 7.23-7.35 (1H, m), 7.38-7.50 (2H, m), 7.80-7.89 (2H, m).

(ii) 3-(Furan-2-ylmethoxy)aniline 830 mg (3.8 mmol) of 3-(furan-2-ylmethyl oxy)nitrobenzene was dissolved in 10 mL of ethanol. 1.1 g (19.70 mmol)

of iron and 1 mL of 1N hydrochloric acid (1.0 mmol) were added thereto and heated under reflux for 2 hours. After cooling the reaction solution to room temperature, 1.5 mL of 1N sodium hydroxide was added dropwise, and filtration through celite was carried out. The filtrate was condensed, and ethyl acetate and water were added to the filtrate to separate the solution into organic layer and aqueous layer. The organic layer was separated, washed with a saturated sodium chloride solution, and dried over magnesium sulfate. Thereafter, filtration was carried out, and the filtrate was condensed. The resulting crude product was separated and purified using silica gel column chromatography to give 3-(furan-2-ylmethoxy)aniline (yield: 86%).

$^1$H-NMR (CDCl$_3$) δ: 3.66 (2H, s), 4.95 (2H, s), 6.24-6.44 (5H, m), 7.06 (1H, dd, J=8.4, 8.2 Hz), 7.44 (1H, dd, J=1.8, 0.9 Hz).

(iii) 5-Chloro-2-([(2-([3-(furan-2-ylmethoxy)phenyl]amino)-2-oxoethoxy)acetyl]amino)benzoic acid.methyl ester Using the same method as in Example 1-(ii), 3-(furan-2-ylmethoxy)aniline was reacted with the (2-([4-chloro-2-(methoxycarbonyl)phenyl]amino)-2-oxoethoxy)acetic acid obtained in Example 1-(i) to give 5-chloro-2-([(2-([3-(furan-2-ylmethoxy)phenyl]amino)-2-oxoethoxy)acetyl]amino)benzoic acid.methyl ester (yield: 66%).

$^1$H-NMR (CDCl$_3$) δ: 3.85 (3H, s), 4.25 (4H, s), 5.01 (2H, s), 6.38 (1H, dd, J=3.3, 1.8 Hz), 6.44 (1H, dd, J=3.3, 0.8 Hz), 6.78 (1H, ddd, J=8.1, 2.4, 1.0 Hz), 7.25 (1H, dd, J=8.1, 8.0 Hz), 7.33-7.40 (1H, m), 7.45 (1H, dd, J=1.8, 0.8 Hz), 7.49-7.54 (1H, m), 7.54 (1H, dd, J=9.2, 2.6 Hz), 8.05 (1H, d, J=2.6 Hz), 8.76 (1H, s), 8.79 (1H, d, J=9.2 Hz), 12.0 (1H, s).

(iv) 5-Chloro-2-([(2-([3-(furan-2-ylmethoxy)phenyl]amino)-2-oxoethoxy)acetyl]amino)benzoic acid Using the same method as in Example 1-(iii), the target 5-chloro-2-([(2-([3-(furan-2-ylmethoxy)phenyl]amino)-2-oxoethoxy)acetyl]amino)benzoic acid was obtained from 5-chloro-2-([(2-([3-(furan-2-ylmethoxy)phenyl]amino)-2-oxoethoxy)acetyl]amino)benzoic acid.methyl ester (yield: 76%).

$^1$H-NMR (DMSO-d$_6$) δ: 4.26 (2H, s), 4.28 (2H, s), 5.05 (2H, s), 6.46 (1H, dd, J=3.0, 1.7 Hz), 6.59 (1H, d, J=3.0 Hz), 6.70-6.79 (1H, m), 7.22 (1H, dd, J=8.0, 8.0 Hz), 7.27-7.36 (1H, m), 7.47-7.54 (1H, m), 7.65-7.71 (1H, m), 7.66 (1H, dd, J=9.0, 2.7 Hz), 7.97 (1H, d, J=2.7 Hz), 8.66 (1H, d, J=9.0 Hz), 9.81 (1H, s), 12.3 (1H, s).

Example 66

Production of 5-chloro-2-([(2-([3-(furan-3-yl)benzyl]amino)-2-oxoethoxy)acetyl]amino)benzoic acid (66)

The target compound (66) was synthesized according to the following Steps (i) to (iv).

(i) [3-(Furan-3-yl)benzyl]carbamic acid.tert-butyl

Using the same method as in Example 5-(i), 3-(4,4,5,5-tetramethyl-1,3,2-dioxaborolan-2-yl)furan was reacted with the (3-bromobenzyl)carbamic acid.tert-butyl to give [3-(furan-3-yl)benzyl]carbamic acid.tert-butyl (yield: 96%).

$^1$H-NMR (CDCl$_3$) δ: 1.47 (9H, s), 4.33 (2H, d, J=5.8 Hz), 4.85 (1H, s), 6.69 (1H, dd, J=1.9, 0.9 Hz), 7.14-7.21 (1H, m), 7.28-7.42 (3H, m), 7.47 (1H, dd, J=1.9, 1.7 Hz), 7.70-7.74 (1H, m).

(ii) 3-(Furan-3-yl)benzylamine.hydrochloride

Using the same method as in Example 61-(ii), 3-(furan-3-yl)benzylamine.hydrochloride was quantitatively obtained from [3-(furan-3-yl)benzyl]carbamic acid tert-butyl.

$^1$H-NMR (DMSO-d$_6$) δ: 3.96-4.10 (2H, m), 6.99 (1H, dd, J=1.7, 0.7 Hz), 7.34-7.47 (2H, m), 7.58-7.66 (1H, m), 7.77 (1H, dd, J=1.8, 1.7 Hz), 7.87 (1H, s), 8.20 (1H, s), 8.59 (3H, s).

(iii) 5-Chloro-2-([(2-([3-(furan-3-yl)benzyl]amino)-2-oxoethoxy)acetyl]amino)benzoic acid.methyl ester Using the same method as in Example 1-(ii), 3-(furan-3-yl)benzylamine.hydrochloride was reacted with the (2-([4-chloro-2-(methoxycarbonyl)phenyl]amino)-2-oxoethoxy)acetic acid obtained in Example 1-(i) to give 5-chloro-2-([(2-([3-(furan-3-yl)benzyl]amino)-2-oxoethoxy)acetyl]amino)benzoic acid.methyl ester (yield: 77%). Note that 3-(furan-3-yl)benzylamine.hydrochloride was neutralized in DMA by adding an equivalent amount of triethylamine, and then used in the reaction.

$^1$H-NMR (CDCl$_3$) δ: 3.58 (3H, s), 4.20 (2H, s), 4.23 (2H, s), 4.65 (2H, d, J=5.9 Hz), 6.63-6.69 (1H, m), 7.19-7.48 (5H, m), 7.51 (1H, dd, J=9.0, 2.5 Hz), 7.68-7.73 (1H, m), 7.73-7.82 (1H, m), 7.96 (1H, d, J=2.5 Hz), 8.74 (1H, d, J=9.0 Hz), 11.8 (1H, s).

(iv) 5-Chloro-2-([(2-([3-(furan-3-yl)benzyl]amino)-2-oxoethoxy)acetyl]amino)benzoic acid Using the same method as in Example 1-(iii), the target 5-chloro-2-([(2-([3-(furan-3-yl)benzyl]amino)-2-oxoethoxy)acetyl]amino)benzoic acid was obtained from 5-chloro-2-([(2-oxo-2-([3-(furan-3-yl)benzyl]amino)ethoxy)acetyl]amino)benzoic acid.methyl ester (yield: 85%).

$^1$H-NMR (DMSO-d$_6$) δ: 4.18 (2H, s), 4.23 (2H, s), 4.40 (2H, d, J=6.0 Hz), 6.89-6.94 (1H, m), 7.20 (1H, d, J=7.6 Hz), 7.34 (1H, dd, J=7.6, 7.5 Hz), 7.43-7.55 (2H, m), 7.69 (1H, dd, J=9.0, 2.6 Hz), 7.71-7.76 (1H, m), 7.97 (1H, d, J=2.6 Hz), 8.14 (1H, s), 8.45 (1H, t, J=6.0 Hz), 8.65 (1H, d, J=9.0 Hz), 11.9 (1H, s).

Example 67

Production of 5-chloro-2-([(2-([3-(furan-2-yl)benzyl]amino)-2-oxoethoxy)acetyl]amino)benzoic acid (67)

The target compound (67) was synthesized according to the following Steps (i) to (iv).

(i) [3-(Furan-2-yl)benzyl]carbamic acid.tert-butyl

Using the same method as in Example 19-(ii), 2-furanboronic acid was reacted with the (3-bromobenzyl)carbamic acid.tert-butyl to give [3-(furan-2-yl)benzyl]carbamic acid.tert-butyl (yield: 84%).

$^1$H-NMR (CDCl$_3$) δ: 1.47 (9H, s), 4.34 (2H, d, J=5.9 Hz), 4.86 (1H, s), 6.47 (1H, dd, J=3.4, 1.8 Hz), 6.66 (1H, dd, J=3.4, 0.5 Hz), 7.14-7.22 (1H, m), 7.35 (1H, dd, J=8.3, 7.8 Hz), 7.47 (1H, dd, J=1.8, 0.5 Hz), 7.54-7.61 (2H, m).

(ii) 3-(Furan-2-yl)benzylamine.hydrochloride

The same method as in Example 61-(ii), 3-(furan-2-yl)benzylamine.hydrochloride was obtained from [3-(furan-2-yl)benzyl]carbamic acid tert-butyl (yield: 92%).

$^1$H-NMR (DMSO-d$_6$) δ: 4.05 (2H, s), 6.63 (1H, dd, J=3.3, 1.8 Hz), 6.98 (1H, d, J=3.3 Hz), 7.32-7.63 (2H, m), 7.66-7.74 (1H, m), 7.76-7.82 (1H, m), 7.91 (1H, s), 8.59 (3H, s).

(iii) 5-Chloro-2-([(2-([3-(furan-2-yl)benzyl]amino)-2-oxoethoxy)acetyl]amino)benzoic acid.methyl ester Using the same method as in Example 1 (ii), 3-(furan-2-yl)benzylamine hydrochloride was reacted with the (2-([4-chloro-2-(methoxycarbonyl)phenyl]amino)-2-oxoethoxy) acetic acid obtained in Example 1-(i) to give 5-chloro-2-([(2-([3-(furan-2-yl)benzyl]amino)-2-oxoethoxy)acetyl]amino) benzoic acid.methyl ester (yield: 84%). Note that 3-(furan-2-yl)benzylamine.hydrochloride was neutralized in DMA by adding an equivalent amount of triethylamine, and then used in the reaction.

$^1$H-NMR (CDCl$_3$) δ: 3.59 (3H, s), 4.20 (2H, s), 4.24 (2H, s), 4.67 (2H, d, J=6.0 Hz), 6.45 (1H, dd, J=3.4, 1.6 Hz), 6.63 (1H, d, J=3.4 Hz), 7.18-7.39 (2H, m), 7.43 (1H, d, J=1.6 Hz), 7.51 (1H, dd, J=9.0, 2.6 Hz), 7.51-7.59 (1H, m), 7.64 (1H, s), 7.72-7.88 (1H, m), 7.96 (1H, d, J=2.6 Hz), 8.74 (1H, d, J=9.0 Hz), 11.9 (1H, s).

(iv) 5-Chloro-2-([(2-([3-(furan-2-yl)benzyl]amino)-2-oxoethoxy)acetyl]amino)benzoic acid Using the same method as in Example 1-(iii), the target 5-chloro-2-([(2-([3-(furan-2-yl)benzyl]amino)-2-oxoethoxy)acetyl]amino)benzoic acid was obtained from 5-chloro-2-([(2-([3-(furan-2-yl)benzyl]amino)-2-oxoethoxy)acetyl]amino)benzoic acid.methyl ester (yield: 34%).

$^1$H-NMR (DMSO-d$_6$) δ: 4.18 (2H, s), 4.23 (2H, s), 4.41 (2H, d, J=6.1 Hz), 6.59 (1H, dd, J=3.3, 1.7 Hz), 6.92 (1H, d, J=3.3 Hz), 7.23 (1H, d, J=7.7 Hz), 7.38 (1H, dd, J=7.8, 7.7 Hz), 7.58 (1H, d, J=7.8 Hz), 7.64 (1H, s), 7.70 (1H, dd, J=9.1, 2.6 Hz), 7.71-7.77 (1H, m), 7.97 (1H, d, J=2.6 Hz), 8.51 (1H, t, J=6.1 Hz), 8.66 (1H, d, J=9.1 Hz), 11.9 (1H, s).

Example 68

Production of 5-chloro-2-([(2-oxo-2-([3-(1H-pyrazol-4-yl)phenyl]amino)ethoxy)acetyl]amino)benzoic acid (68)

The target compound (68) was synthesized according to either the following synthesization steps (i) to (iv) and (vii), or the steps (v), (vi), and (vii).

(i) 4-(3-Nitrophenyl)-1H-pyrazole-1-carboxylic acid.tert-butyl

Using the same method as in Example 5-(i), 4-(4,4,5,5-tetramethyl-1,3,2-dioxaborolan-2-yl)-1H-pyrazole-1-carboxylic acid.tert-butyl was reacted with 1-bromo-3-nitrobenzene to give 4-(3-nitrophenyl)-1H-pyrazole-1-carboxylic acid.tert-butyl (yield: 64%).

$^1$H-NMR (CDCl$_3$) δ: 1.70 (9H, s), 7.59 (1H, dd, J=8.2, 8.0 Hz), 7.82-7.89 (1H, m), 8.05-8.08 (1H, m), 8.13-8.20 (1H, m), 8.38 (1H, dd, J=2.0, 1.7 Hz), 8.42-8.45 (1H, m).

(ii) 4-(3-Nitrophenyl)-1H-pyrazole

Using the same method as in Example 61-(ii), 4-(3-nitrophenyl)-1H-pyrazole.hydrochloride was obtained from 4-(3-nitrophenyl)-1H-pyrazole-1-carboxylic acid tert-butyl. Thereafter, a saturated aqueous sodium bicarbonate solution was added thereto and stirred. The precipitate was collected by filtration, washed with water, and dried under reduced pressure at 50° for 5 hours to give 4-(3-nitrophenyl)-1H-pyrazole (yield: 99%).

$^1$H-NMR (DMSO-d$_6$) δ: 7.65 (1H, dd, J=8.1, 7.8 Hz), 7.99-8.06 (1H, m), 8.06-8.14 (1H, m), 8.30 (2H, s), 8.43 (1H, dd, J=1.9, 1.9 Hz).

(iii) 3-(1H-Pyrazol-4-yl)aniline

A 5 mL ethyl acetate solution of 300 mg (1.59 mmol) of 4-(3-nitrophenyl)-1H-pyrazole was added to 30 mg of 5% Pd—C, and stirred under a hydrogen atmosphere at room temperature overnight. The reaction solution was filtered through celite, and the filtrate was condensed and dried to give 252 mg of 3-(1H-pyrazol-4-yl)aniline (yield: 99%).

$^1$H-NMR (DMSO-d$_6$) δ: 5.01 (2H, s), 6.36-6.44 (1H, m), 6.70-6.78 (2H, m), 6.99 (1H, dd, J=7.6, 7.6 Hz), 7.87 (2H, s), 12.9 (1H, s).

(iv) 5-Chloro-2-([(2-oxo-2-([3-(1H-pyrazol-4-yl)phenyl]amino)ethoxy)acetyl]amino)benzoic acid.methyl ester Using the same method as in Example 1-(ii), 3-(1H-pyrazol-4-yl)aniline was reacted with the (2-([4-chloro-2-(methoxycarbonyl)phenyl]amino)-2-oxoethoxy)acetic acid obtained in Example 1-(i) to give 5-chloro-2-([(2-oxo-2-([3-(1H-pyrazol-4-yl)phenyl]amino)ethoxy)acetyl]amino)benzoic acid.methyl ester (yield: 72%).

$^1$H-NMR (DMSO-d$_6$) δ: 3.81 (3H, s), 4.32 (2H, s), 4.33 (2H, s), 7.22-7.38 (2H, m), 7.44-7.58 (1H, m), 7.75 (1H, dd, J=9.0, 2.7 Hz), 7.80-7.84 (1H, m), 7.96 (1H, d, J=2.7 Hz), 7.97 (2H, s), 8.63 (1H, d, J=9.0 Hz), 9.76 (1H, s), 11.47 (1H, s), 13.0 (1H, s).

(v) 4-(3-([(2-([4-Chloro-2-(methoxycarbonyl)phenyl]amino)-2-oxoethoxy)acetyl]amino)phenyl)-1H-pyrazole-1-carboxylic acid.tert-butyl Using the same method as in Example 5-(i), 4-(4,4,5,5-tetramethyl-1,3,2-dioxaborolan-2-yl)-1H-pyrazole-1-carboxylic acid.tert-butyl was reacted with the 2-[((2-[(3-bromophenyl)amino]-2-oxoethoxy)acetyl]amino]-5-chlorobenzoic acid.methyl ester obtained in Example 19-(i) to give 4-(3-([(2-([4-chloro-2-(methoxycarbonyl)phenyl]amino)-2-oxoethoxy)acetyl]amino)phenyl)-1H-pyrazole-1-carboxylic acid.tert-butyl (yield: 13%).

$^1$H-NMR (CDCl$_3$) δ: 1.69 (9H, s), 3.77 (3H, s), 4.28 (2H, s), 4.30 (2H, s), 7.28-7.78 (5H, m), 8.00 (1H, d, J=0.8 Hz), 8.04 (1H, d, J=2.4 Hz), 8.33 (1H, d, J=0.8 Hz), 8.78 (1H, d, J=9.0 Hz), 8.89 (1H, s), 11.9 (1H, s).

(vi) 5-Chloro-2-([(2-oxo-2-([3-(1H-pyrazol-4-yl)phenyl]amino)ethoxy)acetyl]amino)benzoic acid.methyl ester Using the same method as in Example 68-(ii), 5-chloro-2-([(2-oxo-2-([3-(1H-pyrazol-4-yl)phenyl]amino)ethoxy)acetyl]amino)benzoic acid.methyl ester was obtained from 4-(3-([(2-([4-chloro-2-(methoxycarbonyl)phenyl]amino)-2-oxoethoxy)acetyl]amino)phenyl)-1H-pyrazole-1-carboxylic acid.tert-butyl (yield: 52%).

(vii) 5-Chloro-2-([(2-oxo-2-([3-(1H-pyrazol-4-yl)phenyl]amino)ethoxy)acetyl]amino)benzoic acid Using the same method as in Example 1-(iii), the target 5-chloro-2-([(2-oxo-2-([3-(1H-pyrazol-4-yl)phenyl]amino)ethoxy)acetyl]amino)benzoic acid was obtained from 5-chloro-2-([(2-oxo-2-([3-(1H-pyrazol-4-yl)phenyl]amino)ethoxy)acetyl]amino)benzoic acid.methyl ester (yield: 70%).

$^1$H-NMR (DMSO-$d_6$) δ: 4.30 (2H, s), 4.31 (2H, s), 7.25-7.37 (2H, m), 7.47-7.57 (1H, m), 7.71 (1H, dd, J=9.0, 2.7 Hz), 7.82-7.88 (1H, m), 7.98 (1H, d, J=2.7 Hz), 7.99 (2H, s), 8.69 (1H, d, J=9.0 Hz), 9.78 (1H, s), 12.0 (1H, s).

Example 69

Production of 5-chloro-2-[((2-oxo-2-[(3-(1-[(phosphonatoxy)methyl]-1H-pyrazol-4-yl)phenyl)amino]ethoxy)acetyl)amino]benzoic acid.trisodium salt (69)

The target compound (69) was synthesized according to the following Steps (i) to (v).

(i) Phosphoric acid di-tert-butyl[4-(3-nitrophenyl)-1H-pyrazol-1-yl]methyl

In an argon atmosphere, a DMF solution (5 mL) of 250 mg (1.32 mmol) of 4-(3-nitrophenyl)-1H-pyrazole obtained in Example 68-(ii) was ice-cooled, and 185 mg (4.62 mmol) of 60% sodium hydride was added over 5 minutes in installments.

After stirring the mixture at room temperature for 1 hour, a DMF solution (2 mL) of 445 mg (1.72 mmol) of phosphoric acid di-tert-butylchloromethyl was added thereto dropwise for 5 minutes, and stirring was conducted at room temperature overnight. Under ice-cooling, water was added to the reaction solution to quench the liquid, and extraction was carried out with methylene chloride. The organic layer was separated, washed with a saturated aqueous sodium bicarbonate solution and a saturated sodium chloride solution, dried over sodium sulfate, filtered, condensed, and dried under reduced pressure. The resulting crude product was separated and purified using silica gel column chromatography to quantitatively give phosphoric acid.di-tert-butyl[4-(3-nitrophenyl)-1H-pyrazol-1-yl]methyl.

$^1$H-NMR (DMSO-$d_6$) δ: 1.39 (18H, s), 5.86 (2H, d, J=10.7 Hz), 7.69 (1H, dd, J=8.1, 7.8 Hz), 8.04-8.15 (2H, m), 8.28 (1H, s), 8.45 (1H, dd, J=2.0, 1.8 Hz), 8.63 (1H, s).

(ii) Phosphoric acid.[4-(3-aminophenyl)-1H-pyrazol-1-yl]methyl.di-tert-butyl

Using the same method as in Example 68-(iii), phosphoric acid.[4-(3-aminophenyl)-1H-pyrazol-1-yl]methyl.di-tert-butyl was obtained from phosphoric acid.di-tert-butyl[4-(3-nitrophenyl)-1H-pyrazol-1-yl]methyl (yield: 96%).

$^1$H-NMR (DMSO-$d_6$) δ: 1.38 (18H, s), 5.09 (2H, s), 5.83 (2H, d, J=10.8 Hz), 6.40-6.48 (1H, m), 6.68-6.77 (2H, m), 7.01 (1H, dd, J=7.8, 7.6 Hz), 7.89 (1H, s), 8.15 (1H, s).

(iii) 5-Chloro-2-([2-([3-(1-([(di-tert-butoxyphosphoryl)oxy]methyl)-1H-pyrazol-4-yl)phenyl]amino)-2-oxoethoxy)acetyl]amino)benzoic acid.methyl ester Using the same method as in Example 1-(ii), phosphoric acid.[4-(3-aminophenyl)-1H-pyrazol-1-yl]methyl.di-tert-butyl was reacted with the (2-([4-chloro-2-(methoxycarbonyl)phenyl]amino)-2-oxoethoxy)acetic acid obtained in Example 1-(i) to give 5-chloro-2-([2-([3-(1-([(di-tert-butoxyphosphoryl)oxy]methyl)-1H-pyrazol-4-yl)phenyl]amino)-2-oxoethoxy)acetyl]amino)benzoic acid.methyl ester (yield: 45%).

$^1$H-NMR (DMSO-$d_6$) δ: 1.38 (18H, s), 3.81 (3H, s), 4.31 (2H, s), 4.34 (2H, s), 5.86 (2H, d, J=10.8 Hz), 7.34 (2H, d, J=5.1 Hz), 7.47-7.57 (1H, m), 7.76 (1H, dd, J=9.0, 2.7 Hz), 7.88 (1H, s), 7.97 (1H, d, J=2.7 Hz), 7.99 (1H, s), 8.27 (1H, s), 8.63 (1H, d, J=9.0 Hz), 9.82 (1H, s), 11.5 (1H, s).

(iv) 5-Chloro-2-[((2-oxo-2-[(3-(1-[(phosphonooxy)methyl]-1H-pyrazol-4-yl)phenyl)amino]ethoxy)acetyl)amino]benzoic acid.methyl ester Using the same method as in Example 61-(ii), 5-chloro-2-[((2-oxo-2-[(3-(1-[(phosphonooxy)methyl]-1H-pyrazol-4-yl)phenyl)amino]ethoxy)acetyl)amino]benzoic acid.methyl ester was obtained from 5-chloro-2-([2-([3-(1-([(di-tert-butoxyphosphoryl)oxy]methyl)-1H-pyrazol-4-yl)phenyl]amino)-2-oxoethoxy)acetyl]amino)benzoic acid.methyl ester (yield: 99%).

$^1$H-NMR (DMSO-$d_6$) δ: 3.82 (3H, s), 4.32 (2H, s), 4.34 (2H, s), 5.81 (2H, d, J=9.8 Hz), 7.34 (2H, d, J=5.0 Hz), 7.47-7.57 (1H, m), 7.76 (1H, dd, J=9.0, 2.7 Hz), 7.88 (1H, s), 7.95 (1H, s), 7.97 (1H, d, J=2.7 Hz), 8.25 (1H, s), 8.63 (1H, d, J=9.0 Hz), 9.83 (1H, s), 11.5 (1H, s).

(v) 5-Chloro-2-[((2-oxo-2-[(3-(1-[(phosphonatoxy)methyl]-1H-pyrazol-4-yl)phenyl)amino]ethoxy)acetyl)amino]benzoic acid.trisodium salt 1.42 mL (1.42 mmol) of 1N aqueous sodium hydroxide solution was added to a THF solution (8 mL) of 261 mg (0.472 mmol) of 5-chloro-2-[((2-oxo-2-[(3-(1-[(phosphonooxy)methyl]-1H-pyrazol-4-yl)phenyl)amino]ethoxy)acetyl)amino]benzoic acid.methyl ester under ice-cooling, and heated under stirring at 50° C. for 6 hours. The reaction solution was condensed to yield a solid. IPE was added to the solid, and the mixture was filtered. The resulting solid was washed with IPE, and dried under reduced pressure at 50° C. for 3 hours, thereby quantitatively giving the target 5-chloro-2-[((2-oxo-2-[(3-(1-[(phosphonatoxy)methyl]-1H-pyrazol-4-yl)phenyl)amino]ethoxy)acetyl)amino]benzoic acid.trisodium salt.

$^1$H-NMR (D$_2$O) δ: 4.17 (2H, s), 4.23 (2H, s), 5.70 (2H, d, J=6.3 Hz), 7.24-7.54 (4H, m), 7.78 (1H, s), 7.85 (1H, d, J=2.2 Hz), 7.95 (1H, s), 8.17 (1H, d, J=8.9 Hz), 8.19 (1H, s).

Example 70

Production of 5-chloro-2-([(2-([3-(1,3-oxazol-5-yl)phenyl]amino)-2-oxoethoxy)acetyl]amino)benzoic acid (70)

The target compound (70) was synthesized according to the following Steps (i) to (ii).

(i) 5-Chloro-2-([(2-([3-(1,3-oxazol-5-yl)phenyl]amino)-2-oxoethoxy)acetyl]amino)benzoic acid.methyl ester Using the same method as in Example 15-(i), 3-(1,3-oxazol-5-yl)aniline was reacted with the (2-([4-chloro-2-(methoxycarbonyl)phenyl]amino)-2-oxoethoxy)acetic acid obtained in Example 1-(i) to give 5-chloro-2-([(2-([3-(1,3-oxazol-5-yl)phenyl]amino)-2-oxoethoxy)acetyl]amino)benzoic acid.methyl ester (yield: 65%).

¹H-NMR (DMSO-d₆) δ: 3.83 (3H, s), 4.32 (2H, s), 4.35 (2H, s), 7.42-7.52 (2H, m), 7.50-7.68 (1H, m), 7.60 (1H, s), 7.75 (1H, dd, J=9.1, 2.6 Hz), 7.96 (1H, d, J=2.6 Hz), 8.08 (1H, s), 8.47 (1H, s), 8.63 (1H, d, J=9.1 Hz), 9.96 (1H, s), 11.5 (1H, s).

(ii) 5-Chloro-2-([(2-([3-(1,3-oxazol-5-yl)phenyl]amino)-2-oxoethoxy)acetyl]amino)benzoic acid Using the same method as in Example 1-(iii), the target 5-chloro-2-([(2-([3-(1,3-oxazol-5-yl)phenyl]amino)-2-oxoethoxy)acetyl]amino)benzoic acid was obtained from 5-chloro-2-([(2-([3-(1,3-oxazol-5-yl)phenyl]amino)-2-oxoethoxy)acetyl]amino)benzoic acid.methyl ester (yield: 88%).
¹H-NMR (DMSO-d₆) δ: 4.31 (2H, s), 4.34 (2H, s), 7.38-7.51 (2H, m), 7.61-7.69 (1H, m), 7.66 (1H, s), 7.72 (1H, dd, J=9.0, 2.7 Hz), 7.98 (1H, d, J=2.7 Hz), 8.11 (1H, s), 8.47 (1H, s), 8.71 (1H, d, J=9.0 Hz), 9.97 (1H, s), 11.9 (1H, s).

Example 71

Production of 5-chloro-2-([(2-([3-(isoxazol-5-yl)phenyl]amino)-2-oxoethoxy)acetyl]amino)benzoic acid (71)

The target compound (71) was synthesized according to the following Steps (i) to (ii).

(i) 5-Chloro-2-([(2-([3-(isoxazol-5-yl)phenyl]amino)-2-oxoethoxy)acetyl]amino)benzoic acid.methyl ester Using the same method as in Example 15-(i), 3-(isoxazol-5-yl)aniline was reacted with the (2-([4-chloro-2-(methoxycarbonyl)phenyl]amino)-2-oxoethoxy)acetic acid obtained in Example 1-(i) to give 5-chloro-2-([(2-([3-(isoxazol-5-yl)phenyl]amino)-2-oxoethoxy)acetyl]amino)benzoic acid.methyl ester (yield: 56%).
¹H-NMR (CDCl₃) δ: 3.84 (3H, s), 4.28 (2H, s), 4.31 (2H, s), 6.56 (1H, d, J=1.9 Hz), 7.46 (1H, t, J=7.9 Hz), 7.55 (1H, dd, J=9.1, 2.6 Hz), 7.55-7.62 (1H, m), 7.91 (1H, ddd, J=8.0, 1.7, 1,2 Hz), 8.05 (1H, d, J=2.6 Hz), 8.14 (1H, t, J=1.7 Hz), 8.30 (1H, d, J=1.9 Hz), 8.78 (1H, d, J=9.1 Hz), 8.96 (1H, s), 11.9 (1H, s).

(ii) 5-Chloro-2-([(2-([3-(isoxazol-5-yl)phenyl]amino)-2-oxoethoxy)acetyl]amino)benzoic acid Using the same method as in Example 1-(iii), the target 5-chloro-2-([(2-([3-(isoxazol-5-yl)phenyl]amino)-2-oxoethoxy)acetyl]amino)benzoic acid was obtained from 5-chloro-2-([(2-([3-(isoxazol-5-yl)phenyl]amino)-2-oxoethoxy)acetyl]amino)benzoic acid.methyl ester (yield: 87%).
¹H-NMR (DMSO-d₆) δ: 4.32 (2H, s), 4.36 (2H, s), 7.00 (1H, d, J=1.9 Hz), 7.71 (1H, t, J=7.8 Hz), 7.62 (1H, dt, J=7.8, 1.5 Hz), 7.72 (1H, dd, J=9.0, 2.7 Hz), 7.74-7.82 (1H, m), 7.98 (1H, d, J=2.7 Hz), 8.26 (1H, t, J=1.5 Hz), 8.68 (1H, d, J=1.9 Hz), 8.72 (1H, d, J=9.0 Hz), 10.0 (1H, s), 11.9 (1H, s).

Example 72

Production of 5-chloro-2-([(2-oxo-2-([3-(thiophene-3-yl)benzyl]amino)ethoxy)acetyl]amino)benzoic acid (72)

The target compound (72) was synthesized according to the following Steps (i) to (iii).

(i) 2-[((2-[(3-Bromobenzyl)amino]-2-oxoethoxy)acetyl)amino]-5-chlorobenzoic acid.methyl ester Using the same method as in Example 15-(i), 3-bromobenzylamine was reacted with the (2-([4-chloro-2-(methoxycarbonyl)phenyl]amino)-2-oxoethoxy)acetic acid obtained in Example 1-(i) to give 2-[((2-[(3-bromobenzyl)amino]-2-oxoethoxy)acetyl)amino]-5-chlorobenzoic acid.methyl ester (yield: 78%).
¹H-NMR (CDCl₃) δ: 3.65 (3H, s), 4.21 (2H, s), 4.23 (2H, s), 4.61 (2H, d, J=6.3 Hz), 7.19 (1H, t, J=7.6 Hz), 7.28 (1H, dt, J=7.6, 1.7 Hz), 7.40 (1H, dt, J=7.6, 1.7 Hz), 7.49 (1H, t, J=1.7 Hz), 7.53 (1H, dd, J=9.0, 2.5 Hz), 7.83 (1H, t, J=6.3 Hz), 8.00 (1H, d, J=2.5 Hz), 8.76 (1H, d, J=9.0 Hz), 12.8 (1H, s).

(ii) 5-Chloro-2-([(2-oxo-2-([3-(thiophene-3-yl)benzyl]amino)ethoxy)acetyl]amino)benzoic acid.methyl ester Using the same method as in Example 19-(ii), 3-thiopheneboronic acid was reacted with the 2-[((2-[(3-bromobenzyl)amino]-2-oxoethoxy)acetyl)amino]-5-chlorobenzoic acid methyl ester to give 5-chloro-2-([(2-oxo-2-([3-(thiophene-3-yl)benzyl]amino)ethoxy)acetyl]amino)benzoic acid.methyl ester (yield: 77%).
¹H-NMR (CDCl₃) δ: 3.55 (3H, s), 4.20 (2H, s), 4.24 (2H, s), 4.68 (2H, d, J=6.2 Hz), 7.22-7.58 (8H, m), 7.81 (1H, t, J=6.2 Hz), 7.95 (1H, d, J=2.6 Hz), 8.74 (1H, d, J=9.0), 11.9 (1H, s).

(iii) 5-Chloro-2-([(2-oxo-2-([3-(thiophene-3-yl)benzyl]amino)ethoxy)acetyl]amino)benzoic acid Using the same method as in Example 1-(iii), the target 5-chloro-2-([(2-oxo-2-([3-(thiophene-3-yl)benzyl]amino)ethoxy)acetyl]amino)benzoic acid was obtained from 5-chloro-2-([(2-oxo-2-([3-(thiophene-3-yl)benzyl]amino)ethoxy)acetyl]amino)benzoic acid.methyl ester (yield: 73%).
¹H-NMR (DMSO-d₆) δ: 4.19 (2H, s), 4.24 (2H, s), 4.32 (2H, d, J=6.1 Hz), 7.23 (1H, d, J=7.7 Hz), 7.37 (1H, t, J=7.7 Hz), 7.53 (1H, dd, J=5.0, 1.3 Hz), 7.59 (1H, d, J=7.7 Hz), 7.59-7.67 (2H, m), 7.70 (1H, dd, J=9.0, 2.6 Hz), 7.83 (1H, dd, J=2.9, 1.3 Hz), 7.971H, d, J=2.6 Hz), 8.50 (1H, t, J=6.1 Hz), 8.67 (1H, d, J=9.0 Hz), 11.9 (1H, s).

Example 73

Production of 5-chloro-2-([(2-oxo-2-([3-(thiophen-2-yl)benzyl]amino)ethoxy)acetyl]amino)benzoic acid (73)

The target compound (73) was synthesized according to the following Steps (i) to (ii).

(i) 5-Chloro-2-([(2-oxo-2-([3-(thiophen-2-yl)benzyl]amino)ethoxy)acetyl]amino)benzoic acid.methyl ester Using the same method as in Example 19-(ii), 2-thiopheneboronic acid was reacted with the 2-[((2-[(3-bromobenzyl)amino]-2-oxoethoxy)acetyl)amino]-5-chlorobenzoic acid.methyl ester obtained in Example 72-(i) to give 5-chloro-2-([(2-oxo-2-([3-(thiophen-2-yl)benzyl]amino)ethoxy)acetyl]amino)benzoic acid.methyl ester (yield: 67%).
¹H-NMR (CDCl₃) δ: 3.58 (3H, s), 4.20 (2H, s), 4.24 (2H, s), 4.67 (2H, d, J=6.2 Hz), 7.06 (1H, dd, J=5.2, 3.6 Hz), 7.22-7.31 (3H, m), 7.33 (1H, t, J=7.7 Hz), 7.46-7.58 (2H, m), 7.51 (1H, dd, J=9.1, 2.6 Hz), 7.83 (1H, t, J=6.2 Hz), 7.96 (1H, d, J=2.6 Hz), 8.74 (1H, d, J=9.1 Hz), 11.9 (1H, s).

(ii) 5-Chloro-2-([(2-oxo-2-([3-(thiophen-2-yl)benzyl]amino)ethoxy)acetyl]amino)benzoic acid Using the same method as in Example 1-(iii), the target 5-chloro-2-([(2-oxo-2-([3-(thiophen-2-yl)benzyl]amino)ethoxy)acetyl]amino)benzoic acid was obtained from 5-chloro-2-([(2-oxo-2-([3-(thiophen-2-yl)benzyl]amino)ethoxy)acetyl]amino)benzoic acid.methyl ester (yield: 59%).
$^1$H-NMR (DMSO-$d_6$) δ: 4.19 (2H, s), 4.24 (2H, s), 4.41 (2H, d, J=6.0 Hz), 7.13 (1H, dd, J=4.6, 3.9 Hz), 7.25 (1H, d, J=7.5 Hz), 7.37 (1H, t, J=7.5 Hz), 7.45-7.65 (4H, m), 7.71 (1H, dd, J=8.9, 2.4 Hz), 7.97 (1H, d, J=2.4 Hz), 8.53 (1H, t, J=6.0 Hz), 8.67 (1H, d, J=8.9 Hz), 11.9 (1H, s).

Example 74

Production of 5-chloro-2-([([3-(furan-2-yl)benzyl]amino) (oxo)acetyl]amino)benzoic acid (74)

The target compound (74) was synthesized according to the following Steps (i) to (iv).

(i) [(3-Bromobenzyl)amino](oxo)acetic acid

Using the same method as in Example 20-(i), chloro glyoxylic acid ethyl was reacted with 3-bromobenzylamine to give [(3-bromobenzyl)amino](oxo)acetic acid.ethylester. Thereafter, [(3-bromobenzyl)amino](oxo)acetic acid was obtained using the same method as in Example 1-(iii) (yield: 40%).
$^1$H-NMR (DMSO-$d_6$) δ: 4.32 (2H, d, J=6.4 Hz), 7.22-7.52 (4H, m), 9.44 (1H, t, J=6.4 Hz), 13.9 (1H, br).

(ii) 2-(([(3-Bromobenzyl)amino](oxo)acetyl)amino)-5-chlorobenzoic acid.methyl ester Using the same method as in Example 15-(i), 2-amino-5-chlorobenzoic acid methyl was reacted with the [(3-bromobenzyl)amino](oxo)acetic acid to give 2-(([(3-bromobenzyl)amino](oxo)acetyl)amino)-5-chlorobenzoic acid.methyl ester (yield: 93%).
$^1$H-NMR (CDCl$_3$) δ: 4.00 (3H, s), 4.55 (2H, d, J=6.4 Hz), 7.16-7.30 (2H, m), 7.40-7.50 (2H, m), 7.54 (1H, dd, J=9.0, 2.5 Hz), 7.83 (1H, t, J=6.4 Hz), 8.07 (1H, d, J=2.5 Hz), 8.67 (1H, d, J=9.0 Hz), 12.7 (1H, s).

(iii) 5-Chloro-2-([([3-(furan-2-yl)benzyl]amino) (oxo)acetyl]amino)benzoic acid.methyl ester Using the same method as in Example 19-(ii), 2-furanboronic acid was reacted with the 2-(([(3-bromobenzyl)amino](oxo)acetyl)amino)-5-chlorobenzoic acid.methyl ester to quantitatively give 5-chloro-2-([([3-(furan-2-yl)benzyl]amino)(oxo)acetyl]amino)benzoic acid.methyl ester.
$^1$H-NMR (CDCl$_3$) δ: 4.00 (3H, s), 4.60 (2H, d, J=6.2 Hz), 6.47 (1H, dd, J=3.4, 1.8 Hz), 6.67 (1H, dd, J=3.4, 0.5 Hz), 7.22 (1H, d, J=7.5 Hz), 7.37 (1H, t, J=7.5 Hz), 7.47 (1H, dd, J=1.8, 0.5 Hz), 7.54 (1H, dd, J=8.9, 2.5 Hz), 7.57-7.65 (2H, m), 7.81 (1H, t, J=6.2 Hz), 8.07 (1H, d, J=2.5 Hz), 8.67 (1H, d, J=8.9 Hz), 12.7 (1H, s).

(iv) 5-Chloro-2-([([3-(furan-2-yl)benzyl]amino) (oxo)acetyl]amino)benzoic acid

Using the same method as in Example 1-(iii), the target 5-chloro-2-([([3-(furan-2-yl)benzyl]amino)(oxo)acetyl]amino)benzoic acid was obtained from 5-chloro-2-([([3-(furan-2-yl)benzyl]amino)(oxo)acetyl]amino)benzoic acid.methyl ester (yield: 64%).
$^1$H-NMR (DMSO-$d_6$) δ: 4.45 (2H, d, J=6.3 Hz), 6.60 (1H, dd, J=3.4, 1.8 Hz), 6.95 (1H, dd, J=3.4, 0.5 Hz), 7.25 (1H, d, J=7.6 Hz), 7.39 (1H, t, J=7.6 Hz), 7.61 (1H, d, J=7.6 Hz), 7.67 (1H, s), 7.76 (1H, dd, J=9.0, 2.6 Hz), 7.76 (1H, dd, J=1.8, 0.5 Hz), 7.99 (1H, d, J=2.6 Hz), 8.70 (1H, d, J=9.0 Hz), 9.75 (1H, t, J=6.3 Hz), 12.6 (1H, s).

Example 75

Production of 5-chloro-2-([(2-([3-(5-chlorothiophen-2-yl)benzyl]amino)-2-oxoethoxy)acetyl]amino)benzoic acid (75)

The target compound (75) was synthesized according to the following Steps (i) to (ii).

(i) 5-Chloro-2-([(2-([3-(5-chlorothiophen-2-yl)benzyl]amino)-2-oxoethoxy)acetyl]amino)benzoic acid. methyl ester Using the same method as in Example 19-(ii), 5-chloro-2-thiopheneboronic acid was reacted with the 2-(([(3-bromobenzyl)amino](oxo)acetyl)amino)-5-chlorobenzoic acid.methyl ester obtained in Example 72-(i) to give 5-chloro-2-([(2-([3-(5-chlorothiophen-2-yl)benzyl]amino)-2-oxoethoxy)acetyl]amino)benzoic acid.methyl ester (yield: 74%).
$^1$H-NMR (CDCl$_3$) δ: 3.59 (3H, s), 4.21 (2H, s), 4.24 (2H, s), 4.65 (2H, d, J=6.3 Hz), 6.86 (1H, s, J=3.8 Hz), 7.04 (1H, d, J=3.8 Hz), 7.21-7.47 (4H, m), 7.52 (1H, dd, J=9.0, 2.6 Hz), 7.84 (1H, t, J=6.3 Hz), 7.97 (1H, d, J=2.6 Hz), 8.74 (1H, d, J=9.0 Hz), 11.8 (1H, s).

(ii) 5-Chloro-2-([(2-([3-(5-chlorothiophen-2-yl)benzyl]amino)-2-oxoethoxy)acetyl]amino)benzoic acid Using the same method as in Example 1-(iii), the target 5-chloro-2-([(2-([3-(5-chlorothiophen-2-yl)benzyl]amino)-2-oxoethoxy)acetyl]amino)benzoic acid was obtained from 5-chloro-2-([(2-([3-(5-chlorothiophen-2-yl)benzyl]amino)-2-oxoethoxy)acetyl]amino)benzoic acid.methyl ester (yield: 63%).
$^1$H-NMR (DMSO-$d_6$) δ: 4.19 (2H, s), 4.24 (2H, s), 4.41 (2H, d, J=6.1 Hz), 7.15 (1H, d, J=3.9 Hz), 7.27 (1H, d, J=7.5 Hz), 7.37 (1H, d, J=3.9 Hz), 7.33-7.56 (3H, m), 7.71 (1H, dd, J=9.0, 2.6 Hz), 7.97 (1H, d, J=2.6 Hz), 8.51 (1H, t, J=6.1 Hz), 8.67 (1H, d, J=9.0 Hz), 11.9 (1H, s), 14.1 (1H, br).

Example 76

Production of 5-chloro-2-([(2-([3-(5-methylthiophen-2-yl)benzyl]amino)-2-oxoethoxy)acetyl] amino)benzoic acid (76)

The target compound (76) was synthesized according to the following Steps (i) to (ii).

(i) 5-Chloro-2-([(2-([3-(5-methylthiophen-2-yl)benzyl]amino)-2-oxoethoxy)acetyl]amino)benzoic acid. methyl ester Using the same method as in Example 19-(ii), 5-methyl-2-thiopheneboronic acid was reacted with the 2-(([(3-bromobenzyl)amino](oxo)acetyl)amino)-5-chlorobenzoic acid. methyl ester obtained in Example 72-(i) to give 5-chloro-2-

([2-([3-(5-methylthiophen-2-yl)benzyl]amino)-2-oxoethoxy)acetyl]amino)benzoic acid.methyl ester (yield: 78%).

¹H-NMR (CDCl₃) δ: 2.47 (3H, d, J=0.9 Hz), 3.57 (3H, s), 4.20 (2H, s), 4.23 (2H, s), 4.65 (2H, d, J=6.2 Hz), 6.67-6.72 (1H, m), 7.06 (1H, d, J=3.5 Hz), 7.21 (1H, dt, J=7.6, 1.4 Hz), 7.30 (1H, t, J=7.6 Hz), 7.50 (1H, dd, J=9.1, 2.5 Hz), 7.40-7.54 (2H, m), 7.81 (1H, t, J=6.2 Hz), 7.95 (1H, d, J=2.5 Hz), 8.74 (1H, d, J=9.1 Hz), 11.9 (1H, s).

(ii) 5-Chloro-2-([(2-([3-(5-methylthiophen-2-yl)benzyl]amino)-2-oxoethoxy)acetyl]amino)benzoic acid Using the same method as in Example 1-(iii), the target 5-chloro-2-([(2-([3-(5-methylthiophen-2-yl)benzyl]amino)-2-oxoethoxy)acetyl]amino)benzoic acid was obtained from 5-chloro-2-([(2-([3-(5-methylthiophen-2-yl)benzyl]amino)-2-oxoethoxy)acetyl]amino)benzoic acid.methyl ester (yield: 74.0%).

¹H-NMR (DMSO-d₆) δ: 2.45 (3H, s), 4.18 (2H, s), 4.24 (2H, s), 4.39 (2H, d, J=6.1 Hz), 6.81 (1H, dd, J=3.4, 1.1 Hz), 7.20 (1H, d, J=7.5 Hz), 7.27 (1H, d, J=3.5 Hz), 7.34 (1H, t, J=7.5 Hz), 7.42-7.53 (2H, m), 7.71 (1H, dd, J=9.0, 2.7 Hz), 7.97 (1H, d, J=2.7 Hz), 8.51 (1H, t, J=6.1 Hz), 8.67 (1H, d, J=9.0 Hz), 11.9 (1H, s), 14.2 (1H, br).

Example 77

Production of 5-chloro-2-([(2-([3-(furan-3-yl)phenyl]amino)-2-oxoethoxy)acetyl]amino)benzoic acid.N-methyl-D-glucamine salt (77)

The target compound (77) was synthesized according to the following step.

9 mL of methanol and 136.6 mg (0.70 mmol) of N-methyl-D-glucamine were added to 300 mg (0.70 mmol) of 5-chloro-2-([(2-([3-(furan-3-yl)phenyl]amino)-2-oxoethoxy)acetyl]amino)benzoic acid obtained in Example 58, and the mixture was stirred for 0.5 hours. Thereafter, the solvent was distilled off under reduced pressure, 10 mL of water was added thereto, and dissolution and freeze-drying were carried out to quantitatively give 5-chloro-2-([(2-([3-(furan-3-yl)phenyl]amino)-2-oxoethoxy)acetyl]amino)benzoic acid.N-methyl-D-glucamine salt.

¹H-NMR (D₂O) δ: 2.75 (3H, s), 3.07-3.28 (2H, m), 3.58-3.89 (5H, m), 4.03-4.15 (1H, m), 4.09 (2H, s), 4.12 (2H, s), 6.72 (1H, s), 7.19-7.33 (2H, m), 7.33 (1H, dd, J=8.9, 2.4 Hz), 7.45 (1H, s), 7.53 (1H, d, J=7.7 Hz), 7.62 (1H, s), 7.80 (1H, s), 7.84 (1H, d, J=2.4 Hz), 8.16 (1H, d, J=8.9 Hz).

Example 78

Production of 5-chloro-2-([(2-([3-(furan-3-yl)phenyl]amino)-2-oxoethoxy)acetyl]amino)benzoic acid.2-amino-2-hydroxymethyl-1,3-propanediol salt (78)

The target compound (78) was synthesized according to the following step.

Using the same method as in Example 77, 2-amino-2-hydroxymethyl-1,3-propanediol was reacted with 5-chloro-2-([(2-([3-(furan-3-yl)phenyl]amino)-2-oxoethoxy)acetyl]amino)benzoic acid obtained in Example 58 to quantitatively give 5-chloro-2-([(2-([3-(furan-3-yl)phenyl]amino)-2-oxoethoxy)acetyl]amino)benzoic acid.2-amino-2-hydroxymethyl-1,3-propanediol salt.

¹H-NMR (D₂O) δ: 3.69 (6H, s), 4.10 (2H, s), 4.13 (2H, s), 6.74 (1H, s), 7.18-7.41 (3H, m), 7.44-7.59 (2H, m), 7.63 (1H, s), 7.78-7.89 (2H, m), 7.17 (1H, d, J=8.7 Hz).

Example 79

Production of 5-chloro-2-([(2-([3-(isoxazole-3-yl)phenyl]amino)-2-oxoethoxy)acetyl]amino)benzoic acid (79)

The target compound (79) was synthesized according to the following Steps (i) to (ii).

(i) 5-Chloro-2-([(2-([3-(isoxazole-3-yl)phenyl]amino)-2-oxoethoxy)acetyl]amino)benzoic acid.methyl ester Using the same method as in Example 15-(i), 3-(isoxazole-3-yl)aniline was reacted with the (2-([4-chloro-2-(methoxycarbonyl)phenyl]amino)-2-oxoethoxy)acetic acid obtained in Example 1-(i) to give 5-chloro-2-([(2-([3-(isoxazole-3-yl)phenyl]amino)-2-oxoethoxy)acetyl]amino)benzoic acid.methyl ester (yield: 82%).

¹H-NMR (CDCl₃) δ: 3.82 (3H, s), 4.28 (2H, s), 4.31 (2H, s), 6.69 (1H, d, J=1.7 Hz), 7.46 (1H, t, J=7.9 Hz), 7.55 (1H, dd, J=9.0, 2.6 Hz), 7.56-7.64 (1H, m), 7.94 (1H, ddd, J=7.9, 2.0, 1.2 Hz), 8.05 (1H, d, J=2.6 Hz), 8.15 (1H, t, J=1.7 Hz), 8.48 (1H, d, J=1.7 Hz), 8.78 (1H, d, J=9.0 Hz), 8.96 (1H, s), 12.0 (1H, s).

(ii) 5-Chloro-2-([(2-([3-(isoxazole-3-yl)phenyl]amino)-2-oxoethoxy)acetyl]amino)benzoic acid Using the same method as in Example 1-(iii), the target 5-chloro-2-([(2-([3-(isoxazole-3-yl)phenyl]amino)-2-oxoethoxy)acetyl]amino)benzoic acid was obtained from 5-chloro-2-([(2-([3-(isoxazole-3-yl)phenyl]amino)-2-oxoethoxy)acetyl]amino)benzoic acid.methyl ester (yield: 94%).

¹H-NMR (DMSO-d₆) δ: 4.31 (2H, s), 4.35 (2H, s), 7.10 (1H, d, J=1.7 Hz), 7.49 (1H, t, J=7.8 HZ), 7.61 (1H, dt, J=7.8, 1.4 Hz), 7.72 (1H, dd, J=9.0, 2.7 Hz), 7.80 (1H, ddd, J=7.8, 2.0, 1.3 Hz), 7.99 (1H, d, J=2.7 Hz), 8.27 (1H, t, J=1.7 Hz), 8.70 (1H, d, J=9.0 Hz), 9.03 (1H, d, J=1.7 Hz), 10.0 (1H, s), 11.9 (1H, s).

Example 80

Production of 5-chloro-2-([(2-([3-(5-methylfuran-3-yl)phenyl]amino)-2-oxoethoxy)acetyl]amino)benzoic acid (80)

The target compound (80) was synthesized according to the following Steps (i) to (iii).

(i) 3-(5-Methylfuran-3-yl)aniline 500 mg (3.1 mmol) of 4-bromo-2-methylfuran was dissolved in 12 mL of toluene, and then 3 mL of methanol, 638 mg (4.7 mmol) of m-aminophenyl boronic acid, and 3 mL of 2M aqueous sodium carbonate solution were added thereto. Subsequently, 180 mg (0.16 mmol) of triphenylphosphine palladium was added, and the mixture was stirred at 100° C. for 17 hours. After cooling, anhydrous magnesium sulfate was added to the mixture, and the mixture was stirred. Filtration was then conducted, and the filtrate was condensed. The resulting product was separated and purified using silica gel column chromatography to give 3-(5-methylfuran-3-yl)aniline (yield: 52%).

$^1$H-NMR (CDCl$_3$) δ: 2.30 (3H, d, J=1.0 Hz), 3.66 (2H, br), 6.23 (1H, quintet, J=1.0 Hz), 6.51-6.56 (1H, m), 6.73-6.88 (2H, m), 7.12 (1H, t, J=7.8 Hz), 7.52 (1H, s).

(ii) 5-Chloro-2-([(2-([3-(5-methylfuran-3-yl)phenyl]amino)-2-oxoethoxy)acetyl]amino)benzoic acid.m-ethyl ester 380 mg (2.2 mmol) of (2-[(4-chloro-2-(methoxycarbonyl)phenyl)amino]-2-oxoethoxy)acetic acid was dissolved in 7 mL of THF. 361 mg (2.9 mmol) of oxalyl chloride and a catalytic quantity of DMF were added thereto under ice-cooling, and stirred at room temperature for 2 hours. Thereafter, the solvent was distilled off under reduced pressure. The DMA solution of 380 mg (2.2 mmol) of 3-(5-methylfuran-3-yl)aniline was added to the resulting residue, and stirred for 1 hour. After completion of the reaction, an aqueous sodium bicarbonate solution (was added dropwise, and extraction was carried out using ethyl acetate. The organic layer was washed with an aqueous sodium bicarbonate solution and water, dried over anhydrous magnesium sulfate, and filtered, and the filtrate was condensed. The resulting crude product was separated and purified using silica gel column chromatography to give 5-chloro-2-([(2-([3-(5-methylfuran-3-yl)phenyl]amino)-2-oxoethoxy)acetyl]amino)benzoic acid.m-ethyl ester (yield: 32%).

$^1$H-NMR (CDCl$_3$) δ: 2.33 (3H, d, J=1.0 Hz), 3.75 (3H, s), 4.28 (2H, s), 4.29 (2H, s), 6.29 (1H, quintet, J=1.0 Hz), 7.25-7.59 (5H, m), 7.82 (1H, s), 8.05 (1H, d, J=2.6 Hz), 8.79 (1H, d, J=9.2 Hz), 8.82 (1H, br), 11.9 (1H, br).

(iii) 5-Chloro-2-([(2-([3-(5-methylfuran-3-yl)phenyl]amino)-2-oxoethoxy)acetyl]amino)benzoic acid 320 mg (0.70 mmol) of 5-chloro-2-([(2-([3-(5-methylfuran-3-yl)phenyl]amino)-2-oxoethoxy)acetyl]amino)benzoic acid.methyl ester was suspended in 5 mL of methanol. 1N sodium hydroxide was added thereto and stirred at 50° C. for 3 hours. Thereafter, cooling was conducted, and the solvent was distilled off under reduced pressure. After the residue was neutralized by adding 2N hydrochloric acid, the residue was extracted with ethyl acetate. The organic layer was washed with water, dried over anhydrous magnesium sulfate, and filtered, and the filtrate was condensed. The resulting crude product was separated and purified using silica gel column chromatography to give the target 5-chloro-2-([(2-([3-(5-methylfuran-3-yl)phenyl]amino)-2-oxoethoxy)acetyl]amino) benzoic acid (yield: 22%).

$^1$H-NMR (DMSO-d$_6$) δ: 2.30 (3H, d, J=1.0 Hz), 4.30 (2H, s), 4.31 (2H, s), 6.46 (1H, quintet, J=1.0 Hz) 7.28-7.50 (3H, m), 7.54 (1H, dt, J=7.0, 2.0 Hz), 7.72 (1H, dd, J=9.0, 2.8 Hz), 7.83 (1H, s), 7.93 (1H, d, J=1.0 Hz), 7.98 (1H, d, J=2.8 Hz), 8.70 (1H, d, J=9.0 Hz), 9.80 (1H, br), 11.9 (1H, br).

Test Example

Measurement of PAI-1 Inhibitory Activity

Each of the compounds (1) to (77) prepared in Examples 1 to 77 was evaluated for inhibitory activity against human PAI-1 (manufactured by Molecular Innovation Inc. (USA); the same applies hereinafter).

More specifically, human-derived PAI-1 was added to a 0.1% Tween 80-containing 100 mM Tris-HCl (pH 8) solution containing each of the above compounds in a given concentration (20 μM or 50 μM), and incubated at 37° C. for 15 minutes. Subsequently, human-derived tissue plasminogen activator (t-PA) (manufactured by American Diagnostica, Inc. (USA); the same applies hereinafter) adjusted to 0.3 pmol/μL, was added thereto, and further incubated at 37° C. for 15 minutes. Then, 1.25 mM of S-2288 synthesized substrate (manufactured by Chromogenix) (Italy); the same applies hereinafter), which was a chromogenic substrate, was added thereto. Each of the final mixtures contained 100 mM Tris-HCl (pH 8), 30 mM NaCl, 1% DMSO, 0.1% Tween 80, 67 nM PAI-1, 9.8 nMt-PA, 1 mM S-2288 synthesized substrate, and each of the compounds (50 μM or 20 μM).

Free radical p-nitranilide removed from the chromogenic substrate (S-2288) by t-PA action was measured using a spectrophotometer at an absorbance of 405 nm at 5-minute intervals for 30 minutes. A system that did not contain the compounds (1) to (14) was similarly evaluated, and the PAI-1 activity of this system after 30 minutes was taken as 100% to evaluate the PAI-1 activity of the systems to which each of the test compounds was added. The results are together shown in FIGS. 1 to 7.

Reference Test Example

2-[3-(3'-carboxy-4'-phenylthiophen-2'-ylcarbamoyl)-pentanoylamino]-4-phenylthiophen-3-carboxylic acid (hereinafter referred to as a "compound a"), and 2-[3-(3'-carboxy-4'-thienylthiophen-2'-ylcarbamoyl)-pentanoylamino]-4-thienylthiophen-3-carboxylic acid (hereinafter referred to as a "compound b") were each evaluated for (1) PAI-1 inhibitory activity, (2) fibrinolytic action, and (3) effects on bleomycin-induced pulmonary fibrosis.

(1) PAI-1 Inhibitory Activity Assay

The compounds a and b (test compounds) were evaluated for inhibitory action on human PAI-1 (produced by Molecular Innovations Inc. (USA); the same applies hereinafter). More specifically, human-derived PAI-1 was added to a 0.1% Tween 80-containing 100 mM Tris-HCl (pH 8) solution containing each of the test compounds at a given concentration (20, 35, or 50 μM), and incubated at 37° C. for 15 minutes. Subsequently, human-derived tissue plasminogen activator (t-PA) (produced by American Diagnostica, Inc. (U.S.A.); the same applies hereinafter) adjusted to 0.53 pmol/μL was added thereto, and further incubated at 37° C. for 15 minutes. Then, 1.25 mM of S-2288 synthesized substrate (manufactured by Chromogenix (Italy); the same applies hereinafter), which was a chromogenic substrate, was added thereto. Each of the final mixtures contained 100 mM Tris-HCl (pH 8), 30 mM NaCl, 1% DMSO, 0.1% Tween 80, 67 nM PAI-1, 9.8 nM t-PA, 1 mM S-2288, and the test compound a or b (20, 35, or 50 μM).

P-nitranilide removed from the chromogenic substrate (S-2288) by t-PA action was measured using a spectrophotometer at an absorbance of 405 nm at 5-minute intervals for 30 minutes. A system that did not contain the test compounds was similarly evaluated, and the PAI-1 activity of this system (control system) after 30 minutes was taken as 100% to evaluate the PAI-1 activity of the systems to which each of the test compounds was added.

Comparative tests were carried out in the same manner using, in place of the above test compounds, a compound (tiplaxtinin) of the formula below used as an antithrombotic drug in US clinical trials (provided that the given concentrations were 20, 35, and 50 μM).

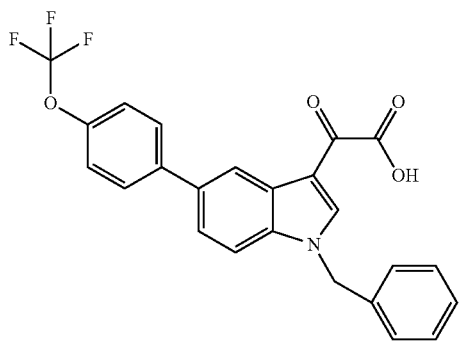 [SMILES: O=C(O)C(=O)c1cn(Cc2ccccc2)c2ccc(-c3ccc(OC(F)(F)F)cc3)cc12]

The results are shown in FIGS. 8 (A) to (C). FIGS. 8 (A), (B), and (C) each show PAI-1 activity (%) when the compound a (concentrations: 20, 35, and 50 μM), the compound b (concentrations: 20, 35, and 50 μM), and tiplaxtinin (comparative compound) (concentrations: 20, 35, and 50 μM) are added, respectively. The results reveal that the compounds a and b have higher PAI-1 activity inhibitory action at concentrations of 35 μM and 50 μM than tiplaxtinin (comparative compound) (PAI-1 inhibitory activity).

(2) Evaluation of Fibrinolytic Action

The compounds a and b were evaluated for fibrinolytic action in accordance with the document (Matsuo, O. et al., Haemostasis, 16, 43-50 (1986)).

More specifically, an aqueous solution (containing 25 mM barbital-sodium, 50 mM NaCl, and 25 mM $CaCl_2$) containing a concentration of 1.5 mg/mL of fibrinogen (produced by Organon Teknica) was added, on a 9 cm-plate, to thrombin dissolved in 0.2 mL of physiological saline (10NIH U/mL: produced by Mochida Pharmaceutical Co., Ltd.), and the mixture was allowed to stand at room temperature for 2 hours. Using this mixture, fibrinolysis assay was conducted.

Namely, a mixture of PAI-1, t-PA, and each of the test compounds was dropped onto the plate and incubated at room temperature for 18 hours. After the incubation, fibrinolysis due to plasminogen activation was measured from the lysis area on the plate.

The results demonstrate that the compounds a and b inhibit fibrinolysis suppression caused by PAI-1.

(3) Evaluation of Effects on Bleomycin-Induced Pulmonary Fibrosis

In order to evaluate the in vivo antifibrotic action of the compound b having PAI-1 inhibitory activity, the following experiments were carried out using an animal (mouse) model with pulmonary fibrosis artificially induced by bleomycin.

A C57BL/6 mouse (male, body weight: 19 to 21 g) was intraperitoneally anesthetized with pentobarbital, and an incision was made on the cervical organ. Ten mice were used as controls. The control mice (n=10) were endotracheally administered bleomycin (produced by Nippon Kayaku Co., Ltd.) (1.5 U/kg) lysed in physiological saline, twice a day for 14 days. On the other hand, the test mice were subjected to forcible oral administration with the compound b (200 mg/kg), suspended in a 0.5% carboxymethyl cellulose aqueous solution, twice a day for 14 days, in addition to the above endotracheal administration. Then, the lung tissues taken from these control mice and the test mice were analyzed, and further assayed for hydroxyproline levels. The hydroxyproline levels in the lung tissues were assayed in terms of the level in the hydrolysate of the lung tissues as described in the method of Kivirikko et al. (Anal. Biochem. 19, 249-255 (1967)). The levels (severity) of pulmonary fibrosis were scored from 0 to 8, based on the method of Ashcort et al. (J. Clin. Pathol. 41, 467-470 (1988)). Further, the control mice and the test mice were assayed for plasma PAI-1 activity (ng/mL).

FIG. 9 shows the results of the lung tissue analysis (a: fibrosis scores, b: tissue stained images), and the following table shows the hydroxyproline level (n=10, mean±SE) in the lung tissues and plasma PAI-1 activity (n=10, mean±SE).

TABLE 1

| Treatment | Hydroxyproline level in the lung tissues (μg/lung) | Plasma PAI-1 activity (ng/mL) |
|---|---|---|
| Control (untreated) | 140.2 ± 4.8 | 0.8 ± 0.1 |
| Bleomycin (0.5% CMC) | 232.9 ± 8.5[a] | 1.7 ± 0.2[a] |
| Bleomycin + compound b (0.5% CMC) (200 mg/kg, p.o., twice/day) | 204.2 ± 9.5[b] | 1.2 ± 0.1[b] |

[a]$P < 0.001$ vs control by Mann Whitney U test
[b]$P < 0.05$ vs control by Mann Whitney U test The results reveal that the administration of the compound b significantly reduces the hydroxyproline level in the lung tissues, which has been dramatically increased by the administration of bleomycin. The results further demonstrate that the administration of bleomycin remarkably increases plasma PAI-1 activity, and that such increases in plasma PAI-1 activity can be significantly reduced by the administration of the compound b.

As is clearly shown in FIG. 9, pulmonary fibrosis induced by the administered bleomycin (fibrosis score: 4.7±0.17, Control group: 0.5±0.17, P<0.001) is significantly ameliorated by the administration of the compound b (fibrosis score: 2.9±0.42, P<0.01). These results agree with the results of the above PAI-1 activity.

These results suggest that the compound b and other compounds having PAI-1 inhibitory action have properties that prevent the process of pulmonary fibrosis, in addition to a fibrinolytic system-promoting action. It has already been reported by Eitzman et al. that a strong relationship is observed between PAI-1 expression and accumulation of collagen in the lung tissues of mice in which the PAI-1 gene is overexpressed or deficient (J. Clin. Invest. 97, 232-237 (1996)). The above results, showing that pulmonary fibrosis is alleviated by the compound b having a strong PAI-1 inhibitory activity, suggest that PAI-1 is not a simply an indicator of pulmonary fibrosis, but the primary factor thereof. Fibril formation occurs in many tissues and organs such as the heart, blood vessels, liver, kidneys, etc., in addition to lungs. For this reason, this finding is critical.

Additionally, PAI-1 is also known to be involved in radiation injuries, and in the development and metastasis of cancer. More specifically, some studies on humans or animals have reported increased expression of PAI-1 in radiation injuries and growth and metastasis of cancer, in addition to thrombosis, fibrosis, and atherosclerosis (Thromb. Haemost. 2005 April; 93 (4), pp. 631-640). Another finding relating to PAI-1 is that in myocardial infarction, for example, cardiomyocytes and mast cells are involved in the expression of PAI-1, playing a critical role in interstitial and perivascular fibrosis (Am. J. Pathol. 2004 February; 164 (2): 449-456). It is also suggested that in atherosclerosis and vascular restenosis, intravascular fibrin deposition is involved in intimal hyperplasia, and that PAI-1 plays a key role in fibrin homeostasis (Trends Cardiovasc. Med. 2004 July; 14 (5); 196-202). In liver fibrosis in cirrhotic liver, PAI-1 increased together with u-PA, u-PAR, and t-PA increased in fibrotic liver is suggested to be associated with the inhibition of matrix degradation in cirrhotic liver. This implies that PAI-1 has an important role in the development of liver fibrosis in cirrhotic liver (J. Hepatol. 1999. October; 31 (4): 703-711). Furthermore, it is known that PAI-1 is related to expansion of the mesangium in diabetic nephropathy (J. Lab. Clin. Med. 2004 August; 144 (2): 69-77), and that PAI-1 is involved in the development and metastasis of breast cancer (Oncogene. 2003 July 10; 22 (28): 4389-4397). Regarding radiation injuries, it is reported that in radiation therapy for abdominal and pelvic cancers, radiation-induced PAI-1 plays a critical role in intestinal damage (Am. J. Pathol. 2008 March; 172 (3): 691-701). From such numerous findings relating to PAI-1, PAI-1 is considered to be deeply associated with the development of many diseases in various organs.

Moreover, regarding Alzheimer's disease, whose onset is said to be triggered by the accumulation of amyloid-β peptide (Aβ) in the brain, it has recently been reported that the degradation of Aβ is promoted by inhibiting PAI-1 (Jacobsen J S et al., Proc. Natl. Acad. Sci. USA, 105 (25), 8754-8759, 2008), suggesting the possibility that PAI-1 inhibitors are useful as therapeutic agents for Alzheimer's disease.

In light of the above, the compound (I) of the present invention is expected to prevent or treat various diseases whose onset is associated with PAI-1 (e.g., thrombosis, tissue fibrosis such as pulmonary fibrosis, angiopathy, heart disorders such as myocardial infarction, liver cirrhosis, kidney diseases, radiation injuries, and development and metastasis of cancer) and Alzheimer's disease, on the basis of the PAI-1 inhibitory action.

The invention claimed is:
1. A compound of Formula (I) or a salt thereof:

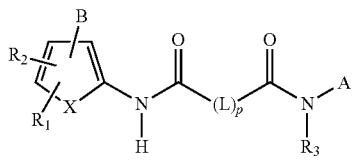

wherein
$R_1$ and $R_2$ are the same or different, and each represents hydrogen, halogen, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic-alkyl, heterocyclic-alkyloxy; aryl optionally having one or two substituents; 5- to 6-membered ring heteroaryl optionally having one or two substituents, or benzo-fused heteroaryl optionally having one or two substituents; amino or carbamoyl, each of which is optionally substituted with one or two substituents; or cyano, carboxy, or alkoxycarbonyl; and $R_1$ and $R_2$ are optionally adjoined with each other to form a ring;
$R_3$ is hydrogen, alkyl, cycloalkyl, or aryl optionally having one or two substituents;
X is $-C(R_5)=C(R_6)-$, $-C(R_7)=N-$, or $-N=C(R_8)-$, wherein $R_5$, $R_6$, $R_7$ and $R_8$ each represents hydrogen, halogen, alkyl optionally having one or two substituents, or alkoxy;
L is alkylene (some carbon atoms in the alkylene optionally form a cycloalkyl ring), alkenylene, alkynylene, cycloalkylene, alkyleneoxyalkylene, alkylenethioalkylene, alkylene-SO-alkylene, or alkylene-$SO_2$-alkylene, each of which is optionally substituted with one or two substituents; or alkylene-N($R_9$)-alkylene optionally substituted with one or two substituents, wherein $R_9$ represents hydrogen, or alkyl optionally having one or two substituents;
p represents an integer of 0 or 1;
A is a group represented by any one of the following Formulae (a), (b) or (c):

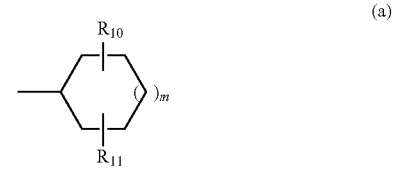

wherein $R_{10}$ and $R_{11}$ are the same or different, and each represents hydrogen or straight- or branched-chain alkyl; and m represents an integer of 0 to 10,

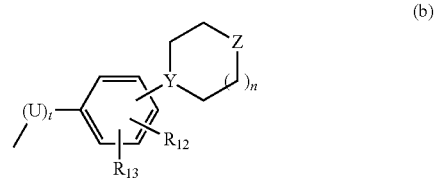

wherein
$R_{12}$ and $R_{13}$ are the same or different, and each represents hydrogen; halogen; or alkyl optionally having one or two substituents, cycloalkyl optionally having one or two substituents, or alkoxy optionally having one or two substituents;
Y represents CH or nitrogen;
Z represents $CH_2$, oxygen, or N-alkyl;
n represents an integer of 0 to 3;
U represents alkylene; and
t represents an integer of 0 or 1,

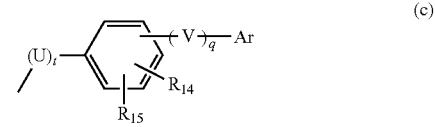

wherein
$R_{14}$ and $R_{15}$ are the same or different, and each represents hydrogen; halogen; or alkyl optionally having one or two substituents, cycloalkyl optionally having one or two substituents, or alkoxy optionally having one or two substituents;
V is alkylene, alkyleneoxyalkylene, oxyalkylene, alkyleneoxy, or oxygen;
q represents an integer of 0 or 1;
U and t are as defined above; and
Ar represents aryl having one or two substituents (the one or two substituents optionally form a ring with a part of carbon atoms in the aryl group), 5- to 6-membered ring aryl group having one or two identical or different heteroatoms optionally having one or two substituents, or benzo-fused heteroaryl optionally having one to three substituents; and B represents COOR$_{16}$, wherein R$_{16}$ represents hydrogen; alkyl, aryl or aralkyl; a group represented by CH(R$_{17}$)—O—COR$_{18}$ or —CH(R$_{17}$)—O—CO—OR$_{18}$, wherein R$_{17}$ is hydrogen or alkyl, and R$_{18}$ is alkyl or cycloalkyl; a (5-alkyl-2-oxo-1,3-dioxolen-4-yl)methyl group represented by the following formula:

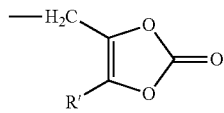

wherein R' represents alkyl; or a heterocyclic group: a 1H-tetrazol-5-yl group; a 4,5-dihydro-5-oxo-4H-1,2,4-oxadiazol-3-yl group; a 4,5-dihydro-5-thioxo-4H-1,2,4-oxadiazol-3-yl group; or a 4,5-dihydro-5-oxo-1,2,4-thiadiazol-3-yl group, represented by the following formulae (sequentially from the left)

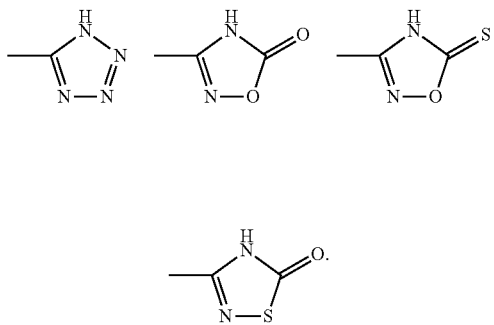

2. The compound or a salt thereof according to claim 1, wherein the X in Formula (I) is vinylene.

3. The compound or a salt thereof according to claim 1, wherein the compound represented by Formula (I) is a compound represented by Formula (II-1):

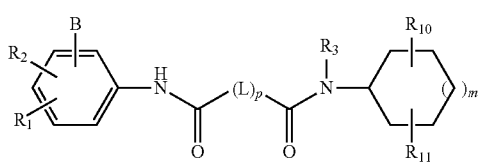

(II-1)

wherein
R$_1$ and R$_2$ are the same or different, and each represents hydrogen, halogen, alkyl, or aryl optionally having one or two substituents;
R$_3$ represents hydrogen, cycloalkyl, or aryl optionally having one or two substituents;
R$_{10}$ and R$_{11}$ represent hydrogen;
L represents alkylene, alkyleneoxyalkylene, or alkylenethioalkylene; and
m, p and B are as defined above.

4. The compound or a salt thereof according to claim 1, wherein the compound represented by Formula (I) is a compound represented by Formula (II-2):

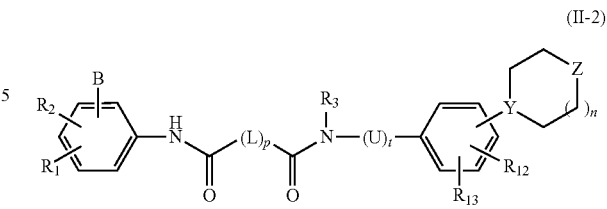

(II-2)

wherein
R$_1$ and R$_2$ are the same or different, and each represents hydrogen, halogen, alkyl, or aryl optionally having one or two substituents;
R$_3$, R$_{12}$ and R$_{13}$ are hydrogen;
Y is CH;
Z is CH$_2$;
L is alkylene, alkyleneoxyalkylene, or alkylenethioalkylene; and
n, p, U, t and B are as defined in claim 1.

5. The compound or a salt thereof according to claim 1, wherein the compound represented by Formula (I) is a compound represented by Formula (II-3):

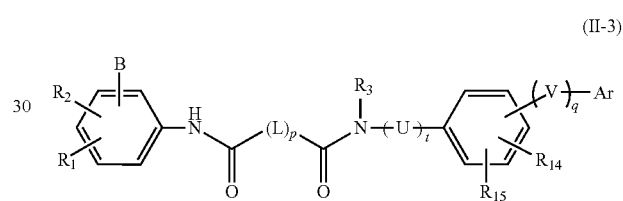

(II-3)

wherein
R$_1$ and R$_2$ are the same or different, and each represents hydrogen, halogen, alkyl, or aryl optionally having one or two substituents;
R$_3$ is hydrogen or alkyl;
R$_{14}$ and R$_{15}$ are the same or different, and each represents hydrogen, alkyl, or halogen;
V is alkylene, oxyalkylene, or oxygen;
Ar is aryl optionally having one or two substituents, aryl group having one or two identical or different heteroatoms optionally having one or two substituents, or benzo-fused heteroaryl optionally having one or three substituents;
L is alkylene, alkyleneoxyalkylene, alkylenethioalkylene, alkylene-SO-alkylene, alkylene-SO$_2$-alkylene; and
q, U, t, p, and B are as defined in claim 1.

6. The compound or a salt thereof according to claim 1, wherein the compound (I) is at least one member selected from the group consisting of compounds (9), (11), (15) and (28); the group consisting of compounds (10), (26) and (27); the group consisting of compounds (1) to (8), (12) to (14), (16) to (25), and (29) to (80) below;

(1) 5-chloro-2-{[(2-oxo-2-{[4-(pyridin-4-yl)phenyl]amino}ethoxy)acetyl]amino}benzoic acid,
(2) 5-chloro-2-{[(2-oxo-2-{[3-(pyridin-4-yl)phenyl]amino}ethoxy)acetyl]amino}benzoic acid,
(3) 5-chloro-2-[({2-[(4'-fluorobiphenyl-2-yl)amino]-2-oxoethoxy}acetyl)amino]benzoic acid,
(4) 5-chloro-2-{[(2-oxo-2-{[2-(pyridin-4-yl)phenyl]amino}ethoxy)acetyl]amino}benzoic acid hydrochloride, (5) 5-chloro-2-[({2-[(4'-fluoro-4-methylbiphenyl-3-yl)amino]-2-oxoethoxy}acetyl)amino]benzoic acid
(6) 5-chloro-2-[({2-oxo-2-[(3',4,5'-trimethylbiphenyl-3-yl)amino]ethoxy}acetyl)amino]benzoic acid,
(7) 5-chloro-2-[({2-[(4'-fluorobiphenyl-4-yl)amino]-2-oxoethoxy}acetyl)amino]benzoic acid,
(8) 5-chloro-2-[({2-[(4'-fluorobiphenyl-3-yl)amino]-2-oxoethoxy}acetyl)amino]benzoic acid,
(9) 5-chloro-2-({[2-(dicyclohexylamino)-2-oxoethoxy]acetyl}amino)benzoic acid,
(10) 5-chloro-2-[({2-[(4-cyclohexylphenyl)amino]-2-oxoethoxy}acetyl)amino]benzoic acid,
(11) 5-chloro-2-({[2-(cyclododecylamino)-2-oxoethoxy]acetyl}amino)benzoic acid,
(12) 5-chloro-2-{[({2-[(4'-fluorobiphenyl-3-yl)amino]-2-oxoethyl}sulfanyl)acetyl]amino}benzoic acid,
(13) 5-chloro-2-{[({2-[(4'-fluorobiphenyl-3-yl)amino]-2-oxoethyl}sulfinyl)acetyl]amino}benzoic acid,
(14) 5-chloro-2-{[({2-[(4'-fluorobiphenyl-3-yl)amino]-2-oxoethyl}sulfonyl)acetyl]amino}benzoic acid,
(15) 5-chloro-2-[({2-[cyclohexyl(phenyl)amino]-2-oxoethoxy}acetyl)amino]benzoic acid,
(16) 5-chloro-2-{[(2-oxo-2-{[3-(pyridin-4-yl)phenyl]amino}ethyl)acetyl]amino}benzoic acid[(2,2-dimethylpropanoyl)oxy]methyl ester,
(17) 5-chloro-2-{[(2-oxo-2-{[3-(pyridin-4-yl)phenyl]amino}ethoxy)acetyl]amino}benzoic acid 1-{[(cyclohexyloxy)carbonyl]oxy}ethyl ester,
(18) 5-chloro-2-{[(2-oxo-2-{[3-(pyridin-4-yl)phenyl]amino}ethoxy)acetyl]amino}benzoic acid (5-methyl-2-oxo-1,3-dioxol-4-yl)methyl ester,
(19) 5-chloro-2-{[(2-oxo-2-{[3-(pyridin-3-yl)phenyl]amino}ethoxy)acetyl]amino}benzoic acid,
(20) 5-chloro-2-({[(4'-fluoro-4-methylbiphenyl-3-yl)amino](oxo)acetyl}amino)benzoic acid
(21) 5-chloro-2-{[(2-oxo-2-{[3-(pyridin-2-yl)phenyl]amino}ethoxy)acetyl]amino}benzoic acid,
(22) 5-chloro-2-[({2-[(4'-fluoro-4-methylbiphenyl-3-yl)(2-methylpropyl)amino]-2-oxoethoxy}acetyl)amino]benzoic acid,
(23) 4'-fluoro-4-[({2-[(4'-fluoro-4-methylbiphenyl-3-yl)amino]-2-oxoethoxy}acetyl)amino]biphenyl-3-carboxylic acid,
(24) 5-chloro-2-{[({2-oxo-2-[(3',4,5'-trimethylbiphenyl-3-yl)amino]ethyl}sulfanyl)acetyl]amino}benzoic acid,
(25) 5-chloro-2-({[(2-oxo-2-{[3-(pyridin-4-yl)phenyl]amino}ethyl)sulfanyl]acetyl}amino)benzoic acid,
(26) 5-chloro-2-[({2-[(3-cyclohexylphenyl)amino]-2-oxoethoxy}acetyl)amino]benzoic acid,
(27) 5-chloro-2-{[({2-[(4-cyclohexylphenyl)amino]-2-oxoethyl}sulfanyl)acetyl]amino}benzoic acid,
(28) 5-chloro-2-[({[2-(cyclododecylamino)-2-oxoethyl]sulfanyl}acetyl)amino]benzoic acid,
(29) 5-chloro-2-[({2-[ethyl(4'-fluoro-4-methylbiphenyl-3-yl)amino]-2-oxoethoxy}acetyl)amino]benzoic acid,
(30) 5-chloro-2-{[({2-[ethyl(4'-fluoro-4-methylbiphenyl-3-yl)amino]-2-oxoethyl}sulfanyl)acetyl]amino}benzoic acid,
(31) 5-chloro-2-({5-[ethyl(4'-fluoro-4-methylbiphenyl-3-yl)amino]-5-oxopentanoyl}amino)benzoic acid,
(32) 5-chloro-2-{[(2-{[5-(furan-3-yl)-2-methylphenyl]amino}-2-oxoethoxy)acetyl]amino}benzoic acid,
(33) 5-chloro-2-({[(2-{[5-(furan-3-yl)-2-methylphenyl]amino}-2-oxoethyl)sulfanyl]acetyl}amino)benzoic acid,
(34) 5-chloro-2-[(5-{[5-(furan-3-yl)-2-methylphenyl]amino}-5-oxopentanoyl)amino]benzoic acid,
(35) 5-chloro-2-{[(2-{ethyl[5-(furan-3-yl)-2-methylphenyl]amino}-2-oxoethoxy)acetyl]amino}benzoic acid,
(36) 5-chloro-2-({[(2-{ethyl[5-(furan-3-yl)-2-methylphenyl]amino}-2-oxoethyl)sulfanyl]acetyl}amino)benzoic acid,
(37) 5-chloro-2-[(5-{ethyl[5-(furan-3-yl)-2-methylphenyl]amino}-5-oxopentanoyl)amino]benzoic acid,
(38) 5-chloro-2-[({2-[(2'-methoxy-4-methylbiphenyl-3-yl)amino]-2-oxoethoxy}acetyl)amino]benzoic acid,
(39) 5-chloro-2-[({2-[(3'-methoxy-4-methylbiphenyl-3-yl)amino]-2-oxoethoxy}acetyl)amino]benzoic acid,
(40) 5-chloro-2-[({2-[(4'-methoxy-4-methylbiphenyl-3-yl)amino]-2-oxoethoxy}acetyl)amino]benzoic acid,
(41) 2-{[(2-{[5-(1,3-benzodioxol-5-yl)-2-methylphenyl]amino}-2-oxoethoxy)acetyl]amino}-5-chlorobenzoic acid,
(42) 5-chloro-2-{[(2-{[2-methyl-5-(quinolin-8-yl)phenyl]amino}-2-oxoethoxy)acetyl]amino}benzoic acid,
(43) 2-{[(2-{[3'-(acetylamino)-4-methylbiphenyl-3-yl]amino}-2-oxoethoxy)acetyl]amino}-5-chlorobenzoic acid,
(44) 2-{[(2-{[4'-(acetylamino)-4-methylbiphenyl-3-yl]amino}-2-oxoethoxy)acetyl]amino}-5-chlorobenzoic acid,
(45) 5-chloro-2-{[{[3-(furan-3-yl)phenyl]amino}(oxo)acetyl]amino}benzoic acid,
(46) 5-chloro-2-({[(2-{[3-(furan-3-yl)phenyl]amino}-2-oxoethyl)sulfanyl]acetyl}amino)benzoic acid,
(47) 5-chloro-2-{[(2-{[3-(2,6-dimethoxypyridin-3-yl)phenyl]amino}-2-oxoethoxy)acetyl]amino}benzoic acid,
(48) 5-chloro-2-{[(2-oxo-2-{[3-(1H-pyrrol-1-yl)phenyl]amino}ethoxy)acetyl]amino}benzoic acid,
(49) 5-chloro-2-{[(2-{[2-fluoro-5-(furan-3-yl)phenyl]amino}-2-oxoethoxy)acetyl]amino}benzoic acid,
(50) 5-chloro-2-{[(2-{[4-fluoro-3-(furan-3-yl)phenyl]amino}-2-oxoethoxy)acetyl]amino}benzoic acid,
(51) 2-{[(2-{[3-(1-benzofuran-2-yl)phenyl]amino}-2-oxoethoxy)acetyl]amino}-5-chlorobenzoic acid,
(52) 5-chloro-2-[(3-{[3-(furan-3-yl)phenyl]amino}-3-oxopropanoyl)amino]benzoic acid,
(53) 5-chloro-2-{[{[3-(furan-3-yl)benzyl]amino}(oxo)acetyl]amino}benzoic acid,
(54) 5-chloro-2-{[(2-{[3-(furan-2-ylmethyl)phenyl]amino}-2-oxoethoxy)acetyl]amino}benzoic acid,
(55) 5-chloro-2-{[(2-{[3-(furan-3-ylmethyl)phenyl]amino}-2-oxoethoxy)acetyl]amino}benzoic acid,
(56) 5-chloro-2-[({2-oxo-2-[(2-phenoxyphenyl)amino]ethoxy}acetyl)amino]benzoic acid,
(57) 5-chloro-2-{[({2-oxo-2-[(2-phenoxyphenyl)amino]ethyl}sulfanyl)acetyl]amino}benzoic acid,
(58) 5-chloro-2-{[(2-{[3-(furan-3-yl)phenyl]amino}-2-oxoethoxy)acetyl]amino}benzoic acid,
(59) 5-chloro-2-{[(2-oxo-2-{[3-(thiophen-3-yl)phenyl]amino}ethoxy)acetyl]amino}benzoic acid,
(60) 5-chloro-2-{[(2-{[3-(1-methyl-1H-pyrazol-4-yl)phenyl]amino}-2-oxoethoxy)acetyl]amino}benzoic acid,
(61) 5-chloro-2-{[(2-{[3-(furan-2-yl)phenyl]amino}-2-oxoethoxy)acetyl]amino}benzoic acid,
(62) 5-chloro-2-{[(2-{[3-(3,5-dimethylisoxazol-4-yl)phenyl]amino}-2-oxoethoxy)acetyl]amino}benzoic acid,
(63) 5-chloro-2-{[(2-oxo-2-{[3-(thiophen-2-yl)phenyl]amino}ethoxy)acetyl]amino}benzoic acid,
(64) 5-chloro-2-{[(2-{[4-(furan-3-yl)phenyl]amino}-2-oxoethoxy)acetyl]amino}benzoic acid,
(65) 5-chloro-2-{[(2-{[3-(furan-2-ylmethoxy)phenyl]amino}-2-oxoethoxy)acetyl]amino}benzoic acid,

(66) 5-chloro-2-{[(2-{[3-(furan-3-yl)benzyl]amino}-2-oxoethoxy)acetyl]amino}benzoic acid,
(67) 5-chloro-2-{[(2-{[3-(furan-2-yl)benzyl]amino}-2-oxoethoxy)acetyl]amino}benzoic acid,
(68) 5-chloro-2-{[(2-oxo-2-{[3-(1H-pyrazol-4-yl)phenyl]amino}ethoxy)acetyl]amino}benzoic acid,
(69) 5-chloro-2-[({2-oxo-2-[(3-{1-[(phosphonateoxy)methyl]-1H-pyrazol-4-yl}phenyl)amino]ethoxy}acetyl)amino]benzoic acid,
(70) 5-chloro-2-{[(2-{[3-(1,3-oxazol-5-yl)phenyl]amino}-2-oxoethoxy)acetyl]amino}benzoic acid,
(71) 5-chloro-2-{[(2-{[3-(isoxazol-5-yl)phenyl]amino}-2-oxoethoxy)acetyl]amino}benzoic acid,
(72) 5-chloro-2-{[(2-oxo-2-{[3-(thiophen-3-yl)benzyl]amino}ethoxy)acetyl]amino}benzoic acid,
(73) 5-chloro-2-{[(2-oxo-2-{[3-(thiophen-2-yl)benzyl]amino}ethoxy)acetyl]amino}benzoic acid,
(74) 5-chloro-2-{[{[3-(furan-2-yl)benzyl]amino}(oxo)acetyl]amino}benzoic acid,
(75) 5-chloro-2-{[(2-{[3-(5-chlorothiophen-2-yl)benzyl]amino}-2-oxoethoxy)acetyl]amino}benzoic acid,
(76) 5-chloro-2-{[(2-{[3-(5-methylthiophen-2-yl)benzyl]amino}-2-oxoethoxy)acetyl]amino}benzoic acid,
(77) 5-chloro-2-{[(2-{[3-(furan-3-yl)phenyl]amino}-2-oxoethoxy)acetyl]amino}benzoic acid,
(78) 5-chloro-2-{[(2-{[3-(furan-3-yl)phenyl]amino}-2-oxoethoxy)acetyl]amino}benzoic acid,
(79) 5-chloro-2-{[(2-{[3-(isoxazol-3-yl)phenyl]amino}-2-oxoethoxy)acetyl]amino}benzoic acid, and
(80) 5-chloro-2-{[(2-{[3-(5-methylfuran-3-yl)phenyl]amino}-2-oxoethoxy)acetyl]amino}benzoic acid.

7. A method for producing a compound of claim 1 represented by the following Formula (I-1), comprising the step (a):

(a) a step of condensing a compound (1) and a compound (2) to form an ester compound (I-1), the compounds being represented by the formulae below:

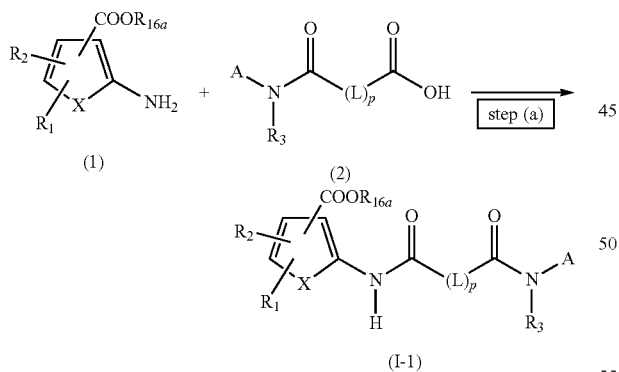

wherein $R_1$ to $R_3$, X, L, p and A are as defined in claim 1, and $R_{16a}$ is alkyl, aryl, or aralkyl.

8. A method for producing a compound of claim 1 represented by the following Formula (I-1), comprising the steps (b), (c) and (d):

(b) a step of reacting a compound (1) and a compound (3) to produce a compound (4), the compounds being represented by the formulae below;
(c) a step of selectively removing the $R_{19}$ of the compound (4) produced in the step (b) above to produce a compound (5); and
(d) a step of reacting the compound (5) produced in the step (C) above and a compound (6) to form an ester compound (I-1),

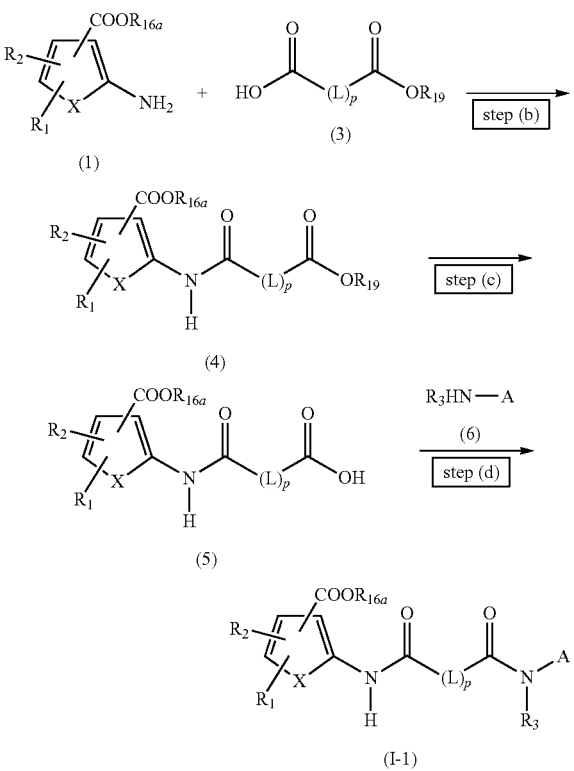

wherein $R_1$ to $R_3$, X, L, A and p are as defined in claim 1, $R_{16a}$ is alkyl, aryl, or aralkyl, and $R_{19}$ is alkyl, aryl or aralkyl.

9. A method for producing a compound of claim 1 represented by the following Formula (I-1), comprising the steps (e) and (f):

(e) a step of reacting a compound (1) and an intramolecular anhydride (7) of a dicarboxylic acid to form an ester carboxylic acid compound (5), the compounds being represented by the formulae below; and
(f) a step of reacting the ester carboxylic acid (5) formed in the step (e) above and a compound (6) to form an ester compound (I-1),

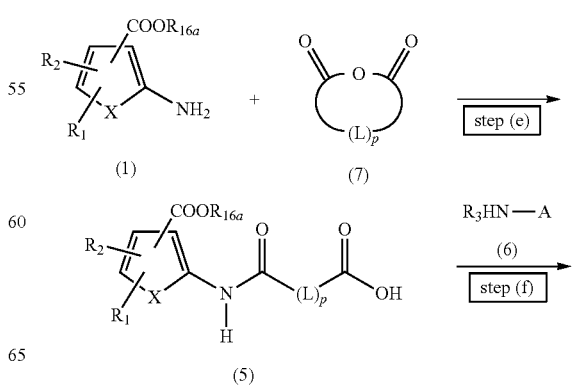

-continued

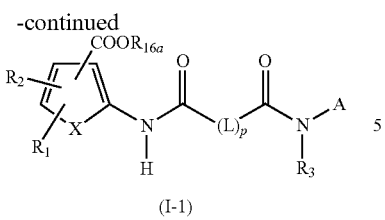
(I-1)

wherein $R_1$ to $R_3$, X, L and A are as defined in claim 1, $R_{16a}$ is alkyl, aryl, or aralkyl, and p is 1.

10. A method for producing a carboxylic acid compound of claim 1 represented by the following Formula (I-2), comprising the step (g) of removing the $R_{16a}$ of the ester compound of claim 1 represented by the following Formula (I-1),

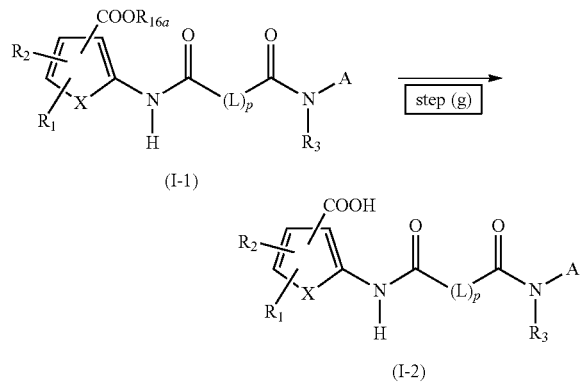

wherein $R_1$ to $R_3$, X, L, p and A are as defined in claim 1, and $R_{16a}$ is alkyl, aryl, or aralkyl.

11. A method for producing a compound of claim 1 represented by the following Formula (I-1'), comprising the step (h) of esterifying the carboxylic acid compound of claim 1 represented by the following Formula (I-2),

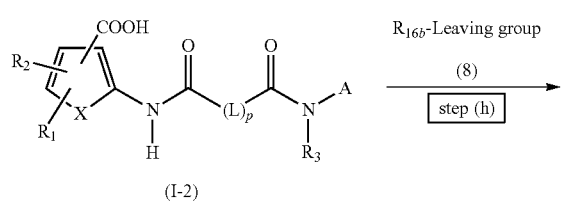

-continued

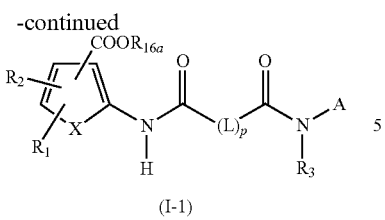
(I-1')

wherein $R_1$ to $R_3$, X, L, p, and A are as defined in claim 1, $R_{16b}$ is alkyl, phenyl, benzyl, a (5-alkyl-2-oxo-1,3-dioxolen-4-yl)methyl group, or a group represented by —CH($R_{17}$)—O—CO$R_{18}$ or —CH($R_{17}$)—O—CO—O$R_{18}$, wherein $R_{17}$ is hydrogen or alkyl, and $R_{18}$ is alkyl or cycloalkyl.

12. A method for producing a compound of claim 1 represented by the following Formula (I-8), comprising the step (n):

(n) a step of oxidizing a compound (I-7) to produce a compound (I-8),

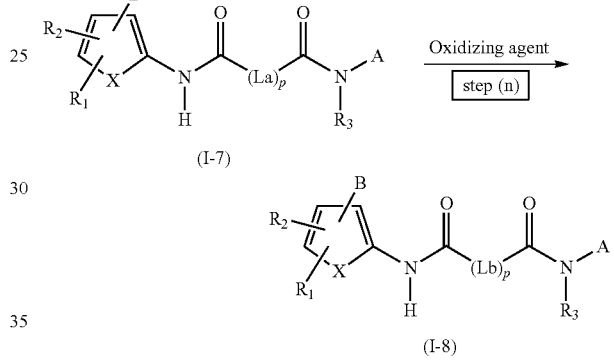

wherein B, $R_1$ to $R_3$, X and A are as defined in claim 1, La represents alkylenethioalkylene, Lb represents alkylene-SO-alkylene, and p represents 1.

13. A method for producing a compound of claim 1 represented by the following Formula (I-9), comprising the step (o) or (p):

(o) a step of further oxidizing the compound of claim 1 represented by the following Formula (I-8) to produce the compound (I-9); or (p) a step of reacting an excessive amount of an oxidizing agent with a compound (I-7) to produce the compound (I-9),

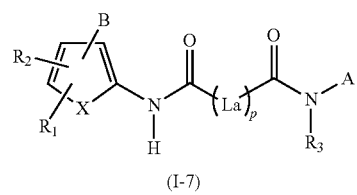
(I-7)

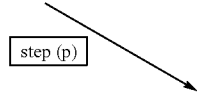

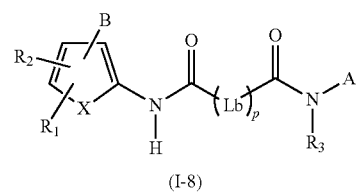
(I-8)

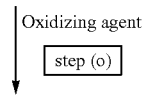

-continued

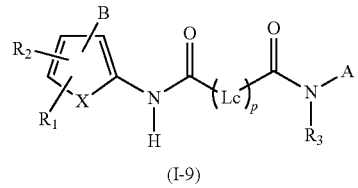

(I-9)

wherein B, $R_1$ to $R_3$, X and A are as defined in claim 1, La represents alkylenethioalkylene, Lb represents alkylene-SO-alkylene, Lc represents alkylene-$SO_2$-alkylene, and p represents 1.

14. A method for producing a compound of claim 1 represented by the following Formula (I-1), comprising the step (q) and (r):
- (q) a step of subjecting a compound (5) to a reaction with a compound (6) to produce a compound (16), which has halogen or trifluoromethanesulfonyloxy as a substituent; and
- (r) a step of reacting the compound (16) obtained in the above step (q) and a compound (17) to produce the compound (I-1),

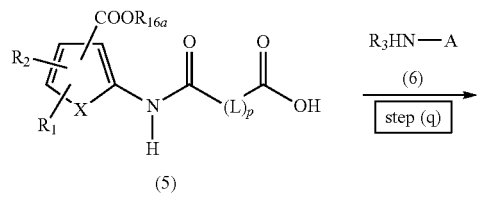

(5)

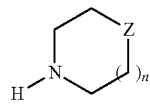
(6)
step (q)

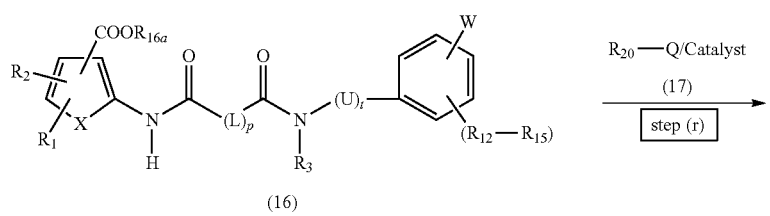

(16)

$R_{20}$—Q/Catalyst
(17)
step (r)

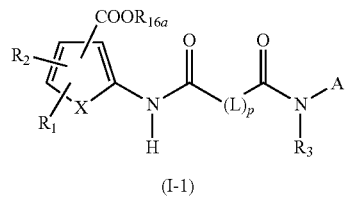

(I-1)

wherein $R_1$ to $R_3$, $R_{12}$ to $R_{15}$, X, L, p, U, t, and A are as defined in claim 1; and $R_{16a}$ is alkyl, aryl, or aralkyl, W represents halogen or trifluoromethanesulfonyloxy; $R_{20}$ represents cycloalkyl, cycloalkoxy, aryl, aryloxy, aralkyl, aralkyloxy, heterocyclic group, heterocyclic-alkyl, or heterocyclic-alkyloxy; Q is —$B(OR_{21})OR_{21}$, wherein $R_{21}$ represents hydrogen or alkyl, and when $R_{21}$ is alkyl, both alkyl groups are optionally joined to form a ring, or —ZnW, wherein Zn represents zinc, and W represents halogen; or $R_{20}$-Q together represent $R_{20}$—OH or a cyclic amine having a structure represented by the following formula:

$$\underset{H}{N}\diagup\diagdown\underset{( \ )_n}{\diagdown\diagup}Z$$

wherein Z and n are as defined in claim 1.

15. A plasminogen activator inhibitor-1 (PAI-1) inhibitor comprising a compound or a salt thereof according to claim 1 as an active ingredient.

16. A pharmaceutical composition comprising a compound or a salt thereof according to claim 1 and a pharmacologically acceptable carrier or additive.

17. The pharmaceutical composition according to claim 16, the composition being a fibrinolysis promoter or an anti-fibrosis agent.

* * * * *

UNITED STATES PATENT AND TRADEMARK OFFICE
CERTIFICATE OF CORRECTION

PATENT NO.       : 8,415,479 B2
APPLICATION NO.  : 12/935609
DATED            : April 9, 2013
INVENTOR(S)      : Miyata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 48 days.

Signed and Sealed this
First Day of September, 2015

Michelle K. Lee
*Director of the United States Patent and Trademark Office*